(12) United States Patent
Salas et al.

(10) Patent No.: US 10,875,924 B2
(45) Date of Patent: Dec. 29, 2020

(54) ANTI-GPIIB/IIIA ANTIBODIES AND USES THEREOF

(71) Applicant: Biogen MA Inc., Cambridge, MA (US)

(72) Inventors: Joe Salas, Wayland, MA (US); Karl Hanf, Billerica, MA (US); Arjan van der Flier, Somerville, MA (US); Bradley R. Pearse, Somerville, MA (US)

(73) Assignee: Biogen MA Inc., Cambridge, MA (US)

( * ) Notice: Subject to any disclaimer, the term of this patent is extended or adjusted under 35 U.S.C. 154(b) by 357 days.

(21) Appl. No.: 15/521,102

(22) PCT Filed: Oct. 23, 2015

(86) PCT No.: PCT/US2015/057187
§ 371 (c)(1),
(2) Date: Apr. 21, 2017

(87) PCT Pub. No.: WO2016/065301
PCT Pub. Date: Apr. 28, 2016

(65) Prior Publication Data
US 2017/0355771 A1    Dec. 14, 2017

Related U.S. Application Data

(60) Provisional application No. 62/067,783, filed on Oct. 23, 2014, provisional application No. 62/110,883, filed on Feb. 2, 2015, provisional application No. 62/184,044, filed on Jun. 24, 2015.

(51) Int. Cl.
| C07K 16/36 | (2006.01) |
| C07K 16/28 | (2006.01) |
| C12N 9/64 | (2006.01) |
| G01N 33/569 | (2006.01) |
| A61K 39/00 | (2006.01) |

(52) U.S. Cl.
CPC ........ *C07K 16/2848* (2013.01); *C12N 9/6437* (2013.01); *C12Y 304/21021* (2013.01); *G01N 33/56966* (2013.01); *A61K 2039/505* (2013.01); *C07K 2317/24* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/90* (2013.01); *C07K 2317/92* (2013.01); *C07K 2317/94* (2013.01); *C07K 2319/00* (2013.01); *C07K 2319/30* (2013.01); *C07K 2319/31* (2013.01); *C07K 2319/33* (2013.01); *C07K 2319/74* (2013.01); *G01N 2333/70557* (2013.01)

(58) Field of Classification Search
None
See application file for complete search history.

(56) References Cited

U.S. PATENT DOCUMENTS

| 5,530,101 A * | 6/1996 | Queen .................... C07K 16/00 424/133.1 |
| 5,714,350 A * | 2/1998 | Co .......................... C07K 16/00 424/133.1 |
| 5,770,198 A * | 6/1998 | Coller ................ C07K 16/2848 424/153.1 |
| 5,777,085 A * | 7/1998 | Co ...................... C07K 16/2848 435/320.1 |
| 8,455,627 B2 * | 6/2013 | Linhard ............. C07K 16/2848 530/388.22 |
| 9,365,650 B2 | 6/2016 | Peter |
| 9,702,879 B2 | 7/2017 | Barneo Serra et al. |
| 10,364,288 B2 * | 7/2019 | Salas .................... C12N 9/6437 |
| 2002/0009753 A1 | 1/2002 | Bednar et al. |
| 2009/0104187 A1* | 4/2009 | Kovacevich ......... C07K 16/241 424/133.1 |
| 2010/0135991 A1 | 6/2010 | Huang et al. |
| 2011/0045008 A1 | 2/2011 | Simon et al. |
| 2011/0165175 A1 | 7/2011 | Linhard et al. |
| 2013/0108629 A1 | 5/2013 | Dumont et al. |
| 2014/0243502 A1 | 8/2014 | Peter |
| 2014/0271685 A1 | 9/2014 | Liu |
| 2016/0115234 A1 | 4/2016 | Salas et al. |
| 2016/0311923 A1 | 10/2016 | Gros |
| 2017/0342152 A1 | 11/2017 | Pearse et al. |
| 2020/0102391 A1 | 4/2020 | Salas |

FOREIGN PATENT DOCUMENTS

| EP | 2025685 | 2/2009 |
| WO | 1999019463 | 4/1999 |
| WO | 2004005890 | 4/2004 |
| WO | WO-2005079479 A2 * | 9/2005 | ......... C07K 16/1027 |
| WO | 2009140593 | 11/2009 |

(Continued)

OTHER PUBLICATIONS

Edwards et al., J Mol Biol. Nov. 14, 2003;334(1): 103-18.*
Llyod et al., Protein Eng Des Sel. Mar. 2009;22(3):159-68. doi: 10.1093/protei n/gzn058. Epub Oct. 29, 2008.*
Goel et al., J Immunol. Dec. 15, 2004; 173(12):7358-67.*
Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Newman et al., "Synergistic action of murine monoclonal antibodies that inhibit ADP-induced platelet aggregation without blocking fibrinogen binding," Blood, American Society of Hematology, p. 668-676 (Feb. 1987).

(Continued)

*Primary Examiner* — Michael Szperka
(74) *Attorney, Agent, or Firm* — Fish & Richardson P.C.

(57) ABSTRACT

Antibodies and antibody fragments that specifically bind to glycoprotein IIb/IIIa (GPIIb/IIIa) are disclosed. Chimeric molecules comprising such antibodies or antigen-binding fragments are also disclosed. In addition, methods of using the disclosed antibodies, antibody fragments, and chimeric molecules, e.g., to target agents to platelets and for the treatment or prevention of diseases or disorders are provided.

16 Claims, 20 Drawing Sheets

Specification includes a Sequence Listing.

(56) References Cited

FOREIGN PATENT DOCUMENTS

| WO | 2009140598 | 11/2009 | | |
|---|---|---|---|---|
| WO | 2010091122 | 8/2010 | | |
| WO | 2010115866 | 10/2010 | | |
| WO | 2011112549 | 9/2011 | | |
| WO | 2012006633 | 1/2012 | | |
| WO | 2012078813 | 6/2012 | | |
| WO | 2012170969 | 12/2012 | | |
| WO | 2013016454 | 1/2013 | | |
| WO | 2014193305 | 11/2014 | | |
| WO | WO-2014190305 A2 * | 11/2014 | ......... | C07K 14/755 |
| WO | 2014194282 | 12/2014 | | |
| WO | 2016065301 | 4/2016 | | |
| WO | 2016070050 | 5/2016 | | |
| WO | WO 2017/152102 | 9/2017 | | |
| WO | WO 2018/098363 | 5/2018 | | |
| WO | WO 2018/160704 | 9/2018 | | |
| WO | WO 2018/208868 | 11/2018 | | |

OTHER PUBLICATIONS

Newman et al., "Quantitation of Membrane Glycoprotein IIIa on Intact Human Platelets Using the Monoclonal Antibody, AP-3," Blood, 66(1):227-232 (Jan. 1985).

Quinn et al., "Quantifying GPIIb/IIIa Receptor Binding Using 2 Monoclonal Antibodies: Discriminating Abciximab and Small Molecular Weight Antagonists," Circulation, 2231-2238 (May 1999).

Li et al., "Platelet Fragmentation requires a Specific Structural Conformation of Human Monoclonal Antibody against beta3 Integrin," Journal of Biological Chemistry, 283(6):3224-3230 (Feb. 2008).

O'Toole et al., "Affinity Modulation of the Alpha-I-I-B-Beta-3 Integrin Platelet GPIIB-IIIA is an Intrinsic Property of the Receptor," Cell Regulation, Bethesda, MD, US, 1(12):883-893 (Nov. 1990).

Pidard et al., "Interaction of AP-2, a Monoclonal Antibody Specific for the Human Platelet Glycoprotein IIb-IIIa Complex, with Intact Platelets," The Journal of Biological Chemistry, 12582-12586 (Oct. 1983).

Shattil et al., "changes in the platelet membrane glycoprotein IIb.IIIa complex during platelet activation," Journal of Biological Chemistry, 11107-11114 (Sep. 1985).

Anderson et al., "Anti-GPIIb/IIIa (CD41) monoclonal antibody-induced platelet activation requires Fc receptor-dependent cell-cell interaction," British Journal of Haematol, Sep. 1991, 79(1):75-83.

Bi et al., "Targeted disruption of the mouse factor VIII gene produces a model of haemophilia ," A. Nat. Genet. 1995, 10(1):119-121.

Dumont et al., "Prolonged activity of a recombinant factor VIII-Fc fusion protein in hemophilia A mice and dogs," Blood, 2012, 119(13):3024-3030.

Emambokus and Frampton, "The glycoprotein IIb molecule is expressed on early murine hematopoietic progenitors and regulates their numbers in sites of hematopoiesis," Immunity, 2003, 19(1):33-45.

European Search Report in European Application No. 14801129.9, dated Dec. 22, 2016, 11 pages.

Frelinger et al., "Selective Inhibition of Integrin Function by Antibodies Specific for Ligand-occupied Receptor Conformers," The Journal of Biological Chemistry, Apr. 1990, 265(11):6346-6352.

International Preliminary Report on Patentability in International Application No. PCT/US2014/040370, dated Dec. 1, 2015, 9 pages.

International Preliminary Report on Patentability in International Application No. PCT/US2014/039420, dated Nov. 24, 2015, 8 pages.

International Search Report and Written Opinion in International Application No. PCT/US2014/040370, dated Jan. 9, 2015, 13 pages.

International Search Report and Written Opinion in International Application No. PCT/US2014/039420, dated Dec. 9, 2014, 13 pages.

International Search Report in International Application No. PCT/US2015/057187, dated Feb. 23, 2016, 12 pages.

International Preliminary Report on Patentability in International Application No. PCT/US2015/057187, dated Apr. 25, 2017, 7 pages.

Invitation to Pay Additional Fees in International Application No. PCT/US2015/058326, dated Feb. 8, 2016, 13 pages.

International Search Report and Written Opinion in International Application No. PCT/US2015/058326, dated Apr. 20, 2016, 26 pages.

International Preliminary Report on Patentability in International Application No. PCT/US2015/058326, dated May 2, 2017, 17 pages.

Jurlander et al., "Recombinant activated factor VII (rFVIIa): characterization, manufacturing, and clinical development," Semin. Thromb. Hemost., 2001, 27(4):373-84.

Kosugi, "Platelet-associated anti-GPIIb-IIIa autoantibodies in chronic immune thrombocytopenic purpura recognizing epitopes close to the ligand-binding site of glycoprotein (GP) IIb," Blood, Sep. 2001, 98(6):1819-1827.

Mekrache et al., "Activation of recombinant alphaIIbbeta3 expressed in Chinese hamster ovary cells exposes different binding sites for fibrinogen or von Willebrand factor: evidence using monoclonal antibodies to alphaIIbbeta3,"British Journal of Haematol, 2002, 116(3):636-644.

Pan et al., "Enhanced efficacy of recombinant FVIII in noncovalent complex with PEGylated liposome in hemophilia A mice," Blood, Sep. 2009, 114:2802-2811.

Rostin et al., "B-Domain Deleted Recombinant Coagulation Factor VIII Modified with Monomethoxy Polyethylene Glycol," Bioconj. Chem., 2000, 11:387-396.

Schulte, "Use of albumin fusion technology to prolong the half-life of recombinant factor VIIa," Thromb. Res. 2008;122 Suppl 4:S14-19.

Schwarz et al., "Conformation-specific blockade of the integrin GPIIb/IIIa: a novel antiplatelet strategy that selectively targets activated platelets," Circulation Research, American Heart Associa., 99(1):25-33 (Jul. 2006).

Schwarz et al., "Reversibility versus Persistence of GPIIb/IIIa Blocker-Induced Conformational Change of GPIIb/IIIa (αIIbβ3), CD41/CD61)," Journal of Pharmacology and Experimental Therapeutics, Aug. 2004, 308(3):1002-1011.

Shibeko et al., "Predicting dosing advantages of factor VIIa variants with altered tissue factor-dependent and lipid-dependent activities," J Thromb Haemost, 12(8):1302-1312, Aug. 1, 2014.

Spira et al., "Prolonged bleeding-free period following prophylactic infusion of recombinant factor VIII reconstituted with pegylated liposomes," Blood, Dec. 2006, 108:3668-3673.

Stennicke et al., "Generation and biochemical characterization of glycoPEGylated factor VIIa derivatives," Thromb Haemost., Nov. 2008, 100:920-928.

Supplementary European Search Report in European Application No. 14801129.9, dated Mar. 30, 2017, 17 pages.

Thornton et al., "Identification of distal regulatory regions in the human alpha IIb gene locus necessary for consistent, high-level megakaryocyte expression," Blood, 2002, 100(10):12 pages.

Stoll et al., "Targeting Ligand-Induced Binding Sites on GPIIb/IIIa via Single-Chain Antibody Allows Effective Anticoagulation Without Bleeding Time Prolongation," Arterioscler Thromb Vasc Biol, 2007, 27(5):1206-1212.

White et al. [online], "Common Bleeding Episodes," National Hemophilia Foundation, 2013, [retrieved on Oct. 22, 2018], retrieved from: URL<https://www.hemophilia.org/sites/default/files/document/files/Nurses-Guide-Chapter-4-Common-Bleeding-Episodes.pdf>, pp. 1-14.

World Health Organization [online], "Blood products and related biologicals," Aug. 2018, [retrieved on Oct. 22, 2018], retrieved from: URL<www.who.int/bloodproducts/ivd/coagulation_disorders/en/>, 2 pages.

U.S. Appl. No. 14/890,653, filed Nov. 12, 2015, Salas.

(56) References Cited

OTHER PUBLICATIONS

U.S. Appl. No. 16/438,639, filed Jun. 12, 2019, Salas.
U.S. Appl. No. 15/521,683, filed Apr. 25, 2017, Pearse.
U.S. Appl. No. 16/721,162, filed Dec. 19, 2019, Pearse.

* cited by examiner

| | |
|---|---|
| 34D10 VH: | EVKLVESGGGLVKPGGSLKLSCAASGFTFSAYAMSWVRQTPEKRLEWVASISSGGTTYYPDSVKRRFTISRDNARNILYLQMSSLRSEDTAMYYCTRGDYGYALDYWGQGTSVTVSS (SEQ ID NO:1) |
| h34D10 VH0: (CDR graft) | EVQLVESGGGLVQPGGSLRLSCAASGFTFSAYAMSWVRQAPGKGLEWVSSISSGGTTYYPDSVKRQFTISRDNAKNTLYLQMNSLRAEDMAVYYCTRGDYGYALDYWGQGTLVTVSS (SEQ ID NO:3) |
| h34D10 VH1: | EVQLVQSGGGLVQPGeSLRLSCAASGFTFSAYAMSWVRQAPGKGLEWVSSISSGGTTYYPDSVKRQFTISRDNAKNTLYLQMNSLRAEDMAVYYCTRGDYGYALDYWGQGTLVTVSS (SEQ ID NO:5) |
| h34D10 VH2: | EVQLVQSGGGLVKPGeSLRLSCAASGFTFSAYAMSWVRQAPGKGLVWVaSISSGGTTYYPDSVKRrFTISRDNAKNTLYLQMNSLRAEDtAVYYCTRGDYGYALDYWGQGTLVTVSS (SEQ ID NO:7) |
| h34D10 VH3: | EVQLVQSGGGLVKPGeSLRLSCAASGFTFSAYAMSWVRQAPGKGLeWVaSISSGGTTYYPDSVKRrFTISRDNAKNTLYLQMNSLRAEDtAVYYCTRGDYGYALDYWGQGTLVTVSS (SEQ ID NO:9) |
| h34D10 VH4: | EVQLVQSGGGLVKPGeSLRLSCAASGFTFSAYAMSWVRQAPGKGLeWVaSISSGGTTYYPDSVKRrFTISRDNsrNTLYLQMNSLRAEDtAVYYCTRGDYGYALDYWGQGTLVTVSS (SEQ ID NO:11) |
| h34D10 VH5: | EVKLVESGGGLVKPGGSLRLSCAASGFTFSAYAMSWVRQAPGKGLeWVaSISSGGTTYYPDSVKRrFTISRDNArNTLYLQMNSLRAEDtAVYYCTRGDYGYALDYWGQGTLVTVSS (SEQ ID NO:12) |

FIG. 1

34D10 VL:   ENVLTQSPAIMSASLGEKVTMSCRASSSVNYMYWYQQKSDASPKLWIYYTSNLAPGVPARFSGSGSGNSYSLTISSMEGEDAATYYCQQFSSSPWTFGGGTKLEIK (SEQ ID NO:2)

34D10 VL0:  EIVMTQSPATLSVSPGERATLSCRASSSVNYMYWYQQKPGQAPRLLIYYTSNLAPGIPARFSGSGSGTEFTLTISSLQSEDFAVYYCQQFSSSPWTFGQGTKVEIK (SEQ ID NO:4)
(CDR graft)

34D10 VL1:  EIVITQSPATLSVSPGERATLSCRASSSVNYMYWYQQKPGQAPRLLIYYTSNLAPGVPARFSGSGSGTEFTLTISSLQSEDFAVYYCQQFSSSPWTFGQGTKVEIK (SEQ ID NO:6)

34D10 VL2:  EIVITQSPATLSaSPGERvTmSCRASSSVNYMYWYQQKPGQsPRLLIYYTSNLAPGVPARFSGSGSGTEyLTISSLQSEDFAVYYCQQFSSSPWTFGQGTKVEIK (SEQ ID NO:8)

34D10 VL3:  EnVMTQSPATLSaSPGERvTmSCRASSSVNYMYWYQQKPGQsPRLLIYYTSNLAPGVPARFSGSGSGTEyLTISSLQSEDFAVYYCQQFSSSPWTFGQGTKVEIK (SEQ ID NO:10)

FIG. 2

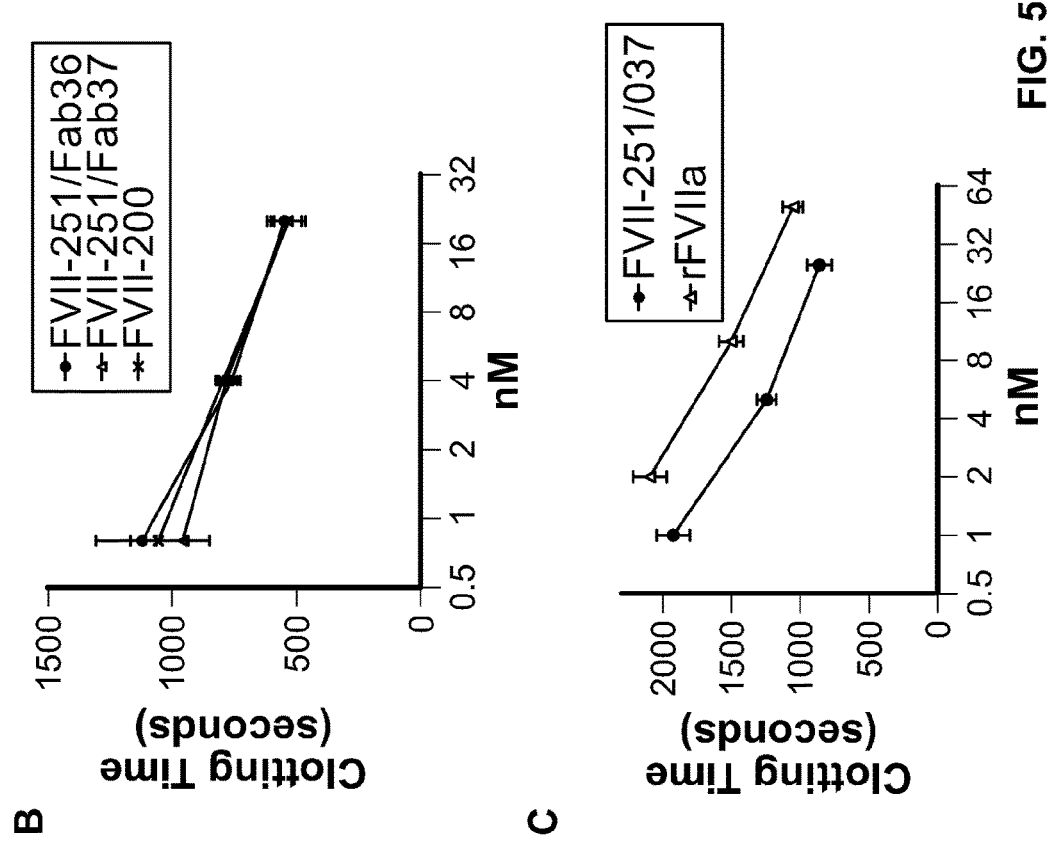
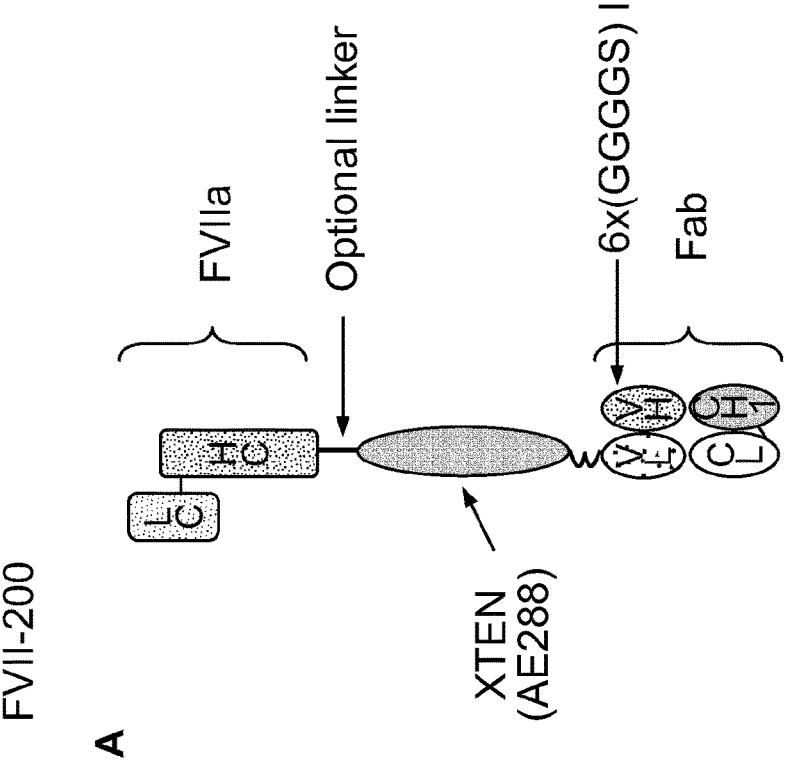
FIG. 5

VH-VL: scFv derived, e.g., from h34D10 (note that an Fab of h34D10 can be used instead of an scFv)
H1: E.g., half-life extending peptide
H2: E.g., clotting factor (e.g., FVIIa)
∽ An optional linker

| | | |
|---|---|---|
| h34D10 VH2: | EVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYGYALDYWGQGTLVTVSS | (SEQ ID NO:7) |
| VH100: | EVQLVESGGGLVKPGGSLRLSCAASGFTFgAYAMSWVRQAPGKGLVWVASISSGGTTYYPDSVKRQFTISRDNAKNTLYLQMNSLRAEDTAVYYCTRGGDYsYALDYWGQGTLVTVSS | (SEQ ID NO:197) |
| VH101: | EVQLVESGGGLVKPGGSLRLSCAASGFTFSAYAMSWVRQAPGKGLVWVASISSGGTTYYPDSVeRQFTISRDNAKNTLYLQMNSLRAEDTAVYYCTRGGDYsYALDYWGQGTLVTVSS | (SEQ ID NO:198) |
| VH102: | EVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYsYALDYWGQGTLVTVSf | (SEQ ID NO:199) |
| VH103: | EVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYsYALDYWGQGTLVTVSS | (SEQ ID NO:200) |
| VH104: | EVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYsYALDYWGrGTLVTVSS | (SEQ ID NO:201) |
| VH105: | EVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYsYALDYWGQGTLVTVSS | (SEQ ID NO:202) |
| VH106: | EVQLVEcGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYsYALDYWGQGTLVTVSS | (SEQ ID NO:203) |
| VH107: | EVQLVESGGGLVKPGeSLRLSCAASGFTFnAYAMSWVRQAPGKGLVWVASISSGGTTYYPDSVKRQFTISRDNAKNTLYLQMNSLRAEDTAVYYCTRGGDYGYALDYWGQGTLVTVSS | (SEQ ID NO:204) |
| VH108: | EVQLVESGGGLVKPGGSLRLSCAASGFTFSAYAMSWVRQAPGeGLVWVASISSGGTTYYPDSVKRQFTISRDNAKNTLYLQMNSLRAEDTAVYYCTRGGDYGYALDYWGQGTLVTVSS | (SEQ ID NO:205) |
| VH109: | EVQLVESGGGLVKPGGSLRLSCAASGFTFnAYAMSWVRQAPGeGLVWVASISSGGTTYYPDSVKRQFTISRDNAKNTLYLQMNSLRAEDTAVYYCTRGGDYGYALDYWGQGTLVTVSS | (SEQ ID NO:206) |
| VH110: | EVQLVESGGGLVKPGGSLRLSCAASGFTFSAYAMSWVRQAPGKGLVWvAgISSGGTTYYPDSVKRQFTISRDNArnTLYLQMNSLRAEDTAVYYCTRGGDYGYALDYWGQGTLVTVSS | (SEQ ID NO:207) |
| VH111: | EVQLVESGGGLVKPGGSLRLSCAASGFTFSAYAMSWVRQAPGKGLVWVASISSdGTTYYPDSVKRQFTISRDNAKNTLYLQMNSLRAEDTAVYYCTRGGDYGYALDYWGQGTLVTVSS | (SEQ ID NO:208) |
| VH112: | EVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYGYALDYWGQGTLVTVSS | (SEQ ID NO:209) |
| VH113: | EVQLVESGGGLVKPGGSLRLSCAASGFTFSAYAMSWVRQAPGKGLVWVAgISSGGTTYYPDSVKRQFTISRDNAKNTLYLQMNSLRAEDTAVYYCTRGGDYGYALDYWGQGTLVTVSS | (SEQ ID NO:210) |
| VH114: | EmQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYGYALDYWGQGTLVTVSS | (SEQ ID NO:211) |
| VH115: | gVQLVESGGGLVKPGGSLRLSCAASGFTFSAYAMSWVRQAPGKGLVWVASISSGGTTYYPDSVKRQFTISRDdAKNTLYLQMNSLRAEDTAVYYCTRGGDYGYALDYWGQGTLVTVSS | (SEQ ID NO:212) |
| VH116: | EVQLVESGGGLVKPGGSLRLSCAASGFTFSAYAMSWVRQAPGKGLVWVASISSGGTTYYPDSVKRQFTISRDdAKNTLYLQMNSLRAEDTAVYYCTRGGDYGYALDYWGQGTLVTVSS | (SEQ ID NO:213) |
| VH117: | EaQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYGYALDYWGQGTLVTVSS | (SEQ ID NO:214) |
| VH118: | gVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYGYALDYWGQGaLVTVSS | (SEQ ID NO:215) |
| VH119: | gVQLVESGGGLVKPGGSLRLSCAASGFTFSAYAMSWVRQAPGKGLVWVASISSGGTTYYPDSVKRQFTISRDNAKNTLYLQMNSLRAEDTAVYYCTRGGDYGYALDYWGQGTLVTVSS | (SEQ ID NO:216) |
| VH120: | EVQLVESGGGLVePGGSLRLSCAASGFTFSAYAMSWVRQAPGeGLVWVASISSGGTTYYPDSVKRQFTISRDNAKNTLYLQMNSLRAEDTAVYYCTRGGDYGYALDYWGQGTLVTVSS | (SEQ ID NO:217) |
| VH121: | EVQLVESGGGLVKPGGSLRLSCAASGFTFSAYAMSWVRQAPGeGLVWVASISSGGTTYYPDSVKRQFTISRDNAKNTLYLQMNSLRAEDTAVYYCTRGGDYGYALDYWGQGTLVTVSS | (SEQ ID NO:218) |

FIG. 11

| VH | KD (M) | K$_{dis}$ (1/s) |
| --- | --- | --- |
| VH100 | 2.90E-08 | 8.22E-03 |
| VH101 | 2.50E-08 | 8.36E-03 |
| VH102 | 3.60E-08 | 9.77E-03 |
| VH103 | 3.70E-08 | 1.03E-02 |
| VH104 | 3.10E-08 | 1.13E-02 |
| VH105 | 4.20E-08 | 1.14E-02 |
| VH106 | 4.40E-08 | 1.27E-02 |
| VH107 | 4.80E-08 | 1.42E-02 |
| VH108 | 4.90E-08 | 1.93E-02 |
| VH109 | 1.20E-07 | 3.10E-02 |
| VH110 | 1.30E-07 | 3.37E-02 |
| VH111 | 1.50E-07 | 3.52E-02 |
| VH112 | 1.60E-07 | 3.52E-02 |
| VH113 | 1.60E-07 | 3.72E-02 |
| VH114 | 1.30E-07 | 3.93E-02 |
| VH115 | 1.20E-07 | 4.29E-02 |
| VH116 | 1.30E-07 | 4.32E-02 |
| VH117 | 1.60E-07 | 4.35E-02 |
| VH118 | 2.00E-07 | 4.78E-02 |
| VH119 | 1.40E-07 | 4.82E-02 |
| VH120 | 2.40E-07 | 4.92E-02 |
| VH121 | 2.30E-07 | 4.94E-02 |
| Parent | 1.55E-07 | 5.63E-02 |

| VH | DSFT$_m$(°C) |
|---|---|
| VH100 | 78 |
| VH101 | 78 |
| VH102 | 79 |
| VH103 | 76 |
| VH104 | 79 |
| VH105 | 79 |
| VH106 | 79 |
| VH107 | 78 |
| VH108 | 79 |
| VH109 | 78 |
| VH110 | 80 |
| VH111 | 79 |
| VH112 | 76 |
| VH113 | 78 |
| VH114 | 79 |
| VH115 | 80 |
| VH116 | 80 |
| VH117 | 78 |
| VH118 | 80 |
| VH119 | 81 |
| VH120 | 80 |
| VH121 | 80 |
| Parent | 81 |

FIG. 13

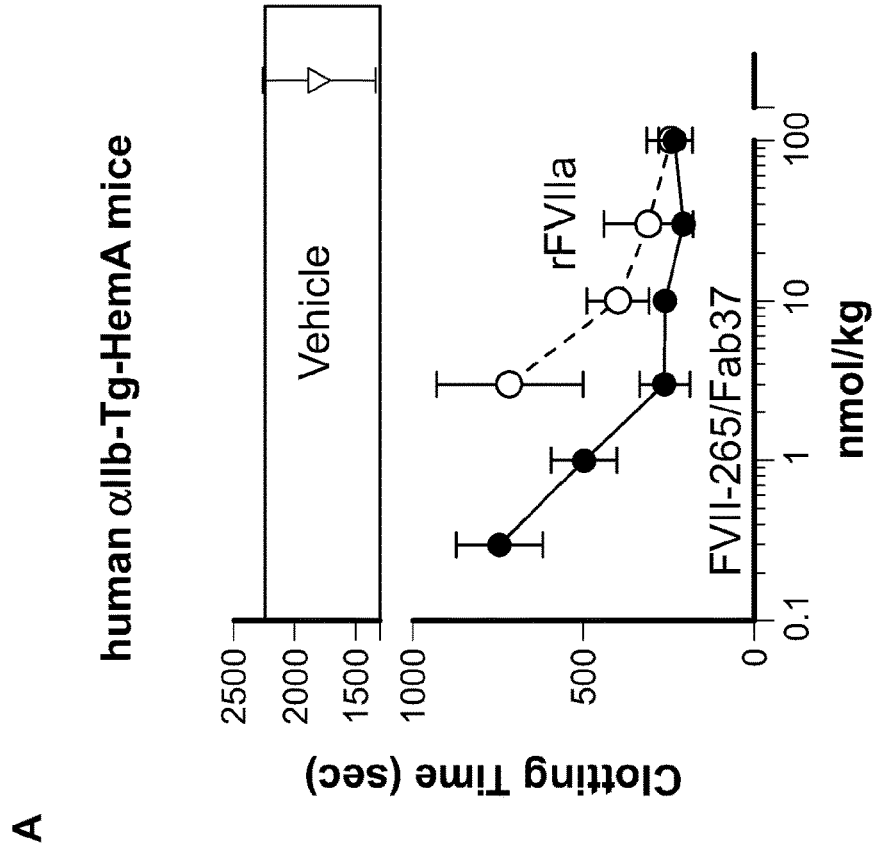
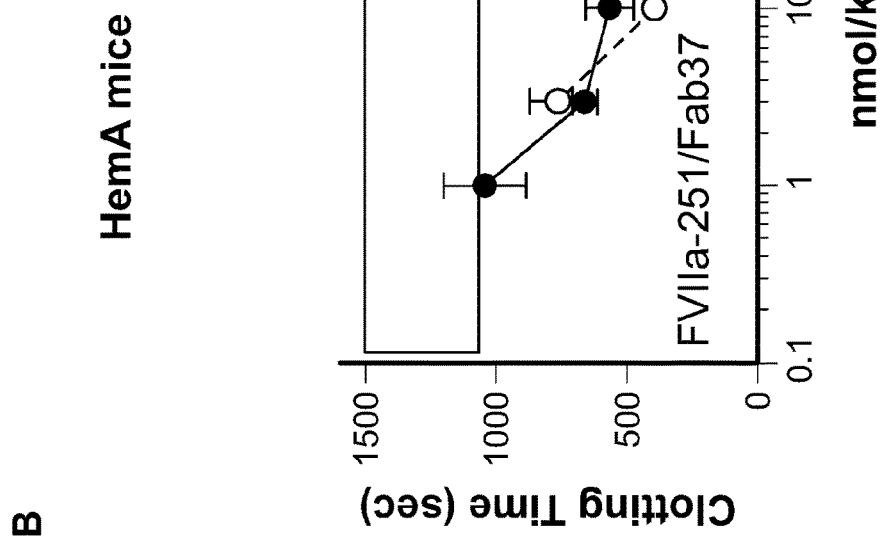
FIG. 14

SEQUENCE LISTING

<160> NUMBER OF SEQ ID NOS: 252

<210> SEQ ID NO 1
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ala Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Thr Thr Tyr Tyr Pro Asp Ser Val Lys
    50                  55                  60

Arg Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Thr
                85                  90                  95

Arg Gly Gly Asp Tyr Gly Tyr Ala Leu Asp Tyr Trp Gly Gln Gly Thr
            100                 105                 110

Ser Val Thr Val Ser Ser
        115

<210> SEQ ID NO 2
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ser Ser Ser Pro Trp Thr
                85                  90                  95

Phe Gly Gly Gly Thr Lys Leu Glu Ile Lys
            100                 105

<210> SEQ ID NO 3
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ser Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Met Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 4
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ala Ser Ser Ser Val Asn Tyr Met
            20                  25                  30

Tyr Trp Tyr Gln Gln Lys Pro Gly Gln Ala Pro Arg Leu Leu Ile Tyr
        35                  40                  45

Tyr Thr Ser Asn Leu Ala Pro Gly Ile Pro Ala Arg Phe Ser Gly Ser
    50                  55                  60

Gly Ser Gly Thr Glu Phe Thr Leu Thr Ile Ser Ser Leu Gln Ser Glu
65                  70                  75                  80

Asp Phe Ala Val Tyr Tyr Cys Gln Gln Phe Ser Ser Ser Pro Trp Thr
                85                  90                  95

Phe Gly Gln Gly Thr Lys Val Glu Ile Lys
            100                 105

<210> SEQ ID NO 5
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Val Gln Leu Val Gln Ser Gly Gly Gly Leu Val Gln Pro Gly Glu
1               5                   10                  15

Ser Leu Arg Leu Ser Cys Ala Ala Ser Gly Phe Thr Phe Ser Ala Tyr
            20                  25                  30

```
Ala Met Ser Trp Val Arg Gln Ala Pro Gly Lys Gly Leu Glu Trp Val
            35                  40                  45

Ser Ser Ile Ser Ser Gly Gly Thr Thr Tyr Tyr Pro Asp Ser Val Lys
 50                  55                  60

Arg Arg Phe Thr Ile Ser Arg Asp Asn Ala Lys Asn Thr Leu Tyr Leu
 65                  70                  75                  80

Gln Met Asn Ser Leu Arg Ala Glu Asp Met Ala Val Tyr Tyr Cys Thr
                 85                  90                  95

Arg Gly Gly Asp Tyr Gly Tyr Ala Leu Asp Tyr Trp Gly Gln Gly Thr
                100                 105                 110

Leu Val Thr Val Ser Ser
            115
```

<210> SEQ ID NO 6
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

```
Glu Ile Val Leu Thr Gln Ser Pro Ala Thr Leu Ser Val Ser Pro Gly
 1               5                  10                  15

Glu Arg Ala Thr Leu Ser Cys Arg Ala Ser Ser Ser Val Asn Tyr Met
                 20                  25                  30

Tyr Trp Tyr Gln Gln Lys Pro Gly Gln Ala Pro Arg Leu Leu Ile Tyr
             35                  40                  45

Tyr Thr Ser Asn Leu Ala Pro Gly Val Pro Ala Arg Phe Ser Gly Ser
 50                  55                  60

Gly Ser Gly Thr Glu Phe Thr Leu Thr Ile Ser Ser Leu Gln Ser Glu
 65                  70                  75                  80

Asp Phe Ala Val Tyr Tyr Cys Gln Gln Phe Ser Ser Ser Pro Trp Thr
                 85                  90                  95

Phe Gly Gln Gly Thr Lys Val Glu Ile Lys
            100                 105
```

<210> SEQ ID NO 7
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ala Tyr
                 20                  25                  30

Ala Met Ser Trp Val Arg Gln Ala Pro Gly Lys Gly Leu Val Trp Val
             35                  40                  45

Ala Ser Ile Ser Ser Gly Gly Thr Thr Tyr Tyr Pro Asp Ser Val Lys
 50                  55                  60

Arg Gln Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Thr
```

85                  90                  95

Arg Gly Gly Asp Tyr Gly Tyr Ala Leu Asp Tyr Trp Gly Gln Gly Thr
                100                 105                 110

Leu Val Thr Val Ser Ser
        115

<210> SEQ ID NO 8
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Ile Val Leu Thr Gln Ser Pro Ala Thr Leu Ser Ala Ser Pro Gly
1               5                   10                  15

Glu Arg Val Thr Met Ser Cys Arg Ala Ser Ser Ser Val Asn Tyr Met
            20                  25                  30

Tyr Trp Tyr Gln Gln Lys Pro Gly Gln Ser Pro Arg Leu Leu Ile Tyr
        35                  40                  45

Tyr Thr Ser Asn Leu Ala Pro Gly Val Pro Ala Arg Phe Ser Gly Ser
    50                  55                  60

Gly Ser Gly Thr Glu Tyr Thr Leu Thr Ile Ser Ser Leu Gln Ser Glu
65                  70                  75                  80

Asp Phe Ala Val Tyr Tyr Cys Gln Gln Phe Ser Ser Ser Pro Trp Thr
                85                  90                  95

Phe Gly Gln Gly Thr Lys Val Glu Ile Lys
                100                 105

<210> SEQ ID NO 9
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Glu Val Gln Leu Val Gln Ser Gly Gly Gly Leu Val Lys Pro Gly Glu
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Arg Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
                100                 105                 110

Leu Val Thr Val Ser Ser
        115

<210> SEQ ID NO 10

```
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Glu Asn Val Met Thr Gln Ser Pro Ala Thr Leu Ser Ala Ser Pro Gly
1               5                   10                  15

Glu Arg Val Thr Met Ser Cys Arg Ala Ser Ser Ser Val Asn Tyr Met
                20                  25                  30

Tyr Trp Tyr Gln Gln Lys Pro Gly Gln Ser Pro Arg Leu Leu Ile Tyr
            35                  40                  45

Tyr Thr Ser Asn Leu Ala Pro Gly Val Pro Ala Arg Phe Ser Gly Ser
        50                  55                  60

Gly Ser Gly Thr Glu Tyr Thr Leu Thr Ile Ser Ser Leu Gln Ser Glu
65                  70                  75                  80

Asp Phe Ala Val Tyr Tyr Cys Gln Gln Phe Ser Ser Ser Pro Trp Thr
                85                  90                  95

Phe Gly Gln Gly Thr Lys Val Glu Ile Lys
            100                 105

<210> SEQ ID NO 11
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Val Gln Leu Val Gln Ser Gly Gly Gly Leu Val Lys Pro Gly Glu
1               5                   10                  15

Ser Leu Arg Leu Ser Cys Ala Ala Ser Gly Phe Thr Phe Ser Ala Tyr
                20                  25                  30

Ala Met Ser Trp Val Arg Gln Ala Pro Gly Lys Gly Leu Glu Trp Val
            35                  40                  45

Ala Ser Ile Ser Ser Gly Gly Thr Thr Tyr Tyr Pro Asp Ser Val Lys
        50                  55                  60

Arg Arg Phe Thr Ile Ser Arg Asp Asn Ser Arg Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 12
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

```
Glu Val Lys Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys
    50                  55                  60

Arg Arg Phe Thr Ile Ser Arg Asp Asn Ala Arg Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
            115
```

```
<210> SEQ ID NO 13
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
gaggtgcagc tggtggagtc tggaggaggc ttggtacagc ctggagggtc cctgagactc      60
tcctgtgcag cctctggatt cacctttagc gcctatgcca tgagctgggt ccgccaggct     120
ccagggaagg gctggtgtg gtctcaagc attagtagtg gtggtaccac atactaccca      180
gactccgtga agaggcagtt caccatctcc agagacaatg ccagaacac gctgtatctg      240 caaatgaaca gcctgagagc cgaggacatg gccgtatatt actgtaccag aggaggggat     300
tatggctacg ctctcgacta ctggggccag ggaaccctgg tcaccgtctc ctca           354
```

```
<210> SEQ ID NO 14
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
gaggtgcagc tggtgcagtc tggaggaggc ttggtacagc ctggagagtc cctgagactc      60
tcctgtgcag cctctggatt cacctttagc gcctatgcca tgagctgggt ccgccaggct     120
ccagggaagg gctggagtg gtctcaagc attagtagtg gtggtaccac atactaccca      180
gactccgtga agaggagatt caccatctcc agagacaatg ccagaacac gctgtatctg      240 caaatgaaca gcctgagagc cgaggacatg gccgtatatt actgtaccag aggaggggat     300
tatggctacg ctctcgacta ctggggccag ggaaccctgg tcaccgtctc ctca           354
```

```
<210> SEQ ID NO 15
<211> LENGTH: 354
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic polynucleotide"

<400> SEQUENCE: 15
gaggtgcagc tggtggagtc tggaggaggc ttggtaaagc ctggaggatc cctgagactc      60
tcctgtgcag cctctggatt cacctttagc gcctatgcca tgagctgggt ccgccaggct     120
ccagggaagg ggctggtctg ggtcgctagc attagtagtg gtggtaccac atactaccca     180
gactccgtga agaggcagtt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca           354

<210> SEQ ID NO 16
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
gaggtgcagc tggtgcagtc tggaggaggc ttggtaaagc ctggagagtc cctgagactc      60
tcctgtgcag cctctggatt cacctttagc gcctatgcca tgagctgggt ccgccaggct     120
ccagggaagg ggctggagtg ggtcgctagc attagtagtg gtggtaccac atactaccca     180
gactccgtga agaggagatt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca           354

<210> SEQ ID NO 17
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
gaggtgcagc tggtgcagtc tggaggaggc ttggtaaagc ctggagagtc cctgagactc      60
tcctgtgcag cctctggatt cacctttagc gcctatgcca tgagctgggt ccgccaggct     120
ccagggaagg ggctggagtg ggtcgctagc attagtagtg gtggtaccac atactaccca     180
gactccgtga agaggagatt caccatctcc agagacaata gtcgcaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca           354

<210> SEQ ID NO 18
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
gaggtgaagc tggtggagtc tggaggaggc ttggtaaagc ctggaggctc cctgagactc      60

```
tcctgtgcag cctctggatt caccttagc gcctatgcca tgagctgggt ccgccaggct    120
ccagggaagg ggctggagtg ggtcgctagc attagtagtg gtggtaccac atactaccca   180
gactccgtga agaggagatt caccatctcc agagacaatg ctcgcaacac gctgtatctg   240
caaatgaaca gcctgagagc cgaggacaca gccgtatatt actgtaccag aggaggggat   300
tatggctacg ctctcgacta ctggggccag ggaaccctgg tcaccgtctc ctca         354
```

<210> SEQ ID NO 19
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

```
gaaattgtaa tgacacagtc tccagccacc ctgtctgtgt ctcctggcga aagagccacc    60
ctctcctgcc gcgccagtag cagtgttaac tacatgtact ggtatcaaca gaaacctggc   120
caggctccca ggctcctcat ctattacaca tccaacttgg ccctggcat cccagccagg    180 ttcagtggca gtgggtctgg gacagagttc actctcacca tcagcagcct acagagcgaa   240
gattttgcag tttattactg tcagcagttc agcagttcac cttggacgtt cggccaaggg   300
accaaggtgg aaatcaaa                                                 318
```

<210> SEQ ID NO 20
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

```
gaaattgtac tcacacagtc tccagccacc ctgtctgtgt ctcctggcga aagagccacc    60
ctctcctgcc gcgccagtag cagtgttaac tacatgtact ggtatcaaca gaaacctggc   120
caggctccca ggctcctcat ctattacaca tccaacttgg ccctggcgt tccagccagg    180 ttcagtggca gtgggtctgg gacagagttc actctcacca tcagcagcct acagagcgaa   240
gattttgcag tttattactg tcagcagttc agcagttcac cttggacgtt cggccaaggg   300
accaaggtgg aaatcaaa                                                 318
```

<210> SEQ ID NO 21
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
gaaattgtac tcacacagtc tccagccacc ctgtctgcct ctcctggcga aagagtgacc    60
atgtcctgcc gcgccagtag cagtgttaac tacatgtact ggtatcaaca gaaacctggc   120
cagtcaccca ggctcctcat ctattacaca tccaacttgg ccctggcgt tccagccagg    180 ttcagtggca gtgggtctgg gacagagtac actctcacca tcagcagcct acagagcgaa   240
gattttgcag tttattactg tcagcagttc agcagttcac cttggacgtt cggccaaggg   300
```

```
accaaggtgg aaatcaaa                                                    318
```

<210> SEQ ID NO 22
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
gaaaacgtaa tgacacagtc tccagccacc ctgtctgcct ctcctggcga aagagtgacc    60
atgtcctgcc gcgccagtag cagtgttaac tacatgtact ggtatcaaca gaaacctggc   120
cagtcaccca ggctcctcat ctattacaca tccaacttgg ccctggcgt tccagccagg    180
ttcagtggca gtgggtctgg gacagagtac actctcacca tcagcagcct acagagcgaa   240
gattttgcag tttattactg tcagcagttc agcagttcac cttggacgtt cggccaaggg   300
accaaggtgg aaatcaaa                                                  318
```

<210> SEQ ID NO 23
<211> LENGTH: 994
<212> TYPE: PRT
<213> ORGANISM: Homo sapiens

<400> SEQUENCE: 23

```
Met Ala Arg Ala Leu Cys Pro Leu Gln Ala Leu Trp Leu Leu Glu Trp
 1               5                  10                  15

Val Leu Leu Leu Leu Gly Pro Cys Ala Ala Pro Pro Ala Trp Ala Leu
                20                  25                  30

Asn Leu Asp Pro Val Gln Leu Thr Phe Tyr Ala Gly Pro Asn Gly Ser
            35                  40                  45

Gln Phe Gly Phe Ser Leu Asp Phe His Lys Asp Ser His Gly Arg Val
        50                  55                  60

Ala Ile Val Val Gly Ala Pro Arg Thr Leu Gly Pro Ser Gln Glu Glu
 65                  70                  75                  80

Thr Gly Gly Val Phe Leu Cys Pro Trp Arg Ala Glu Gly Gly Gln Cys
                85                  90                  95

Pro Ser Leu Leu Phe Asp Leu Arg Asp Glu Thr Arg Asn Val Gly Ser
            100                 105                 110

Gln Thr Leu Gln Thr Phe Lys Ala Arg Gln Gly Leu Gly Ala Ser Val
        115                 120                 125

Val Ser Trp Ser Asp Val Ile Val Ala Cys Ala Pro Trp Gln His Trp
    130                 135                 140

Asn Val Leu Glu Lys Thr Glu Glu Ala Glu Lys Thr Pro Val Gly Ser
145                 150                 155                 160

Cys Phe Leu Ala Gln Pro Glu Ser Gly Arg Arg Ala Glu Tyr Ser Pro
                165                 170                 175

Cys Arg Gly Asn Thr Leu Ser Arg Ile Tyr Val Glu Asn Asp Phe Ser
            180                 185                 190

Trp Asp Lys Arg Tyr Cys Glu Ala Gly Phe Ser Ser Val Val Thr Gln
        195                 200                 205

Ala Gly Glu Leu Val Leu Gly Ala Pro Gly Gly Tyr Tyr Phe Leu Gly
    210                 215                 220

Leu Leu Ala Gln Ala Pro Val Ala Asp Ile Phe Ser Ser Tyr Arg Pro
225                 230                 235                 240
```

```
Gly Ile Leu Leu Trp His Val Ser Ser Gln Ser Leu Ser Phe Asp Ser
                245                 250                 255

Ser Asn Pro Glu Tyr Phe Asp Gly Tyr Trp Gly Tyr Ser Val Ala Val
            260                 265                 270

Gly Glu Phe Asp Gly Asp Leu Asn Thr Thr Glu Tyr Val Val Gly Ala
        275                 280                 285

Pro Thr Trp Ser Trp Thr Leu Gly Ala Val Glu Ile Leu Asp Ser Tyr
    290                 295                 300

Tyr Gln Arg Leu His Arg Leu Arg Gly Glu Gln Met Ala Ser Tyr Phe
305                 310                 315                 320

Gly His Ser Val Ala Val Thr Asp Val Asn Gly Asp Gly Arg His Asp
                325                 330                 335

Leu Leu Val Gly Ala Pro Leu Tyr Met Glu Ser Arg Ala Asp Arg Lys
            340                 345                 350

Leu Ala Glu Val Gly Arg Val Tyr Leu Phe Leu Gln Pro Arg Gly Pro
        355                 360                 365

His Ala Leu Gly Ala Pro Ser Leu Leu Thr Gly Thr Gln Leu Tyr
    370                 375                 380

Gly Arg Phe Gly Ser Ala Ile Ala Pro Leu Gly Asp Leu Asp Arg Asp
385                 390                 395                 400

Gly Tyr Asn Asp Ile Ala Val Ala Ala Pro Tyr Gly Gly Pro Ser Gly
                405                 410                 415

Arg Gly Gln Val Leu Val Phe Leu Gly Gln Ser Glu Gly Leu Arg Ser
            420                 425                 430

Arg Pro Ser Gln Val Leu Asp Ser Pro Phe Pro Thr Gly Ser Ala Phe
        435                 440                 445

Gly Phe Ser Leu Arg Gly Ala Val Asp Ile Asp Asp Asn Gly Tyr Pro
    450                 455                 460

Asp Leu Ile Val Gly Ala Tyr Gly Ala Asn Gln Val Ala Val Tyr Arg
465                 470                 475                 480

Ala Gln Pro Val Val Lys Ala Ser Val Gln Leu Leu Val Gln Asp Ser
                485                 490                 495

Leu Asn Pro Ala Val Lys Ser Cys Val Leu Pro Gln Thr Lys Thr Pro
            500                 505                 510

Val Ser Cys Phe Asn Ile Gln Met Cys Val Gly Ala Thr Gly His Asn
        515                 520                 525

Ile Pro Gln Lys Leu Ser Leu Asn Ala Glu Leu Gln Leu Asp Arg Gln
    530                 535                 540

Lys Pro Arg Gln Gly Arg Arg Val Leu Leu Leu Gly Ser Gln Gln Ala
545                 550                 555                 560

Gly Thr Thr Leu Asn Leu Asp Leu Gly Gly Lys His Ser Pro Ile Cys
                565                 570                 575

His Thr Thr Met Ala Phe Leu Arg Asp Glu Ala Asp Phe Arg Asp Lys
            580                 585                 590

Leu Ser Pro Ile Val Leu Ser Leu Asn Val Ser Leu Pro Pro Thr Glu
        595                 600                 605

Ala Gly Met Ala Pro Ala Val Val Leu His Gly Asp Thr His Val Gln
    610                 615                 620

Glu Gln Thr Arg Ile Val Leu Asp Cys Gly Glu Asp Asp Val Cys Val
625                 630                 635                 640

Pro Gln Leu Gln Leu Thr Ala Ser Val Thr Gly Ser Pro Leu Leu Val
                645                 650                 655
```

Gly Ala Asp Asn Val Leu Glu Leu Gln Met Asp Ala Ala Asn Glu Gly
                660                 665                 670

Glu Gly Ala Tyr Glu Ala Glu Leu Ala Val His Leu Pro Gln Gly Ala
            675                 680                 685

His Tyr Met Arg Ala Leu Ser Asn Val Glu Gly Phe Glu Arg Leu Ile
        690                 695                 700

Cys Asn Gln Lys Lys Glu Asn Glu Thr Arg Val Val Leu Cys Glu Leu
705                 710                 715                 720

Gly Asn Pro Met Lys Lys Asn Ala Gln Ile Gly Ile Ala Met Leu Val
                725                 730                 735

Ser Val Gly Asn Leu Glu Glu Ala Gly Glu Ser Val Ser Phe Gln Leu
            740                 745                 750

Gln Ile Arg Ser Lys Asn Ser Gln Asn Pro Asn Ser Lys Ile Val Leu
        755                 760                 765

Leu Asp Val Pro Val Arg Ala Glu Ala Gln Val Glu Leu Arg Gly Asn
770                 775                 780

Ser Phe Pro Ala Ser Leu Val Val Ala Ala Glu Glu Gly Glu Arg Glu
785                 790                 795                 800

Gln Asn Ser Leu Asp Ser Trp Gly Pro Lys Val Glu His Thr Tyr Glu
                805                 810                 815

Leu His Asn Asn Gly Pro Gly Thr Val Asn Gly Leu His Leu Ser Ile
            820                 825                 830

His Leu Pro Gly Gln Ser Gln Pro Ser Asp Leu Leu Tyr Ile Leu Asp
        835                 840                 845

Ile Gln Pro Gln Gly Gly Leu Gln Cys Phe Pro Gln Pro Pro Val Asn
850                 855                 860

Pro Leu Lys Val Asp Trp Gly Leu Pro Ile Pro Ser Pro Ser Pro Ile
865                 870                 875                 880

His Pro Ala His His Lys Arg Asp Arg Arg Gln Ile Phe Leu Pro Glu
                885                 890                 895

Pro Glu Gln Pro Ser Arg Leu Gln Asp Pro Val Leu Val Ser Cys Asp
            900                 905                 910

Ser Ala Pro Cys Thr Val Val Gln Cys Asp Leu Gln Glu Met Ala Arg
        915                 920                 925

Gly Gln Arg Ala Met Val Thr Val Leu Ala Phe Leu Trp Leu Pro Ser
930                 935                 940

Leu Tyr Gln Arg Pro Leu Asp Gln Phe Val Leu Gln Ser His Ala Trp
945                 950                 955                 960

Phe Asn Val Ser Ser Leu Pro Tyr Ala Val Pro Pro Leu Ser Leu Pro
                965                 970                 975

Arg Gly Glu Ala Gln Val Trp Thr Gln Leu Leu Arg Ala Leu Glu Glu
            980                 985                 990

Arg Ala

<210> SEQ ID NO 24
<211> LENGTH: 716
<212> TYPE: PRT
<213> ORGANISM: Homo sapiens

<400> SEQUENCE: 24

Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

```
Thr Arg Gly Val Ser Ser Cys Gln Gln Cys Leu Ala Val Ser Pro Met
         35                  40                  45

Cys Ala Trp Cys Ser Asp Glu Ala Leu Pro Leu Gly Ser Pro Arg Cys
 50                  55                  60

Asp Leu Lys Glu Asn Leu Leu Lys Asp Asn Cys Ala Pro Glu Ser Ile
 65                  70                  75                  80

Glu Phe Pro Val Ser Glu Ala Arg Val Leu Glu Asp Arg Pro Leu Ser
                 85                  90                  95

Asp Lys Gly Ser Gly Asp Ser Ser Gln Val Thr Gln Val Ser Pro Gln
             100                 105                 110

Arg Ile Ala Leu Arg Leu Arg Pro Asp Asp Ser Lys Asn Phe Ser Ile
         115                 120                 125

Gln Val Arg Gln Val Glu Asp Tyr Pro Val Asp Ile Tyr Tyr Leu Met
 130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                 165                 170                 175

Ile Gly Phe Gly Ala Phe Val Asp Lys Pro Val Ser Pro Tyr Met Tyr
             180                 185                 190

Ile Ser Pro Pro Glu Ala Leu Glu Asn Pro Cys Tyr Asp Met Lys Thr
         195                 200                 205

Thr Cys Leu Pro Met Phe Gly Tyr Lys His Val Leu Thr Leu Thr Asp
 210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                 245                 250                 255

Val Cys Asp Glu Lys Ile Gly Trp Arg Asn Asp Ala Ser His Leu Leu
             260                 265                 270

Val Phe Thr Thr Asp Ala Lys Thr His Ile Ala Leu Asp Gly Arg Leu
         275                 280                 285

Ala Gly Ile Val Gln Pro Asn Asp Gly Gln Cys His Val Gly Ser Asp
 290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                 325                 330                 335

Thr Glu Asn Val Val Asn Leu Tyr Gln Asn Tyr Ser Glu Leu Ile Pro
             340                 345                 350

Gly Thr Thr Val Gly Val Leu Ser Met Asp Ser Ser Asn Val Leu Gln
         355                 360                 365

Leu Ile Val Asp Ala Tyr Gly Lys Ile Arg Ser Lys Val Glu Leu Glu
 370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                 405                 410                 415

Ile Gly Asp Thr Val Ser Phe Ser Ile Glu Ala Lys Val Arg Gly Cys
             420                 425                 430

Pro Gln Glu Lys Glu Lys Ser Phe Thr Ile Lys Pro Val Gly Phe Lys
         435                 440                 445

Asp Ser Leu Ile Val Gln Val Thr Phe Asp Cys Asp Cys Ala Cys Gln
```

```
                450             455             460
Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
                500                 505                 510

Ser Pro Arg Glu Gly Gln Pro Val Cys Ser Gln Arg Gly Glu Cys Leu
            515                 520                 525

Cys Gly Gln Cys Val Cys His Ser Ser Asp Phe Gly Lys Ile Thr Gly
        530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
                580                 585                 590

Cys Met Ser Ser Asn Gly Leu Leu Cys Ser Gly Arg Gly Lys Cys Glu
                595                 600                 605

Cys Gly Ser Cys Val Cys Ile Gln Pro Gly Ser Tyr Gly Asp Thr Cys
            610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Gly Ala Leu His Asp Glu Asn Thr
                645                 650                 655

Cys Asn Arg Tyr Cys Arg Asp Glu Ile Glu Ser Val Lys Glu Leu Lys
                660                 665                 670

Asp Thr Gly Lys Asp Ala Val Asn Cys Thr Tyr Lys Asn Glu Asp Asp
            675                 680                 685

Cys Val Val Arg Phe Gln Tyr Tyr Glu Asp Ser Ser Gly Lys Ser Ile
        690                 695                 700

Leu Tyr Val Val Glu Glu Pro Glu Cys Pro Lys Gly
705                 710                 715

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ala Tyr Ala Met Ser
1               5

<210> SEQ ID NO 26
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ser Ile Ser Ser Gly Gly Thr Thr Tyr Tyr Pro Asp Ser Val Lys Arg
1               5                   10                  15
```

```
<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Gly Asp Tyr Gly Tyr Ala Leu Asp Tyr
1               5                   10

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Arg Ala Ser Ser Ser Val Asn Tyr Met Tyr
1               5                   10

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Tyr Thr Ser Asn Leu Ala Pro
1               5

<210> SEQ ID NO 30
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Gln Phe Ser Ser Ser Pro Trp Thr
1               5

<210> SEQ ID NO 31
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

```
<210> SEQ ID NO 32
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Trp Val Arg Gln Ala Pro Gly Lys Gly Leu Val Trp Val
1               5                   10

<210> SEQ ID NO 33
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gln Phe Thr Ile Ser Arg Asp Asn Ala Lys Asn Thr Leu Tyr Leu Gln
1               5                   10                  15

Met Asn Ser Leu Arg Ala Glu Asp Met Ala Val Tyr Tyr Cys Thr Arg
            20                  25                  30

<210> SEQ ID NO 34
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Trp Gly Gln Gly Thr Leu Val Thr Val Ser Ser
1               5                   10

<210> SEQ ID NO 35
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Glu Val Gln Leu Val Gln Ser Gly Gly Gly Leu Val Gln Pro Gly Glu
1               5                   10                  15

Ser Leu Arg Leu Ser Cys Ala Ala Ser Gly Phe Thr Phe Ser
            20                  25                  30

<210> SEQ ID NO 36
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Trp Val Arg Gln Ala Pro Gly Lys Gly Leu Glu Trp Val Ser
```

<210> SEQ ID NO 37
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Trp Val Arg Gln Ala Pro Gly Lys Gly Leu Val Trp Val Ala
1               5                   10

<210> SEQ ID NO 39
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

Gln Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 40
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

Glu Val Gln Leu Val Gln Ser Gly Gly Gly Leu Val Lys Pro Gly Glu
1               5                   10                  15

Ser Leu Arg Leu Ser Cys Ala Ala Ser Gly Phe Thr Phe Ser
            20                  25                  30

<210> SEQ ID NO 41
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 41

Trp Val Arg Gln Ala Pro Gly Lys Gly Leu Glu Trp Val Ala
1               5                   10

<210> SEQ ID NO 42
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 43
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Arg Phe Thr Ile Ser Arg Asp Asn Ser Arg Asn Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 44
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Glu Val Lys Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 45
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Arg Phe Thr Ile Ser Arg Asp Asn Ala Arg Asn Thr Leu Tyr Leu Gln
1               5                   10                  15

Met Asn Ser Leu Arg Ala Glu Asp Thr Ala Val Tyr Tyr Cys Thr Arg
            20                  25                  30

-continued

```
<210> SEQ ID NO 46
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Trp Tyr Gln Gln Lys Pro Gly Gln Ala Pro Arg Leu Leu Ile Tyr
1               5                   10                  15

<210> SEQ ID NO 48
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Phe Gly Gln Gly Thr Lys Val Glu Ile Lys
1               5                   10

<210> SEQ ID NO 50
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Glu Ile Val Leu Thr Gln Ser Pro Ala Thr Leu Ser Val Ser Pro Gly
```

-continued

```
                1               5                  10                  15
Glu Arg Ala Thr Leu Ser Cys
            20

<210> SEQ ID NO 51
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gly Val Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 52
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Glu Ile Val Leu Thr Gln Ser Pro Ala Thr Leu Ser Ala Ser Pro Gly
1               5                   10                  15

Glu Arg Val Thr Met Ser Cys
            20

<210> SEQ ID NO 53
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Trp Tyr Gln Gln Lys Pro Gly Gln Ser Pro Arg Leu Leu Ile Tyr
1               5                   10                  15

<210> SEQ ID NO 54
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gly Val Pro Ala Arg Phe Ser Gly Ser Gly Ser Gly Thr Glu Tyr Thr
1               5                   10                  15

Leu Thr Ile Ser Ser Leu Gln Ser Glu Asp Phe Ala Val Tyr Tyr Cys
            20                  25                  30

<210> SEQ ID NO 55
<211> LENGTH: 23
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 55

Glu Asn Val Met Thr Gln Ser Pro Ala Thr Leu Ser Ala Ser Pro Gly
1               5                   10                  15

Glu Arg Val Thr Met Ser Cys
            20

<210> SEQ ID NO 56
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 57
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 58
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Gln Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly
                325
```

<210> SEQ ID NO 59
<211> LENGTH: 666
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

```
gaggtgcagc tggtggagtc tggaggaggc ttggtacagc ctggagggtc cctgagactc      60
tcctgtgcag cctctggatt cacctttagc gcctatgcca tgagctgggt ccgccaggct     120
ccagggaagg ggctggtgtg ggtctcaagc attagtagtg gtggtaccac atactaccca     180
gactccgtga agaggcagtt caccatctcc agagacaatg ccaagaacac gctgtatctg     240
caaatgaaca gcctgagagc cgaggacatg gccgtatatt actgtaccag aggaggggat     300
tatggctacg ctctcgacta ctggggccag ggaaccctgg tcaccgtctc ctcagcctcc     360
accaagggcc catcggtctt cccgctagca ccctcctcca gagcacctc tggggggcaca     420
gcggccctgg gctgcctggt caaggactac ttccccgaac cggtgacggt gtcgtggaac     480
tcaggcgccc tgaccagcgg cgtccacacc ttcccggctg tcctacagtc tagcggactc     540
tactccctca gcagcgtagt gaccgtgccc tcttctagct tgggcaccca gacctacatc     600
tgcaacgtga atcacaagcc cagcaacacc aaggtggaca gaaagttga gcccaaatct     660
tgttag                                                                666
```

<210> SEQ ID NO 60
<211> LENGTH: 666
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60

```
gaggtgcagc tggtgcagtc tggaggaggc ttggtacagc ctggagagtc cctgagactc      60
tcctgtgcag cctctggatt cacctttagc gcctatgcca tgagctgggt ccgccaggct     120
ccagggaagg ggctggagtg ggtctcaagc attagtagtg gtggtaccac atactaccca     180
gactccgtga agaggagatt caccatctcc agagacaatg ccaagaacac gctgtatctg     240
caaatgaaca gcctgagagc cgaggacatg gccgtatatt actgtaccag aggaggggat     300
tatggctacg ctctcgacta ctggggccag ggaaccctgg tcaccgtctc ctcagcctcc     360
accaagggcc catcggtctt cccgctagca ccctcctcca gagcacctc tggggggcaca     420
gcggccctgg gctgcctggt caaggactac ttccccgaac cggtgacggt gtcgtggaac     480
tcaggcgccc tgaccagcgg cgtccacacc ttcccggctg tcctacagtc tagcggactc     540
tactccctca gcagcgtagt gaccgtgccc tcttctagct tgggcaccca gacctacatc     600
tgcaacgtga atcacaagcc cagcaacacc aaggtggaca gaaagttga gcccaaatct     660
tgttag                                                                666
```

<210> SEQ ID NO 61
<211> LENGTH: 666
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

```
gaggtgcagc tggtggagtc tggaggaggc ttggtaaagc ctggaggatc cctgagactc    60
tcctgtgcag cctctggatt cacctttagc gcctatgcca tgagctgggt ccgccaggct   120
ccagggaagg ggctggtctg ggtcgctagc attagtagtg gtggtaccac atactaccca   180
gactccgtga agaggcagtt caccatctcc agagacaatg ccaagaacac gctgtatctg   240
caaatgaaca gcctgagagc cgaggacaca gccgtatatt actgtaccag aggaggggat   300
tatggctacg ctctcgacta ctggggccag ggaaccctgg tcaccgtctc ctcagcctcc   360
accaagggcc catcggtctt cccgctagca ccctcctcca agagcacctc tgggggcaca   420
gcggccctgg gctgcctggt caaggactac ttccccgaac cggtgacggt gtcgtggaac   480
tcaggcgccc tgaccagcgg cgtccacacc ttcccggctg tcctacagtc tagcggactc   540
tactccctca gcagcgtagt gaccgtgccc tcttctagct gggcaccca gacctacatc    600 tgcaacgtga atcacaagcc cagcaacacc aaggtggaca agaaagttga gcccaaatct   660
tgttag                                                              666
```

<210> SEQ ID NO 62
<211> LENGTH: 666
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

```
gaggtgcagc tggtgcagtc tggaggaggc ttggtaaagc ctggagagtc cctgagactc    60
tcctgtgcag cctctggatt cacctttagc gcctatgcca tgagctgggt ccgccaggct   120
ccagggaagg ggctggagtg ggtcgctagc attagtagtg gtggtaccac atactaccca   180
gactccgtga agaggagatt caccatctcc agagacaatg ccaagaacac gctgtatctg   240
caaatgaaca gcctgagagc cgaggacaca gccgtatatt actgtaccag aggaggggat   300
tatggctacg ctctcgacta ctggggccag ggaaccctgg tcaccgtctc ctcagcctcc   360
accaagggcc catcggtctt cccgctagca ccctcctcca agagcacctc tgggggcaca   420
gcggccctgg gctgcctggt caaggactac ttccccgaac cggtgacggt gtcgtggaac   480
tcaggcgccc tgaccagcgg cgtccacacc ttcccggctg tcctacagtc tagcggactc   540
tactccctca gcagcgtagt gaccgtgccc tcttctagct gggcaccca gacctacatc    600 tgcaacgtga atcacaagcc cagcaacacc aaggtggaca agaaagttga gcccaaatct   660
tgttag                                                              666
```

<210> SEQ ID NO 63
<211> LENGTH: 666
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
gaggtgcagc tggtgcagtc tggaggaggc ttggtaaagc ctggagagtc cctgagactc    60
tcctgtgcag cctctggatt cacctttagc gcctatgcca tgagctgggt ccgccaggct   120
ccagggaagg ggctggagtg ggtcgctagc attagtagtg gtggtaccac atactaccca   180
```

```
gactccgtga agaggagatt caccatctcc agagacaata gtcgcaacac gctgtatctg    240
caaatgaaca gcctgagagc cgaggacaca gccgtatatt actgtaccag aggaggggat    300
tatggctacg ctctcgacta ctggggccag ggaaccctgg tcaccgtctc ctcagcctcc    360
accaagggcc catcggtctt cccgctagca ccctcctcca agagcacctc tgggggcaca    420
gcggccctgg gctgcctggt caaggactac ttccccgaac cggtgacggt gtcgtggaac    480
tcaggcgccc tgaccagcgg cgtccacacc ttcccggctg tcctacagtc tagcggactc    540
tactccctca gcagcgtagt gaccgtgccc tcttctagct gggcacccca gacctacatc    600
tgcaacgtga atcacaagcc cagcaacacc aaggtggaca gaaagttga gcccaaatct    660 tgttag                                                               666
```

<210> SEQ ID NO 64
<211> LENGTH: 666
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 64

```
gaggtgaagc tggtggagtc tggaggaggc ttggtaaagc ctggaggctc cctgagactc    60
tcctgtgcag cctctggatt cacctttagc gcctatgcca tgagctgggt ccgccaggct    120
ccagggaagg ggctggagtg ggtcgctagc attagtagtg gtggtaccac atactaccca    180
gactccgtga agaggagatt caccatctcc agagacaatg ctcgcaacac gctgtatctg    240
caaatgaaca gcctgagagc cgaggacaca gccgtatatt actgtaccag aggaggggat    300
tatggctacg ctctcgacta ctggggccag ggaaccctgg tcaccgtctc ctcagcctcc    360
accaagggcc catcggtctt cccgctagca ccctcctcca agagcacctc tgggggcaca    420
gcggccctgg gctgcctggt caaggactac ttccccgaac cggtgacggt gtcgtggaac    480
tcaggcgccc tgaccagcgg cgtccacacc ttcccggctg tcctacagtc tagcggactc    540
tactccctca gcagcgtagt gaccgtgccc tcttctagct gggcacccca gacctacatc    600
tgcaacgtga atcacaagcc cagcaacacc aaggtggaca gaaagttga gcccaaatct    660 tgttag                                                               666
```

<210> SEQ ID NO 65
<211> LENGTH: 708
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

```
atggacatga gggtccccgc tcagctcctg gggctccttc tgctctggct ccctggagca    60
cgatgtgaaa ttgtaatgac acagtctcca gccaccctgt ctgtgtctcc aggcgaaaga    120
gccaccctct cctgccgcgc cagtagcagt gttaactaca tgtactggta tcaacagaaa    180
cctggccagg ctcccaggct cctcatctat tacacatcca acttggcccc tggcatccca    240
gccaggttca gtggcagtgg gtctgggaca gagttcactc tcaccatcag cagcctacag    300
agcgaagatt ttgcagtttta ttactgtcag cagttcagca gttcaccttg gacgttcggc    360
caagggacca aggtggaaat caaacgtacg gtggctgcac catctgtctt catcttcccg    420
```

```
ccatctgatg agcagttgaa atctggaact gcctctgttg tgtgcctgct gaataacttc      480
tatcccagag aggccaaagt acagtggaag gtggataacg ccctccaatc gggtaactcc      540
caggagagtg tcacagagca ggacagcaag gacagcacct acagcctcag cagcaccctg      600
acgctgagca aagcagacta cgagaaacac aaagtctacg cctgcgaagt cacccatcag      660
ggcctgagct cgcccgtcac aaagagcttc aacaggggag agtgttag                   708
```

<210> SEQ ID NO 66
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66

```
gaaattgtac tcacacagtc tccagccacc ctgtctgtgt ctcctggcga aagagccacc       60
ctctcctgcc gcgccagtag cagtgttaac tacatgtact ggtatcaaca gaaacctggc      120
caggctccca ggctcctcat ctattacaca tccaacttgg cccctggcgt tccagccagg      180
ttcagtggca gtgggtctgg gacagagttc actctcacca tcagcagcct acagagcgaa      240
gattttgcag tttattactg tcagcagttc agcagttcac cttggacgtt cggccaaggg      300
accaaggtgg aaatcaaacg tacggtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                         642
```

<210> SEQ ID NO 67
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 67

```
gaaattgtac tcacacagtc tccagccacc ctgtctgcct ctcctggcga aagagtgacc       60
atgtcctgcc gcgccagtag cagtgttaac tacatgtact ggtatcaaca gaaacctggc      120
cagtcaccca ggctcctcat ctattacaca tccaacttgg cccctggcgt tccagccagg      180
ttcagtggca gtgggtctgg gacagagtac actctcacca tcagcagcct acagagcgaa      240
gattttgcag tttattactg tcagcagttc agcagttcac cttggacgtt cggccaaggg      300
accaaggtgg aaatcaaacg tacggtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                         642
```

<210> SEQ ID NO 68
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68

```
gaaaacgtaa tgacacagtc tccagccacc ctgtctgcct ctcctggcga aagagtgacc      60
atgtcctgcc gcgccagtag cagtgttaac tacatgtact ggtatcaaca gaaacctggc     120
cagtcaccca ggctcctcat ctattacaca tccaacttgg cccctggcgt tccagccagg     180
ttcagtggca gtgggtctgg gacagagtac actctcacca tcagcagcct acagagcgaa     240
gattttgcag tttattactg tcagcagttc agcagttcac cttggacgtt cggccaaggg     300
accaaggtgg aaatcaaacg tacggtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                        642
```

<210> SEQ ID NO 69
<211> LENGTH: 406
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

```
Ala Asn Ala Phe Leu Glu Glu Leu Arg Pro Gly Ser Leu Glu Arg Glu
1               5                  10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175
```

```
Leu Cys Gly Gly Thr Leu Ile Asn Thr Ile Trp Val Val Ser Ala Ala
                180                 185                 190

His Cys Phe Asp Lys Ile Lys Asn Trp Arg Asn Leu Ile Ala Val Leu
            195                 200                 205

Gly Glu His Asp Leu Ser Glu His Asp Gly Asp Glu Gln Ser Arg Arg
        210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 70
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Ser Ser Ser Pro Trp Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
```

```
            115                 120                 125
Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
                195                 200                 205

Asn Arg Asn Glu Cys
    210

<210> SEQ ID NO 71
<211> LENGTH: 649
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255
```

```
His Val Val Pro Leu Cys Leu Pro Glu Arg Thr Phe Ser Glu Arg Thr
            260                 265                 270
Leu Ala Phe Val Arg Phe Ser Leu Val Ser Gly Trp Gly Gln Leu Leu
            275                 280                 285
Asp Arg Gly Ala Thr Ala Leu Glu Leu Met Val Leu Asn Val Pro Arg
            290                 295                 300
Leu Met Thr Gln Asp Cys Leu Gln Gln Ser Arg Lys Val Gly Asp Ser
305                 310                 315                 320
Pro Asn Ile Thr Glu Tyr Met Phe Cys Ala Gly Tyr Ser Asp Gly Ser
                325                 330                 335
Lys Asp Ser Cys Lys Gly Asp Ser Gly Gly Pro His Ala Thr His Tyr
            340                 345                 350
Arg Gly Thr Trp Tyr Leu Thr Gly Ile Val Ser Trp Gly Gln Gly Cys
            355                 360                 365
Ala Thr Val Gly His Phe Gly Val Tyr Thr Arg Val Ser Gln Tyr Ile
            370                 375                 380
Glu Trp Leu Gln Lys Leu Met Arg Ser Glu Pro Arg Pro Gly Val Leu
385                 390                 395                 400
Leu Arg Ala Pro Phe Pro Gly Gly Gly Ser Gly Gly Gly Gly Ser
                405                 410                 415
Gly Gly Gly Gly Ser Gly Gly Gly Ser Gly Gly Gly Gly Ser Gly
            420                 425                 430
Gly Gly Gly Ser Glu Asn Val Leu Thr Gln Ser Pro Ala Ile Met Ser
            435                 440                 445
Ala Ser Leu Gly Glu Lys Val Thr Met Ser Cys Arg Ala Ser Ser Ser
450                 455                 460
Val Asn Tyr Met Tyr Trp Tyr Gln Gln Lys Ser Asp Ala Ser Pro Lys
465                 470                 475                 480
Leu Trp Ile Tyr Tyr Thr Ser Asn Leu Ala Pro Gly Val Pro Ala Arg
                485                 490                 495
Phe Ser Gly Ser Gly Ser Gly Asn Ser Tyr Ser Leu Thr Ile Ser Ser
                500                 505                 510
Met Glu Gly Glu Asp Ala Ala Thr Tyr Tyr Cys Gln Gln Phe Ser Ser
            515                 520                 525
Ser Pro Trp Thr Phe Gly Gly Gly Thr Lys Leu Glu Ile Lys Arg Ala
            530                 535                 540
Asp Ala Ala Pro Thr Val Ser Ile Phe Pro Pro Ser Ser Glu Gln Leu
545                 550                 555                 560
Thr Ser Gly Gly Ala Ser Val Val Cys Phe Leu Asn Asn Phe Tyr Pro
                565                 570                 575
Lys Asp Ile Asn Val Lys Trp Lys Ile Asp Gly Ser Glu Arg Gln Asn
            580                 585                 590
Gly Val Leu Asn Ser Trp Thr Asp Gln Asp Ser Lys Asp Ser Thr Tyr
            595                 600                 605
Ser Met Ser Ser Thr Leu Thr Leu Thr Lys Asp Glu Tyr Glu Arg His
            610                 615                 620
Asn Ser Tyr Thr Cys Glu Ala Thr His Lys Thr Ser Thr Ser Pro Ile
625                 630                 635                 640
Val Lys Ser Phe Asn Arg Asn Glu Cys
                645

<210> SEQ ID NO 72
<211> LENGTH: 218
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72
```

| | | | | | | | | | | | | | | |
|---|---|---|---|---|---|---|---|---|---|---|---|---|---|---|
| Glu | Val | Lys | Leu | Val | Glu | Ser | Gly | Gly | Gly | Leu | Val | Lys | Pro | Gly |
| 1 | | | | 5 | | | | | 10 | | | | | 15 |
| Ser | Leu | Lys | Leu | Ser | Cys | Ala | Ala | Ser | Gly | Phe | Thr | Phe | Ser | Ala | Tyr |
| | | | 20 | | | | | 25 | | | | | 30 |
| Ala | Met | Ser | Trp | Val | Arg | Gln | Thr | Pro | Glu | Lys | Arg | Leu | Glu | Trp | Val |
| | | 35 | | | | | 40 | | | | | 45 |
| Ala | Ser | Ile | Ser | Ser | Gly | Gly | Thr | Thr | Tyr | Tyr | Pro | Asp | Ser | Val | Lys |
| | 50 | | | | | 55 | | | | | 60 |
| Arg | Arg | Phe | Thr | Ile | Ser | Arg | Asp | Asn | Ala | Arg | Asn | Ile | Leu | Tyr | Leu |
| 65 | | | | | 70 | | | | | 75 | | | | | 80 |
| Gln | Met | Ser | Ser | Leu | Arg | Ser | Glu | Asp | Thr | Ala | Met | Tyr | Tyr | Cys | Thr |
| | | | | 85 | | | | | 90 | | | | | 95 |
| Arg | Gly | Gly | Asp | Tyr | Gly | Tyr | Ala | Leu | Asp | Tyr | Trp | Gly | Gln | Gly | Thr |
| | | | 100 | | | | | 105 | | | | | 110 |
| Ser | Val | Thr | Val | Ser | Ser | Ala | Lys | Thr | Thr | Ala | Pro | Ser | Val | Tyr | Pro |
| | | 115 | | | | | 120 | | | | | 125 |
| Leu | Ala | Pro | Val | Cys | Gly | Asp | Thr | Thr | Gly | Ser | Ser | Val | Thr | Leu | Gly |
| | 130 | | | | | 135 | | | | | 140 |
| Cys | Leu | Val | Lys | Gly | Tyr | Phe | Pro | Glu | Pro | Val | Thr | Leu | Thr | Trp | Asn |
| 145 | | | | | 150 | | | | | 155 | | | | | 160 |
| Ser | Gly | Ser | Leu | Ser | Ser | Gly | Val | His | Thr | Phe | Pro | Ala | Val | Leu | Gln |
| | | | 165 | | | | | 170 | | | | | 175 |
| Ser | Asp | Leu | Tyr | Thr | Leu | Ser | Ser | Val | Thr | Val | Thr | Ser | Ser | Thr |
| | | | 180 | | | | | 185 | | | | | 190 |
| Trp | Pro | Ser | Gln | Ser | Ile | Thr | Cys | Asn | Val | Ala | His | Pro | Ala | Ser | Ser |
| | | | 195 | | | | | 200 | | | | | 205 |
| Thr | Lys | Val | Asp | Lys | Lys | Ile | Glu | Pro | Arg |
| | 210 | | | | | 215 |

```
<210> SEQ ID NO 73
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73
```

| | | | | | | | | | | | | | | |
|---|---|---|---|---|---|---|---|---|---|---|---|---|---|---|
| Glu | Ile | Val | Met | Thr | Gln | Ser | Pro | Ala | Thr | Leu | Ser | Val | Ser | Pro | Gly |
| 1 | | | | 5 | | | | | 10 | | | | | 15 |
| Glu | Arg | Ala | Thr | Leu | Ser | Cys | Arg | Ala | Ser | Ser | Ser | Val | Asn | Tyr | Met |
| | | | 20 | | | | | 25 | | | | | 30 |
| Tyr | Trp | Tyr | Gln | Gln | Lys | Pro | Gly | Gln | Ala | Pro | Arg | Leu | Leu | Ile | Tyr |
| | | 35 | | | | | 40 | | | | | 45 |
| Tyr | Thr | Ser | Asn | Leu | Ala | Pro | Gly | Ile | Pro | Ala | Arg | Phe | Ser | Gly | Ser |
| | 50 | | | | | 55 | | | | | 60 |
| Gly | Ser | Gly | Thr | Glu | Phe | Thr | Leu | Thr | Ile | Ser | Ser | Leu | Gln | Ser | Glu |
| 65 | | | | | 70 | | | | | 75 | | | | | 80 |
| Asp | Phe | Ala | Val | Tyr | Tyr | Cys | Gln | Gln | Phe | Ser | Ser | Ser | Pro | Trp | Thr |

```
            85                  90                  95
Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 74
<211> LENGTH: 649
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
            35                  40                  45

Gln Cys Ala Ser Ser Pro Cys Gln Asn Gly Gly Ser Cys Lys Asp Gln
        50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
            85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
            115                 120                 125

Pro Thr Val Glu Tyr Pro Cys Gly Lys Ile Pro Ile Leu Glu Lys Arg
            130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
            165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
            195                 200                 205

Gly Glu His Asp Leu Ser Glu His Asp Gly Asp Glu Gln Ser Arg Arg
            210                 215                 220
```

```
Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro Gly Gly Gly Ser Gly Gly Gly Ser
                405                 410                 415

Gly Gly Gly Ser Gly Gly Gly Ser Gly Gly Gly Ser
            420                 425                 430

Gly Gly Gly Ser Glu Ile Val Met Thr Gln Ser Pro Ala Thr Leu Ser
            435                 440                 445

Val Ser Pro Gly Glu Arg Ala Thr Leu Ser Cys Arg Ala Ser Ser Ser
450                 455                 460

Val Asn Tyr Met Tyr Trp Tyr Gln Gln Lys Pro Gly Gln Ala Pro Arg
465                 470                 475                 480

Leu Leu Ile Tyr Tyr Thr Ser Asn Leu Ala Pro Gly Ile Pro Ala Arg
                485                 490                 495

Phe Ser Gly Ser Gly Ser Gly Thr Glu Phe Thr Leu Thr Ile Ser Ser
            500                 505                 510

Leu Gln Ser Glu Asp Phe Ala Val Tyr Tyr Cys Gln Gln Phe Ser Ser
        515                 520                 525

Ser Pro Trp Thr Phe Gly Gln Gly Thr Lys Val Glu Ile Lys Arg Thr
    530                 535                 540

Val Ala Ala Pro Ser Val Phe Ile Phe Pro Pro Ser Asp Glu Gln Leu
545                 550                 555                 560

Lys Ser Gly Thr Ala Ser Val Val Cys Leu Leu Asn Asn Phe Tyr Pro
                565                 570                 575

Arg Glu Ala Lys Val Gln Trp Lys Val Asp Asn Ala Leu Gln Ser Gly
            580                 585                 590

Asn Ser Gln Glu Ser Val Thr Glu Gln Asp Ser Lys Asp Ser Thr Tyr
        595                 600                 605

Ser Leu Ser Ser Thr Leu Thr Leu Ser Lys Ala Asp Tyr Glu Lys His
    610                 615                 620

Lys Val Tyr Ala Cys Glu Val Thr His Gln Gly Leu Ser Ser Pro Val
625                 630                 635                 640
```

Thr Lys Ser Phe Asn Arg Gly Glu Cys
            645

<210> SEQ ID NO 75
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys
    210                 215                 220

<210> SEQ ID NO 76
<211> LENGTH: 221
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Val Lys Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Glu Trp Val
        35                  40                  45

Ala Ser Ile Ser Ser Gly Gly Thr Thr Tyr Tyr Pro Asp Ser Val Lys

```
               50                  55                  60
Arg Arg Phe Thr Ile Ser Arg Asp Asn Ala Arg Asn Thr Leu Tyr Leu
 65                  70                  75                  80

Gln Met Asn Ser Leu Arg Ala Glu Asp Thr Ala Val Tyr Tyr Cys Thr
                 85                  90                  95

Arg Gly Gly Asp Tyr Gly Tyr Ala Leu Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys
            210                 215                 220

<210> SEQ ID NO 77
<211> LENGTH: 944
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Ala Asn Ala Phe Leu Glu Glu Leu Arg Pro Gly Ser Leu Glu Arg Glu
1               5                  10                  15

Cys Lys Glu Glu Gln Cys Ser Phe Glu Glu Ala Arg Glu Ile Phe Lys
                20                  25                  30

Asp Ala Glu Arg Thr Lys Leu Phe Trp Ile Ser Tyr Ser Asp Gly Asp
            35                  40                  45

Gln Cys Ala Ser Ser Pro Cys Gln Asn Gly Gly Ser Cys Lys Asp Gln
        50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
                100                 105                 110

Arg Cys His Glu Gly Tyr Ser Leu Leu Ala Asp Gly Val Ser Cys Thr
            115                 120                 125

Pro Thr Val Glu Tyr Pro Cys Gly Lys Ile Pro Ile Leu Glu Lys Arg
        130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
                180                 185                 190
```

```
His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
                260                 265                 270

Leu Ala Phe Val Arg Phe Ser Leu Val Ser Gly Trp Gly Gln Leu Leu
            275                 280                 285

Asp Arg Gly Ala Thr Ala Leu Glu Leu Met Val Leu Asn Val Pro Arg
        290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
            355                 360                 365

Ala Thr Val Gly His Phe Gly Val Tyr Thr Arg Val Ser Gln Tyr Ile
        370                 375                 380

Glu Trp Leu Gln Lys Leu Met Arg Ser Glu Pro Arg Pro Gly Val Leu
385                 390                 395                 400

Leu Arg Ala Pro Phe Pro Gly Ser Pro Gly Thr Ser Glu Ser Ala Thr
                405                 410                 415

Pro Glu Ser Gly Pro Gly Ser Glu Pro Ala Thr Ser Gly Ser Glu Thr
                420                 425                 430

Pro Gly Thr Ser Glu Ser Ala Thr Pro Glu Ser Gly Pro Gly Ser Glu
            435                 440                 445

Pro Ala Thr Ser Gly Ser Glu Thr Pro Gly Thr Ser Glu Ser Ala Thr
        450                 455                 460

Pro Glu Ser Gly Pro Gly Thr Ser Thr Glu Pro Ser Glu Gly Ser Ala
465                 470                 475                 480

Pro Gly Ser Pro Ala Gly Ser Pro Thr Ser Thr Glu Glu Gly Thr Ser
                485                 490                 495

Glu Ser Ala Thr Pro Glu Ser Gly Pro Gly Ser Glu Pro Ala Thr Ser
                500                 505                 510

Gly Ser Glu Thr Pro Gly Thr Ser Glu Ser Ala Thr Pro Glu Ser Gly
            515                 520                 525

Pro Gly Ser Pro Ala Gly Ser Pro Thr Ser Thr Glu Glu Gly Ser Pro
        530                 535                 540

Ala Gly Ser Pro Thr Ser Thr Glu Glu Gly Thr Ser Thr Glu Pro Ser
545                 550                 555                 560

Glu Gly Ser Ala Pro Gly Thr Ser Glu Ser Ala Thr Pro Glu Ser Gly
                565                 570                 575

Pro Gly Thr Ser Glu Ser Ala Thr Pro Glu Ser Gly Pro Gly Thr Ser
                580                 585                 590

Glu Ser Ala Thr Pro Glu Ser Gly Pro Gly Ser Glu Pro Ala Thr Ser
            595                 600                 605
```

Gly Ser Glu Thr Pro Gly Ser Glu Pro Ala Thr Gly Ser Glu Thr
            610                 615                 620

Pro Gly Ser Pro Ala Gly Ser Pro Thr Ser Thr Glu Glu Gly Thr Ser
625                 630                 635                 640

Thr Glu Pro Ser Glu Gly Ser Ala Pro Gly Thr Ser Thr Glu Pro Ser
                645                 650                 655

Glu Gly Ser Ala Pro Gly Ser Glu Pro Ala Thr Gly Ser Glu Thr
            660                 665                 670

Pro Gly Thr Ser Glu Ser Ala Thr Pro Glu Ser Gly Pro Gly Thr Ser
                675                 680                 685

Thr Glu Pro Ser Glu Gly Ser Ala Pro Gly Ser Ser Gly Gly Gly
            690                 695                 700

Gly Ser Gly Gly Gly Ser Gly Gly Gly Ser Gly Gly Gly
705                 710                 715                 720

Ser Gly Gly Gly Gly Ser Gly Gly Gly Ser Glu Ile Val Met Thr
                725                 730                 735

Gln Ser Pro Ala Thr Leu Ser Val Ser Pro Gly Glu Arg Ala Thr Leu
            740                 745                 750

Ser Cys Arg Ala Ser Ser Val Asn Tyr Met Tyr Trp Tyr Gln Gln
                755                 760                 765

Lys Pro Gly Gln Ala Pro Arg Leu Leu Ile Tyr Tyr Thr Ser Asn Leu
            770                 775                 780

Ala Pro Gly Ile Pro Ala Arg Phe Ser Gly Ser Gly Ser Gly Thr Glu
785                 790                 795                 800

Phe Thr Leu Thr Ile Ser Ser Leu Gln Ser Glu Asp Phe Ala Val Tyr
                805                 810                 815

Tyr Cys Gln Gln Phe Ser Ser Pro Trp Thr Phe Gly Gln Gly Thr
            820                 825                 830

Lys Val Glu Ile Lys Arg Thr Val Ala Ala Pro Ser Val Phe Ile Phe
                835                 840                 845

Pro Pro Ser Asp Glu Gln Leu Lys Ser Gly Thr Ala Ser Val Val Cys
850                 855                 860

Leu Leu Asn Asn Phe Tyr Pro Arg Glu Ala Lys Val Gln Trp Lys Val
865                 870                 875                 880

Asp Asn Ala Leu Gln Ser Gly Asn Ser Gln Glu Ser Val Thr Glu Gln
                885                 890                 895

Asp Ser Lys Asp Ser Thr Tyr Ser Leu Ser Ser Thr Leu Thr Leu Ser
            900                 905                 910

Lys Ala Asp Tyr Glu Lys His Lys Val Tyr Ala Cys Glu Val Thr His
            915                 920                 925

Gln Gly Leu Ser Ser Pro Val Thr Lys Ser Phe Asn Arg Gly Glu Cys
930                 935                 940

<210> SEQ ID NO 78
<211> LENGTH: 976
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys

```
                    20                  25                  30
Asp Ala Glu Arg Thr Lys Leu Phe Trp Ile Ser Tyr Ser Asp Gly Asp
                35                  40                  45

Gln Cys Ala Ser Ser Pro Cys Gln Asn Gly Gly Ser Cys Lys Asp Gln
            50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
                100                 105                 110

Arg Cys His Glu Gly Tyr Ser Leu Leu Ala Asp Gly Val Ser Cys Thr
            115                 120                 125

Pro Thr Val Glu Tyr Pro Cys Gly Lys Ile Pro Ile Leu Glu Lys Arg
            130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
                180                 185                 190

His Cys Phe Asp Lys Ile Lys Asn Trp Arg Asn Leu Ile Ala Val Leu
            195                 200                 205

Gly Glu His Asp Leu Ser Glu His Asp Gly Asp Glu Gln Ser Arg Arg
            210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
                260                 265                 270

Leu Ala Phe Val Arg Phe Ser Leu Val Ser Gly Trp Gly Gln Leu Leu
            275                 280                 285

Asp Arg Gly Ala Thr Ala Leu Glu Leu Met Val Leu Asn Val Pro Arg
            290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
            355                 360                 365

Ala Thr Val Gly His Phe Gly Val Tyr Thr Arg Val Ser Gln Tyr Ile
            370                 375                 380

Glu Trp Leu Gln Lys Leu Met Arg Ser Glu Pro Arg Pro Gly Val Leu
385                 390                 395                 400

Leu Arg Ala Pro Phe Pro Gly Ser Pro Gly Thr Ser Glu Ser Ala Thr
                405                 410                 415

Pro Glu Ser Gly Pro Gly Ser Glu Pro Ala Thr Ser Gly Ser Glu Thr
                420                 425                 430

Pro Gly Thr Ser Glu Ser Ala Thr Pro Glu Ser Gly Pro Gly Ser Glu
            435                 440                 445
```

```
Pro Ala Thr Ser Gly Ser Glu Thr Pro Gly Thr Ser Glu Ser Ala Thr
    450                 455                 460
Pro Glu Ser Gly Pro Gly Thr Ser Thr Glu Pro Ser Glu Gly Ser Ala
465                 470                 475                 480
Pro Gly Ser Pro Ala Gly Ser Pro Thr Ser Thr Glu Glu Gly Thr Ser
                485                 490                 495
Glu Ser Ala Thr Pro Glu Ser Gly Pro Gly Ser Glu Pro Ala Thr Ser
            500                 505                 510
Gly Ser Glu Thr Pro Gly Thr Ser Glu Ser Ala Thr Pro Glu Ser Gly
        515                 520                 525
Pro Gly Ser Pro Ala Gly Ser Pro Thr Ser Thr Glu Glu Gly Ser Pro
    530                 535                 540
Ala Gly Ser Pro Thr Ser Thr Glu Glu Gly Thr Ser Thr Glu Pro Ser
545                 550                 555                 560
Glu Gly Ser Ala Pro Gly Thr Ser Glu Ser Ala Thr Pro Glu Ser Gly
                565                 570                 575
Pro Gly Thr Ser Glu Ser Ala Thr Pro Glu Ser Gly Pro Gly Thr Ser
            580                 585                 590
Glu Ser Ala Thr Pro Glu Ser Gly Pro Gly Ser Glu Pro Ala Thr Ser
        595                 600                 605
Gly Ser Glu Thr Pro Gly Ser Glu Pro Ala Thr Ser Gly Ser Glu Thr
    610                 615                 620
Pro Gly Ser Pro Ala Gly Ser Pro Thr Ser Thr Glu Glu Gly Thr Ser
625                 630                 635                 640
Thr Glu Pro Ser Glu Gly Ser Ala Pro Gly Thr Ser Thr Glu Pro Ser
                645                 650                 655
Glu Gly Ser Ala Pro Gly Ser Glu Pro Ala Thr Ser Gly Ser Glu Thr
            660                 665                 670
Pro Gly Thr Ser Glu Ser Ala Thr Pro Glu Ser Gly Pro Gly Thr Ser
        675                 680                 685
Thr Glu Pro Ser Glu Gly Ser Ala Pro Gly Ser Ser Ser Gly Gly Gly
    690                 695                 700
Gly Ser Gly Gly Gly Ser Gly Gly Gly Ser Gly Gly Gly Ser Gly Gly
705                 710                 715                 720
Ser Gly Gly Gly Gly Ser Gly Gly Gly Ser Glu Asn Val Leu Thr
                725                 730                 735
Gln Ser Pro Ala Ile Met Ser Ala Ser Leu Gly Glu Lys Val Thr Met
            740                 745                 750
Ser Cys Arg Ala Ser Ser Ser Val Asn Tyr Met Tyr Trp Tyr Gln Gln
        755                 760                 765
Lys Ser Asp Ala Ser Pro Lys Leu Trp Ile Tyr Tyr Thr Ser Asn Leu
    770                 775                 780
Ala Pro Gly Val Pro Ala Arg Phe Ser Gly Ser Gly Ser Gly Asn Ser
785                 790                 795                 800
Tyr Ser Leu Thr Ile Ser Ser Met Glu Gly Glu Asp Ala Ala Thr Tyr
                805                 810                 815
Tyr Cys Gln Gln Phe Ser Ser Ser Pro Trp Thr Phe Gly Gly Gly Thr
            820                 825                 830
Lys Leu Glu Ile Lys Arg Gly Gly Gly Gly Ser Gly Gly Gly Gly Ser
        835                 840                 845
Gly Gly Gly Gly Ser Gly Gly Gly Gly Ser Glu Val Lys Leu Val Glu
    850                 855                 860
```

Ser Gly Gly Gly Leu Val Lys Pro Gly Gly Ser Leu Lys Leu Ser Cys
865                 870                 875                 880

Ala Ala Ser Gly Phe Thr Phe Ser Ala Tyr Ala Met Ser Trp Val Arg
            885                 890                 895

Gln Thr Pro Glu Lys Arg Leu Glu Trp Val Ala Ser Ile Ser Ser Gly
        900                 905                 910

Gly Thr Thr Tyr Tyr Pro Asp Ser Val Lys Arg Phe Thr Ile Ser
    915                 920                 925

Arg Asp Asn Ala Arg Asn Ile Leu Tyr Leu Gln Met Ser Ser Leu Arg
    930                 935                 940

Ser Glu Asp Thr Ala Met Tyr Tyr Cys Thr Arg Gly Gly Asp Tyr Gly
945                 950                 955                 960

Tyr Ala Leu Asp Tyr Trp Gly Gln Gly Thr Ser Val Thr Val Ser Ser
                965                 970                 975

<210> SEQ ID NO 79
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly

```
                        245                 250                 255
Asp Glu Gln Ser Arg Val Ala Gln Val Ile Ile Pro Ser Thr Tyr
            260                 265                 270

Val Pro Gly Thr Thr Asn His Asp Ile Ala Leu Leu Arg Leu His Gln
            275                 280                 285

Pro Val Val Leu Thr Asp His Val Val Pro Leu Cys Leu Pro Glu Arg
            290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
            325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
            355                 360                 365

Gly Tyr Ser Asp Gly Ser Lys Asp Ser Cys Lys Gly Asp Ser Gly Gly
            370                 375                 380

Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
            405                 410                 415

Arg Val Ser Gln Tyr Ile Glu Trp Leu Gln Lys Leu Met Arg Ser Glu
            420                 425                 430

Pro Arg Pro Gly Val Leu Leu Arg Ala Pro Phe Pro
            435                 440

<210> SEQ ID NO 80
<211> LENGTH: 152
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
            35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
            85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
            115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg
145                 150
```

```
<210> SEQ ID NO 81
<211> LENGTH: 254
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn
            20                  25                  30

Thr Ile Trp Val Val Ser Ala Ala His Cys Phe Asp Lys Ile Lys Asn
        35                  40                  45

Trp Arg Asn Leu Ile Ala Val Leu Gly Glu His Asp Leu Ser Glu His
    50                  55                  60

Asp Gly Asp Glu Gln Ser Arg Arg Val Ala Gln Val Ile Ile Pro Ser
65                  70                  75                  80

Thr Tyr Val Pro Gly Thr Thr Asn His Asp Ile Ala Leu Leu Arg Leu
                85                  90                  95

His Gln Pro Val Val Leu Thr Asp His Val Val Pro Leu Cys Leu Pro
            100                 105                 110

Glu Arg Thr Phe Ser Glu Arg Thr Leu Ala Phe Val Arg Phe Ser Leu
        115                 120                 125

Val Ser Gly Trp Gly Gln Leu Leu Asp Arg Gly Ala Thr Ala Leu Glu
    130                 135                 140

Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

Cys Ala Gly Tyr Ser Asp Gly Ser Lys Asp Ser Cys Lys Gly Asp Ser
            180                 185                 190

Gly Gly Pro His Ala Thr His Tyr Arg Gly Thr Trp Tyr Leu Thr Gly
        195                 200                 205

Ile Val Ser Trp Gly Gln Gly Cys Ala Thr Val Gly His Phe Gly Val
    210                 215                 220

Tyr Thr Arg Val Ser Gln Tyr Ile Glu Trp Leu Gln Lys Leu Met Arg
225                 230                 235                 240

Ser Glu Pro Arg Pro Gly Val Leu Leu Arg Ala Pro Phe Pro
                245                 250

<210> SEQ ID NO 82
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Leu Gln Gln Ser Arg Lys Val Gly Asp Ser Pro Asn
1               5                   10

<210> SEQ ID NO 83
<211> LENGTH: 7
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Glu Ala Ser Tyr Pro Gly Lys
1               5

<210> SEQ ID NO 84
<211> LENGTH: 461
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
```

```
                    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 85
<211> LENGTH: 488
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190
```

-continued

```
Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 86
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Glu Ser Pro Gly Gly Ser Ser Gly Ser Glu Ser
1               5                   10

<210> SEQ ID NO 87
<211> LENGTH: 12
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 87

Gly Ser Glu Gly Ser Ser Gly Pro Gly Glu Ser Ser
1               5                   10

<210> SEQ ID NO 88
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Ser Ser Glu Ser Gly Ser Ser Glu Gly Gly Pro
1               5                   10

<210> SEQ ID NO 89
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Ser Gly Gly Glu Pro Ser Glu Ser Gly Ser Ser
1               5                   10

<210> SEQ ID NO 90
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gly Ser Pro Ala Gly Ser Pro Thr Ser Thr Glu Glu
1               5                   10

<210> SEQ ID NO 91
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gly Ser Glu Pro Ala Thr Ser Gly Ser Glu Thr Pro
1               5                   10

<210> SEQ ID NO 92
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 92

Gly Thr Ser Glu Ser Ala Thr Pro Glu Ser Gly Pro
1               5                   10

<210> SEQ ID NO 93
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Thr Ser Thr Glu Pro Ser Glu Gly Ser Ala Pro
1               5                   10

<210> SEQ ID NO 94
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gly Ser Thr Ser Glu Ser Pro Ser Gly Thr Ala Pro
1               5                   10

<210> SEQ ID NO 95
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gly Thr Ser Thr Pro Glu Ser Gly Ser Ala Ser Pro
1               5                   10

<210> SEQ ID NO 96
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Thr Ser Pro Ser Gly Glu Ser Ser Thr Ala Pro
1               5                   10

<210> SEQ ID NO 97
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Ser Thr Ser Ser Thr Ala Glu Ser Pro Gly Pro
1               5                   10
```

```
<210> SEQ ID NO 98
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Thr Pro Gly Ser Gly Thr Ala Ser Ser Ser Pro
1               5                   10

<210> SEQ ID NO 99
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Ser Ser Thr Pro Ser Gly Ala Thr Gly Ser Pro
1               5                   10

<210> SEQ ID NO 100
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Ser Ser Pro Ser Ala Ser Thr Gly Thr Gly Pro
1               5                   10

<210> SEQ ID NO 101
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Ala Ser Pro Gly Thr Ser Ser Thr Gly Ser Pro
1               5                   10

<210> SEQ ID NO 102
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gly Glu Pro Ala Gly Ser Pro Thr Ser Thr Ser Glu
1               5                   10

<210> SEQ ID NO 103
<211> LENGTH: 12
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gly Thr Gly Glu Pro Ser Ser Thr Pro Ala Ser Glu
1               5                   10

<210> SEQ ID NO 104
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gly Ser Gly Pro Ser Thr Glu Ser Ala Pro Thr Glu
1               5                   10

<210> SEQ ID NO 105
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Gly Ser Glu Thr Pro Ser Gly Pro Ser Glu Thr Ala
1               5                   10

<210> SEQ ID NO 106
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Gly Pro Ser Glu Thr Ser Thr Ser Glu Pro Gly Ala
1               5                   10

<210> SEQ ID NO 107
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Ser Pro Ser Glu Pro Thr Glu Gly Thr Ser Ala
1               5                   10

<210> SEQ ID NO 108
<211> LENGTH: 12
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 108

Gly Ser Gly Ala Ser Glu Pro Thr Ser Thr Glu Pro
1               5                   10

<210> SEQ ID NO 109
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Ser Glu Pro Ala Thr Ser Gly Thr Glu Pro Ser
1               5                   10

<210> SEQ ID NO 110
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Gly Thr Ser Glu Pro Ser Thr Ser Glu Pro Gly Ala
1               5                   10

<210> SEQ ID NO 111
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Gly Thr Ser Thr Glu Pro Ser Glu Pro Gly Ser Ala
1               5                   10

<210> SEQ ID NO 112
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Gly Ser Thr Ala Gly Ser Glu Thr Ser Thr Glu Ala
1               5                   10

<210> SEQ ID NO 113
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 113
```

Gly Ser Glu Thr Ala Thr Ser Gly Ser Glu Thr Ala
1               5                   10

<210> SEQ ID NO 114
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Gly Thr Ser Glu Ser Ala Thr Ser Glu Ser Gly Ala
1               5                   10

<210> SEQ ID NO 115
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Gly Thr Ser Thr Glu Ala Ser Glu Gly Ser Ala Ser
1               5                   10

<210> SEQ ID NO 116
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 117
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Thr Gly Gly Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 118
<211> LENGTH: 42

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Gly Thr Ser Glu Ser Ala Thr Pro Glu Ser Gly Pro Gly Ser Glu Pro
1               5                   10                  15

Ala Thr Ser Gly Ser Glu Thr Pro Gly Thr Ser Glu Ser Ala Thr Pro
            20                  25                  30

Glu Ser Gly Pro Gly Ser Glu Pro Ala Thr
        35                  40

<210> SEQ ID NO 119
<211> LENGTH: 78
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Gly Ala Pro Thr Ser Glu Ser Ala Thr Pro Glu Ser Gly Pro Gly Ser
1               5                   10                  15

Glu Pro Ala Thr Ser Gly Ser Glu Thr Pro Gly Thr Ser Glu Ser Ala
            20                  25                  30

Thr Pro Glu Ser Gly Pro Gly Ser Glu Pro Ala Thr Ser Gly Ser Glu
        35                  40                  45

Thr Pro Gly Thr Ser Glu Ser Ala Thr Pro Glu Ser Gly Pro Gly Thr
    50                  55                  60

Ser Thr Glu Pro Ser Glu Gly Ser Ala Pro Gly Ala Ser Ser
65                  70                  75

<210> SEQ ID NO 120
<211> LENGTH: 72
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gly Thr Ser Glu Ser Ala Thr Pro Glu Ser Gly Pro Gly Ser Glu Pro
1               5                   10                  15

Ala Thr Ser Gly Ser Glu Thr Pro Gly Thr Ser Glu Ser Ala Thr Pro
            20                  25                  30

Glu Ser Gly Pro Gly Ser Glu Pro Ala Thr Ser Gly Ser Glu Thr Pro
        35                  40                  45

Gly Thr Ser Glu Ser Ala Thr Pro Glu Ser Gly Pro Gly Thr Ser Thr
    50                  55                  60

Glu Pro Ser Glu Gly Ser Ala Pro
65                  70

<210> SEQ ID NO 121
<211> LENGTH: 72
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 121

Ser Pro Ala Gly Ser Pro Thr Ser Thr Glu Glu Gly Thr Ser Glu Ser
1               5                   10                  15

Ala Thr Pro Glu Ser Gly Pro Gly Ser Glu Pro Ala Thr Ser Gly Ser
                20                  25                  30

Glu Thr Pro Gly Thr Ser Glu Ser Ala Thr Pro Glu Ser Gly Pro Gly
            35                  40                  45

Thr Ser Thr Glu Pro Ser Glu Gly Ser Ala Pro Gly Thr Ser Thr Glu
        50                  55                  60

Pro Ser Glu Gly Ser Ala Pro Gly
65                  70

<210> SEQ ID NO 122
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Gly Ser Glu Pro Ala Thr Ser Gly Ser Glu Thr Pro Gly Thr Ser Glu
1               5                   10                  15

Ser Ala Thr Pro Glu Ser Gly Pro Gly Ser Glu Pro Ala Thr Ser Gly
                20                  25                  30

Ser Glu Thr Pro Gly Ser Pro Ala Gly Ser Pro Thr Ser Thr Glu Glu
            35                  40                  45

Gly Thr Ser Thr Glu Pro Ser Glu Gly Ser Ala Pro Gly Ser Glu Pro
        50                  55                  60

Ala Thr Ser Gly Ser Glu Thr Pro Gly Ser Pro Ala Thr Ser Gly Ser
65                  70                  75                  80

Ser Glu Thr Pro Gly Ser Glu Pro Ala Thr Ser Gly Ser Glu Thr Pro
                85                  90                  95

Gly Thr Ser Thr Glu Pro Ser Glu Gly Ser Ala Pro Gly Thr Ser Glu
            100                 105                 110

Ser Ala Pro Glu Ser Gly Pro Gly Ser Glu Pro Ala Thr Ser Gly Ser
        115                 120                 125

Glu Thr Pro Gly Thr Ser Thr Glu Pro Ser Glu Gly Ser Ala Pro
    130                 135                 140

<210> SEQ ID NO 123
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Gly Thr Ser Glu Ser Ala Thr Pro Glu Ser Gly Pro Gly Ser Glu Pro
1               5                   10                  15

Ala Thr Ser Gly Ser Glu Thr Pro Gly Thr Ser Glu Ser Ala Thr Pro
                20                  25                  30

Glu Ser Gly Pro Gly Ser Glu Pro Ala Thr Ser Gly Ser Glu Thr Pro
            35                  40                  45

```
Gly Thr Ser Glu Ser Ala Thr Pro Glu Ser Gly Pro Gly Thr Ser Thr
        50                  55                  60

Glu Pro Ser Glu Gly Ser Ala Pro Gly Ser Pro Ala Gly Ser Pro Thr
 65                  70                  75                  80

Ser Thr Glu Glu Gly Thr Ser Glu Ser Ala Thr Pro Glu Ser Gly Pro
                85                  90                  95

Gly Ser Glu Pro Ala Thr Ser Gly Ser Glu Thr Pro Gly Thr Ser Glu
               100                 105                 110

Ser Ala Thr Pro Glu Ser Gly Pro Gly Ser Pro Ala Gly Ser Pro Thr
           115                 120                 125

Ser Thr Glu Glu Gly Ser Pro Ala Gly Ser Pro Thr Ser Thr Glu Glu
           130                 135                 140
```

<210> SEQ ID NO 124
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 124

```
Gly Ser Pro Ala Gly Ser Pro Thr Ser Thr Glu Glu Gly Thr Ser Glu
 1               5                  10                  15

Ser Ala Thr Pro Glu Ser Gly Pro Gly Thr Ser Thr Glu Pro Ser Glu
                20                  25                  30

Gly Ser Ala Pro Gly Ser Pro Ala Gly Ser Pro Thr Ser Thr Glu Glu
            35                  40                  45

Gly Thr Ser Thr Glu Pro Ser Glu Gly Ser Ala Pro Gly Thr Ser Thr
        50                  55                  60

Glu Pro Ser Glu Gly Ser Ala Pro Gly Thr Ser Glu Ser Ala Thr Pro
 65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
               100                 105                 110

Gly Ser Pro Thr Ser Thr Glu Glu Gly Thr Ser Glu Ser Ala Thr Pro
           115                 120                 125

Glu Ser Gly Pro Gly Thr Ser Thr Glu Pro Ser Glu Gly Ser Ala Pro
           130                 135                 140
```

<210> SEQ ID NO 125
<211> LENGTH: 144
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

```
Gly Thr Pro Gly Ser Gly Thr Ala Ser Ser Pro Gly Ser Ser Thr
 1               5                  10                  15

Pro Ser Gly Ala Thr Gly Ser Pro Gly Ser Pro Ser Ala Ser Thr
                20                  25                  30

Gly Thr Gly Pro Gly Ser Ser Pro Ser Ala Ser Thr Gly Thr Gly Pro
            35                  40                  45
```

```
Gly Ala Ser Pro Gly Thr Ser Ser Thr Gly Ser Pro Gly Ala Ser Pro
 50                  55                  60

Gly Thr Ser Ser Thr Gly Ser Pro Gly Ser Ser Thr Pro Ser Gly Ala
 65                  70                  75                  80

Thr Gly Ser Pro Gly Ser Ser Pro Ser Ala Ser Thr Gly Thr Gly Pro
                 85                  90                  95

Gly Ala Ser Pro Gly Thr Ser Ser Thr Gly Ser Pro Gly Ser Ser Pro
                100                 105                 110

Ser Ala Ser Thr Gly Thr Gly Pro Gly Thr Pro Gly Ser Gly Thr Ala
            115                 120                 125

Ser Ser Ser Pro Gly Ser Ser Thr Pro Ser Gly Ala Thr Gly Ser Pro
            130                 135                 140
```

<210> SEQ ID NO 126
<211> LENGTH: 288
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

```
Gly Thr Ser Glu Ser Ala Thr Pro Glu Ser Gly Pro Gly Ser Glu Pro
 1               5                  10                  15

Ala Thr Ser Gly Ser Glu Thr Pro Gly Thr Ser Glu Ser Ala Thr Pro
                 20                  25                  30

Glu Ser Gly Pro Gly Ser Glu Pro Ala Thr Ser Gly Ser Glu Thr Pro
                 35                  40                  45

Gly Thr Ser Glu Ser Ala Thr Pro Glu Ser Gly Pro Gly Thr Ser Thr
 50                  55                  60

Glu Pro Ser Glu Gly Ser Ala Pro Gly Ser Pro Ala Gly Ser Pro Thr
 65                  70                  75                  80

Ser Thr Glu Glu Gly Thr Ser Glu Ser Ala Thr Pro Glu Ser Gly Pro
                 85                  90                  95

Gly Ser Glu Pro Ala Thr Ser Gly Ser Glu Thr Pro Gly Thr Ser Glu
                100                 105                 110

Ser Ala Thr Pro Glu Ser Gly Pro Gly Ser Pro Ala Gly Ser Pro Thr
            115                 120                 125

Ser Thr Glu Glu Gly Ser Pro Ala Gly Ser Pro Thr Ser Thr Glu Glu
            130                 135                 140

Gly Thr Ser Thr Glu Pro Ser Glu Gly Ser Ala Pro Gly Thr Ser Glu
145                 150                 155                 160

Ser Ala Thr Pro Glu Ser Gly Pro Gly Thr Ser Glu Ser Ala Thr Pro
                165                 170                 175

Glu Ser Gly Pro Gly Thr Ser Glu Ser Ala Thr Pro Glu Ser Gly Pro
                180                 185                 190

Gly Ser Glu Pro Ala Thr Ser Gly Ser Glu Thr Pro Gly Ser Glu Pro
            195                 200                 205

Ala Thr Ser Gly Ser Glu Thr Pro Gly Ser Pro Ala Gly Ser Pro Thr
            210                 215                 220

Ser Thr Glu Glu Gly Thr Ser Thr Glu Pro Ser Glu Gly Ser Ala Pro
225                 230                 235                 240

Gly Thr Ser Thr Glu Pro Ser Glu Gly Ser Ala Pro Gly Ser Glu Pro
                245                 250                 255

Ala Thr Ser Gly Ser Glu Thr Pro Gly Thr Ser Glu Ser Ala Thr Pro
```

Glu Ser Gly Pro Gly Thr Ser Thr Glu Pro Ser Glu Gly Ser Ala Pro
            260                 265                 270
275                 280                 285

<210> SEQ ID NO 127
<211> LENGTH: 288
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Pro Gly Ala Ser Pro Gly Thr Ser Ser Thr Gly Ser Pro Gly Ala Ser
1               5                   10                  15

Pro Gly Thr Ser Ser Thr Gly Ser Pro Gly Thr Pro Gly Ser Gly Thr
            20                  25                  30

Ala Ser Ser Ser Pro Gly Ser Ser Thr Pro Ser Gly Ala Thr Gly Ser
            35                  40                  45

Pro Gly Thr Pro Gly Ser Gly Thr Ala Ser Ser Pro Gly Ser Ser
    50                  55                  60

Thr Pro Ser Gly Ala Thr Gly Ser Pro Gly Thr Pro Gly Ser Gly Thr
65                  70                  75                  80

Ala Ser Ser Ser Pro Gly Ser Ser Thr Pro Ser Gly Ala Thr Gly Ser
            85                  90                  95

Pro Gly Ser Ser Thr Pro Ser Gly Ala Thr Gly Ser Pro Gly Ser Ser
            100                 105                 110

Pro Ser Ala Ser Thr Gly Thr Gly Pro Gly Ser Ser Pro Ser Ala Ser
            115                 120                 125

Thr Gly Thr Gly Pro Gly Ala Ser Pro Gly Thr Ser Ser Thr Gly Ser
    130                 135                 140

Pro Gly Thr Pro Gly Ser Gly Thr Ala Ser Ser Pro Gly Ser Ser
145                 150                 155                 160

Thr Pro Ser Gly Ala Thr Gly Ser Pro Gly Ser Ser Pro Ser Ala Ser
            165                 170                 175

Thr Gly Thr Gly Pro Gly Ser Ser Pro Ser Ala Ser Thr Gly Thr Gly
            180                 185                 190

Pro Gly Ala Ser Pro Gly Thr Ser Ser Thr Gly Ser Pro Gly Ala Ser
            195                 200                 205

Pro Gly Thr Ser Ser Thr Gly Ser Pro Gly Ser Ser Thr Pro Ser Gly
    210                 215                 220

Ala Thr Gly Ser Pro Gly Ser Ser Pro Ser Ala Ser Thr Gly Thr Gly
225                 230                 235                 240

Pro Gly Ala Ser Pro Gly Thr Ser Ser Thr Gly Ser Pro Gly Ser Ser
            245                 250                 255

Pro Ser Ala Ser Thr Gly Thr Gly Pro Gly Thr Pro Gly Ser Gly Thr
            260                 265                 270

Ala Ser Ser Ser Pro Gly Ser Ser Thr Pro Ser Gly Ala Thr Gly Ser
            275                 280                 285

<210> SEQ ID NO 128
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 128

```
Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
        35                  40                  45

Gly Thr Ser Thr Glu Pro Ser Glu Gly Ser Ala Pro Gly Thr Ser Thr
    50                  55                  60

Glu Pro Ser Glu Gly Ser Ala Pro Gly Thr Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
                100                 105                 110

Gly Ser Pro Thr Ser Thr Glu Glu Gly Thr Ser Glu Ser Ala Thr Pro
            115                 120                 125

Glu Ser Gly Pro Gly Thr Ser Thr Glu Pro Ser Glu Gly Ser Ala Pro
    130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
                180                 185                 190

Gly Thr Ser Glu Ser Ala Thr Pro Glu Ser Gly Pro Gly Thr Ser Thr
            195                 200                 205

Glu Pro Ser Glu Gly Ser Ala Pro Gly Thr Ser Glu Ser Ala Thr Pro
    210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Thr Ser Glu Ser Ala Thr Pro
                260                 265                 270

Glu Ser Gly Pro Gly Thr Ser Glu Ser Ala Thr Pro Glu Ser Gly Pro
            275                 280                 285

Gly Ser Pro Ala Gly Ser Pro Thr Ser Thr Glu Glu Gly Thr Ser Glu
    290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
                340                 345                 350

Glu Pro Ser Glu Gly Ser Ala Pro Gly Thr Ser Thr Glu Pro Ser Glu
            355                 360                 365

Gly Ser Ala Pro Gly Thr Ser Thr Glu Pro Ser Glu Gly Ser Ala Pro
    370                 375                 380

Gly Thr Ser Thr Glu Pro Ser Glu Gly Ser Ala Pro Gly Thr Ser Thr
385                 390                 395                 400
```

```
Glu Pro Ser Glu Gly Ser Ala Pro Gly Ser Pro Ala Gly Ser Pro Thr
                405                 410                 415

Ser Thr Glu Glu Gly Thr Ser Thr Glu Pro Ser Glu Gly Ser Ala Pro
                420                 425                 430

Gly Thr Ser Glu Ser Ala Thr Pro Glu Ser Gly Pro Gly Ser Glu Pro
                435                 440                 445

Ala Thr Ser Gly Ser Glu Thr Pro Gly Thr Ser Glu Ser Ala Thr Pro
                450                 455                 460

Glu Ser Gly Pro Gly Ser Pro Ala Thr Ser Gly Ser Glu Thr Pro
465                 470                 475                 480

Gly Thr Ser Glu Ser Ala Thr Pro Glu Ser Gly Pro Gly Thr Ser Thr
                485                 490                 495

Glu Pro Ser Glu Gly Ser Ala Pro Gly Thr Ser Glu Ser Ala Thr Pro
                500                 505                 510

Glu Ser Gly Pro Gly Ser Pro Ala Gly Ser Pro Thr Ser Thr Glu Glu
                515                 520                 525

Gly Ser Pro Ala Gly Ser Pro Thr Ser Thr Glu Glu Gly Ser Pro Ala
                530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
                565                 570                 575

<210> SEQ ID NO 129
<211> LENGTH: 576
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

Pro Gly Thr Pro Gly Ser Gly Thr Ala Ser Ser Ser Pro Gly Ser Ser
1               5                   10                  15

Thr Pro Ser Gly Ala Thr Gly Ser Pro Gly Ser Ser Pro Ser Ala Ser
                20                  25                  30

Thr Gly Thr Gly Pro Gly Ser Ser Pro Ser Ala Ser Thr Gly Thr Gly
                35                  40                  45

Pro Gly Ser Ser Thr Pro Ser Gly Ala Thr Gly Ser Pro Gly Ser Ser
                50                  55                  60

Thr Pro Ser Gly Ala Thr Gly Ser Pro Gly Ala Ser Pro Gly Thr Ser
65                  70                  75                  80

Ser Thr Gly Ser Pro Gly Ala Ser Pro Gly Thr Ser Ser Thr Gly Ser
                85                  90                  95

Pro Gly Ala Ser Pro Gly Thr Ser Ser Thr Gly Ser Pro Gly Thr Pro
                100                 105                 110

Gly Ser Gly Thr Ala Ser Ser Ser Pro Gly Ala Ser Pro Gly Thr Ser
                115                 120                 125

Ser Thr Gly Ser Pro Gly Ala Ser Pro Gly Thr Ser Ser Thr Gly Ser
                130                 135                 140

Pro Gly Ala Ser Pro Gly Thr Ser Ser Thr Gly Ser Pro Gly Ser Ser
145                 150                 155                 160

Pro Ser Ala Ser Thr Gly Thr Gly Pro Gly Thr Pro Gly Ser Gly Thr
                165                 170                 175

Ala Ser Ser Ser Pro Gly Ala Ser Pro Gly Thr Ser Ser Thr Gly Ser
```

```
                180                 185                 190
Pro Gly Ala Ser Pro Gly Thr Ser Ser Thr Gly Ser Pro Gly Ala Ser
            195                 200                 205
Pro Gly Thr Ser Ser Thr Gly Ser Pro Gly Ser Ser Thr Pro Ser Gly
        210                 215                 220
Ala Thr Gly Ser Pro Gly Ser Ser Thr Pro Ser Gly Ala Thr Gly Ser
225                 230                 235                 240
Pro Gly Ala Ser Pro Gly Thr Ser Ser Thr Gly Ser Pro Gly Thr Pro
            245                 250                 255
Gly Ser Gly Thr Ala Ser Ser Pro Gly Ser Ser Thr Pro Ser Gly
        260                 265                 270
Ala Thr Gly Ser Pro Gly Ser Ser Thr Pro Ser Gly Ala Thr Gly Ser
        275                 280                 285
Pro Gly Ser Ser Thr Pro Ser Gly Ala Thr Gly Ser Pro Gly Ser Ser
        290                 295                 300
Pro Ser Ala Ser Thr Gly Thr Gly Pro Gly Ala Ser Pro Gly Thr Ser
305                 310                 315                 320
Ser Thr Gly Ser Pro Gly Ala Ser Pro Gly Thr Ser Ser Thr Gly Ser
            325                 330                 335
Pro Gly Thr Pro Gly Ser Gly Thr Ala Ser Ser Ser Pro Gly Ala Ser
            340                 345                 350
Pro Gly Thr Ser Ser Thr Gly Ser Pro Gly Ala Ser Pro Gly Thr Ser
        355                 360                 365
Ser Thr Gly Ser Pro Gly Ala Ser Pro Gly Thr Ser Ser Thr Gly Ser
        370                 375                 380
Pro Gly Ala Ser Pro Gly Thr Ser Ser Thr Gly Ser Pro Gly Thr Pro
385                 390                 395                 400
Gly Ser Gly Thr Ala Ser Ser Ser Pro Gly Ser Ser Thr Pro Ser Gly
            405                 410                 415
Ala Thr Gly Ser Pro Gly Thr Pro Gly Ser Gly Thr Ala Ser Ser Ser
        420                 425                 430
Pro Gly Ser Ser Thr Pro Ser Gly Ala Thr Gly Ser Pro Gly Thr Pro
        435                 440                 445
Gly Ser Gly Thr Ala Ser Ser Ser Pro Gly Ser Ser Thr Pro Ser Gly
        450                 455                 460
Ala Thr Gly Ser Pro Gly Ser Ser Thr Pro Ser Gly Ala Thr Gly Ser
465                 470                 475                 480
Pro Gly Ser Ser Pro Ser Ala Ser Thr Gly Thr Gly Pro Gly Ser Ser
            485                 490                 495
Pro Ser Ala Ser Thr Gly Thr Gly Pro Gly Ala Ser Pro Gly Thr Ser
            500                 505                 510
Ser Thr Gly Ser Pro Gly Thr Pro Gly Ser Gly Thr Ala Ser Ser Ser
        515                 520                 525
Pro Gly Ser Ser Thr Pro Ser Gly Ala Thr Gly Ser Pro Gly Ser Ser
        530                 535                 540
Pro Ser Ala Ser Thr Gly Thr Gly Pro Gly Ser Ser Pro Ser Ala Ser
545                 550                 555                 560
Thr Gly Thr Gly Pro Gly Ala Ser Pro Gly Thr Ser Ser Thr Gly Ser
            565                 570                 575

<210> SEQ ID NO 130
<211> LENGTH: 864
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 130

Gly Ser Pro Ala Gly Ser Pro Thr Ser Thr Glu Glu Gly Thr Ser Glu
1               5                   10                  15

Ser Ala Thr Pro Glu Ser Gly Pro Gly Thr Ser Thr Glu Pro Ser Glu
            20                  25                  30

Gly Ser Ala Pro Gly Ser Pro Ala Gly Ser Pro Thr Ser Thr Glu Glu
        35                  40                  45

Gly Thr Ser Thr Glu Pro Ser Glu Gly Ser Ala Pro Gly Thr Ser Thr
50                  55                  60

Glu Pro Ser Glu Gly Ser Ala Pro Gly Thr Ser Glu Ser Ala Thr Pro
65                  70                  75                  80

Glu Ser Gly Pro Gly Ser Glu Pro Ala Thr Ser Gly Ser Glu Thr Pro
                85                  90                  95

Gly Ser Glu Pro Ala Thr Ser Gly Ser Glu Thr Pro Gly Ser Pro Ala
                100                 105                 110

Gly Ser Pro Thr Ser Thr Glu Glu Gly Thr Ser Glu Ser Ala Thr Pro
            115                 120                 125

Glu Ser Gly Pro Gly Thr Ser Thr Glu Pro Ser Glu Gly Ser Ala Pro
130                 135                 140

Gly Thr Ser Thr Glu Pro Ser Glu Gly Ser Ala Pro Gly Ser Pro Ala
145                 150                 155                 160

Gly Ser Pro Thr Ser Thr Glu Glu Gly Thr Ser Thr Glu Pro Ser Glu
                165                 170                 175

Gly Ser Ala Pro Gly Thr Ser Thr Glu Pro Ser Glu Gly Ser Ala Pro
                180                 185                 190

Gly Thr Ser Glu Ser Ala Thr Pro Glu Ser Gly Pro Gly Thr Ser Thr
                195                 200                 205

Glu Pro Ser Glu Gly Ser Ala Pro Gly Thr Ser Glu Ser Ala Thr Pro
            210                 215                 220

Glu Ser Gly Pro Gly Ser Glu Pro Ala Thr Ser Gly Ser Glu Thr Pro
225                 230                 235                 240

Gly Thr Ser Thr Glu Pro Ser Glu Gly Ser Ala Pro Gly Thr Ser Thr
                245                 250                 255

Glu Pro Ser Glu Gly Ser Ala Pro Gly Thr Ser Glu Ser Ala Thr Pro
            260                 265                 270

Glu Ser Gly Pro Gly Thr Ser Glu Ser Ala Thr Pro Glu Ser Gly Pro
                275                 280                 285

Gly Ser Pro Ala Gly Ser Pro Thr Ser Thr Glu Glu Gly Thr Ser Glu
    290                 295                 300

Ser Ala Thr Pro Glu Ser Gly Pro Gly Ser Glu Pro Ala Thr Ser Gly
305                 310                 315                 320

Ser Glu Thr Pro Gly Thr Ser Glu Ser Ala Thr Pro Glu Ser Gly Pro
                325                 330                 335

Gly Thr Ser Thr Glu Pro Ser Glu Gly Ser Ala Pro Gly Thr Ser Thr
            340                 345                 350

Glu Pro Ser Glu Gly Ser Ala Pro Gly Thr Ser Thr Glu Pro Ser Glu
                355                 360                 365

Gly Ser Ala Pro Gly Thr Ser Thr Glu Pro Ser Glu Gly Ser Ala Pro
    370                 375                 380
```

```
Gly Thr Ser Thr Glu Pro Ser Glu Gly Ser Ala Pro Gly Thr Ser Thr
385                 390                 395                 400

Glu Pro Ser Glu Gly Ser Ala Pro Gly Ser Pro Ala Gly Ser Pro Thr
            405                 410                 415

Ser Thr Glu Glu Gly Thr Ser Thr Glu Pro Ser Glu Gly Ser Ala Pro
        420                 425                 430

Gly Thr Ser Glu Ser Ala Thr Pro Glu Ser Gly Pro Gly Ser Glu Pro
        435                 440                 445

Ala Thr Ser Gly Ser Glu Thr Pro Gly Thr Ser Glu Ser Ala Thr Pro
    450                 455                 460

Glu Ser Gly Pro Gly Ser Glu Pro Ala Thr Ser Gly Ser Glu Thr Pro
465                 470                 475                 480

Gly Thr Ser Glu Ser Ala Thr Pro Glu Ser Gly Pro Gly Thr Ser Thr
            485                 490                 495

Glu Pro Ser Glu Gly Ser Ala Pro Gly Thr Ser Glu Ser Ala Thr Pro
            500                 505                 510

Glu Ser Gly Pro Gly Ser Pro Ala Gly Ser Pro Thr Ser Thr Glu Glu
            515                 520                 525

Gly Ser Pro Ala Gly Ser Pro Thr Ser Thr Glu Glu Gly Ser Pro Ala
530                 535                 540

Gly Ser Pro Thr Ser Thr Glu Glu Gly Thr Ser Glu Ser Ala Thr Pro
545                 550                 555                 560

Glu Ser Gly Pro Gly Thr Ser Thr Glu Pro Ser Glu Gly Ser Ala Pro
            565                 570                 575

Gly Thr Ser Glu Ser Ala Thr Pro Glu Ser Gly Pro Gly Ser Glu Pro
            580                 585                 590

Ala Thr Ser Gly Ser Glu Thr Pro Gly Thr Ser Glu Ser Ala Thr Pro
    595                 600                 605

Glu Ser Gly Pro Gly Ser Glu Pro Ala Thr Ser Gly Ser Glu Thr Pro
            610                 615                 620

Gly Thr Ser Glu Ser Ala Thr Pro Glu Ser Gly Pro Gly Thr Ser Thr
625                 630                 635                 640

Glu Pro Ser Glu Gly Ser Ala Pro Gly Ser Pro Ala Gly Ser Pro Thr
            645                 650                 655

Ser Thr Glu Glu Gly Thr Ser Glu Ser Ala Thr Pro Glu Ser Gly Pro
        660                 665                 670

Gly Ser Glu Pro Ala Thr Ser Gly Ser Glu Thr Pro Gly Thr Ser Glu
        675                 680                 685

Ser Ala Thr Pro Glu Ser Gly Pro Gly Ser Pro Ala Gly Ser Pro Thr
    690                 695                 700

Ser Thr Glu Glu Gly Ser Pro Ala Gly Ser Pro Thr Ser Thr Glu Glu
705                 710                 715                 720

Gly Thr Ser Thr Glu Pro Ser Glu Gly Ser Ala Pro Gly Thr Ser Glu
            725                 730                 735

Ser Ala Thr Pro Glu Ser Gly Pro Gly Thr Ser Glu Ser Ala Thr Pro
    740                 745                 750

Glu Ser Gly Pro Gly Thr Ser Glu Ser Ala Thr Pro Glu Ser Gly Pro
            755                 760                 765

Gly Ser Glu Pro Ala Thr Ser Gly Ser Glu Thr Pro Gly Ser Glu Pro
        770                 775                 780

Ala Thr Ser Gly Ser Glu Thr Pro Gly Ser Pro Ala Gly Ser Pro Thr
    785                 790                 795                 800

Ser Thr Glu Glu Gly Thr Ser Thr Glu Pro Ser Glu Gly Ser Ala Pro
```

```
                     805                 810                 815

Gly Thr Ser Thr Glu Pro Ser Glu Gly Ser Ala Pro Gly Ser Glu Pro
            820                 825                 830

Ala Thr Ser Gly Ser Glu Thr Pro Gly Thr Ser Glu Ser Ala Thr Pro
            835                 840                 845

Glu Ser Gly Pro Gly Thr Ser Thr Glu Pro Ser Glu Gly Ser Ala Pro
    850                 855                 860

<210> SEQ ID NO 131
<211> LENGTH: 864
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 131

Gly Ala Ser Pro Gly Thr Ser Ser Thr Gly Ser Pro Gly Ser Ser Pro
1               5                   10                  15

Ser Ala Ser Thr Gly Thr Gly Pro Gly Ser Ser Pro Ser Ala Ser Thr
            20                  25                  30

Gly Thr Gly Pro Gly Thr Pro Gly Ser Gly Thr Ala Ser Ser Ser Pro
        35                  40                  45

Gly Ser Ser Thr Pro Ser Gly Ala Thr Gly Ser Pro Gly Ser Ser Pro
    50                  55                  60

Ser Ala Ser Thr Gly Thr Gly Pro Gly Ala Ser Pro Gly Thr Ser Ser
65                  70                  75                  80

Thr Gly Ser Pro Gly Thr Pro Gly Ser Gly Thr Ala Ser Ser Ser Pro
                85                  90                  95

Gly Ser Ser Thr Pro Ser Gly Ala Thr Gly Ser Pro Gly Thr Pro Gly
            100                 105                 110

Ser Gly Thr Ala Ser Ser Ser Pro Gly Ala Ser Pro Gly Thr Ser Ser
        115                 120                 125

Thr Gly Ser Pro Gly Ala Ser Pro Gly Thr Ser Ser Thr Gly Ser Pro
    130                 135                 140

Gly Thr Pro Gly Ser Gly Thr Ala Ser Ser Ser Pro Gly Ser Ser Thr
145                 150                 155                 160

Pro Ser Gly Ala Thr Gly Ser Pro Gly Ala Ser Pro Gly Thr Ser Ser
                165                 170                 175

Thr Gly Ser Pro Gly Thr Pro Gly Ser Gly Thr Ala Ser Ser Ser Pro
            180                 185                 190

Gly Ser Ser Thr Pro Ser Gly Ala Thr Gly Ser Pro Gly Ser Ser Pro
        195                 200                 205

Ser Ala Ser Thr Gly Thr Gly Pro Gly Ser Ser Pro Ser Ala Ser Thr
    210                 215                 220

Gly Thr Gly Pro Gly Ser Ser Thr Pro Ser Gly Ala Thr Gly Ser Pro
225                 230                 235                 240

Gly Ser Ser Thr Pro Ser Gly Ala Thr Gly Ser Pro Gly Ala Ser Pro
                245                 250                 255

Gly Thr Ser Ser Thr Gly Ser Pro Gly Ala Ser Pro Gly Thr Ser Ser
            260                 265                 270

Thr Gly Ser Pro Gly Ala Ser Pro Gly Thr Ser Ser Thr Gly Ser Pro
        275                 280                 285

Gly Thr Pro Gly Ser Gly Thr Ala Ser Ser Ser Pro Gly Ala Ser Pro
    290                 295                 300
```

-continued

Gly Thr Ser Ser Thr Gly Ser Pro Gly Ala Ser Pro Gly Thr Ser Ser
305                 310                 315                 320

Thr Gly Ser Pro Gly Ala Ser Pro Gly Thr Ser Ser Thr Gly Ser Pro
            325                 330                 335

Gly Ser Ser Pro Ser Ala Ser Thr Gly Thr Gly Pro Gly Thr Pro Gly
            340                 345                 350

Ser Gly Thr Ala Ser Ser Ser Pro Gly Ala Ser Pro Gly Thr Ser Ser
            355                 360                 365

Thr Gly Ser Pro Gly Ala Ser Pro Gly Thr Ser Ser Thr Gly Ser Pro
            370                 375                 380

Gly Ala Ser Pro Gly Thr Ser Ser Thr Gly Ser Pro Gly Ser Ser Thr
385                 390                 395                 400

Pro Ser Gly Ala Thr Gly Ser Pro Gly Ser Ser Thr Pro Ser Gly Ala
            405                 410                 415

Thr Gly Ser Pro Gly Ala Ser Pro Gly Thr Ser Ser Thr Gly Ser Pro
            420                 425                 430

Gly Thr Pro Gly Ser Gly Thr Ala Ser Ser Ser Pro Gly Ser Ser Thr
            435                 440                 445

Pro Ser Gly Ala Thr Gly Ser Pro Gly Ser Ser Thr Pro Ser Gly Ala
            450                 455                 460

Thr Gly Ser Pro Gly Ser Ser Thr Pro Ser Gly Ala Thr Gly Ser Pro
465                 470                 475                 480

Gly Ser Ser Pro Ser Ala Ser Thr Gly Thr Gly Pro Gly Ala Ser Pro
            485                 490                 495

Gly Thr Ser Ser Thr Gly Ser Pro Gly Ala Ser Pro Gly Thr Ser Ser
            500                 505                 510

Thr Gly Ser Pro Gly Thr Pro Gly Ser Gly Thr Ala Ser Ser Ser Pro
            515                 520                 525

Gly Ala Ser Pro Gly Thr Ser Ser Thr Gly Ser Pro Gly Ala Ser Pro
530                 535                 540

Gly Thr Ser Ser Thr Gly Ser Pro Gly Ala Ser Pro Gly Thr Ser Ser
545                 550                 555                 560

Thr Gly Ser Pro Gly Ala Ser Pro Gly Thr Ser Ser Thr Gly Ser Pro
            565                 570                 575

Gly Thr Pro Gly Ser Gly Thr Ala Ser Ser Ser Pro Gly Ser Ser Thr
            580                 585                 590

Pro Ser Gly Ala Thr Gly Ser Pro Gly Thr Pro Gly Ser Gly Thr Ala
            595                 600                 605

Ser Ser Ser Pro Gly Ser Ser Thr Pro Ser Gly Ala Thr Gly Ser Pro
            610                 615                 620

Gly Thr Pro Gly Ser Gly Thr Ala Ser Ser Ser Pro Gly Ser Ser Thr
625                 630                 635                 640

Pro Ser Gly Ala Thr Gly Ser Pro Gly Ser Ser Thr Pro Ser Gly Ala
            645                 650                 655

Thr Gly Ser Pro Gly Ser Ser Pro Ser Ala Ser Thr Gly Thr Gly Pro
            660                 665                 670

Gly Ser Ser Pro Ser Ala Ser Thr Gly Thr Gly Pro Gly Ala Ser Pro
            675                 680                 685

Gly Thr Ser Ser Thr Gly Ser Pro Gly Thr Pro Gly Ser Gly Thr Ala
            690                 695                 700

Ser Ser Ser Pro Gly Ser Ser Thr Pro Ser Gly Ala Thr Gly Ser Pro
705                 710                 715                 720

```
Gly Ser Ser Pro Ser Ala Ser Thr Gly Thr Gly Pro Gly Ser Ser Pro
                725                 730                 735

Ser Ala Ser Thr Gly Thr Gly Pro Gly Ala Ser Pro Gly Thr Ser Ser
                740                 745                 750

Thr Gly Ser Pro Gly Ala Ser Pro Gly Thr Ser Ser Thr Gly Ser Pro
                755                 760                 765

Gly Ser Ser Thr Pro Ser Gly Ala Thr Gly Ser Pro Gly Ser Ser Pro
                770                 775                 780

Ser Ala Ser Thr Gly Thr Gly Pro Gly Ala Ser Pro Gly Thr Ser Ser
785                 790                 795                 800

Thr Gly Ser Pro Gly Ser Ser Pro Ser Ala Ser Thr Gly Thr Gly Pro
                805                 810                 815

Gly Thr Pro Gly Ser Gly Thr Ala Ser Ser Pro Gly Ser Ser Thr
                820                 825                 830

Pro Ser Gly Ala Thr Gly Ser Pro Gly Ser Ser Thr Pro Ser Gly Ala
                835                 840                 845

Thr Gly Ser Pro Gly Ala Ser Pro Gly Thr Ser Ser Thr Gly Ser Pro
                850                 855                 860

<210> SEQ ID NO 132
<211> LENGTH: 474
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

```
                210                 215                 220
Pro Gly Lys Gly Gly Gly Ser Gly Gly Gly Ser Gly Gly
225                 230                 235                 240

Gly Ser Gly Gly Gly Ser Asp Lys Thr His Thr Cys Pro Cys
                    245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
        290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 133
<211> LENGTH: 591
<212> TYPE: PRT
<213> ORGANISM: Homo sapiens

<400> SEQUENCE: 133

Arg Gly Val Phe Arg Arg Asp Ala His Lys Ser Glu Val Ala His Arg
1               5                   10                  15

Phe Lys Asp Leu Gly Glu Glu Asn Phe Lys Ala Leu Val Leu Ile Ala
            20                  25                  30

Phe Ala Gln Tyr Leu Gln Gln Cys Pro Phe Glu Asp His Val Lys Leu
        35                  40                  45

Val Asn Glu Val Thr Glu Phe Ala Lys Thr Cys Val Ala Asp Glu Ser
    50                  55                  60

Ala Glu Asn Cys Asp Lys Ser Leu His Thr Leu Phe Gly Asp Lys Leu
65                  70                  75                  80

Cys Thr Val Ala Thr Leu Arg Glu Thr Tyr Gly Glu Met Ala Asp Cys
                85                  90                  95

Cys Ala Lys Gln Glu Pro Glu Arg Asn Glu Cys Phe Leu Gln His Lys
            100                 105                 110
```

Asp Asp Asn Pro Asn Leu Pro Arg Leu Val Arg Pro Glu Val Asp Val
            115                 120                 125

Met Cys Thr Ala Phe His Asp Asn Glu Thr Phe Leu Lys Lys Tyr
130                 135                 140

Leu Tyr Glu Ile Ala Arg Arg His Pro Tyr Phe Tyr Ala Pro Glu Leu
145                 150                 155                 160

Leu Phe Phe Ala Lys Arg Tyr Lys Ala Ala Phe Thr Glu Cys Cys Gln
                165                 170                 175

Ala Ala Asp Lys Ala Ala Cys Leu Leu Pro Lys Leu Asp Glu Leu Arg
            180                 185                 190

Asp Glu Gly Lys Ala Ser Ser Ala Lys Gln Arg Leu Lys Cys Ala Ser
            195                 200                 205

Leu Gln Lys Phe Gly Glu Arg Ala Phe Lys Ala Trp Ala Val Ala Arg
210                 215                 220

Leu Ser Gln Arg Phe Pro Lys Ala Glu Phe Ala Glu Val Ser Lys Leu
225                 230                 235                 240

Val Thr Asp Leu Thr Lys Val His Thr Glu Cys Cys His Gly Asp Leu
                245                 250                 255

Leu Glu Cys Ala Asp Asp Arg Ala Asp Leu Ala Lys Tyr Ile Cys Glu
            260                 265                 270

Asn Gln Asp Ser Ile Ser Ser Lys Leu Lys Glu Cys Cys Glu Lys Pro
            275                 280                 285

Leu Leu Glu Lys Ser His Cys Ile Ala Glu Val Glu Asn Asp Glu Met
            290                 295                 300

Pro Ala Asp Leu Pro Ser Leu Ala Ala Asp Phe Val Glu Ser Lys Asp
305                 310                 315                 320

Val Cys Lys Asn Tyr Ala Glu Ala Lys Asp Val Phe Leu Gly Met Phe
                325                 330                 335

Leu Tyr Glu Tyr Ala Arg Arg His Pro Asp Tyr Ser Val Val Leu Leu
            340                 345                 350

Leu Arg Leu Ala Lys Thr Tyr Glu Thr Thr Leu Glu Lys Cys Cys Ala
            355                 360                 365

Ala Ala Asp Pro His Glu Cys Tyr Ala Lys Val Phe Asp Glu Phe Lys
            370                 375                 380

Pro Leu Val Glu Glu Pro Gln Asn Leu Ile Lys Gln Asn Cys Glu Leu
385                 390                 395                 400

Phe Glu Gln Leu Gly Glu Tyr Lys Phe Gln Asn Ala Leu Leu Val Arg
                405                 410                 415

Tyr Thr Lys Lys Val Pro Gln Val Ser Thr Pro Thr Leu Val Glu Val
            420                 425                 430

Ser Arg Asn Leu Gly Lys Val Gly Ser Lys Cys Cys Lys His Pro Glu
            435                 440                 445

Ala Lys Arg Met Pro Cys Ala Glu Asp Tyr Leu Ser Val Val Leu Asn
450                 455                 460

Gln Leu Cys Val Leu His Glu Lys Thr Pro Val Ser Asp Arg Val Thr
465                 470                 475                 480

Lys Cys Cys Thr Glu Ser Leu Val Asn Arg Arg Pro Cys Phe Ser Ala
                485                 490                 495

Leu Glu Val Asp Glu Thr Tyr Val Pro Lys Glu Phe Asn Ala Glu Thr
            500                 505                 510

Phe Thr Phe His Ala Asp Ile Cys Thr Leu Ser Glu Lys Glu Arg Gln
            515                 520                 525

Ile Lys Lys Gln Thr Ala Leu Val Glu Leu Val Lys His Lys Pro Lys

```
                  530               535               540
Ala Thr Lys Glu Gln Leu Lys Ala Val Met Asp Asp Phe Ala Phe
545                 550               555               560

Val Glu Lys Cys Cys Lys Ala Asp Asp Lys Glu Thr Cys Phe Ala Glu
                565               570               575

Glu Gly Lys Lys Leu Val Ala Ala Ser Gln Ala Ala Leu Gly Leu
                580               585               590
```

<210> SEQ ID NO 134
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (2)..(2)
<223> OTHER INFORMATION: /replace="Asn" or "Ser" or "Thr" or "Trp"
<220> FEATURE:
<221> NAME/KEY: VARIANT
<222> LOCATION: (3)..(3)
<223> OTHER INFORMATION: /replace="Gln" or "His" or "Ile" or "Leu" or "Lys"
<220> FEATURE:
<221> NAME/KEY: VARIANT
<222> LOCATION: (4)..(4)
<223> OTHER INFORMATION: /replace="Asp" or "Phe" or "Trp" or "Tyr"
<220> FEATURE:
<221> NAME/KEY: VARIANT
<222> LOCATION: (5)..(5)
<223> OTHER INFORMATION: /replace="Gly" or "Leu" or "Phe" or "Ser" or "Thr"
<220> FEATURE:
<221> NAME/KEY: MISC_FEATURE
<222> LOCATION: (1)..(6)
<223> OTHER INFORMATION: /note="Variant residues given in the sequence have no preference with respect to those in the annotations for variant positions"

<400> SEQUENCE: 134

```
Cys Asp Asn Ala Asp Cys
1               5
```

<210> SEQ ID NO 135
<211> LENGTH: 11
<212> TYPE: PRT
<213> ORGANISM: Unknown
<220> FEATURE:
<221> NAME/KEY: source
<223> OTHER INFORMATION: /note="Description of Unknown: Albumin-binding peptide"

<400> SEQUENCE: 135

```
Asp Ile Cys Leu Pro Arg Trp Gly Cys Leu Trp
1               5                   10
```

<210> SEQ ID NO 136
<211> LENGTH: 18
<212> TYPE: PRT
<213> ORGANISM: Unknown
<220> FEATURE:
<221> NAME/KEY: source
<223> OTHER INFORMATION: /note="Description of Unknown: Albumin-binding peptide"

<400> SEQUENCE: 136

```
Arg Leu Ile Glu Asp Ile Cys Leu Pro Arg Trp Gly Cys Leu Trp Glu
1               5                   10                  15
```

Asp Asp

<210> SEQ ID NO 137
<211> LENGTH: 20
<212> TYPE: PRT
<213> ORGANISM: Unknown
<220> FEATURE:
<221> NAME/KEY: source
<223> OTHER INFORMATION: /note="Description of Unknown: Albumin-binding peptide"

<400> SEQUENCE: 137

Gln Arg Leu Met Glu Asp Ile Cys Leu Pro Arg Trp Gly Cys Leu Trp
1               5                   10                  15

Glu Asp Asp Phe
            20

<210> SEQ ID NO 138
<211> LENGTH: 21
<212> TYPE: PRT
<213> ORGANISM: Unknown
<220> FEATURE:
<221> NAME/KEY: source
<223> OTHER INFORMATION: /note="Description of Unknown: Albumin-binding peptide"

<400> SEQUENCE: 138

Gln Gly Leu Ile Gly Asp Ile Cys Leu Pro Arg Trp Gly Cys Leu Trp
1               5                   10                  15

Gly Asp Ser Val Lys
            20

<210> SEQ ID NO 139
<211> LENGTH: 20
<212> TYPE: PRT
<213> ORGANISM: Unknown
<220> FEATURE:
<221> NAME/KEY: source
<223> OTHER INFORMATION: /note="Description of Unknown: Albumin-binding peptide"

<400> SEQUENCE: 139

Gly Glu Trp Trp Glu Asp Ile Cys Leu Pro Arg Trp Gly Cys Leu Trp
1               5                   10                  15

Glu Glu Glu Asp
            20

<210> SEQ ID NO 140
<211> LENGTH: 32
<212> TYPE: PRT
<213> ORGANISM: Homo sapiens

<400> SEQUENCE: 140

Asp Pro Arg Phe Gln Asp Ser Ser Ser Lys Ala Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 141
<211> LENGTH: 28
<212> TYPE: PRT
<213> ORGANISM: Homo sapiens

<400> SEQUENCE: 141

```
Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25
```

<210> SEQ ID NO 142
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

```
Ala Ser Pro Ala Ala Pro Ala Pro Ala Ser Pro Ala Ala Pro Ala Pro
1               5                   10                  15

Ser Ala Pro Ala
            20
```

<210> SEQ ID NO 143
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

```
Ala Ala Pro Ala Ser Pro Ala Pro Ala Ala Pro Ser Ala Pro Ala Pro
1               5                   10                  15

Ala Ala Pro Ser
            20
```

<210> SEQ ID NO 144
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

```
Ala Pro Ser Ser Pro Ser Pro Ser Ala Pro Ser Ser Pro Ser Pro Ala
1               5                   10                  15

Ser Pro Ser Ser
            20
```

<210> SEQ ID NO 145
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

```
Ala Pro Ser Ser Pro Ser Pro Ser Ala Pro Ser Ser Pro Ser Pro Ala
1               5                   10                  15

Ser Pro Ser
```

<210> SEQ ID NO 146

```
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ser Ser Pro Ser Ala Pro Ser Pro Ser Ser Pro Ala Ser Pro Ser Pro
1               5                   10                  15

Ser Ser Pro Ala
            20

<210> SEQ ID NO 147
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 148
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Ala Ser Ala Ala Ala Pro Ala Ala Ser Ala Ala Ser Ala Pro
1               5                   10                  15

Ser Ala Ala Ala
            20

<210> SEQ ID NO 149
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(20)
<223> OTHER INFORMATION: /replace=" "
<220> FEATURE:
<221> NAME/KEY: MISC_FEATURE
<222> LOCATION: (1)..(20)
<223> OTHER INFORMATION: /note="This sequence may encompass 1-20 "Gly"
      repeating units"
<220> FEATURE:
<221> NAME/KEY: MISC_FEATURE
<222> LOCATION: (1)..(20)
<223> OTHER INFORMATION: /note="Variant residues given in the sequence
      have no preference with respect to those in the annotations
      for variant positions"

<400> SEQUENCE: 149
```

Gly Gly Gly Gly Gly Gly Gly Gly Gly Gly Gly Gly Gly Gly
1               5                   10                  15

Gly Gly Gly Gly
            20

<210> SEQ ID NO 150
<211> LENGTH: 100
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (6)..(100)
<223> OTHER INFORMATION: /replace=" "
<220> FEATURE:
<221> NAME/KEY: MISC_FEATURE
<222> LOCATION: (1)..(100)
<223> OTHER INFORMATION: /note="This sequence may encompass 1-20 "Gly
      Gly Gly Gly Ser" repeating units"
<220> FEATURE:
<221> NAME/KEY: MISC_FEATURE
<222> LOCATION: (1)..(100)
<223> OTHER INFORMATION: /note="Variant residues given in the sequence
      have no preference with respect to those in the annotations
      for variant positions"

<400> SEQUENCE: 150

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Ser Gly Gly Gly Ser Gly Gly Gly Gly
    50                  55                  60

Ser Gly Gly Gly Ser Gly Gly Gly Ser Gly Gly Gly Gly Ser
65                  70                  75                  80

Gly Gly Gly Gly Ser Gly Gly Gly Ser Gly Gly Gly Ser Gly
                85                  90                  95

Gly Gly Gly Ser
            100

<210> SEQ ID NO 151
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (7)..(101)
<223> OTHER INFORMATION: /replace=" "
<220> FEATURE:
<221> NAME/KEY: MISC_FEATURE
<222> LOCATION: (2)..(101)
<223> OTHER INFORMATION: /note="This region may encompass 1-20 "Gly Gly
      Gly Gly Ser" repeating units"
<220> FEATURE:
<221> NAME/KEY: MISC_FEATURE
<222> LOCATION: (1)..(101)
<223> OTHER INFORMATION: /note="Variant residues given in the sequence
      have no preference with respect to those in the annotations
      for variant positions"

<400> SEQUENCE: 151

```
Ser Gly Gly Gly Ser Gly Gly Gly Ser Gly Gly Gly Ser
1               5                   10                  15
Gly Gly Gly Gly Ser Gly Gly Gly Ser Gly Gly Gly Ser Gly
                20                  25                  30
Gly Gly Gly Ser Gly Gly Gly Ser Gly Gly Gly Ser Gly Gly
            35                  40                  45
Gly Gly Ser Gly Gly Gly Ser Gly Gly Gly Ser Gly Gly Gly
        50                  55                  60
Gly Ser Gly Gly Gly Ser Gly Gly Gly Ser Gly Gly Gly
65                  70                  75                  80
Ser Gly Gly Gly Ser Gly Gly Gly Ser Gly Gly Gly Ser
                85                  90                  95
Gly Gly Gly Gly Ser
            100
```

<210> SEQ ID NO 152
<211> LENGTH: 4544
<212> TYPE: PRT
<213> ORGANISM: Homo sapiens

<400> SEQUENCE: 152

```
Met Leu Thr Pro Pro Leu Leu Leu Leu Pro Leu Leu Ser Ala Leu
1               5                   10                  15
Val Ala Ala Ala Ile Asp Ala Pro Lys Thr Cys Ser Pro Lys Gln Phe
                20                  25                  30
Ala Cys Arg Asp Gln Ile Thr Cys Ile Ser Lys Gly Trp Arg Cys Asp
            35                  40                  45
Gly Glu Arg Asp Cys Pro Asp Gly Ser Asp Glu Ala Pro Glu Ile Cys
        50                  55                  60
Pro Gln Ser Lys Ala Gln Arg Cys Gln Pro Asn Glu His Asn Cys Leu
65                  70                  75                  80
Gly Thr Glu Leu Cys Val Pro Met Ser Arg Leu Cys Asn Gly Val Gln
                85                  90                  95
Asp Cys Met Asp Gly Ser Asp Glu Gly Pro His Cys Arg Glu Leu Gln
            100                 105                 110
Gly Asn Cys Ser Arg Leu Gly Cys Gln His His Cys Val Pro Thr Leu
        115                 120                 125
Asp Gly Pro Thr Cys Tyr Cys Asn Ser Ser Phe Gln Leu Gln Ala Asp
130                 135                 140
Gly Lys Thr Cys Lys Asp Phe Asp Glu Cys Ser Val Tyr Gly Thr Cys
145                 150                 155                 160
Ser Gln Leu Cys Thr Asn Thr Asp Gly Ser Phe Ile Cys Gly Cys Val
                165                 170                 175
Glu Gly Tyr Leu Leu Gln Pro Asp Asn Arg Ser Cys Lys Ala Lys Asn
            180                 185                 190
Glu Pro Val Asp Arg Pro Pro Val Leu Leu Ile Ala Asn Ser Gln Asn
        195                 200                 205
Ile Leu Ala Thr Tyr Leu Ser Gly Ala Gln Val Ser Thr Ile Thr Pro
210                 215                 220
Thr Ser Thr Arg Gln Thr Thr Ala Met Asp Phe Ser Tyr Ala Asn Glu
225                 230                 235                 240
Thr Val Cys Trp Val His Val Gly Asp Ser Ala Ala Gln Thr Gln Leu
                245                 250                 255
```

```
Lys Cys Ala Arg Met Pro Gly Leu Lys Gly Phe Val Asp Glu His Thr
                260                 265                 270

Ile Asn Ile Ser Leu Ser Leu His His Val Glu Gln Met Ala Ile Asp
            275                 280                 285

Trp Leu Thr Gly Asn Phe Tyr Phe Val Asp Asp Ile Asp Asp Arg Ile
        290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
```

-continued

```
            675                 680                 685
Arg Asp Ile Phe Val Thr Ser Lys Thr Val Leu Trp Pro Asn Gly Leu
        690                 695                 700
Ser Leu Asp Ile Pro Ala Gly Arg Leu Tyr Trp Val Asp Ala Phe Tyr
705                 710                 715                 720
Asp Arg Ile Glu Thr Ile Leu Leu Asn Gly Thr Asp Arg Lys Ile Val
                725                 730                 735
Tyr Glu Gly Pro Glu Leu Asn His Ala Phe Gly Leu Cys His His Gly
            740                 745                 750
Asn Tyr Leu Phe Trp Thr Glu Tyr Arg Ser Gly Ser Val Tyr Arg Leu
        755                 760                 765
Glu Arg Gly Val Gly Gly Ala Pro Pro Thr Val Thr Leu Leu Arg Ser
770                 775                 780
Glu Arg Pro Pro Ile Phe Glu Ile Arg Met Tyr Asp Ala Gln Gln Gln
785                 790                 795                 800
Gln Val Gly Thr Asn Lys Cys Arg Val Asn Asn Gly Gly Cys Ser Ser
                805                 810                 815
Leu Cys Leu Ala Thr Pro Gly Ser Arg Gln Cys Ala Cys Ala Glu Asp
            820                 825                 830
Gln Val Leu Asp Ala Asp Gly Val Thr Cys Leu Ala Asn Pro Ser Tyr
        835                 840                 845
Val Pro Pro Pro Gln Cys Gln Pro Gly Glu Phe Ala Cys Ala Asn Ser
850                 855                 860
Arg Cys Ile Gln Glu Arg Trp Lys Cys Asp Gly Asp Asn Asp Cys Leu
865                 870                 875                 880
Asp Asn Ser Asp Glu Ala Pro Ala Leu Cys His Gln His Thr Cys Pro
                885                 890                 895
Ser Asp Arg Phe Lys Cys Glu Asn Asn Arg Cys Ile Pro Asn Arg Trp
            900                 905                 910
Leu Cys Asp Gly Asp Asn Asp Cys Gly Asn Ser Glu Asp Glu Ser Asn
        915                 920                 925
Ala Thr Cys Ser Ala Arg Thr Cys Pro Pro Asn Gln Phe Ser Cys Ala
930                 935                 940
Ser Gly Arg Cys Ile Pro Ile Ser Trp Thr Cys Asp Leu Asp Asp Asp
945                 950                 955                 960
Cys Gly Asp Arg Ser Asp Glu Ser Ala Ser Cys Ala Tyr Pro Thr Cys
                965                 970                 975
Phe Pro Leu Thr Gln Phe Thr Cys Asn Asn Gly Arg Cys Ile Asn Ile
            980                 985                 990
Asn Trp Arg Cys Asp Asn Asp Asn Asp Cys Gly Asp Asn Ser Asp Glu
        995                 1000                1005
Ala Gly Cys Ser His Ser Cys Ser Ser Thr Gln Phe Lys Cys Asn
        1010                1015                1020
Ser Gly Arg Cys Ile Pro Glu His Trp Thr Cys Asp Gly Asp Asn
        1025                1030                1035
Asp Cys Gly Asp Tyr Ser Asp Glu Thr His Ala Asn Cys Thr Asn
        1040                1045                1050
Gln Ala Thr Arg Pro Pro Gly Gly Cys His Thr Asp Glu Phe Gln
        1055                1060                1065
Cys Arg Leu Asp Gly Leu Cys Ile Pro Leu Arg Trp Arg Cys Asp
        1070                1075                1080
Gly Asp Thr Asp Cys Met Asp Ser Ser Asp Glu Lys Ser Cys Glu
        1085                1090                1095
```

```
Gly Val Thr His Val Cys Asp Pro Ser Val Lys Phe Gly Cys Lys
    1100            1105                1110

Asp Ser Ala Arg Cys Ile Ser Lys Ala Trp Val Cys Asp Gly Asp
    1115            1120                1125

Asn Asp Cys Glu Asp Asn Ser Asp Glu Glu Asn Cys Glu Ser Leu
    1130            1135                1140

Ala Cys Arg Pro Pro Ser His Pro Cys Ala Asn Asn Thr Ser Val
    1145            1150                1155

Cys Leu Pro Pro Asp Lys Leu Cys Asp Gly Asn Asp Asp Cys Gly
    1160            1165                1170

Asp Gly Ser Asp Glu Gly Glu Leu Cys Asp Gln Cys Ser Leu Asn
    1175            1180                1185

Asn Gly Gly Cys Ser His Asn Cys Ser Val Ala Pro Gly Glu Gly
    1190            1195                1200

Ile Val Cys Ser Cys Pro Leu Gly Met Glu Leu Gly Pro Asp Asn
    1205            1210                1215

His Thr Cys Gln Ile Gln Ser Tyr Cys Ala Lys His Leu Lys Cys
    1220            1225                1230

Ser Gln Lys Cys Asp Gln Asn Lys Phe Ser Val Lys Cys Ser Cys
    1235            1240                1245

Tyr Glu Gly Trp Val Leu Glu Pro Asp Gly Glu Ser Cys Arg Ser
    1250            1255                1260

Leu Asp Pro Phe Lys Pro Phe Ile Ile Phe Ser Asn Arg His Glu
    1265            1270                1275

Ile Arg Arg Ile Asp Leu His Lys Gly Asp Tyr Ser Val Leu Val
    1280            1285                1290

Pro Gly Leu Arg Asn Thr Ile Ala Leu Asp Phe His Leu Ser Gln
    1295            1300                1305

Ser Ala Leu Tyr Trp Thr Asp Val Val Glu Asp Lys Ile Tyr Arg
    1310            1315                1320

Gly Lys Leu Leu Asp Asn Gly Ala Leu Thr Ser Phe Glu Val Val
    1325            1330                1335

Ile Gln Tyr Gly Leu Ala Thr Pro Glu Gly Leu Ala Val Asp Trp
    1340            1345                1350

Ile Ala Gly Asn Ile Tyr Trp Val Glu Ser Asn Leu Asp Gln Ile
    1355            1360                1365

Glu Val Ala Lys Leu Asp Gly Thr Leu Arg Thr Thr Leu Leu Ala
    1370            1375                1380

Gly Asp Ile Glu His Pro Arg Ala Ile Ala Leu Asp Pro Arg Asp
    1385            1390                1395

Gly Ile Leu Phe Trp Thr Asp Trp Asp Ala Ser Leu Pro Arg Ile
    1400            1405                1410

Glu Ala Ala Ser Met Ser Gly Ala Gly Arg Arg Thr Val His Arg
    1415            1420                1425

Glu Thr Gly Ser Gly Gly Trp Pro Asn Gly Leu Thr Val Asp Tyr
    1430            1435                1440

Leu Glu Lys Arg Ile Leu Trp Ile Asp Ala Arg Ser Asp Ala Ile
    1445            1450                1455

Tyr Ser Ala Arg Tyr Asp Gly Ser Gly His Met Glu Val Leu Arg
    1460            1465                1470

Gly His Glu Phe Leu Ser His Pro Phe Ala Val Thr Leu Tyr Gly
    1475            1480                1485
```

-continued

```
Gly Glu Val Tyr Trp Thr Asp Trp Arg Thr Asn Thr Leu Ala Lys
    1490                1495                1500

Ala Asn Lys Trp Thr Gly His Asn Val Thr Val Val Gln Arg Thr
    1505                1510                1515

Asn Thr Gln Pro Phe Asp Leu Gln Val Tyr His Pro Ser Arg Gln
    1520                1525                1530

Pro Met Ala Pro Asn Pro Cys Glu Ala Asn Gly Gly Gln Gly Pro
    1535                1540                1545

Cys Ser His Leu Cys Leu Ile Asn Tyr Asn Arg Thr Val Ser Cys
    1550                1555                1560

Ala Cys Pro His Leu Met Lys Leu His Lys Asp Asn Thr Thr Cys
    1565                1570                1575

Tyr Glu Phe Lys Lys Phe Leu Leu Tyr Ala Arg Gln Met Glu Ile
    1580                1585                1590

Arg Gly Val Asp Leu Asp Ala Pro Tyr Tyr Asn Tyr Ile Ile Ser
    1595                1600                1605

Phe Thr Val Pro Asp Ile Asp Asn Val Thr Val Leu Asp Tyr Asp
    1610                1615                1620

Ala Arg Glu Gln Arg Val Tyr Trp Ser Asp Val Arg Thr Gln Ala
    1625                1630                1635

Ile Lys Arg Ala Phe Ile Asn Gly Thr Gly Val Glu Thr Val Val
    1640                1645                1650

Ser Ala Asp Leu Pro Asn Ala His Gly Leu Ala Val Asp Trp Val
    1655                1660                1665

Ser Arg Asn Leu Phe Trp Thr Ser Tyr Asp Thr Asn Lys Lys Gln
    1670                1675                1680

Ile Asn Val Ala Arg Leu Asp Gly Ser Phe Lys Asn Ala Val Val
    1685                1690                1695

Gln Gly Leu Glu Gln Pro His Gly Leu Val Val His Pro Leu Arg
    1700                1705                1710

Gly Lys Leu Tyr Trp Thr Asp Gly Asp Asn Ile Ser Met Ala Asn
    1715                1720                1725

Met Asp Gly Ser Asn Arg Thr Leu Leu Phe Ser Gly Gln Lys Gly
    1730                1735                1740

Pro Val Gly Leu Ala Ile Asp Phe Pro Glu Ser Lys Leu Tyr Trp
    1745                1750                1755

Ile Ser Ser Gly Asn His Thr Ile Asn Arg Cys Asn Leu Asp Gly
    1760                1765                1770

Ser Gly Leu Glu Val Ile Asp Ala Met Arg Ser Gln Leu Gly Lys
    1775                1780                1785

Ala Thr Ala Leu Ala Ile Met Gly Asp Lys Leu Trp Trp Ala Asp
    1790                1795                1800

Gln Val Ser Glu Lys Met Gly Thr Cys Ser Lys Ala Asp Gly Ser
    1805                1810                1815

Gly Ser Val Val Leu Arg Asn Ser Thr Thr Leu Val Met His Met
    1820                1825                1830

Lys Val Tyr Asp Glu Ser Ile Gln Leu Asp His Lys Gly Thr Asn
    1835                1840                1845

Pro Cys Ser Val Asn Asn Gly Asp Cys Ser Gln Leu Cys Leu Pro
    1850                1855                1860

Thr Ser Glu Thr Thr Arg Ser Cys Met Cys Thr Ala Gly Tyr Ser
    1865                1870                1875

Leu Arg Ser Gly Gln Gln Ala Cys Glu Gly Val Gly Ser Phe Leu
```

```
            1880                1885                1890
Leu Tyr Ser Val His Glu Gly Ile Arg Gly Ile Pro Leu Asp Pro
    1895                1900                1905

Asn Asp Lys Ser Asp Ala Leu Val Pro Val Ser Gly Thr Ser Leu
    1910                1915                1920

Ala Val Gly Ile Asp Phe His Ala Glu Asn Asp Thr Ile Tyr Trp
    1925                1930                1935

Val Asp Met Gly Leu Ser Thr Ile Ser Arg Ala Lys Arg Asp Gln
    1940                1945                1950

Thr Trp Arg Glu Asp Val Val Thr Asn Gly Ile Gly Arg Val Glu
    1955                1960                1965

Gly Ile Ala Val Asp Trp Ile Ala Gly Asn Ile Tyr Trp Thr Asp
    1970                1975                1980

Gln Gly Phe Asp Val Ile Glu Val Ala Arg Leu Asn Gly Ser Phe
    1985                1990                1995

Arg Tyr Val Val Ile Ser Gln Gly Leu Asp Lys Pro Arg Ala Ile
    2000                2005                2010

Thr Val His Pro Glu Lys Gly Tyr Leu Phe Trp Thr Glu Trp Gly
    2015                2020                2025

Gln Tyr Pro Arg Ile Glu Arg Ser Arg Leu Asp Gly Thr Glu Arg
    2030                2035                2040

Val Val Leu Val Asn Val Ser Ile Ser Trp Pro Asn Gly Ile Ser
    2045                2050                2055

Val Asp Tyr Gln Asp Gly Lys Leu Tyr Trp Cys Asp Ala Arg Thr
    2060                2065                2070

Asp Lys Ile Glu Arg Ile Asp Leu Glu Thr Gly Glu Asn Arg Glu
    2075                2080                2085

Val Val Leu Ser Ser Asn Asn Met Asp Met Phe Ser Val Ser Val
    2090                2095                2100

Phe Glu Asp Phe Ile Tyr Trp Ser Asp Arg Thr His Ala Asn Gly
    2105                2110                2115

Ser Ile Lys Arg Gly Ser Lys Asp Asn Ala Thr Asp Ser Val Pro
    2120                2125                2130

Leu Arg Thr Gly Ile Gly Val Gln Leu Lys Asp Ile Lys Val Phe
    2135                2140                2145

Asn Arg Asp Arg Gln Lys Gly Thr Asn Val Cys Ala Val Ala Asn
    2150                2155                2160

Gly Gly Cys Gln Gln Leu Cys Leu Tyr Arg Gly Arg Gly Gln Arg
    2165                2170                2175

Ala Cys Ala Cys Ala His Gly Met Leu Ala Glu Asp Gly Ala Ser
    2180                2185                2190

Cys Arg Glu Tyr Ala Gly Tyr Leu Leu Tyr Ser Glu Arg Thr Ile
    2195                2200                2205

Leu Lys Ser Ile His Leu Ser Asp Glu Arg Asn Leu Asn Ala Pro
    2210                2215                2220

Val Gln Pro Phe Glu Asp Pro Glu His Met Lys Asn Val Ile Ala
    2225                2230                2235

Leu Ala Phe Asp Tyr Arg Ala Gly Thr Ser Pro Gly Thr Pro Asn
    2240                2245                2250

Arg Ile Phe Phe Ser Asp Ile His Phe Gly Asn Ile Gln Gln Ile
    2255                2260                2265

Asn Asp Asp Gly Ser Arg Arg Ile Thr Ile Val Glu Asn Val Gly
    2270                2275                2280
```

```
Ser Val Glu Gly Leu Ala Tyr His Arg Gly Trp Asp Thr Leu Tyr
2285                2290                2295

Trp Thr Ser Tyr Thr Thr Ser Thr Ile Thr Arg His Thr Val Asp
2300                2305                2310

Gln Thr Arg Pro Gly Ala Phe Glu Arg Glu Thr Val Ile Thr Met
2315                2320                2325

Ser Gly Asp Asp His Pro Arg Ala Phe Val Leu Asp Glu Cys Gln
2330                2335                2340

Asn Leu Met Phe Trp Thr Asn Trp Asn Glu Gln His Pro Ser Ile
2345                2350                2355

Met Arg Ala Ala Leu Ser Gly Ala Asn Val Leu Thr Leu Ile Glu
2360                2365                2370

Lys Asp Ile Arg Thr Pro Asn Gly Leu Ala Ile Asp His Arg Ala
2375                2380                2385

Glu Lys Leu Tyr Phe Ser Asp Ala Thr Leu Asp Lys Ile Glu Arg
2390                2395                2400

Cys Glu Tyr Asp Gly Ser His Arg Tyr Val Ile Leu Lys Ser Glu
2405                2410                2415

Pro Val His Pro Phe Gly Leu Ala Val Tyr Gly Glu His Ile Phe
2420                2425                2430

Trp Thr Asp Trp Val Arg Arg Ala Val Gln Arg Ala Asn Lys His
2435                2440                2445

Val Gly Ser Asn Met Lys Leu Leu Arg Val Asp Ile Pro Gln Gln
2450                2455                2460

Pro Met Gly Ile Ile Ala Val Ala Asn Asp Thr Asn Ser Cys Glu
2465                2470                2475

Leu Ser Pro Cys Arg Ile Asn Asn Gly Gly Cys Gln Asp Leu Cys
2480                2485                2490

Leu Leu Thr His Gln Gly His Val Asn Cys Ser Cys Arg Gly Gly
2495                2500                2505

Arg Ile Leu Gln Asp Asp Leu Thr Cys Arg Ala Val Asn Ser Ser
2510                2515                2520

Cys Arg Ala Gln Asp Glu Phe Glu Cys Ala Asn Gly Glu Cys Ile
2525                2530                2535

Asn Phe Ser Leu Thr Cys Asp Gly Val Pro His Cys Lys Asp Lys
2540                2545                2550

Ser Asp Glu Lys Pro Ser Tyr Cys Asn Ser Arg Cys Lys Lys
2555                2560                2565

Thr Phe Arg Gln Cys Ser Asn Gly Arg Cys Val Ser Asn Met Leu
2570                2575                2580

Trp Cys Asn Gly Ala Asp Asp Cys Gly Asp Gly Ser Asp Glu Ile
2585                2590                2595

Pro Cys Asn Lys Thr Ala Cys Gly Val Gly Glu Phe Arg Cys Arg
2600                2605                2610

Asp Gly Thr Cys Ile Gly Asn Ser Ser Arg Cys Asn Gln Phe Val
2615                2620                2625

Asp Cys Glu Asp Ala Ser Asp Glu Met Asn Cys Ser Ala Thr Asp
2630                2635                2640

Cys Ser Ser Tyr Phe Arg Leu Gly Val Lys Gly Val Leu Phe Gln
2645                2650                2655

Pro Cys Glu Arg Thr Ser Leu Cys Tyr Ala Pro Ser Trp Val Cys
2660                2665                2670
```

```
Asp Gly Ala Asn Asp Cys Gly Asp Tyr Ser Asp Glu Arg Asp Cys
2675                2680                2685

Pro Gly Val Lys Arg Pro Arg Cys Pro Leu Asn Tyr Phe Ala Cys
2690                2695                2700

Pro Ser Gly Arg Cys Ile Pro Met Ser Trp Thr Cys Asp Lys Glu
2705                2710                2715

Asp Asp Cys Glu His Gly Glu Asp Glu Thr His Cys Asn Lys Phe
2720                2725                2730

Cys Ser Glu Ala Gln Phe Glu Cys Gln Asn His Arg Cys Ile Ser
2735                2740                2745

Lys Gln Trp Leu Cys Asp Gly Ser Asp Asp Cys Gly Asp Gly Ser
2750                2755                2760

Asp Glu Ala Ala His Cys Glu Gly Lys Thr Cys Gly Pro Ser Ser
2765                2770                2775

Phe Ser Cys Pro Gly Thr His Val Cys Val Pro Glu Arg Trp Leu
2780                2785                2790

Cys Asp Gly Asp Lys Asp Cys Ala Asp Gly Ala Asp Glu Ser Ile
2795                2800                2805

Ala Ala Gly Cys Leu Tyr Asn Ser Thr Cys Asp Asp Arg Glu Phe
2810                2815                2820

Met Cys Gln Asn Arg Gln Cys Ile Pro Lys His Phe Val Cys Asp
2825                2830                2835

His Asp Arg Asp Cys Ala Asp Gly Ser Asp Glu Ser Pro Glu Cys
2840                2845                2850

Glu Tyr Pro Thr Cys Gly Pro Ser Glu Phe Arg Cys Ala Asn Gly
2855                2860                2865

Arg Cys Leu Ser Ser Arg Gln Trp Glu Cys Asp Gly Glu Asn Asp
2870                2875                2880

Cys His Asp Gln Ser Asp Glu Ala Pro Lys Asn Pro His Cys Thr
2885                2890                2895

Ser Pro Glu His Lys Cys Asn Ala Ser Ser Gln Phe Leu Cys Ser
2900                2905                2910

Ser Gly Arg Cys Val Ala Glu Ala Leu Leu Cys Asn Gly Gln Asp
2915                2920                2925

Asp Cys Gly Asp Ser Ser Asp Glu Arg Gly Cys His Ile Asn Glu
2930                2935                2940

Cys Leu Ser Arg Lys Leu Ser Gly Cys Ser Gln Asp Cys Glu Asp
2945                2950                2955

Leu Lys Ile Gly Phe Lys Cys Arg Cys Arg Pro Gly Phe Arg Leu
2960                2965                2970

Lys Asp Asp Gly Arg Thr Cys Ala Asp Val Asp Glu Cys Ser Thr
2975                2980                2985

Thr Phe Pro Cys Ser Gln Arg Cys Ile Asn Thr His Gly Ser Tyr
2990                2995                3000

Lys Cys Leu Cys Val Glu Gly Tyr Ala Pro Arg Gly Gly Asp Pro
3005                3010                3015

His Ser Cys Lys Ala Val Thr Asp Glu Glu Pro Phe Leu Ile Phe
3020                3025                3030

Ala Asn Arg Tyr Tyr Leu Arg Lys Leu Asn Leu Asp Gly Ser Asn
3035                3040                3045

Tyr Thr Leu Leu Lys Gln Gly Leu Asn Asn Ala Val Ala Leu Asp
3050                3055                3060

Phe Asp Tyr Arg Glu Gln Met Ile Tyr Trp Thr Asp Val Thr Thr
```

```
            3065                3070                3075
Gln Gly Ser Met Ile Arg Arg Met His Leu Asn Gly Ser Asn Val
        3080                3085                3090
Gln Val Leu His Arg Thr Gly Leu Ser Asn Pro Asp Gly Leu Ala
        3095                3100                3105
Val Asp Trp Val Gly Gly Asn Leu Tyr Trp Cys Asp Lys Gly Arg
        3110                3115                3120
Asp Thr Ile Glu Val Ser Lys Leu Asn Gly Ala Tyr Arg Thr Val
        3125                3130                3135
Leu Val Ser Ser Gly Leu Arg Glu Pro Arg Ala Leu Val Val Asp
        3140                3145                3150
Val Gln Asn Gly Tyr Leu Tyr Trp Thr Asp Trp Gly Asp His Ser
        3155                3160                3165
Leu Ile Gly Arg Ile Gly Met Asp Gly Ser Ser Arg Ser Val Ile
        3170                3175                3180
Val Asp Thr Lys Ile Thr Trp Pro Asn Gly Leu Thr Leu Asp Tyr
        3185                3190                3195
Val Thr Glu Arg Ile Tyr Trp Ala Asp Ala Arg Glu Asp Tyr Ile
        3200                3205                3210
Glu Phe Ala Ser Leu Asp Gly Ser Asn Arg His Val Val Leu Ser
        3215                3220                3225
Gln Asp Ile Pro His Ile Phe Ala Leu Thr Leu Phe Glu Asp Tyr
        3230                3235                3240
Val Tyr Trp Thr Asp Trp Glu Thr Lys Ser Ile Asn Arg Ala His
        3245                3250                3255
Lys Thr Thr Gly Thr Asn Lys Thr Leu Leu Ile Ser Thr Leu His
        3260                3265                3270
Arg Pro Met Asp Leu His Val Phe His Ala Leu Arg Gln Pro Asp
        3275                3280                3285
Val Pro Asn His Pro Cys Lys Val Asn Asn Gly Gly Cys Ser Asn
        3290                3295                3300
Leu Cys Leu Leu Ser Pro Gly Gly Gly His Lys Cys Ala Cys Pro
        3305                3310                3315
Thr Asn Phe Tyr Leu Gly Ser Asp Gly Arg Thr Cys Val Ser Asn
        3320                3325                3330
Cys Thr Ala Ser Gln Phe Val Cys Lys Asn Asp Lys Cys Ile Pro
        3335                3340                3345
Phe Trp Trp Lys Cys Asp Thr Glu Asp Asp Cys Gly Asp His Ser
        3350                3355                3360
Asp Glu Pro Pro Asp Cys Pro Glu Phe Lys Cys Arg Pro Gly Gln
        3365                3370                3375
Phe Gln Cys Ser Thr Gly Ile Cys Thr Asn Pro Ala Phe Ile Cys
        3380                3385                3390
Asp Gly Asp Asn Asp Cys Gln Asp Asn Ser Asp Glu Ala Asn Cys
        3395                3400                3405
Asp Ile His Val Cys Leu Pro Ser Gln Phe Lys Cys Thr Asn Thr
        3410                3415                3420
Asn Arg Cys Ile Pro Gly Ile Phe Arg Cys Asn Gly Gln Asp Asn
        3425                3430                3435
Cys Gly Asp Gly Glu Asp Glu Arg Asp Cys Pro Glu Val Thr Cys
        3440                3445                3450
Ala Pro Asn Gln Phe Gln Cys Ser Ile Thr Lys Arg Cys Ile Pro
        3455                3460                3465
```

-continued

Arg Val Trp Val Cys Asp Arg Asp Asn Asp Cys Val Asp Gly Ser
3470          3475              3480

Asp Glu Pro Ala Asn Cys Thr Gln Met Thr Cys Gly Val Asp Glu
3485          3490              3495

Phe Arg Cys Lys Asp Ser Gly Arg Cys Ile Pro Ala Arg Trp Lys
3500          3505              3510

Cys Asp Gly Glu Asp Cys Gly Asp Gly Ser Asp Glu Pro Lys
3515          3520              3525

Glu Glu Cys Asp Glu Arg Thr Cys Glu Pro Tyr Gln Phe Arg Cys
3530          3535              3540

Lys Asn Asn Arg Cys Val Pro Gly Arg Trp Gln Cys Asp Tyr Asp
3545          3550              3555

Asn Asp Cys Gly Asp Asn Ser Asp Glu Glu Ser Cys Thr Pro Arg
3560          3565              3570

Pro Cys Ser Glu Ser Glu Phe Ser Cys Ala Asn Gly Arg Cys Ile
3575          3580              3585

Ala Gly Arg Trp Lys Cys Asp Gly Asp His Asp Cys Ala Asp Gly
3590          3595              3600

Ser Asp Glu Lys Asp Cys Thr Pro Arg Cys Asp Met Asp Gln Phe
3605          3610              3615

Gln Cys Lys Ser Gly His Cys Ile Pro Leu Arg Trp Arg Cys Asp
3620          3625              3630

Ala Asp Ala Asp Cys Met Asp Gly Ser Asp Glu Glu Ala Cys Gly
3635          3640              3645

Thr Gly Val Arg Thr Cys Pro Leu Asp Glu Phe Gln Cys Asn Asn
3650          3655              3660

Thr Leu Cys Lys Pro Leu Ala Trp Lys Cys Asp Gly Glu Asp Asp
3665          3670              3675

Cys Gly Asp Asn Ser Asp Glu Asn Pro Glu Glu Cys Ala Arg Phe
3680          3685              3690

Val Cys Pro Pro Asn Arg Pro Phe Arg Cys Lys Asn Asp Arg Val
3695          3700              3705

Cys Leu Trp Ile Gly Arg Gln Cys Asp Gly Thr Asp Asn Cys Gly
3710          3715              3720

Asp Gly Thr Asp Glu Glu Asp Cys Glu Pro Pro Thr Ala His Thr
3725          3730              3735

Thr His Cys Lys Asp Lys Lys Glu Phe Leu Cys Arg Asn Gln Arg
3740          3745              3750

Cys Leu Ser Ser Ser Leu Arg Cys Asn Met Phe Asp Asp Cys Gly
3755          3760              3765

Asp Gly Ser Asp Glu Glu Cys Ser Ile Asp Pro Lys Leu Thr
3770          3775              3780

Ser Cys Ala Thr Asn Ala Ser Ile Cys Gly Asp Glu Ala Arg Cys
3785          3790              3795

Val Arg Thr Glu Lys Ala Ala Tyr Cys Ala Cys Arg Ser Gly Phe
3800          3805              3810

His Thr Val Pro Gly Gln Pro Gly Cys Gln Asp Ile Asn Glu Cys
3815          3820              3825

Leu Arg Phe Gly Thr Cys Ser Gln Leu Cys Asn Asn Thr Lys Gly
3830          3835              3840

Gly His Leu Cys Ser Cys Ala Arg Asn Phe Met Lys Thr His Asn
3845          3850              3855

Thr Cys Lys Ala Glu Gly Ser Glu Tyr Gln Val Leu Tyr Ile Ala
3860            3865               3870

Asp Asp Asn Glu Ile Arg Ser Leu Phe Pro Gly His Pro His Ser
3875            3880               3885

Ala Tyr Glu Gln Ala Phe Gln Gly Asp Glu Ser Val Arg Ile Asp
3890            3895               3900

Ala Met Asp Val His Val Lys Ala Gly Arg Val Tyr Trp Thr Asn
3905            3910               3915

Trp His Thr Gly Thr Ile Ser Tyr Arg Ser Leu Pro Pro Ala Ala
3920            3925               3930

Pro Pro Thr Thr Ser Asn Arg His Arg Arg Gln Ile Asp Arg Gly
3935            3940               3945

Val Thr His Leu Asn Ile Ser Gly Leu Lys Met Pro Arg Gly Ile
3950            3955               3960

Ala Ile Asp Trp Val Ala Gly Asn Val Tyr Trp Thr Asp Ser Gly
3965            3970               3975

Arg Asp Val Ile Glu Val Ala Gln Met Lys Gly Glu Asn Arg Lys
3980            3985               3990

Thr Leu Ile Ser Gly Met Ile Asp Glu Pro His Ala Ile Val Val
3995            4000               4005

Asp Pro Leu Arg Gly Thr Met Tyr Trp Ser Asp Trp Gly Asn His
4010            4015               4020

Pro Lys Ile Glu Thr Ala Ala Met Asp Gly Thr Leu Arg Glu Thr
4025            4030               4035

Leu Val Gln Asp Asn Ile Gln Trp Pro Thr Gly Leu Ala Val Asp
4040            4045               4050

Tyr His Asn Glu Arg Leu Tyr Trp Ala Asp Ala Lys Leu Ser Val
4055            4060               4065

Ile Gly Ser Ile Arg Leu Asn Gly Thr Asp Pro Ile Val Ala Ala
4070            4075               4080

Asp Ser Lys Arg Gly Leu Ser His Pro Phe Ser Ile Asp Val Phe
4085            4090               4095

Glu Asp Tyr Ile Tyr Gly Val Thr Tyr Ile Asn Asn Arg Val Phe
4100            4105               4110

Lys Ile His Lys Phe Gly His Ser Pro Leu Val Asn Leu Thr Gly
4115            4120               4125

Gly Leu Ser His Ala Ser Asp Val Val Leu Tyr His Gln His Lys
4130            4135               4140

Gln Pro Glu Val Thr Asn Pro Cys Asp Arg Lys Lys Cys Glu Trp
4145            4150               4155

Leu Cys Leu Leu Ser Pro Ser Gly Pro Val Cys Thr Cys Pro Asn
4160            4165               4170

Gly Lys Arg Leu Asp Asn Gly Thr Cys Val Pro Val Pro Ser Pro
4175            4180               4185

Thr Pro Pro Pro Asp Ala Pro Arg Pro Gly Thr Cys Asn Leu Gln
4190            4195               4200

Cys Phe Asn Gly Gly Ser Cys Phe Leu Asn Ala Arg Arg Gln Pro
4205            4210               4215

Lys Cys Arg Cys Gln Pro Arg Tyr Thr Gly Asp Lys Cys Glu Leu
4220            4225               4230

Asp Gln Cys Trp Glu His Cys Arg Asn Gly Gly Thr Cys Ala Ala
4235            4240               4245

Ser Pro Ser Gly Met Pro Thr Cys Arg Cys Pro Thr Gly Phe Thr

```
            4250                4255                4260

Gly Pro Lys Cys Thr Gln Gln Val Cys Ala Gly Tyr Cys Ala Asn
        4265                4270                4275

Asn Ser Thr Cys Thr Val Asn Gln Gly Asn Gln Pro Gln Cys Arg
        4280                4285                4290

Cys Leu Pro Gly Phe Leu Gly Asp Arg Cys Gln Tyr Arg Gln Cys
        4295                4300                4305

Ser Gly Tyr Cys Glu Asn Phe Gly Thr Cys Gln Met Ala Ala Asp
        4310                4315                4320

Gly Ser Arg Gln Cys Arg Cys Thr Ala Tyr Phe Glu Gly Ser Arg
        4325                4330                4335

Cys Glu Val Asn Lys Cys Ser Arg Cys Leu Glu Gly Ala Cys Val
        4340                4345                4350

Val Asn Lys Gln Ser Gly Asp Val Thr Cys Asn Cys Thr Asp Gly
        4355                4360                4365

Arg Val Ala Pro Ser Cys Leu Thr Cys Val Gly His Cys Ser Asn
        4370                4375                4380

Gly Gly Ser Cys Thr Met Asn Ser Lys Met Met Pro Glu Cys Gln
        4385                4390                4395

Cys Pro Pro His Met Thr Gly Pro Arg Cys Glu Glu His Val Phe
        4400                4405                4410

Ser Gln Gln Gln Pro Gly His Ile Ala Ser Ile Leu Ile Pro Leu
        4415                4420                4425

Leu Leu Leu Leu Leu Leu Val Leu Val Ala Gly Val Val Phe Trp
        4430                4435                4440

Tyr Lys Arg Arg Val Gln Gly Ala Lys Gly Phe Gln His Gln Arg
        4445                4450                4455

Met Thr Asn Gly Ala Met Asn Val Glu Ile Gly Asn Pro Thr Tyr
        4460                4465                4470

Lys Met Tyr Glu Gly Gly Glu Pro Asp Asp Val Gly Gly Leu Leu
        4475                4480                4485

Asp Ala Asp Phe Ala Leu Asp Pro Asp Lys Pro Thr Asn Phe Thr
        4490                4495                4500

Asn Pro Val Tyr Ala Thr Leu Tyr Met Gly Gly His Gly Ser Arg
        4505                4510                4515

His Ser Leu Ala Ser Thr Asp Glu Lys Arg Glu Leu Leu Gly Arg
        4520                4525                4530

Gly Pro Glu Asp Glu Ile Gly Asp Pro Leu Ala
        4535                4540

<210> SEQ ID NO 153
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(4)
<223> OTHER INFORMATION: /replace=" "
<220> FEATURE:
<221> NAME/KEY: VARIANT
<222> LOCATION: (5)..(5)
<223> OTHER INFORMATION: /replace=" "
<220> FEATURE:
<221> NAME/KEY: VARIANT
<222> LOCATION: (7)..(9)
```

```
<223> OTHER INFORMATION: /replace=" "
<220> FEATURE:
<221> NAME/KEY: VARIANT
<222> LOCATION: (10)..(10)
<223> OTHER INFORMATION: /replace=" "
<220> FEATURE:
<221> NAME/KEY: VARIANT
<222> LOCATION: (12)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" "
<220> FEATURE:
<221> NAME/KEY: VARIANT
<222> LOCATION: (17)..(19)
<223> OTHER INFORMATION: /replace=" "
<220> FEATURE:
<221> NAME/KEY: VARIANT
<222> LOCATION: (20)..(20)
<223> OTHER INFORMATION: /replace=" "
<220> FEATURE:
<221> NAME/KEY: VARIANT
<222> LOCATION: (22)..(24)
<223> OTHER INFORMATION: /replace=" "
<220> FEATURE:
<221> NAME/KEY: VARIANT
<222> LOCATION: (25)..(25)
<223> OTHER INFORMATION: /replace=" "
<220> FEATURE:
<221> NAME/KEY: VARIANT
<222> LOCATION: (27)..(29)
<223> OTHER INFORMATION: /replace=" "
<220> FEATURE:
<221> NAME/KEY: VARIANT
<222> LOCATION: (30)..(30)
<223> OTHER INFORMATION: /replace=" "
<220> FEATURE:
<221> NAME/KEY: VARIANT
<222> LOCATION: (32)..(34)
<223> OTHER INFORMATION: /replace=" "
<220> FEATURE:
<221> NAME/KEY: VARIANT
<222> LOCATION: (35)..(35)
<223> OTHER INFORMATION: /replace=" "
<220> FEATURE:
<221> NAME/KEY: VARIANT
<222> LOCATION: (37)..(39)
<223> OTHER INFORMATION: /replace=" "
<220> FEATURE:
<221> NAME/KEY: VARIANT
<222> LOCATION: (40)..(40)
<223> OTHER INFORMATION: /replace=" "
<220> FEATURE:
<221> NAME/KEY: VARIANT
<222> LOCATION: (42)..(44)
<223> OTHER INFORMATION: /replace=" "
<220> FEATURE:
<221> NAME/KEY: VARIANT
<222> LOCATION: (45)..(45)
<223> OTHER INFORMATION: /replace=" "
<220> FEATURE:
<221> NAME/KEY: VARIANT
<222> LOCATION: (47)..(49)
<223> OTHER INFORMATION: /replace=" "
<220> FEATURE:
<221> NAME/KEY: VARIANT
<222> LOCATION: (50)..(50)
<223> OTHER INFORMATION: /replace=" "
<220> FEATURE:
<221> NAME/KEY: VARIANT
<222> LOCATION: (52)..(54)
<223> OTHER INFORMATION: /replace=" "
<220> FEATURE:
<221> NAME/KEY: VARIANT
<222> LOCATION: (55)..(55)
<223> OTHER INFORMATION: /replace=" "
<220> FEATURE:
<221> NAME/KEY: VARIANT
```

```
<222> LOCATION: (57)..(59)
<223> OTHER INFORMATION: /replace=" "
<220> FEATURE:
<221> NAME/KEY: VARIANT
<222> LOCATION: (60)..(60)
<223> OTHER INFORMATION: /replace=" "
<220> FEATURE:
<221> NAME/KEY: VARIANT
<222> LOCATION: (62)..(64)
<223> OTHER INFORMATION: /replace=" "
<220> FEATURE:
<221> NAME/KEY: VARIANT
<222> LOCATION: (65)..(65)
<223> OTHER INFORMATION: /replace=" "
<220> FEATURE:
<221> NAME/KEY: VARIANT
<222> LOCATION: (67)..(69)
<223> OTHER INFORMATION: /replace=" "
<220> FEATURE:
<221> NAME/KEY: VARIANT
<222> LOCATION: (70)..(70)
<223> OTHER INFORMATION: /replace=" "
<220> FEATURE:
<221> NAME/KEY: VARIANT
<222> LOCATION: (72)..(74)
<223> OTHER INFORMATION: /replace=" "
<220> FEATURE:
<221> NAME/KEY: VARIANT
<222> LOCATION: (75)..(75)
<223> OTHER INFORMATION: /replace=" "
<220> FEATURE:
<221> NAME/KEY: VARIANT
<222> LOCATION: (77)..(79)
<223> OTHER INFORMATION: /replace=" "
<220> FEATURE:
<221> NAME/KEY: VARIANT
<222> LOCATION: (80)..(80)
<223> OTHER INFORMATION: /replace=" "
<220> FEATURE:
<221> NAME/KEY: VARIANT
<222> LOCATION: (82)..(84)
<223> OTHER INFORMATION: /replace=" "
<220> FEATURE:
<221> NAME/KEY: VARIANT
<222> LOCATION: (85)..(85)
<223> OTHER INFORMATION: /replace=" "
<220> FEATURE:
<221> NAME/KEY: VARIANT
<222> LOCATION: (87)..(89)
<223> OTHER INFORMATION: /replace=" "
<220> FEATURE:
<221> NAME/KEY: VARIANT
<222> LOCATION: (90)..(90)
<223> OTHER INFORMATION: /replace=" "
<220> FEATURE:
<221> NAME/KEY: VARIANT
<222> LOCATION: (92)..(94)
<223> OTHER INFORMATION: /replace=" "
<220> FEATURE:
<221> NAME/KEY: VARIANT
<222> LOCATION: (95)..(95)
<223> OTHER INFORMATION: /replace=" "
<220> FEATURE:
<221> NAME/KEY: VARIANT
<222> LOCATION: (97)..(99)
<223> OTHER INFORMATION: /replace=" "
<220> FEATURE:
<221> NAME/KEY: VARIANT
<222> LOCATION: (100)..(100)
<223> OTHER INFORMATION: /replace=" "
<220> FEATURE:
<221> NAME/KEY: VARIANT
<222> LOCATION: (102)..(104)
<223> OTHER INFORMATION: /replace=" "
<220> FEATURE:
<221> NAME/KEY: VARIANT
<222> LOCATION: (105)..(105)
<223> OTHER INFORMATION: /replace=" "
<220> FEATURE:
```

```
<221> NAME/KEY: VARIANT
<222> LOCATION: (107)..(109)
<223> OTHER INFORMATION: /replace=" "
<220> FEATURE:
<221> NAME/KEY: VARIANT
<222> LOCATION: (110)..(110)
<223> OTHER INFORMATION: /replace=" "
<220> FEATURE:
<221> NAME/KEY: VARIANT
<222> LOCATION: (112)..(114)
<223> OTHER INFORMATION: /replace=" "
<220> FEATURE:
<221> NAME/KEY: VARIANT
<222> LOCATION: (115)..(115)
<223> OTHER INFORMATION: /replace=" "
<220> FEATURE:
<221> NAME/KEY: VARIANT
<222> LOCATION: (117)..(119)
<223> OTHER INFORMATION: /replace=" "
<220> FEATURE:
<221> NAME/KEY: VARIANT
<222> LOCATION: (120)..(120)
<223> OTHER INFORMATION: /replace=" "
<220> FEATURE:
<221> NAME/KEY: VARIANT
<222> LOCATION: (122)..(124)
<223> OTHER INFORMATION: /replace=" "
<220> FEATURE:
<221> NAME/KEY: VARIANT
<222> LOCATION: (125)..(125)
<223> OTHER INFORMATION: /replace=" "
<220> FEATURE:
<221> NAME/KEY: VARIANT
<222> LOCATION: (127)..(129)
<223> OTHER INFORMATION: /replace=" "
<220> FEATURE:
<221> NAME/KEY: VARIANT
<222> LOCATION: (130)..(130)
<223> OTHER INFORMATION: /replace=" "
<220> FEATURE:
<221> NAME/KEY: VARIANT
<222> LOCATION: (132)..(134)
<223> OTHER INFORMATION: /replace=" "
<220> FEATURE:
<221> NAME/KEY: VARIANT
<222> LOCATION: (135)..(135)
<223> OTHER INFORMATION: /replace=" "
<220> FEATURE:
<221> NAME/KEY: VARIANT
<222> LOCATION: (137)..(139)
<223> OTHER INFORMATION: /replace=" "
<220> FEATURE:
<221> NAME/KEY: VARIANT
<222> LOCATION: (140)..(140)
<223> OTHER INFORMATION: /replace=" "
<220> FEATURE:
<221> NAME/KEY: VARIANT
<222> LOCATION: (142)..(144)
<223> OTHER INFORMATION: /replace=" "
<220> FEATURE:
<221> NAME/KEY: VARIANT
<222> LOCATION: (145)..(145)
<223> OTHER INFORMATION: /replace=" "
<220> FEATURE:
<221> NAME/KEY: VARIANT
<222> LOCATION: (147)..(149)
<223> OTHER INFORMATION: /replace=" "
<220> FEATURE:
<221> NAME/KEY: VARIANT
<222> LOCATION: (150)..(150)
<223> OTHER INFORMATION: /replace=" "
<220> FEATURE:
<221> NAME/KEY: VARIANT
<222> LOCATION: (152)..(154)
<223> OTHER INFORMATION: /replace=" "
<220> FEATURE:
<221> NAME/KEY: VARIANT
<222> LOCATION: (155)..(155)
<223> OTHER INFORMATION: /replace=" "
```

```
<220> FEATURE:
<221> NAME/KEY: VARIANT
<222> LOCATION: (157)..(159)
<223> OTHER INFORMATION: /replace=" "
<220> FEATURE:
<221> NAME/KEY: VARIANT
<222> LOCATION: (160)..(160)
<223> OTHER INFORMATION: /replace=" "
<220> FEATURE:
<221> NAME/KEY: VARIANT
<222> LOCATION: (162)..(164)
<223> OTHER INFORMATION: /replace=" "
<220> FEATURE:
<221> NAME/KEY: VARIANT
<222> LOCATION: (165)..(165)
<223> OTHER INFORMATION: /replace=" "
<220> FEATURE:
<221> NAME/KEY: VARIANT
<222> LOCATION: (167)..(169)
<223> OTHER INFORMATION: /replace=" "
<220> FEATURE:
<221> NAME/KEY: VARIANT
<222> LOCATION: (170)..(170)
<223> OTHER INFORMATION: /replace=" "
<220> FEATURE:
<221> NAME/KEY: VARIANT
<222> LOCATION: (172)..(174)
<223> OTHER INFORMATION: /replace=" "
<220> FEATURE:
<221> NAME/KEY: VARIANT
<222> LOCATION: (175)..(175)
<223> OTHER INFORMATION: /replace=" "
<220> FEATURE:
<221> NAME/KEY: VARIANT
<222> LOCATION: (177)..(179)
<223> OTHER INFORMATION: /replace=" "
<220> FEATURE:
<221> NAME/KEY: VARIANT
<222> LOCATION: (180)..(180)
<223> OTHER INFORMATION: /replace=" "
<220> FEATURE:
<221> NAME/KEY: VARIANT
<222> LOCATION: (182)..(184)
<223> OTHER INFORMATION: /replace=" "
<220> FEATURE:
<221> NAME/KEY: VARIANT
<222> LOCATION: (185)..(185)
<223> OTHER INFORMATION: /replace=" "
<220> FEATURE:
<221> NAME/KEY: VARIANT
<222> LOCATION: (187)..(189)
<223> OTHER INFORMATION: /replace=" "
<220> FEATURE:
<221> NAME/KEY: VARIANT
<222> LOCATION: (190)..(190)
<223> OTHER INFORMATION: /replace=" "
<220> FEATURE:
<221> NAME/KEY: VARIANT
<222> LOCATION: (192)..(194)
<223> OTHER INFORMATION: /replace=" "
<220> FEATURE:
<221> NAME/KEY: VARIANT
<222> LOCATION: (195)..(195)
<223> OTHER INFORMATION: /replace=" "
<220> FEATURE:
<221> NAME/KEY: VARIANT
<222> LOCATION: (197)..(199)
<223> OTHER INFORMATION: /replace=" "
<220> FEATURE:
<221> NAME/KEY: VARIANT
<222> LOCATION: (200)..(200)
<223> OTHER INFORMATION: /replace=" "
<220> FEATURE:
<221> NAME/KEY: VARIANT
<222> LOCATION: (202)..(204)
<223> OTHER INFORMATION: /replace=" "
<220> FEATURE:
<221> NAME/KEY: VARIANT
<222> LOCATION: (205)..(205)
```

```
<223> OTHER INFORMATION: /replace=" "
<220> FEATURE:
<221> NAME/KEY: VARIANT
<222> LOCATION: (207)..(209)
<223> OTHER INFORMATION: /replace=" "
<220> FEATURE:
<221> NAME/KEY: VARIANT
<222> LOCATION: (210)..(210)
<223> OTHER INFORMATION: /replace=" "
<220> FEATURE:
<221> NAME/KEY: VARIANT
<222> LOCATION: (212)..(214)
<223> OTHER INFORMATION: /replace=" "
<220> FEATURE:
<221> NAME/KEY: VARIANT
<222> LOCATION: (215)..(215)
<223> OTHER INFORMATION: /replace=" "
<220> FEATURE:
<221> NAME/KEY: VARIANT
<222> LOCATION: (217)..(219)
<223> OTHER INFORMATION: /replace=" "
<220> FEATURE:
<221> NAME/KEY: VARIANT
<222> LOCATION: (220)..(220)
<223> OTHER INFORMATION: /replace=" "
<220> FEATURE:
<221> NAME/KEY: VARIANT
<222> LOCATION: (222)..(224)
<223> OTHER INFORMATION: /replace=" "
<220> FEATURE:
<221> NAME/KEY: VARIANT
<222> LOCATION: (225)..(225)
<223> OTHER INFORMATION: /replace=" "
<220> FEATURE:
<221> NAME/KEY: VARIANT
<222> LOCATION: (227)..(229)
<223> OTHER INFORMATION: /replace=" "
<220> FEATURE:
<221> NAME/KEY: VARIANT
<222> LOCATION: (230)..(230)
<223> OTHER INFORMATION: /replace=" "
<220> FEATURE:
<221> NAME/KEY: VARIANT
<222> LOCATION: (232)..(234)
<223> OTHER INFORMATION: /replace=" "
<220> FEATURE:
<221> NAME/KEY: VARIANT
<222> LOCATION: (235)..(235)
<223> OTHER INFORMATION: /replace=" "
<220> FEATURE:
<221> NAME/KEY: VARIANT
<222> LOCATION: (237)..(239)
<223> OTHER INFORMATION: /replace=" "
<220> FEATURE:
<221> NAME/KEY: VARIANT
<222> LOCATION: (240)..(240)
<223> OTHER INFORMATION: /replace=" "
<220> FEATURE:
<221> NAME/KEY: VARIANT
<222> LOCATION: (242)..(244)
<223> OTHER INFORMATION: /replace=" "
<220> FEATURE:
<221> NAME/KEY: VARIANT
<222> LOCATION: (245)..(245)
<223> OTHER INFORMATION: /replace=" "
<220> FEATURE:
<221> NAME/KEY: VARIANT
<222> LOCATION: (247)..(249)
<223> OTHER INFORMATION: /replace=" "
<220> FEATURE:
<221> NAME/KEY: VARIANT
<222> LOCATION: (250)..(250)
<223> OTHER INFORMATION: /replace=" "
<220> FEATURE:
<221> NAME/KEY: MISC_FEATURE
<222> LOCATION: (1)..(250)
<223> OTHER INFORMATION: /note="This sequence may encompass 1-50
      "(Gly)x-(Ser)y" repeating units, wherein x is 1-4 and y is 0-1;
      See specification as filed for detailed description of
``` substitutions and preferred embodiments"
<220> FEATURE:
<221> NAME/KEY: MISC_FEATURE
<222> LOCATION: (1)..(250)
<223> OTHER INFORMATION: /note="Variant residues given in the sequence
      have no preference with respect to those in the annotations
      for variant positions"

<400> SEQUENCE: 153

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20              25                  30

Gly Gly Ser Gly Gly Gly Ser Gly Gly Gly Ser Gly Gly Gly
            35              40              45

Gly Ser Gly Gly Gly Ser Gly Gly Gly Ser Gly Gly Gly Gly
        50              55              60

Ser Gly Gly Gly Ser Gly Gly Gly Ser Gly Gly Gly Gly Ser
65              70              75                  80

Gly Gly Gly Gly Ser Gly Gly Gly Ser Gly Gly Gly Ser Gly
                85              90                  95

Gly Gly Gly Ser Gly Gly Gly Ser Gly Gly Gly Ser Gly Gly
                100             105                 110

Gly Gly Ser Gly Gly Gly Ser Gly Gly Gly Ser Gly Gly Gly
            115             120             125

Gly Ser Gly Gly Gly Ser Gly Gly Gly Ser Gly Gly Gly Gly
        130             135             140

Ser Gly Gly Gly Ser Gly Gly Gly Ser Gly Gly Gly Gly Ser
145             150             155                 160

Gly Gly Gly Gly Ser Gly Gly Gly Ser Gly Gly Gly Ser Gly
                165             170                 175

Gly Gly Gly Ser Gly Gly Gly Ser Gly Gly Gly Ser Gly Gly
                180             185                 190

Gly Gly Ser Gly Gly Gly Ser Gly Gly Gly Ser Gly Gly Gly
            195             200             205

Gly Ser Gly Gly Gly Ser Gly Gly Gly Ser Gly Gly Gly Gly
        210             215             220

Ser Gly Gly Gly Ser Gly Gly Gly Ser Gly Gly Gly Gly Ser
225             230             235                 240

Gly Gly Gly Gly Ser Gly Gly Gly Ser
                245             250
```

<210> SEQ ID NO 154
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

```
Gly Gly Gly Gly
1
```

<210> SEQ ID NO 155
<211> LENGTH: 300
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (4)..(300)
<223> OTHER INFORMATION: /replace=" "
<220> FEATURE:
<221> NAME/KEY: MISC_FEATURE
<222> LOCATION: (1)..(300)
<223> OTHER INFORMATION: /note="This region may encompass 1-100 "Gly Gly
      Ser" repeating units"
<220> FEATURE:
<221> NAME/KEY: MISC_FEATURE
<222> LOCATION: (1)..(300)
<223> OTHER INFORMATION: /note="Variant residues given in the sequence
      have no preference with respect to those in the annotations
      for variant positions"

<400> SEQUENCE: 155
```

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
            85                  90                  95

Gly Gly Ser Gly Gly Ser Gly Gly Ser Gly Gly Ser Gly Gly Ser Gly
        100                 105                 110

Gly Ser Gly Gly Ser Gly Gly Ser Gly Gly Ser Gly Gly Ser Gly Gly
    115                 120                 125

Ser Gly Gly Ser Gly Gly Ser Gly Gly Ser Gly Gly Ser Gly Gly Ser
        130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
            165                 170                 175

Ser Gly Gly Ser Gly Gly Ser Gly Gly Ser Gly Gly Ser Gly Gly Ser
        180                 185                 190

Gly Gly Ser Gly Gly Ser Gly Gly Ser Gly Gly Ser Gly Gly Ser Gly
    195                 200                 205

Gly Ser Gly Gly Ser Gly Gly Ser Gly Gly Ser Gly Gly Ser Gly Gly
    210                 215                 220

Ser Gly Gly Ser Gly Gly Ser Gly Gly Ser Gly Gly Ser Gly Gly Ser
225                 230                 235                 240

Gly Gly Ser Gly Gly Ser Gly Gly Ser Gly Gly Ser Gly Gly Ser Gly
            245                 250                 255

Gly Ser Gly Gly Ser Gly Gly Ser Gly Gly Ser Gly Gly Ser Gly Gly
        260                 265                 270

Ser Gly Gly Ser Gly Gly Ser Gly Gly Ser Gly Gly Ser Gly Gly Ser
    275                 280                 285

Gly Gly Ser Gly Gly Ser Gly Gly Ser Gly Gly Ser
    290                 295                 300

```
<210> SEQ ID NO 156
<211> LENGTH: 400
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(400)
<223> OTHER INFORMATION: /replace=" "
<220> FEATURE:
<221> NAME/KEY: MISC_FEATURE
<222> LOCATION: (1)..(400)
<223> OTHER INFORMATION: /note="This region may encompass 1-100 "Gly Gly
      Gly Ser" repeating units"
<220> FEATURE:
<221> NAME/KEY: MISC_FEATURE
<222> LOCATION: (1)..(400)
<223> OTHER INFORMATION: /note="Variant residues given in the sequence
      have no preference with respect to those in the annotations
      for variant positions"

<400> SEQUENCE: 156
```

| Gly Gly Gly Ser Gly Gly Gly Ser Gly Gly Gly Ser Gly Gly Gly Ser |
|---|
| 1               5                   10                  15 |
| Gly Gly Gly Ser Gly Gly Gly Ser Gly Gly Gly Ser Gly Gly Gly Ser |
|             20                  25                  30 |
| Gly Gly Gly Ser Gly Gly Gly Ser Gly Gly Gly Ser Gly Gly Gly Ser |
|         35                  40                  45 |
| Gly Gly Gly Ser Gly Gly Gly Ser Gly Gly Gly Ser Gly Gly Gly Ser |
|     50                  55                  60 |
| Gly Gly Gly Ser Gly Gly Gly Ser Gly Gly Gly Ser Gly Gly Gly Ser |
| 65                  70                  75                  80 |
| Gly Gly Gly Ser Gly Gly Gly Ser Gly Gly Gly Ser Gly Gly Gly Ser |
|             85                  90                  95 |
| Gly Gly Gly Ser Gly Gly Gly Ser Gly Gly Gly Ser Gly Gly Gly Ser |
|         100                 105                 110 |
| Gly Gly Gly Ser Gly Gly Gly Ser Gly Gly Gly Ser Gly Gly Gly Ser |
|     115                 120                 125 |
| Gly Gly Gly Ser Gly Gly Gly Ser Gly Gly Gly Ser Gly Gly Gly Ser |
| 130                 135                 140 |
| Gly Gly Gly Ser Gly Gly Gly Ser Gly Gly Gly Ser Gly Gly Gly Ser |
| 145                 150                 155                 160 |
| Gly Gly Gly Ser Gly Gly Gly Ser Gly Gly Gly Ser Gly Gly Gly Ser |
|             165                 170                 175 |
| Gly Gly Gly Ser Gly Gly Gly Ser Gly Gly Gly Ser Gly Gly Gly Ser |
|         180                 185                 190 |
| Gly Gly Gly Ser Gly Gly Gly Ser Gly Gly Gly Ser Gly Gly Gly Ser |
|     195                 200                 205 |
| Gly Gly Gly Ser Gly Gly Gly Ser Gly Gly Gly Ser Gly Gly Gly Ser |
| 210                 215                 220 |
| Gly Gly Gly Ser Gly Gly Gly Ser Gly Gly Gly Ser Gly Gly Gly Ser |
| 225                 230                 235                 240 |
| Gly Gly Gly Ser Gly Gly Gly Ser Gly Gly Gly Ser Gly Gly Gly Ser |
|             245                 250                 255 |
| Gly Gly Gly Ser Gly Gly Gly Ser Gly Gly Gly Ser Gly Gly Gly Ser |
|         260                 265                 270 |
| Gly Gly Gly Ser Gly Gly Gly Ser Gly Gly Gly Ser Gly Gly Gly Ser |
|     275                 280                 285 |

```
Gly Gly Gly Ser Gly Gly Gly Ser Gly Gly Gly Ser Gly Gly Gly Ser
        290                 295                 300

Gly Gly Gly Ser Gly Gly Gly Ser Gly Gly Gly Ser Gly Gly Gly Ser
305                 310                 315                 320

Gly Gly Gly Ser Gly Gly Gly Ser Gly Gly Gly Ser Gly Gly Gly Ser
            325                 330                 335

Gly Gly Gly Ser Gly Gly Gly Ser Gly Gly Gly Ser Gly Gly Gly Ser
        340                 345                 350

Gly Gly Gly Ser Gly Gly Gly Ser Gly Gly Gly Ser Gly Gly Gly Ser
    355                 360                 365

Gly Gly Gly Ser Gly Gly Gly Ser Gly Gly Gly Ser Gly Gly Gly Ser
        370                 375                 380

Gly Gly Gly Ser Gly Gly Gly Ser Gly Gly Gly Ser Gly Gly Gly Ser
385                 390                 395                 400

<210> SEQ ID NO 157
<211> LENGTH: 800
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (4)..(300)
<223> OTHER INFORMATION: /replace=" "
<220> FEATURE:
<221> NAME/KEY: MISC_FEATURE
<222> LOCATION: (1)..(300)
<223> OTHER INFORMATION: /note="This region may encompass 1-100 "Gly Gly
      Ser" repeating units"
<220> FEATURE:
<221> NAME/KEY: VARIANT
<222> LOCATION: (306)..(800)
<223> OTHER INFORMATION: /replace=" "
<220> FEATURE:
<221> NAME/KEY: MISC_FEATURE
<222> LOCATION: (301)..(800)
<223> OTHER INFORMATION: /note="This region may encompass 1-100 "Gly Gly
      Gly Gly Ser" repeating units"
<220> FEATURE:
<221> NAME/KEY: MISC_FEATURE
<222> LOCATION: (1)..(800)
<223> OTHER INFORMATION: /note="Variant residues given in the sequence
      have no preference with respect to those in the annotations
      for variant positions"

<400> SEQUENCE: 157

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Gly Ser Gly Gly Ser Gly Gly Ser Gly Gly Ser Gly
            100                 105                 110
```

```
Gly Ser Gly Gly Ser Gly Gly Ser Gly Gly Ser Gly Gly
        115                 120                 125
Ser Gly Gly Ser Gly Gly Ser Gly Gly Ser Gly Gly Ser
        130                 135                 140
Gly Gly Ser Gly Gly Ser Gly Gly Ser Gly Gly Ser Gly
145                 150                 155                 160
Gly Ser Gly Gly Ser Gly Gly Ser Gly Gly Ser Gly Gly
        165                 170                 175
Ser Gly Gly Ser Gly Gly Ser Gly Gly Ser Gly Gly Ser
        180                 185                 190
Gly Gly Ser Gly Gly Ser Gly Gly Ser Gly Gly Ser Gly
        195                 200                 205
Gly Ser Gly Gly Ser Gly Gly Ser Gly Gly Ser Gly Gly
210                 215                 220
Ser Gly Gly Ser Gly Gly Ser Gly Gly Ser Gly Gly Ser
225                 230                 235                 240
Gly Gly Ser Gly Gly Ser Gly Gly Ser Gly Gly Ser Gly
        245                 250                 255
Gly Ser Gly Gly Ser Gly Gly Ser Gly Gly Ser Gly Gly
        260                 265                 270
Ser Gly Gly Ser Gly Gly Ser Gly Gly Ser Gly Gly Ser
        275                 280                 285
Gly Gly Ser Gly Gly Ser Gly Gly Ser Gly Gly Gly Gly
        290                 295                 300
Ser Gly Gly Gly Ser Gly Gly Gly Ser Gly Gly Gly Ser
305                 310                 315                 320
Gly Gly Gly Gly Ser Gly Gly Gly Ser Gly Gly Gly Ser
                325                 330                 335
Gly Gly Gly Ser Gly Gly Gly Ser Gly Gly Gly Ser Gly
                340                 345                 350
Gly Gly Ser Gly Gly Gly Ser Gly Gly Gly Ser Gly Gly
        355                 360                 365
Gly Ser Gly Gly Gly Ser Gly Gly Gly Ser Gly Gly Gly
        370                 375                 380
Ser Gly Gly Gly Ser Gly Gly Gly Ser Gly Gly Gly Ser
385                 390                 395                 400
Gly Gly Gly Gly Ser Gly Gly Gly Gly Ser Gly Gly Gly
                405                 410                 415
Gly Gly Gly Ser Gly Gly Gly Ser Gly Gly Gly Ser Gly
                420                 425                 430
Gly Gly Ser Gly Gly Gly Ser Gly Gly Gly Ser Gly Gly
        435                 440                 445
Gly Ser Gly Gly Gly Ser Gly Gly Gly Ser Gly Gly Gly
        450                 455                 460
Ser Gly Gly Gly Ser Gly Gly Gly Ser Gly Gly Gly Ser
465                 470                 475                 480
Gly Gly Gly Gly Ser Gly Gly Gly Ser Gly Gly Gly Ser Gly
                485                 490                 495
Gly Gly Gly Ser Gly Gly Gly Ser Gly Gly Gly Ser Gly Gly
                500                 505                 510
Gly Gly Ser Gly Gly Gly Ser Gly Gly Gly Ser Gly Gly Gly
        515                 520                 525
Gly Ser Gly Gly Gly Gly Ser Gly Gly Gly Gly Ser Gly Gly Gly Gly
```

```
                530             535             540
Ser Gly Gly Gly Gly Ser Gly Gly Gly Ser Gly Gly Gly Ser
545                 550             555             560

Gly Gly Gly Gly Ser Gly Gly Gly Ser Gly Gly Gly Ser Gly
                565             570             575

Gly Gly Gly Ser Gly Gly Gly Ser Gly Gly Gly Ser Gly Gly
            580             585             590

Gly Gly Ser Gly Gly Gly Ser Gly Gly Gly Ser Gly Gly Gly
        595             600             605

Gly Ser Gly Gly Gly Ser Gly Gly Gly Ser Gly Gly Gly Gly
    610             615             620

Ser Gly Gly Gly Gly Ser Gly Gly Gly Ser Gly Gly Gly Ser
625                 630             635             640

Gly Gly Gly Gly Ser Gly Gly Gly Ser Gly Gly Gly Ser Gly
                645             650             655

Gly Gly Gly Ser Gly Gly Gly Ser Gly Gly Gly Ser Gly Gly
            660             665             670

Gly Gly Ser Gly Gly Gly Ser Gly Gly Gly Ser Gly Gly Gly
        675             680             685

Gly Ser Gly Gly Gly Ser Gly Gly Gly Ser Gly Gly Gly Gly
    690             695             700

Ser Gly Gly Gly Gly Ser Gly Gly Gly Ser Gly Gly Gly Ser
705                 710             715             720

Gly Gly Gly Gly Ser Gly Gly Gly Ser Gly Gly Gly Ser Gly
                725             730             735

Gly Gly Gly Ser Gly Gly Gly Ser Gly Gly Gly Ser Gly Gly
            740             745             750

Gly Gly Ser Gly Gly Gly Ser Gly Gly Gly Ser Gly Gly Gly
        755             760             765

Gly Ser Gly Gly Gly Ser Gly Gly Gly Ser Gly Gly Gly Gly
    770             775             780

Ser Gly Gly Gly Gly Ser Gly Gly Gly Ser Gly Gly Gly Ser
785                 790             795             800

<210> SEQ ID NO 158
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 158

Ser Gly Gly Ser Gly Gly Ser
1               5

<210> SEQ ID NO 159
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Gly Gly Ser Gly Gly Ser Gly Gly Ser Gly Gly Ser Gly Gly Gly
1               5                   10                  15
```

```
<210> SEQ ID NO 160
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Gly Gly Ser Gly Gly Ser Gly Gly Gly Ser Gly Gly Gly Gly Ser
1               5                   10                  15

<210> SEQ ID NO 161
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Gly Gly Ser Gly Gly Ser Gly Gly Ser Gly Gly Ser Gly Gly Ser Gly
1               5                   10                  15

Gly Ser

<210> SEQ ID NO 162
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Gly Gly Gly Gly Ser Gly Gly Gly Gly Ser Gly Gly Gly Gly Ser
1               5                   10                  15

<210> SEQ ID NO 163
<211> LENGTH: 200
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (3)..(200)
<223> OTHER INFORMATION: /replace=" "
<220> FEATURE:
<221> NAME/KEY: MISC_FEATURE
<222> LOCATION: (1)..(200)
<223> OTHER INFORMATION: /note="This region may encompass 1-100 "Gly
      Ala" repeating units"
<220> FEATURE:
<221> NAME/KEY: MISC_FEATURE
<222> LOCATION: (1)..(200)
<223> OTHER INFORMATION: /note="Variant residues given in the sequence
      have no preference with respect to those in the annotations
      for variant positions"

<400> SEQUENCE: 163

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
```

```
            20                  25                  30
Gly Ala Gly Ala Gly Ala Gly Ala Gly Ala Gly Ala Gly Ala Gly Ala
        35                  40                  45

Gly Ala Gly Ala Gly Ala Gly Ala Gly Ala Gly Ala Gly Ala Gly Ala
 50                  55                  60

Gly Ala Gly Ala Gly Ala Gly Ala Gly Ala Gly Ala Gly Ala Gly Ala
 65                  70                  75                  80

Gly Ala Gly Ala Gly Ala Gly Ala Gly Ala Gly Ala Gly Ala Gly Ala
            85                  90                  95

Gly Ala Gly Ala Gly Ala Gly Ala Gly Ala Gly Ala Gly Ala Gly Ala
           100                 105                 110

Gly Ala Gly Ala Gly Ala Gly Ala Gly Ala Gly Ala Gly Ala Gly Ala
       115                 120                 125

Gly Ala Gly Ala Gly Ala Gly Ala Gly Ala Gly Ala Gly Ala Gly Ala
    130                 135                 140

Gly Ala Gly Ala Gly Ala Gly Ala Gly Ala Gly Ala Gly Ala Gly Ala
145                 150                 155                 160

Gly Ala Gly Ala Gly Ala Gly Ala Gly Ala Gly Ala Gly Ala Gly Ala
           165                 170                 175

Gly Ala Gly Ala Gly Ala Gly Ala Gly Ala Gly Ala Gly Ala Gly Ala
        180                 185                 190

Gly Ala Gly Ala Gly Ala Gly Ala
         195                 200

<210> SEQ ID NO 164
<211> LENGTH: 400
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (5)..(400)
<223> OTHER INFORMATION: /replace=" "
<220> FEATURE:
<221> NAME/KEY: MISC_FEATURE
<222> LOCATION: (1)..(400)
<223> OTHER INFORMATION: /note="This sequence may encompass 1-100 "Gly
      Gly Gly Gly" repeating units"
<220> FEATURE:
<221> NAME/KEY: MISC_FEATURE
<222> LOCATION: (1)..(400)
<223> OTHER INFORMATION: /note="Variant residues given in the sequence
      have no preference with respect to those in the annotations
      for variant positions"

<400> SEQUENCE: 164

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
 50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
            85                  90                  95
```

Gly Gly Gly Gly Gly Gly Gly Gly Gly Gly Gly Gly Gly
             100                 105                 110
Gly Gly Gly Gly Gly Gly Gly Gly Gly Gly Gly Gly Gly
             115                 120                 125
Gly Gly Gly Gly Gly Gly Gly Gly Gly Gly Gly Gly Gly
             130                 135             140
Gly Gly Gly Gly Gly Gly Gly Gly Gly Gly Gly Gly Gly
145                  150                 155                 160
Gly Gly Gly Gly Gly Gly Gly Gly Gly Gly Gly Gly Gly
             165                 170                 175
Gly Gly Gly Gly Gly Gly Gly Gly Gly Gly Gly Gly Gly
             180                 185                 190
Gly Gly Gly Gly Gly Gly Gly Gly Gly Gly Gly Gly Gly
             195                 200                 205
Gly Gly Gly Gly Gly Gly Gly Gly Gly Gly Gly Gly Gly
             210                 215                 220
Gly Gly Gly Gly Gly Gly Gly Gly Gly Gly Gly Gly Gly
225                  230                 235                 240
Gly Gly Gly Gly Gly Gly Gly Gly Gly Gly Gly Gly Gly
             245                 250                 255
Gly Gly Gly Gly Gly Gly Gly Gly Gly Gly Gly Gly Gly
             260                 265                 270
Gly Gly Gly Gly Gly Gly Gly Gly Gly Gly Gly Gly Gly
             275                 280                 285
Gly Gly Gly Gly Gly Gly Gly Gly Gly Gly Gly Gly Gly
             290                 295                 300
Gly Gly Gly Gly Gly Gly Gly Gly Gly Gly Gly Gly Gly
305                  310                 315                 320
Gly Gly Gly Gly Gly Gly Gly Gly Gly Gly Gly Gly Gly
             325                 330                 335
Gly Gly Gly Gly Gly Gly Gly Gly Gly Gly Gly Gly Gly
             340                 345                 350
Gly Gly Gly Gly Gly Gly Gly Gly Gly Gly Gly Gly Gly
             355                 360                 365
Gly Gly Gly Gly Gly Gly Gly Gly Gly Gly Gly Gly Gly
             370                 375                 380
Gly Gly Gly Gly Gly Gly Gly Gly Gly Gly Gly Gly Gly
385                  390                 395                 400

<210> SEQ ID NO 165
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 165

Gly Gly Gly Gly Ser
1               5

<210> SEQ ID NO 166
<211> LENGTH: 10
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 166

Gly Gly Gly Gly Ser Gly Gly Gly Gly Ser
1               5                   10

<210> SEQ ID NO 167
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 167

Gly Gly Gly Gly Ser Gly Gly Gly Ser Gly Gly Gly Gly Ser
1               5                   10                  15

<210> SEQ ID NO 168
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Gly Gly Gly Gly Ser Gly Gly Gly Gly Ser Gly Gly Gly Gly Ser Gly
1               5                   10                  15

Gly Gly Gly Ser
            20

<210> SEQ ID NO 169
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 170
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 170

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Gly Ser
            20                  25                  30
```

```
<210> SEQ ID NO 171
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 171

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser
        35

<210> SEQ ID NO 172
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 172

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser
        35                  40

<210> SEQ ID NO 173
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 173

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser
        35                  40                  45

<210> SEQ ID NO 174
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
```

Gly Gly Ser Gly Gly Gly Gly Ser Gly Gly Gly Ser Gly Gly Gly
            35                  40                  45

Gly Ser
    50

<210> SEQ ID NO 175
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Ser Gly Gly Gly Gly Ser
1               5

<210> SEQ ID NO 176
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 176

Ser Gly Gly Gly Gly Ser Gly Gly Gly Gly Ser
1               5                   10

<210> SEQ ID NO 177
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Ser Gly Gly Gly Gly Ser Gly Gly Gly Gly Ser Gly Gly Gly Gly Ser
1               5                   10                  15

<210> SEQ ID NO 178
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 179
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ser Gly Gly Gly Gly Ser Gly Gly Gly Gly Ser Gly Gly Gly Ser
1               5                   10                  15

Gly Gly Gly Gly Ser Gly Gly Gly Gly Ser
            20                  25

<210> SEQ ID NO 180
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 181
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser
        35

<210> SEQ ID NO 182
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser
        35                  40

<210> SEQ ID NO 183
<211> LENGTH: 46
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Ser Gly Gly Gly Gly Ser Gly Gly Gly Ser Gly Gly Gly Gly Ser
1               5                   10                  15

Gly Gly Gly Gly Ser Gly Gly Gly Ser Gly Gly Gly Gly Ser Gly
                20                  25                  30

Gly Gly Gly Ser Gly Gly Gly Ser Gly Gly Gly Ser
            35                  40                  45

<210> SEQ ID NO 184
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 184

Ser Gly Gly Gly Gly Ser Gly Gly Gly Ser Gly Gly Gly Gly Ser
1               5                   10                  15

Gly Gly Gly Gly Ser Gly Gly Gly Ser Gly Gly Gly Gly Ser Gly
                20                  25                  30

Gly Gly Gly Ser Gly Gly Gly Ser Gly Gly Gly Ser Gly Gly
            35                  40                  45

Gly Gly Ser
    50

<210> SEQ ID NO 185
<211> LENGTH: 4
<212> TYPE: PRT
<213> ORGANISM: Unknown
<220> FEATURE:
<221> NAME/KEY: source
<223> OTHER INFORMATION: /note="Description of Unknown: FXIa cleavage
      site peptide"

<400> SEQUENCE: 185

Lys Leu Thr Arg
1

<210> SEQ ID NO 186
<211> LENGTH: 4
<212> TYPE: PRT
<213> ORGANISM: Unknown
<220> FEATURE:
<221> NAME/KEY: source
<223> OTHER INFORMATION: /note="Description of Unknown: FXIa cleavage
      site peptide"

<400> SEQUENCE: 186

Asp Phe Thr Arg
1

<210> SEQ ID NO 187
<211> LENGTH: 9
<212> TYPE: PRT
<213> ORGANISM: Unknown
<220> FEATURE:
<221> NAME/KEY: source
<223> OTHER INFORMATION: /note="Description of Unknown: FXIa cleavage
      site peptide"

<400> SEQUENCE: 187

Thr Gln Ser Phe Asn Asp Phe Thr Arg
1               5

<210> SEQ ID NO 188
<211> LENGTH: 10
<212> TYPE: PRT
<213> ORGANISM: Unknown
<220> FEATURE:
<221> NAME/KEY: source
<223> OTHER INFORMATION: /note="Description of Unknown: FXIa cleavage
      site peptide"

<400> SEQUENCE: 188

Ser Val Ser Gln Thr Ser Lys Leu Thr Arg
1               5                   10

<210> SEQ ID NO 189
<211> LENGTH: 10
<212> TYPE: PRT
<213> ORGANISM: Unknown
<220> FEATURE:
<221> NAME/KEY: source
<223> OTHER INFORMATION: /note="Description of Unknown: Thrombin
      cleavage site peptide"

<400> SEQUENCE: 189

Asp Phe Leu Ala Glu Gly Gly Gly Val Arg
1               5                   10

<210> SEQ ID NO 190
<211> LENGTH: 7
<212> TYPE: PRT
<213> ORGANISM: Unknown
<220> FEATURE:
<221> NAME/KEY: source
<223> OTHER INFORMATION: /note="Description of Unknown: Thrombin
      cleavage site peptide"

<400> SEQUENCE: 190

Thr Thr Lys Ile Lys Pro Arg
1               5

<210> SEQ ID NO 191
<211> LENGTH: 5
<212> TYPE: PRT
<213> ORGANISM: Unknown
<220> FEATURE:
<221> NAME/KEY: source
<223> OTHER INFORMATION: /note="Description of Unknown: Thrombin
      cleavage site peptide"

<400> SEQUENCE: 191

Leu Val Pro Arg Gly
1               5

<210> SEQ ID NO 192
<211> LENGTH: 5
<212> TYPE: PRT
<213> ORGANISM: Unknown
<220> FEATURE:
<221> NAME/KEY: source
<223> OTHER INFORMATION: /note="Description of Unknown: Thrombin
      cleavage site peptide"

<400> SEQUENCE: 192

Ala Leu Arg Pro Arg
1               5

<210> SEQ ID NO 193
<211> LENGTH: 10

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Phe Gly Gly Gly Thr Lys Leu Glu Ile Lys
1               5                   10

<210> SEQ ID NO 194
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 194

Met Asp Met Arg Val Pro Ala Gln Leu Leu Gly Leu Leu Leu Leu Trp
1               5                   10                  15

Leu Pro Gly Ala Arg Cys
            20

<210> SEQ ID NO 195
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Gly Ser Pro Gly Thr Ser Glu Ser Ala Thr Pro Glu Ser Gly Pro Gly
1               5                   10                  15

Ser Glu Pro Ala Thr Ser Gly Ser Glu Thr Pro
            20                  25

<210> SEQ ID NO 196
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Gly Ser Ser Ser
1

<210> SEQ ID NO 197
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Gly Ala Tyr
```

```
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
            100                 105                 110

Leu Val Thr Val Ser Ser
        115

<210> SEQ ID NO 198
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 198

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Glu
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
            100                 105                 110

Leu Val Thr Val Ser Ser
        115

<210> SEQ ID NO 199
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60
```

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
            100                 105                 110

Leu Val Thr Val Ser Phe
        115

<210> SEQ ID NO 200
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 200

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Val Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
            100                 105                 110

Leu Val Thr Val Ser Ser
        115

<210> SEQ ID NO 201
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 201

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

```
Arg Gly Gly Asp Tyr Ser Tyr Ala Leu Asp Tyr Trp Gly Arg Gly Thr
                100                 105                 110

Leu Val Thr Val Ser Ser
        115

<210> SEQ ID NO 202
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 202

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
                100                 105                 110

Leu Val Thr Val Ser Ser
        115

<210> SEQ ID NO 203
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 203

Glu Val Gln Leu Val Glu Cys Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
                100                 105                 110

Leu Val Thr Val Ser Ser
        115
```

<210> SEQ ID NO 204
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 204

Glu Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Glu Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
            100                 105                 110

Leu Val Thr Val Ser Ser
        115

<210> SEQ ID NO 205
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 205

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Asp Gly Thr Thr Tyr Tyr Pro Asp Ser Val Lys
    50                  55                  60

Arg Gln Phe Thr Ile Ser Arg Asp Asn Ala Arg Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Ser Tyr Ala Leu Asp Tyr Trp Gly Gln Gly Thr
            100                 105                 110

Leu Val Thr Val Ser Ser
        115

<210> SEQ ID NO 206
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 206

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Asp Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 207
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 207

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 208
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 208

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Ala Tyr
            20                  25                  30

Ala Met Ser Trp Val Arg Gln Ala Pro Gly Glu Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 209
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 209

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Glu Gly Leu Val Trp Val
        35                  40                  45

Ala Gly Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 210
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 210

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Gly Ile Ser Ser Gly Gly Thr Thr Tyr Tyr Pro Asp Ser Val Lys

```
                    50                  55                  60
Arg Gln Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Thr
                    85                  90                  95

Arg Gly Gly Asp Tyr Gly Tyr Ala Leu Asp Tyr Trp Gly Gln Gly Thr
                100                 105                 110

Leu Val Thr Val Ser Ser
            115

<210> SEQ ID NO 211
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 211

Glu Met Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ala Tyr
                20                  25                  30

Ala Met Ser Trp Val Arg Gln Ala Pro Gly Lys Gly Leu Val Trp Val
            35                  40                  45

Ala Ser Ile Ser Ser Gly Gly Thr Thr Tyr Tyr Pro Asp Ser Val Lys
        50                  55                  60

Arg Gln Phe Thr Ile Ser Arg Asp Asn Ala Lys Asn Thr Leu Tyr Leu
 65                  70                  75                  80

Gln Met Asn Ser Leu Arg Ala Glu Asp Thr Ala Val Tyr Tyr Cys Thr
                    85                  90                  95

Arg Gly Gly Asp Tyr Gly Tyr Ala Leu Asp Tyr Trp Gly Gln Gly Thr
                100                 105                 110

Leu Val Thr Val Ser Ser
            115

<210> SEQ ID NO 212
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 212

Gly Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ala Tyr
                20                  25                  30

Ala Met Ser Trp Val Arg Gln Ala Pro Gly Lys Gly Leu Val Trp Val
            35                  40                  45

Ala Ser Ile Ser Ser Gly Gly Thr Thr Tyr Tyr Pro Asp Ser Val Lys
        50                  55                  60

Arg Gln Phe Thr Ile Ser Arg Asp Asp Ala Lys Asn Thr Leu Tyr Leu
 65                  70                  75                  80

Gln Met Asn Ser Leu Arg Ala Glu Asp Thr Ala Val Tyr Tyr Cys Thr
                    85                  90                  95
```

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 213
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 213

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asp Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 214
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 214

Glu Ala Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 215
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 215

Gly Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Ala
            100                 105                 110

Leu Val Thr Val Ser Ser
        115

<210> SEQ ID NO 216
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 216

Gly Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 217
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 217

Glu Val Gln Leu Val Glu Ser Gly Gly Gly Leu Val Glu Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Lys Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 218
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 218

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ala Tyr
            20                  25                  30

Ala Met Ser Trp Val Arg Gln Ala Pro Gly Glu Gly Leu Val Trp Val
        35                  40                  45

Ala Ser Ile Ser Ser Gly Gly Thr Thr Tyr Tyr Pro Asp Ser Val Lys
    50                  55                  60

Arg Gln Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Gly Asp Tyr Gly Tyr Ala Leu Asp Tyr Trp Gly Gln Gly Thr
            100                 105                 110

Leu Val Thr Val Ser Ser
        115

<210> SEQ ID NO 219
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 219
gaggtgcagc tggtggagtc tggaggaggc ttggtaaagc ctggaggatc cctgagactc     60

```
tcctgtgcag cctctggatt cacctttggc gcctatgcca tgagctgggt ccgccaggct    120
ccagggaagg ggctggtctg ggtcgctagc attagtagtg gtggtaccac atactaccca    180
gactccgtga agaggcagtt caccatctcc agagacaatg ccaagaacac gctgtatctg    240
caaatgaaca gcctgagagc cgaggacaca gccgtatatt actgtaccag aggaggggat    300
tatagctacg ctctcgacta ctggggccag ggaaccctgg tcaccgtctc ctca          354
```

<210> SEQ ID NO 220
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 220

```
gaggtgcagc tggtggagtc tggaggaggc ttggtaaagc ctggaggatc cctgagactc    60
tcctgtgcag cctctggatt cacctttagc gcctatgcca tgagctgggt ccgccaggct    120
ccagggaagg ggctggtctg ggtcgctagc attagtagtg gtggtaccac atactaccca    180
gactccgtgg agaggcagtt caccatctcc agagacaatg ccaagaacac gctgtatctg    240
caaatgaaca gcctgagagc cgaggacaca gccgtatatt actgtaccag aggaggggat    300
tatagctacg ctctcgacta ctggggccag ggaaccctgg tcaccgtctc ctca          354
```

<210> SEQ ID NO 221
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 221

```
gaggtgcagc tggtggagtc tggaggaggc ttggtaaagc ctggaggatc cctgagactc    60
tcctgtgcag cctctggatt cacctttagc gcctatgcca tgagctgggt ccgccaggct    120
ccagggaagg ggctggtctg ggtcgctagc attagtagtg gtggtaccac atactaccca    180
gactccgtga agaggcagtt caccatctcc agagacaatg ccaagaacac gctgtatctg    240
caaatgaaca gcctgagagc cgaggacaca gccgtatatt actgtaccag aggaggggat    300
tatagctacg ctctcgacta ctggggccag ggaaccctgg tcaccgtctc cttcagc       357
```

<210> SEQ ID NO 222
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 222

```
gaggtgcagc tggtggagtc tggaggaggc ttggtaaagc ctggaggatc cctgagactc    60
tcctgtgcag cctctggatt cacctttagc gcctatgcca tgagctgggt ccgccaggct    120
ccagggaagg ggctggtctg ggtcgctagc attagtagtg gtggtaccac atactaccca    180
gactccgtga agaggcagtt caccatctcc agagacaatg ccaagaacac gctgtatctg    240
caagtgaaca gcctgagagc cgaggacaca gccgtatatt actgtaccag aggaggggat    300
```
tatagctacg ctctcgacta ctggggccag ggaaccctgg tcaccgtctc ctca      354

```
<210> SEQ ID NO 223
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 223
```
gaggtgcagc tggtggagtc tggaggaggc ttggtaaagc ctggaggatc cctgagactc      60
tcctgtgcag cctctggatt cacctttagc gcctatgcca tgagctgggt ccgccaggct      120
ccagggaagg ggctggtctg ggtcgctagc attagtagtg gtggtaccac atactaccca      180
gactccgtga agaggcagtt caccatctcc agagacaatg ccaagaacac gctgtatttg      240
caaatgaaca gcctgagagc cgaggacaca gccgtatatt actgtaccag aggaggggat      300
tatagctacg ctctcgacta ctggggccgg ggaaccctgg tcaccgtctc ctca      354

```
<210> SEQ ID NO 224
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
```
gaggtgcagc tggtggagtc tggaggaggc ttggtaaagc ctggaggatc cctgagactc      60
tcctgtgcag cctctggatt cacctttagc gcctatgcca tgagctgggt ccgccaggct      120
ccagggaagg ggctggtctg ggtcgctagc attagtagtg gtggtaccac atactaccca      180
gactccgtga agaggcagtt caccatctcc agagacaatg ccaagaacac gctgtatctg      240
caaatgaaca gcctgagagc cgaggacaca gccgtatatt actgtaccag aggaggggat      300
tatagctacg ctctcgacta ctggggccag ggaaccctgg tcaccgtctc ctca      354

```
<210> SEQ ID NO 225
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 225
```
gaggtgcagc tggtggagtg tggaggaggc ttggtaaagc ctggaggatc cctgagactc      60
tcctgtgcag cctctggatt cacctttagc gcctatgcca tgagctgggt ccgccaggct      120
ccagggaagg ggctggtctg ggtcgctagc attagtagtg gtggtaccac atactaccca      180
gactccgtga agaggcagtt caccatctcc agagacaatg ccaagaacac gctgtatctg      240
caaatgaaca gcctgagagc cgaggacaca gccgtatatt actgtaccag aggaggggat      300
tatagctacg ctctcgacta ctggggccag ggaaccctgg tcaccgtctc ctca      354

```
<210> SEQ ID NO 226
<211> LENGTH: 354
<212> TYPE: DNA
```

<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 226

| | | | | | |
|---|---|---|---|---|---|
| gaggtgcagc | tggtggagtc | tggaggaggc | ttggtaaagc | ctggagaatc | cctgagactc | 60 |
| tcctgtgcag | cctcgggatt | cacctttagc | gcctatgcca | tgagctgggt | ccgccaggct | 120 |
| ccaggggagg | ggctggtctg | ggtcgctagc | attagtagtg | gtggtaccac | atactaccca | 180 |
| gactccgtga | agaggcagtt | caccatctcc | agagacaatg | ccaagaacac | gctgtatctg | 240 |
| caaatgaaca | gcctgagagc | cgaggacaca | gccgtatatt | actgtaccag | aggaggggat | 300 |
| tatagctacg | ctctcgacta | ctggggccag | ggaaccctgg | tcaccgtctc | ctca | 354 |

<210> SEQ ID NO 227
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 227

| | | | | | |
|---|---|---|---|---|---|
| gaggtgcagc | tggtggagtc | tggaggaggc | ttggtaaagc | ctggaggatc | cctgagactc | 60 |
| tcctgtgcag | cctctggatt | cacctttagc | gcctatgcca | tgagctgggt | ccgccaggct | 120 |
| ccagggaagg | ggctggtctg | ggtcgctagc | attagtagtg | atggtaccac | atactaccca | 180 |
| gactccgtga | agaggcagtt | caccatctcc | agagacaatg | ccaggaacac | gctgtatctg | 240 |
| caaatgaaca | gcctgagagc | cgaggacaca | gccgtatatt | actgtaccag | aggaggggac | 300 |
| tatagctacg | ctctcgacta | ctggggccag | gggaccctgg | tcaccgtctc | ctca | 354 |

<210> SEQ ID NO 228
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 228

| | | | | | |
|---|---|---|---|---|---|
| gaggtgcagc | tggtggagtc | tggaggaggc | ttggtaaagc | ctggaggatc | cctgagactc | 60 |
| tcctgtgcag | cctctggatt | cacctttagc | gcctatgcca | tgagctgggt | ccgccaggct | 120 |
| ccagggaagg | ggctggtctg | ggtcgctagc | attagtagtg | gtggtaccac | agactaccca | 180 |
| gactccgtga | agaggcagtt | caccatctcc | agagacaatg | ccaagaacac | gctgtatctg | 240 |
| caaatgaaca | gcctgagagc | cgaggacaca | gccgtatatt | actgtaccag | aggaggggat | 300 |
| tatggctacg | ctctcgacta | ctggggccag | ggaaccctgg | tcaccgtctc | ctca | 354 |

<210> SEQ ID NO 229
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 229

```
gaggtgcagc tggtggagtc tggaggaggc ttggtaaagc ctggaggatc cctgagactc     60
tcctgtgcag cctctggatt cacctttaac gcctatgcaa tgagctgggt ccgccaggct    120
ccagggaagg ggctggtctg ggtcgctagc attagtagtg gtggtaccac atactaccca    180
gactccgtga agaggcagtt caccatctcc agagacaatg ccaagaacac gctgtatctg    240
caaatgaaca gcctgagagc cgaggacaca gccgtatatt actgtaccag aggaggggat    300
tatggctacg ctctcgacta ctggggccag ggaaccctgg tcaccgtctc ctca          354
```

<210> SEQ ID NO 230
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230

```
gaggtgcagc tggtggagtc tggaggaggc ttggtaaagc ctggaggatc cctgagactc     60
tcctgtgcag cctctggatt cacctttaac gcctatgcca tgagctgggt ccgccaggct    120
ccaggggagg ggctggtctg ggtcgctagc attagtagtg gtggtaccac atactaccca    180
gactccgtga agaggcagtt caccatctcc agagacaatg ccaagaacac gctgtatctg    240
caaatgaaca gcctgagagc cgaggacaca gccgtatatt actgcaccag aggaggggat    300
tatggctacg ctctcgacta ctggggccag ggaaccctgg tcaccgtctc ctca          354
```

<210> SEQ ID NO 231
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 231

```
gaggtgcagc tggtggagtc tggaggaggc ttggtaaagc ctggaggatc cctgagactc     60
tcctgtgcag cctctggatt cacctttagc gcctatgcca tgagctgggt ccgccaggct    120
ccaggggagg ggctggtctg ggtcgctggc attagtagtg gtggtaccac atactaccca    180
gactccgtga agaggcagtt caccatctcc agagacaatg ccaagaacac gctgtatctg    240
caaatgaaca gcctgagagc cgaggacaca gccgtatatt actgtaccag aggaggggat    300
tatggctacg ctctcgacta ctggggccag ggaaccctgg tcaccgtctc ctca          354
```

<210> SEQ ID NO 232
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 232

```
gaggtgcagc tggtggagtc tggaggaggc ttggtaaagc ctggaggatc cctgagactc     60
tcctgtgcag cctctggatt cacctttagc gcctatgcca tgagctgggt ccgccaggct    120
ccagggaagg ggctggtctg ggtcgctggc attagtagtg gtggtaccac atactaccca    180
```

```
gactccgtga agaggcagtt caccatctcc agagacaatg ccaagaacac gctgtatctg      240
caaatgaaca gcctgagagc cgaggacaca gccgtatatt actgtaccag aggaggggat      300
tatggctacg ctctcgacta ctggggccag ggaaccctgg tcaccgtctc ctca            354
```

<210> SEQ ID NO 233
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 233

```
gagatgcagc tggtggagtc tggaggaggc ttggtaaagc ctggaggatc cctgagactc      60
tcctgtgcag cctctggatt cacctttagc gcctatgcca tgagctgggt ccgccaggct     120
ccagggaagg ggctggtctg ggtcgctagc attagtagtg gtggtaccac atactaccca     180
gactccgtga agaggcagtt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca           354
```

<210> SEQ ID NO 234
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 234

```
ggggtgcagc tggtggagtc tggaggaggc ttggtaaagc ctggaggatc cctgagactc      60
tcctgtgcag cctctggatt cacctttagc gcctatgcca tgagctgggt ccgccaggct     120
ccagggaagg ggctggtctg ggtcgctagc attagtagtg gtggtaccac atactaccca     180
gactccgtga agaggcagtt caccatctcc agagacgatg ccaagaacac gctgtatctg     240
caaatgaaca gcctgagagc cgaggacaca gccgtatatt actgtactag aggggggat      300 tatggctacg ctctcgacta ctggggccag ggaaccctgg tcaccgtctc ctca           354
```

<210> SEQ ID NO 235
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 235

```
gaggtgcagc tggtggagtc tggaggaggc ttggtaaagc ctggaggatc cctgagactc      60
tcctgtgcag cctctggatt cacctttagc gcctatgcca tgagctgggt ccgccaggct     120
ccagggaagg ggctggtctg ggtcgctagc attagtagtg gtggtaccac atactaccca     180
gactccgtga agaggcagtt caccatctcc agagacgatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca           354
```

<210> SEQ ID NO 236
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 236
gaggcgcagc tggtggagtc tggaggaggc ttggtgaagc ctggaggatc cctgagactc      60
tcctgtgcag cctctggatt cacctttagc gcctatgcca tgagctgggt ccgccaggct     120
ccagggaagg ggctggtctg ggtcgctagc attagtagtg gtggtaccac atactaccca     180
gactccgtga agaggcagtt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca           354

<210> SEQ ID NO 237
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 237
ggggtgcagc tggtggagtc tggaggaggc ttggtaaagc ctggaggatc cctgagactc      60
tcctgtgcag cctctggatt cacctttagc gcctatgcca tgagctgggt ccgccaggct     120
ccagggaagg ggctggtctg ggtcgctagc attagtagtg gtggtaccac atactaccca     180
gactccgtga agaggcagtt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggagccctgg tcaccgtctc ctca           354

<210> SEQ ID NO 238
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 238
ggggtgcagc tggtggagtc tggaggaggc ttggtaaagc ctggaggatc cctgagactc      60
tcctgtgcag cctctggatt cacctttagc gcctatgcca tgagctgggt ccgccaggct     120
ccagggaagg ggctggtctg ggtcgctagc attagtagtg gtggtaccac atactaccca     180
gactccgtga agaggcagtt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca           354

<210> SEQ ID NO 239
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 239

```
gaggtgcagc tggtggagtc tggaggaggc ttggtagagc ctggaggatc cctgagactc      60
tcctgtgcag cctctggatt cacctttagc gcctacgcca tgagctgggt ccgccaggct     120
ccagggaagg ggctggtctg ggtcgctagc attagtagtg gcggtaccac atactaccca     180
gactccgtga agaggcagtt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca            354
```

<210> SEQ ID NO 240
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 240

```
gaggtgcagc tggtggagtc tggaggaggc ttggtaaagc ctggaggatc cctgagactc      60
tcctgtgcag cctctggatt cacctttagc gcctatgcca tgagctgggt ccgccaggct     120
ccaggggagg ggctggtctg ggtcgctagc attagtagtg gtggtaccac atactaccca     180
gactccgtga agaggcagtt caccatctcc agagacaatg ccaagaacac gctgtatctg     240
caaatgaaca gcctgagagc cgaggacaca gccgtatatt actgtaccag aggaggggat     300
tatggctacg ctctcgacta ctggggccag ggaaccctgg tcaccgtctc ctca            354
```

<210> SEQ ID NO 241
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 241

```
Ser Ile Ser Ser Gly Gly Thr Thr Tyr Tyr Pro Asp Ser Val Glu Arg
1               5                   10                  15
```

<210> SEQ ID NO 242
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 242

```
Ser Ile Ser Ser Asp Gly Thr Thr Tyr Tyr Pro Asp Ser Val Lys Arg
1               5                   10                  15
```

<210> SEQ ID NO 243
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 243

Ser Ile Ser Ser Gly Gly Thr Thr Asp Tyr Pro Asp Ser Val Lys Arg
1               5                   10                  15

<210> SEQ ID NO 244
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Gly Ile Ser Ser Gly Gly Thr Thr Tyr Tyr Pro Asp Ser Val Lys Arg
1               5                   10                  15

<210> SEQ ID NO 245
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Gly Gly Asp Tyr Ser Tyr Ala Leu Asp Tyr
1               5                   10

<210> SEQ ID NO 246
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 246

His His His His His His
1               5

<210> SEQ ID NO 247
<211> LENGTH: 940
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 247

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly

```
                    85                  90                  95
Gly Cys Glu Gln Tyr Cys Ser Asp His Thr Gly Thr Lys Arg Ser Cys
                100                 105                 110

Arg Cys His Glu Gly Tyr Ser Leu Leu Ala Asp Gly Val Ser Cys Thr
                115                 120                 125

Pro Thr Val Glu Tyr Pro Cys Gly Lys Ile Pro Ile Leu Glu Lys Arg
            130                 135                 140

Asn Ala Ser Lys Pro Gln Gly Arg Ile Val Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
                180                 185                 190

His Cys Phe Asp Lys Ile Lys Asn Trp Arg Asn Leu Ile Ala Val Leu
                195                 200                 205

Gly Glu His Asp Leu Ser Glu His Asp Gly Asp Glu Gln Ser Arg Arg
                210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
                260                 265                 270

Leu Ala Phe Val Arg Phe Ser Leu Val Ser Gly Trp Gly Gln Leu Leu
                275                 280                 285

Asp Arg Gly Ala Thr Ala Leu Glu Leu Met Val Leu Asn Val Pro Arg
                290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
                355                 360                 365

Ala Thr Val Gly His Phe Gly Val Tyr Thr Arg Val Ser Gln Tyr Ile
                370                 375                 380

Glu Trp Leu Gln Lys Leu Met Arg Ser Glu Pro Arg Pro Gly Val Leu
385                 390                 395                 400

Leu Arg Ala Pro Phe Pro Gly Ser Pro Gly Thr Ser Glu Ser Ala Thr
                405                 410                 415

Pro Glu Ser Gly Pro Gly Ser Glu Pro Ala Thr Ser Gly Ser Glu Thr
                420                 425                 430

Pro Gly Thr Ser Glu Ser Ala Thr Pro Glu Ser Gly Pro Gly Ser Glu
                435                 440                 445

Pro Ala Thr Ser Gly Ser Glu Thr Pro Gly Thr Ser Glu Ser Ala Thr
                450                 455                 460

Pro Glu Ser Gly Pro Gly Thr Ser Thr Glu Pro Ser Glu Gly Ser Ala
465                 470                 475                 480

Pro Gly Ser Pro Ala Gly Ser Pro Thr Ser Thr Glu Glu Gly Thr Ser
                485                 490                 495

Glu Ser Ala Thr Pro Glu Ser Gly Pro Gly Ser Glu Pro Ala Thr Ser
                500                 505                 510
```

-continued

```
Gly Ser Glu Thr Pro Gly Thr Ser Glu Ser Ala Thr Pro Glu Ser Gly
            515                 520                 525

Pro Gly Ser Pro Ala Gly Ser Pro Thr Ser Thr Glu Glu Gly Ser Pro
        530                 535                 540

Ala Gly Ser Pro Thr Ser Thr Glu Glu Gly Thr Ser Thr Glu Pro Ser
545                 550                 555                 560

Glu Gly Ser Ala Pro Gly Thr Ser Glu Ser Ala Thr Pro Glu Ser Gly
                565                 570                 575

Pro Gly Thr Ser Glu Ser Ala Thr Pro Glu Ser Gly Pro Gly Thr Ser
            580                 585                 590

Glu Ser Ala Thr Pro Glu Ser Gly Pro Gly Ser Glu Pro Ala Thr Ser
        595                 600                 605

Gly Ser Glu Thr Pro Gly Ser Glu Pro Ala Thr Ser Gly Ser Glu Thr
    610                 615                 620

Pro Gly Ser Pro Ala Gly Ser Pro Thr Ser Thr Glu Glu Gly Thr Ser
625                 630                 635                 640

Thr Glu Pro Ser Glu Gly Ser Ala Pro Gly Ser Thr Glu Pro Ser
                645                 650                 655

Glu Gly Ser Ala Pro Gly Ser Glu Pro Ala Thr Ser Gly Ser Glu Thr
            660                 665                 670

Pro Gly Thr Ser Glu Ser Ala Thr Pro Glu Ser Gly Pro Gly Thr Ser
        675                 680                 685

Thr Glu Pro Ser Glu Gly Ser Ala Pro Gly Gly Gly Ser Gly Gly
    690                 695                 700

Gly Gly Ser Gly Gly Gly Ser Gly Gly Gly Ser Gly Gly Gly
705                 710                 715                 720

Gly Ser Gly Gly Gly Ser Glu Ile Val Met Thr Gln Ser Pro Ala
                725                 730                 735

Thr Leu Ser Val Ser Pro Gly Glu Arg Ala Thr Leu Ser Cys Arg Ala
            740                 745                 750

Ser Ser Ser Val Asn Tyr Met Tyr Trp Tyr Gln Gln Lys Pro Gly Gln
        755                 760                 765

Ala Pro Arg Leu Leu Ile Tyr Tyr Thr Ser Asn Leu Ala Pro Gly Ile
    770                 775                 780

Pro Ala Arg Phe Ser Gly Ser Gly Ser Gly Thr Glu Phe Thr Leu Thr
785                 790                 795                 800

Ile Ser Ser Leu Gln Ser Glu Asp Phe Ala Val Tyr Tyr Cys Gln Gln
                805                 810                 815

Phe Ser Ser Ser Pro Trp Thr Phe Gly Gln Gly Thr Lys Val Glu Ile
            820                 825                 830

Lys Arg Thr Val Ala Ala Pro Ser Val Phe Ile Phe Pro Pro Ser Asp
        835                 840                 845

Glu Gln Leu Lys Ser Gly Thr Ala Ser Val Val Cys Leu Leu Asn Asn
    850                 855                 860

Phe Tyr Pro Arg Glu Ala Lys Val Gln Trp Lys Val Asp Asn Ala Leu
865                 870                 875                 880

Gln Ser Gly Asn Ser Gln Glu Ser Val Thr Glu Gln Asp Ser Lys Asp
                885                 890                 895

Ser Thr Tyr Ser Leu Ser Ser Thr Leu Thr Leu Ser Lys Ala Asp Tyr
            900                 905                 910

Glu Lys His Lys Val Tyr Ala Cys Glu Val Thr His Gln Gly Leu Ser
        915                 920                 925
```

```
Ser Pro Val Thr Lys Ser Phe Asn Arg Gly Glu Cys
    930                 935                 940

<210> SEQ ID NO 248
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(4)
<223> OTHER INFORMATION: /replace=" "
<220> FEATURE:
<221> NAME/KEY: VARIANT
<222> LOCATION: (5)..(5)
<223> OTHER INFORMATION: /replace=" "
<220> FEATURE:
<221> NAME/KEY: VARIANT
<222> LOCATION: (7)..(9)
<223> OTHER INFORMATION: /replace=" "
<220> FEATURE:
<221> NAME/KEY: VARIANT
<222> LOCATION: (10)..(10)
<223> OTHER INFORMATION: /replace=" "
<220> FEATURE:
<221> NAME/KEY: VARIANT
<222> LOCATION: (12)..(14)
<223> OTHER INFORMATION: /replace=" "
<220> FEATURE:
<221> NAME/KEY: VARIANT
<222> LOCATION: (15)..(15)
<223> OTHER INFORMATION: /replace=" "
<220> FEATURE:
<221> NAME/KEY: VARIANT
<222> LOCATION: (17)..(19)
<223> OTHER INFORMATION: /replace=" "
<220> FEATURE:
<221> NAME/KEY: VARIANT
<222> LOCATION: (20)..(20)
<223> OTHER INFORMATION: /replace=" "
<220> FEATURE:
<221> NAME/KEY: VARIANT
<222> LOCATION: (22)..(24)
<223> OTHER INFORMATION: /replace=" "
<220> FEATURE:
<221> NAME/KEY: VARIANT
<222> LOCATION: (25)..(25)
<223> OTHER INFORMATION: /replace=" "
<220> FEATURE:
<221> NAME/KEY: MISC_FEATURE
<222> LOCATION: (1)..(25)
<223> OTHER INFORMATION: /note="This sequence may encompass 1-5
      "(Gly)x-(Ser)y" Repeating units, wherein x is 1-4 and y is 0-1;
      See specification as filed for detailed description of
      substitutions and preferred embodiments"
<220> FEATURE:
<221> NAME/KEY: MISC_FEATURE
<222> LOCATION: (1)..(25)
<223> OTHER INFORMATION: /note="Variant residues given in the sequence
      have no preference with respect to those in the annotations
      for variant positions"

<400> SEQUENCE: 248

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 249
<211> LENGTH: 100
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(100)
<223> OTHER INFORMATION: /replace=" "
<220> FEATURE:
<221> NAME/KEY: MISC_FEATURE
<222> LOCATION: (1)..(100)
<223> OTHER INFORMATION: /note="This region may encompass 1-100 "Gly"
      repeating units"
<220> FEATURE:
<221> NAME/KEY: MISC_FEATURE
<222> LOCATION: (1)..(100)
<223> OTHER INFORMATION: /note="Variant residues given in the sequence
      have no preference with respect to those in the annotations
      for variant positions"

<400> SEQUENCE: 249

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
                85                  90                  95

Gly Gly Gly Gly
            100

<210> SEQ ID NO 250
<211> LENGTH: 500
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (6)..(500)
<223> OTHER INFORMATION: /replace=" "
<220> FEATURE:
<221> NAME/KEY: MISC_FEATURE
<222> LOCATION: (1)..(500)
<223> OTHER INFORMATION: /note="This region may encompass 1-100 "Gly Gly
      Gly Gly Ser" repeating units"
<220> FEATURE:
<221> NAME/KEY: MISC_FEATURE
<222> LOCATION: (1)..(500)
<223> OTHER INFORMATION: /note="Variant residues given in the sequence
      have no preference with respect to those in the annotations
      for variant positions"

<400> SEQUENCE: 250

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45
```

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser Gly Gly Gly Gly Ser Gly Gly Gly Gly Ser Gly Gly
                100                 105                 110

Gly Gly Ser Gly Gly Gly Gly Ser Gly Gly Gly Gly Ser Gly Gly Gly
            115                 120                 125

Gly Ser Gly Gly Gly Gly Ser Gly Gly Gly Gly Ser Gly Gly Gly Gly
        130                 135                 140

Ser Gly Gly Gly Gly Ser Gly Gly Gly Gly Ser Gly Gly Gly Gly Ser
145                 150                 155                 160

Gly Gly Gly Gly Ser Gly Gly Gly Gly Ser Gly Gly Gly Gly Ser Gly
                165                 170                 175

Gly Gly Gly Ser Gly Gly Gly Gly Ser Gly Gly Gly Gly Ser Gly Gly
                180                 185                 190

Gly Gly Ser Gly Gly Gly Gly Ser Gly Gly Gly Gly Ser Gly Gly Gly
            195                 200                 205

Gly Ser Gly Gly Gly Gly Ser Gly Gly Gly Gly Ser Gly Gly Gly Gly
        210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Gly Gly Gly Gly Ser Gly Gly
                260                 265                 270

Gly Gly Ser Gly Gly Gly Gly Ser Gly Gly Gly Gly Ser Gly Gly Gly
            275                 280                 285

Gly Ser Gly Gly Gly Gly Ser Gly Gly Gly Gly Ser Gly Gly Gly Gly
        290                 295                 300

Ser Gly Gly Gly Gly Ser Gly Gly Gly Gly Ser Gly Gly Gly Gly Ser
305                 310                 315                 320

Gly Gly Gly Gly Ser Gly Gly Gly Gly Ser Gly Gly Gly Gly Ser Gly
                325                 330                 335

Gly Gly Gly Ser Gly Gly Gly Gly Ser Gly Gly Gly Gly Ser Gly Gly
                340                 345                 350

Gly Gly Ser Gly Gly Gly Gly Ser Gly Gly Gly Gly Ser Gly Gly Gly
            355                 360                 365

Gly Ser Gly Gly Gly Gly Ser Gly Gly Gly Gly Ser Gly Gly Gly Gly
        370                 375                 380

Ser Gly Gly Gly Gly Ser Gly Gly Gly Gly Ser Gly Gly Gly Gly Ser
385                 390                 395                 400

Gly Gly Gly Gly Ser Gly Gly Gly Gly Ser Gly Gly Gly Gly Ser Gly
                405                 410                 415

Gly Gly Gly Ser Gly Gly Gly Gly Ser Gly Gly Gly Gly Ser Gly Gly
                420                 425                 430

Gly Gly Ser Gly Gly Gly Gly Ser Gly Gly Gly Gly Ser Gly Gly Gly
            435                 440                 445

Gly Ser Gly Gly Gly Gly Ser Gly Gly Gly Gly Ser Gly Gly Gly Gly
        450                 455                 460

Ser Gly Gly Gly Gly Ser Gly Gly Gly Gly Ser Gly Gly Gly Gly Ser

```
465                 470                 475                 480
Gly Gly Gly Gly Ser Gly Gly Gly Ser Gly Gly Gly Ser Gly
                485                 490                 495

Gly Gly Gly Ser
            500

<210> SEQ ID NO 251
<211> LENGTH: 501
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (7)..(501)
<223> OTHER INFORMATION: /replace=" "
<220> FEATURE:
<221> NAME/KEY: MISC_FEATURE
<222> LOCATION: (2)..(501)
<223> OTHER INFORMATION: /note="This region may encompass 1-100 "Gly Gly
      Gly Gly Ser" repeating units"
<220> FEATURE:
<221> NAME/KEY: MISC_FEATURE
<222> LOCATION: (1)..(501)
<223> OTHER INFORMATION: /note="Variant residues given in the sequence
      have no preference with respect to those in the annotations
      for variant positions"

<400> SEQUENCE: 251

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
                20                  25                  30

Gly Gly Gly Ser Gly Gly Gly Gly Ser Gly Gly Gly Gly Ser Gly Gly
            35                  40                  45

Gly Gly Ser Gly Gly Gly Gly Ser Gly Gly Gly Gly Ser Gly Gly Gly
        50                  55                  60

Gly Ser Gly Gly Gly Gly Ser Gly Gly Gly Gly Ser Gly Gly Gly Gly
65                  70                  75                  80

Ser Gly Gly Gly Gly Ser Gly Gly Gly Gly Ser Gly Gly Gly Gly Ser
                85                  90                  95

Gly Gly Gly Gly Ser Gly Gly Gly Gly Ser Gly Gly Gly Gly Ser Gly
                100                 105                 110

Gly Gly Gly Ser Gly Gly Gly Gly Ser Gly Gly Gly Gly Ser Gly Gly
            115                 120                 125

Gly Gly Ser Gly Gly Gly Gly Ser Gly Gly Gly Gly Ser Gly Gly Gly
        130                 135                 140

Gly Ser Gly Gly Gly Gly Ser Gly Gly Gly Gly Ser Gly Gly Gly Gly
145                 150                 155                 160

Ser Gly Gly Gly Gly Ser Gly Gly Gly Gly Ser Gly Gly Gly Gly Ser
                165                 170                 175

Gly Gly Gly Gly Ser Gly Gly Gly Gly Ser Gly Gly Gly Gly Ser Gly
                180                 185                 190

Gly Gly Gly Ser Gly Gly Gly Gly Ser Gly Gly Gly Gly Ser Gly Gly
            195                 200                 205

Gly Gly Ser Gly Gly Gly Gly Ser Gly Gly Gly Gly Ser Gly Gly Gly
        210                 215                 220

Gly Ser Gly Gly Gly Gly Ser Gly Gly Gly Gly Ser Gly Gly Gly Gly
225                 230                 235                 240
```

Ser Gly Gly Gly Gly Ser Gly Gly Gly Gly Ser Gly Gly Gly Ser
            245                 250                 255

Gly Gly Gly Gly Ser Gly Gly Gly Gly Ser Gly Gly Gly Gly Ser Gly
            260                 265                 270

Gly Gly Gly Ser Gly Gly Gly Gly Ser Gly Gly Gly Gly Ser Gly Gly
        275                 280                 285

Gly Gly Ser Gly Gly Gly Gly Ser Gly Gly Gly Gly Ser Gly Gly Gly
        290                 295                 300

Gly Ser Gly Gly Gly Gly Ser Gly Gly Gly Gly Ser Gly Gly Gly Gly
305                 310                 315                 320

Ser Gly Gly Gly Gly Ser Gly Gly Gly Gly Ser Gly Gly Gly Gly Ser
            325                 330                 335

Gly Gly Gly Gly Ser Gly Gly Gly Gly Ser Gly Gly Gly Gly Ser Gly
            340                 345                 350

Gly Gly Gly Ser Gly Gly Gly Gly Ser Gly Gly Gly Gly Ser Gly Gly
        355                 360                 365

Gly Gly Ser Gly Gly Gly Gly Ser Gly Gly Gly Gly Ser Gly Gly Gly
        370                 375                 380

Gly Ser Gly Gly Gly Gly Ser Gly Gly Gly Gly Ser Gly Gly Gly Gly
385                 390                 395                 400

Ser Gly Gly Gly Gly Ser Gly Gly Gly Gly Ser Gly Gly Gly Gly Ser
            405                 410                 415

Gly Gly Gly Gly Ser Gly Gly Gly Gly Ser Gly Gly Gly Gly Ser Gly
            420                 425                 430

Gly Gly Gly Ser Gly Gly Gly Gly Ser Gly Gly Gly Gly Ser Gly Gly
        435                 440                 445

Gly Gly Ser Gly Gly Gly Gly Ser Gly Gly Gly Gly Ser Gly Gly Gly
        450                 455                 460

Gly Ser Gly Gly Gly Gly Ser Gly Gly Gly Gly Ser Gly Gly Gly Gly
465                 470                 475                 480

Ser Gly Gly Gly Gly Ser Gly Gly Gly Gly Ser Gly Gly Gly Gly Ser
            485                 490                 495

Gly Gly Gly Gly Ser
            500

<210> SEQ ID NO 252
<211> LENGTH: 510
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 252

Glu Gly Thr Ser Glu Ser Ala Thr Pro Glu Ser Gly Pro Gly Ser Glu
1               5                   10                  15

Pro Ala Thr Ser Gly Ser Glu Thr Pro Gly Thr Ser Glu Ser Ala Thr
            20                  25                  30

Pro Glu Ser Gly Pro Gly Ser Glu Pro Ala Thr Ser Gly Ser Glu Thr
        35                  40                  45

Pro Gly Thr Ser Glu Ser Ala Thr Pro Glu Ser Gly Pro Gly Thr Ser
    50                  55                  60

Thr Glu Pro Ser Glu Gly Ser Ala Pro Gly Ser Pro Ala Gly Ser Pro
65                  70                  75                  80

```
Thr Ser Thr Glu Glu Gly Thr Ser Glu Ser Ala Thr Pro Glu Ser Gly
                85                  90                  95
Pro Gly Ser Glu Pro Ala Thr Ser Gly Ser Glu Thr Pro Gly Thr Ser
            100                 105                 110
Glu Ser Ala Thr Pro Glu Ser Gly Pro Gly Ser Pro Ala Gly Ser Pro
        115                 120                 125
Thr Ser Thr Glu Glu Gly Ser Pro Ala Gly Ser Pro Thr Ser Thr Glu
    130                 135                 140
Glu Gly Thr Ser Thr Glu Pro Ser Glu Gly Ser Ala Pro Gly Thr Ser
145                 150                 155                 160
Glu Ser Ala Thr Pro Glu Ser Gly Pro Gly Thr Ser Glu Ser Ala Thr
                165                 170                 175
Pro Glu Ser Gly Pro Gly Thr Ser Glu Ser Ala Thr Pro Glu Ser Gly
            180                 185                 190
Pro Gly Ser Glu Pro Ala Thr Ser Gly Ser Glu Thr Pro Gly Ser Glu
        195                 200                 205
Pro Ala Thr Ser Gly Ser Glu Thr Pro Gly Ser Pro Ala Gly Ser Pro
    210                 215                 220
Thr Ser Thr Glu Glu Gly Thr Ser Thr Glu Pro Ser Glu Gly Ser Ala
225                 230                 235                 240
Pro Gly Thr Ser Thr Glu Pro Ser Glu Gly Ser Ala Pro Gly Ser Glu
                245                 250                 255
Pro Ala Thr Ser Gly Ser Glu Thr Pro Gly Thr Ser Glu Ser Ala Thr
            260                 265                 270
Pro Glu Ser Gly Pro Gly Thr Ser Thr Glu Pro Ser Glu Gly Ser Ala
        275                 280                 285
Pro Glu Val Gln Leu Val Glu Ser Gly Gly Gly Leu Val Lys Pro Gly
    290                 295                 300
Gly Ser Leu Arg Leu Ser Cys Ala Ala Ser Gly Phe Thr Phe Ser Ala
305                 310                 315                 320
Tyr Ala Met Ser Trp Val Arg Gln Ala Pro Gly Lys Gly Leu Val Trp
                325                 330                 335
Val Ala Ser Ile Ser Ser Gly Gly Thr Thr Tyr Tyr Pro Asp Ser Val
            340                 345                 350
Lys Arg Gln Phe Thr Ile Ser Arg Asp Asn Ala Lys Asn Thr Leu Tyr
        355                 360                 365
Leu Gln Met Asn Ser Leu Arg Ala Glu Asp Thr Ala Val Tyr Tyr Cys
    370                 375                 380
Thr Arg Gly Gly Asp Tyr Gly Tyr Ala Leu Asp Tyr Trp Gly Gln Gly
385                 390                 395                 400
Thr Leu Val Thr Val Ser Ser Ala Ser Thr Lys Gly Pro Ser Val Phe
                405                 410                 415
Pro Leu Ala Pro Ser Ser Lys Ser Thr Ser Gly Gly Thr Ala Ala Leu
            420                 425                 430
Gly Cys Leu Val Lys Asp Tyr Phe Pro Glu Pro Val Thr Val Ser Trp
        435                 440                 445
Asn Ser Gly Ala Leu Thr Ser Gly Val His Thr Phe Pro Ala Val Leu
    450                 455                 460
Gln Ser Ser Gly Leu Tyr Ser Leu Ser Val Val Thr Val Pro Ser
465                 470                 475                 480
```

```
Ser Ser Leu Gly Thr Gln Thr Tyr Ile Cys Asn Val Asn His Lys Pro
                485                 490                 495
Ser Asn Thr Lys Val Asp Lys Lys Val Glu Pro Lys Ser Cys
            500             505             510
```

ANTI-GPIIB/IIIA ANTIBODIES AND USES THEREOF

CROSS-REFERENCE TO RELATED APPLICATIONS

This patent application is the National Stage of International Application No. PCT/US2015/057187, filed on Oct. 23, 2015, which claims the benefit of U.S. Provisional Patent Application Nos. 62/067,783, filed Oct. 23, 2014; 62/110,883, filed Feb. 2, 2015; and 62/184,044, filed Jun. 24, 2015, each of which are incorporated by reference in their entirety herein.

SEQUENCE LISTING

The instant application contains a Sequence Listing which has been submitted electronically in ASCII format and is hereby incorporated by reference in its entirety. Said ASCII copy, created on Oct. 23, 2015, is named 13751-0225WO1_SL.txt and is 333,632 bytes in size.

BACKGROUND

Clotting factors have been administered to patients to improve hemostasis for some time. The advent of recombinant DNA technology has significantly improved treatment for patients with clotting disorders, allowing for the development of safe and consistent protein therapeutics. For example, recombinant activated factor VII has become widely used for the treatment of major bleeding, such as that which occurs in patients having hemophilia A or B, deficiency of coagulation Factors XI or VII, defective platelet function, thrombocytopenia, or von Willebrand's disease.

Although such recombinant molecules are effective, there is a need for improved versions which localize the therapeutic agent to sites of coagulation, have improved pharmacokinetic properties, improved manufacturability, reduced thrombogenicity, or enhanced activity, or more than one of these characteristics.

Treatment of hemophilia by replacement therapy is targeting restoration of clotting activity. There are plasma-derived and recombinant clotting factor products available to treat bleeding episodes on-demand or to prevent bleeding episodes from occurring by treating prophylactically. Based on the half-life of these products, treatment regimens require frequent intravenous administration. Such frequent administration is painful and inconvenient. Strategies to extend the half-life of clotting factors include pegylation (Rostin J, et al., *Bioconj. Chem.*, 2000; 11:387-96), glycopegylation (Stennicke H R, et al., *Thromb. Haemost.*, 2008; 100:920-8), formulation with pegylated liposomes (Spira J, et al., *Blood*, 2006; 108:3668-3673, Pan J, et al., *Blood*, 2009; 114:2802-2811) and conjugation with albumin (Schulte S., *Thromb. Res.*, 2008; 122 Suppl 4:S14-9).

Recombinant FVIIa (rFVIIa; Jurlander B et al., *Semin. Thromb. Hemost.*, 2001; 27(4):373-84) is used to treat bleeding episodes in (i) hemophilia patients with neutralizing antibodies against FVIII or FIX (inhibitors), (ii) patients with FVII deficiency, or (iii) patients with hemophilia A or B with inhibitors undergoing surgical procedures. Prior recombinant rFVIIa preparations sometimes display poor efficacy. Repeated doses of FVIIa at high concentration are often required to control a bleed, due to its low affinity for activated platelets, short half-life, and poor enzymatic activity in the absence of tissue factor. Accordingly, there is an unmet medical need for better treatment and prevention options for patients with coagulation disorders (e.g., hemophilia patients with inhibitors in which the activity of the FVIIa protein is increased).

SUMMARY

The present disclosure features antibodies and antigen-binding fragments thereof that bind to GPIIb/IIIa. These antibodies can specifically bind the GPIIb subunit and/or the GPIIb/IIIa complex. They are capable of targeting the non-active form of the GPIIb/IIIa receptor. The anti-GPIIb/IIIa antibodies and antigen-binding fragments thereof described herein can be used, for example, to target or ferry any agent of interest (e.g., a therapeutic molecule such as a clotting factor) to platelets. For example, the clotting factor FVIIa has low affinity for platelets, the site of action for clot formation. Thus, one approach to increase activity of a clotting factor like FVIIa is to target this clotting factor to platelet receptors via targeting moieties (e.g., Fab or scFv of an anti-GPIIb/IIIa antibody), which can increase the affinity of FVIIa for platelets thereby boosting activity. Such chimeric molecules can include a heterologous moiety to improve the pharmacokinetic parameters of the molecules such as its half-life. In addition to their use as targeting moieties, the anti-GPIIb/IIIa antibodies and antigen-binding fragments thereof of this disclosure can be used as diagnostics, for example, by conjugation to a detectable label, and also for isolating or separating platelets from a sample.

In one aspect, this disclosure provides an antibody or antigen-binding fragment thereof that specifically binds to glycoprotein IIb/IIIa (GPIIb/IIIa), wherein the antibody or the antigen-binding fragment thereof comprises a heavy chain variable region that is at least 75% identical to the amino acid sequence set forth in any one of SEQ ID NOs: 3, 5, 7, 9, 11, 12, or 197-218. In certain embodiments, the heavy chain variable region is at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in any one of SEQ ID NOs: 3, 5, 7, 9, 11, 12, or 197-218. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to $5 \times 10^{-8}$M (e.g., $1 \times 10^{-8}$M; $1.5 \times 10^{-8}$M; $2 \times 10^{-8}$M; $2.5 \times 10^{-8}$M; $3 \times 10^{-8}$M; $3.5 \times 10^{-8}$M; $4 \times 10^{-8}$M; $4.5 \times 10^{-8}$M; $5 \times 10^{-8}$M). In certain embodiments, these antibodies have an improved off-rate over an antibody comprising a VH comprising an amino acid sequence set forth in SEQ ID NO:7.

In another aspect, this disclosure provides an antibody or antigen-binding fragment thereof that specifically binds to glycoprotein IIb/IIIa (GPIIb/IIIa), wherein the antibody or the antigen-binding fragment thereof comprises a light chain variable region that is at least 75% identical to the amino acid sequence set forth in any one of SEQ ID NOs: 4, 6, 8, or 10. In certain embodiments, the light chain variable region is at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in any one of SEQ ID NOs: 4, 6, 8, or 10.

In another aspect, this disclosure provides an antibody or antigen-binding fragment thereof that specifically binds to glycoprotein IIb/IIIa (GPIIb/IIIa), wherein the antibody or the antigen-binding fragment thereof comprises a heavy chain variable region that is at least 75% identical to the amino acid sequence set forth in any one of SEQ ID NOs: 3, 5, 7, 9, 11, 12, or 197-218, and a light chain variable region that is at least 75% identical to the amino acid sequence set forth in any one of SEQ ID NOs:4, 6, 8, or 10. In certain embodiments, the heavy chain variable region is at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in any one of SEQ ID NOs: 3, 5, 7, 9, 11, 12, or 197-218 In certain embodiments, the light chain variable region is at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in any one of SEQ ID NOs: 4, 6, 8, or 10. In certain embodiments, the heavy chain variable region is at least 80% identical to the amino acid sequence set forth in any one of SEQ ID NOs: 3, 5, 7, 9, 11, 12, or 197-218 and the light chain variable region is at least 80% identical to the amino acid sequence set forth in any one of SEQ ID NOs: 4, 6, 8, or 10. In certain embodiments, the heavy chain variable region is at least 85% identical to the amino acid sequence set forth in any one of SEQ ID NOs: 3, 5, 7, 9, 11, 12, or 197-218 and the light chain variable region is at least 85% identical to the amino acid sequence set forth in any one of SEQ ID NOs: 4, 6, 8, or 10. In some embodiments, the heavy chain variable region is at least 90% identical to the amino acid sequence set forth in any one of SEQ ID NOs: 3, 5, 7, 9, 11, 12, or 197-218 and the light chain variable region is at least 90% identical to the amino acid sequence set forth in any one of SEQ ID NOs: 4, 6, 8, or 10. In other embodiments, the heavy chain variable region is at least 95% identical to the amino acid sequence set forth in any one of SEQ ID NOs: 3, 5, 7, 9, 11, 12, or 197-218 and the light chain variable region is at least 95% identical to the amino acid sequence set forth in any one of SEQ ID NOs: 4, 6, 8, or 10. In yet other embodiments, the heavy chain variable region is at least 97% identical to the amino acid sequence set forth in any one of SEQ ID NOs: 3, 5, 7, 9, 11, 12, or 197-218 and the light chain variable region is at least 97% identical to the amino acid sequence set forth in any one of SEQ ID NOs: 4, 6, 8, or 10. In a certain embodiment, the heavy chain variable region is identical to the amino acid sequence set forth in any one of SEQ ID NOs: 3, 5, 7, 9, 11, 12, or 197-218 and the light chain variable region is identical to the amino acid sequence set forth in any one of SEQ ID NOs: 4, 6, 8, or 10. In one specific embodiment, the heavy chain variable region is identical to the amino acid sequence set forth in SEQ ID NO: 7 and the light chain variable region is identical to the amino acid sequence set forth in SEQ ID NO:4. In another specific embodiment, the heavy chain variable region is identical to the amino acid sequence set forth in SEQ ID NO: 12 and the light chain variable region is identical to the amino acid sequence set forth in SEQ ID NO:8. In yet another specific embodiment, the heavy chain variable region is identical to the amino acid sequence set forth in SEQ ID NO:11 and the light chain variable region is identical to the amino acid sequence set forth in SEQ ID NO:10. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to $5 \times 10^{-8}$M (e.g., $1 \times 10^{-8}$M; $1.5 \times 10^{-8}$M; $2 \times 10^{-8}$M; $2.5 \times 10^{-8}$M; $3 \times 10^{-8}$M; $3.5 \times 10^{-8}$M; $4 \times 10^{-8}$M; $4.5 \times 10^{-8}$M; $5 \times 10^{-8}$M). In certain embodiments, these antibodies have an improved off-rate over an antibody comprising a VH comprising an amino acid sequence set forth in SEQ ID NO:7.

In another aspect, the disclosure features an antibody or antigen-binding fragment thereof that specifically binds to glycoprotein IIb/IIIa (GPIIb/IIIa), wherein the antibody or the antigen-binding fragment thereof comprises a heavy chain variable region that is at least 75% identical to the amino acid sequence set forth in any one of SEQ ID NOs: 5, 7, 9, 11, 12, or 197-218, and a light chain variable region that is at least 75% identical to the amino acid sequence set forth in SEQ ID NO:4. In one embodiment, the heavy chain variable region that is at least 80% identical to the amino acid sequence set forth in any one of SEQ ID NOs: 5, 7, 9, 11, 12, or 197-218, and the light chain variable region is at least 80% identical to the amino acid sequence set forth in SEQ ID NO:4. In another embodiment, the heavy chain variable region that is at least 85% identical to the amino acid sequence set forth in any one of SEQ ID NOs: 5, 7, 9, 11, 12, or 197-218, and the light chain variable region is at least 85% identical to the amino acid sequence set forth in SEQ ID NO:4. In one embodiment, the heavy chain variable region that is at least 90% identical to the amino acid sequence set forth in any one of SEQ ID NOs: 5, 7, 9, 11, 12, or 197-218, and the light chain variable region is at least 90% identical to the amino acid sequence set forth in SEQ ID NO:4. In another embodiment, the heavy chain variable region that is at least 95% identical to the amino acid sequence set forth in any one of SEQ ID NOs: 5, 7, 9, 11, 12, or 197-218, and the light chain variable region is at least 95% identical to the amino acid sequence set forth in SEQ ID NO:4. In yet another embodiment, the heavy chain variable region that is at least 97% identical to the amino acid sequence set forth in any one of SEQ ID NOs: 5, 7, 9, 11, 12, or 197-218, and the light chain variable region is at least 97% identical to the amino acid sequence set forth in SEQ ID NO:4. In a specific embodiment, the heavy chain variable region that is identical to the amino acid sequence set forth in any one of SEQ ID NOs: 5, 7, 9, 11, 12, or 197-218, and the light chain variable region is identical to the amino acid sequence set forth in SEQ ID NO:4. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to $5 \times 10^{-8}$M (e.g., $1 \times 10^{-8}$M; $1.5 \times 10^{-8}$M; $2 \times 10^{-8}$M; $2.5 \times 10^{-8}$M; $3 \times 10^{-8}$M; $3.5 \times 10^{-8}$M; $4 \times 10^{-8}$M; $4.5 \times 10^{-8}$M; $5 \times 10^{-8}$M). In certain embodiments, these antibodies have an improved off-rate over an antibody comprising a VH comprising an amino acid sequence set forth in SEQ ID NO:7.

In another aspect, the disclosure features an antibody or antigen-binding fragment thereof that specifically binds to glycoprotein IIb/IIIa (GPIIb/IIIa), wherein the antibody or the antigen-binding fragment thereof comprises a heavy chain variable region that is at least 75% identical to the amino acid sequence set forth in any one of SEQ ID NOs: 3, 5, 7, 9, 11, 12, or 197-218, and a light chain variable region that is at least 75% identical to the amino acid sequence set forth in SEQ ID NO:10. In one embodiment, the heavy chain variable region that is at least 80% identical to the amino acid sequence set forth in any one of SEQ ID NOs: 3, 5, 7, 9, 11, 12, or 197-218, and the light chain variable region is at least 80% identical to the amino acid sequence set forth in SEQ ID NO:10. In another embodiment, the heavy chain variable region that is at least 85% identical to the amino acid sequence set forth in any one of SEQ ID NOs: 3, 5, 7, 9, 11, 12, or 197-218, and the light chain variable region is at least 85% identical to the amino acid sequence set forth in SEQ ID NO:10. In one embodiment, the heavy chain variable region that is at least 90% identical to the amino acid sequence set forth in any one of SEQ ID NOs: 3, 5, 7, 9, 11, 12, or 197-218, and the light chain variable region is at least 90% identical to the amino acid sequence set forth in SEQ ID NO:10. In another embodiment, the heavy chain variable region that is at least 95% identical to the amino acid sequence set forth in any one of SEQ ID NOs: 3, 5, 7, 9, 11, 12, or 197-218, and the light chain variable region is at least 95% identical to the amino acid sequence set forth in SEQ ID NO:10. In yet another embodiment, the heavy chain variable region that is at least 97% identical to the amino acid sequence set forth in any one of SEQ ID NOs: 3, 5, 7, 9, 11, 12, or 197-218, and the light chain variable region is at least 97% identical to the amino acid sequence set forth in SEQ ID NO:10. In a specific embodiment, the heavy chain variable region that is identical to the amino acid sequence set forth in any one of SEQ ID NOs: 3, 5, 7, 9, 11, 12, or 197-218, and the light chain variable region is identical to the amino acid sequence set forth in SEQ ID NO:10. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to $5 \times 10^{-8}$M (e.g., $1 \times 10^{-8}$M; $1.5 \times 10^{-8}$M; $2 \times 10^{-8}$M; $2.5 \times 10^{-8}$M; $3 \times 10^{-8}$M; $3.5 \times 10^{-8}$M; $4 \times 10^{-8}$M; $4.5 \times 10^{-8}$M; $5 \times 10^{-8}$M). In certain embodiments, these antibodies have an improved off-rate over an antibody comprising a VH comprising an amino acid sequence set forth in SEQ ID NO:7.

In another aspect, the disclosure relates to an antibody or antigen-binding fragment thereof that specifically binds to glycoprotein IIb/IIIa (GPIIb/IIIa), wherein the antibody or the antigen-binding fragment thereof comprises a heavy chain variable region that is identical to the amino acid sequence set forth in any one of SEQ ID NOs: 3, 5, 7, 9, 11, 12, or 197-218, except for a total of 1 to 10 (i.e., 1, 2, 3, 4, 5, 6, 7, 8, 9, 10) amino acid substitutions, deletions, or insertions. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to $5 \times 10^{-8}$M (e.g., $1 \times 10^{-8}$M; $1.5 \times 10^{-8}$M; $2 \times 10^{-8}$M; $2.5 \times 10^{-8}$M; $3 \times 10^{-8}$M; $3.5 \times 10^{-8}$M; $4 \times 10^{-8}$M; $4.5 \times 10^{-8}$M; $5 \times 10^{-8}$M). In certain embodiments, these antibodies have an improved off-rate over an antibody comprising an amino acid sequence set forth in SEQ ID NO:7.

In a further aspect, the disclosure provides an antibody antigen-binding fragment thereof that specifically binds to glycoprotein IIb/IIIa (GPIIb/IIIa), wherein the antibody or the antigen-binding fragment thereof comprises a light chain variable region that is identical to the amino acid sequence set forth in any one of SEQ ID NOs: 4, 6, 8, or 10, except for a total of 1 to 10 (i.e., 1, 2, 3, 4, 5, 6, 7, 8, 9, 10) amino acid substitutions, deletions, or insertions. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to $5 \times 10^{-8}$M (e.g., $1 \times 10^{-8}$M; $1.5 \times 10^{-8}$M; $2 \times 10^{-8}$M; $2.5 \times 10^{-8}$M; $3 \times 10^{-8}$M; $3.5 \times 10^{-8}$M; $4 \times 10^{-8}$M; $4.5 \times 10^{-8}$M; $5 \times 10^{-8}$M). In certain embodiments, these antibodies have an improved off-rate over an antibody comprising a VH comprising an amino acid sequence set forth in SEQ ID NO:7.

In yet another aspect, the disclosure relates to an antibody or antigen-binding fragment thereof that specifically binds to glycoprotein IIb/IIIa (GPIIb/IIIa), wherein the antibody or the antigen-binding fragment thereof comprises (i) a heavy chain variable region that is identical to the amino acid sequence set forth in any one of SEQ ID NOs: 3, 5, 7, 9, 11, 12, or 197-218, except for a total of 1 to 10 amino acid substitutions, deletions, or insertions; and (ii) a light chain variable region that is identical to the amino acid sequence set forth in any one of SEQ ID NOs: 4, 6, 8, or 10, except for a total of 1 to 10 amino acid substitutions, deletions, or insertions. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to $5 \times 10^{-8}$M (e.g., $1 \times 10^{-8}$M; $1.5 \times 10^{-8}$M; $2 \times 10^{-8}$M; $2.5 \times 10^{-8}$M; $3 \times 10^{-8}$M; $3.5 \times 10^{-8}$M; $4 \times 10^{-8}$M; $4.5 \times 10^{-8}$M; $5 \times 10^{-8}$M). In certain embodiments, these antibodies have an improved off-rate over an antibody comprising a VH comprising an amino acid sequence set forth in SEQ ID NO:7.

In certain embodiments of all of the above aspects, the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGTTYYPDSVKR (SEQ ID NO:26), and GGDYGYALDY (SEQ ID NO:27), respectively.

In other embodiments of all of the above aspects, the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGTTYYPDSVKR (SEQ ID NO:26), and GGDYSYALDY (SEQ ID NO:245), respectively. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to 5×10⁻⁸M (e.g., 1×10⁻⁸M; 1.5×10⁻⁸M; 2×10⁻⁸M; 2.5×10⁻⁸M; 3×10⁻⁸M; 3.5×10⁻⁸M; 4×10⁻⁸M; 4.5×10⁻⁸M; 5×10⁻⁸M). In certain embodiments, these antibodies have an improved off-rate over an antibody comprising a VH comprising an amino acid sequence set forth in SEQ ID NO:7.

In other embodiments of all of the above aspects, the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGTTYYPDSVER (SEQ ID NO:241), and GGDYSYALDY (SEQ ID NO:245), respectively. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to 5×10⁻⁸M (e.g., 1×10⁻⁸M; 1.5×10⁻⁸M; 2×10⁻⁸M; 2.5×10⁻⁸M; 3×10⁻⁸M; 3.5×10⁻⁸M; 4×10⁻⁸M; 4.5×10⁻⁸M; 5×10⁻⁸M). In certain embodiments, these antibodies have an improved off-rate over an antibody comprising a VH comprising an amino acid sequence set forth in SEQ ID NO:7.

In other embodiments of all of the above aspects, the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSDGTTYYPDSVKR (SEQ ID NO:242), and GGDYSYALDY (SEQ ID NO:245), respectively. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to 5×10⁻⁸M (e.g., 1×10⁻⁸M; 1.5×10⁻⁸M; 2×10⁻⁸M; 2.5×10⁻⁸M; 3×10⁻⁸M; 3.5×10⁻⁸M; 4×10⁻⁸M; 4.5×10⁻⁸M; 5×10⁻⁸M). In certain embodiments, these antibodies have an improved off-rate over an antibody comprising a VH comprising an amino acid sequence set forth in SEQ ID NO:7.

In other embodiments of all of the above aspects, the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGTTDYPDSVKR (SEQ ID NO:243), and GGDYGYALDY (SEQ ID NO:27), respectively. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to 5×10⁻⁸M (e.g., 1×10⁻⁸M; 1.5×10⁻⁸M; 2×10⁻⁸M; 2.5×10⁻⁸M; 3×10⁻⁸M; 3.5×10⁻⁸M; 4×10⁻⁸M; 4.5×10⁻⁸M; 5×10⁻⁸M). In certain embodiments, these antibodies have an improved off-rate over an antibody comprising a VH comprising an amino acid sequence set forth in SEQ ID NO:7.

In other embodiments of all of the above aspects, the antibody or the antigen-binding fragment thereof comprises a heavy chain variable region comprising complementarity determining region (CDR)1, CDR2, and CDR3, consisting of the amino acid sequences AYAMS (SEQ ID NO:25), GISSGGTTYYPDSVKR (SEQ ID NO:244), and GGDYGYALDY (SEQ ID NO:27), respectively. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to 5×10⁻⁸M (e.g., 1×10⁻⁸M; 1.5×10⁻⁸M; 2×10⁻⁸M; 2.5×10⁻⁸M; 3×10⁻⁸M; 3.5×10⁻⁸M; 4×10⁻⁸M; 4.5×10⁻⁸M; 5×10⁻⁸M). In certain embodiments, these antibodies have an improved off-rate over an antibody comprising a VH comprising an amino acid sequence set forth in SEQ ID NO:7.

In certain embodiments of all of the above aspects, the antibody or the antigen-binding fragment thereof comprises a light chain variable region comprising CDR1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively. In certain embodiments, these antibodies have an apparent monovalent affinity that is improved over an antibody comprising a VH comprising an amino acid sequence set forth in SEQ ID NO:7. In some embodiments, these antibodies have an apparent monovalent affinity that is about 1 to 5×10⁻⁸M (e.g., 1×10⁻⁸M; 1.5×10⁻⁸M; 2×10⁻⁸M; 2.5×10⁻⁸M; 3×10⁻⁸M; 3.5×10⁻⁸M; 4×10⁻⁸M; 4.5×10⁻⁸M; 5×10⁻⁸M). In certain embodiments, these antibodies have an improved off-rate over an antibody comprising a VH comprising an amino acid sequence set forth in SEQ ID NO:7. In certain embodiments of all of the above aspects, the antibody or the antigen-binding fragment thereof comprises (i) a heavy chain variable region comprising complementarity determining region (CDR)1, CDR2, and CDR3, consisting of the amino acid sequences AYAMS (SEQ ID NO:25), SISSGGTTYYPDSVKR (SEQ ID NO:26), and GGDYGYALDY (SEQ ID NO:27), respectively; and (ii) a light chain variable region comprising CDR1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In certain embodiments of all of the above aspects, the antibody or the antigen-binding fragment thereof comprises (i) a heavy chain variable region comprising complementarity determining region (CDR)1, CDR2, and CDR3, consisting of the amino acid sequences AYAMS (SEQ ID NO:25), SISSGGTTYYPDSVKR (SEQ ID NO:26), and GGDYSYALDY (SEQ ID NO:245), respectively; and (ii) a light chain variable region comprising CDR1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In certain embodiments of all of the above aspects, the antibody or the antigen-binding fragment thereof comprises (i) a heavy chain variable region comprising complementarity determining region (CDR)1, CDR2, and CDR3, consisting of the amino acid sequences AYAMS (SEQ ID NO:25), SISSGGTTYYPDSVER (SEQ ID NO:241), and GGDYSYALDY (SEQ ID NO:245), respectively; and (ii) a light chain variable region comprising CDR1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In certain embodiments of all of the above aspects, the antibody or the antigen-binding fragment thereof comprises (i) a heavy chain variable region comprising complementarity determining region (CDR)1, CDR2, and CDR3, consisting of the amino acid sequences AYAMS (SEQ ID NO:25), SISSDGTTYYPDSVKR (SEQ ID NO:242), and GGDYSYALDY (SEQ ID NO:245), respectively; and (ii) a light chain variable region comprising CDR1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In certain embodiments of all of the above aspects, the antibody or the antigen-binding fragment thereof comprises (i) a heavy chain variable region comprising complementarity determining region (CDR)1, CDR2, and CDR3, consisting of the amino acid sequences AYAMS (SEQ ID NO:25), SISSGGTTDYPDSVKR (SEQ ID NO:243), and GGDYGYALDY (SEQ ID NO:27), respectively; and (ii) a light chain variable region comprising CDR1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In certain embodiments of all of the above aspects, the antibody or the antigen-binding fragment thereof comprises (i) a heavy chain variable region comprising complementarity determining region (CDR)1, CDR2, and CDR3, consisting of the amino acid sequences AYAMS (SEQ ID NO:25), GISSGGTTYYPDSVKR (SEQ ID NO:244), and GGDYGYALDY (SEQ ID NO:27), respectively; and (ii) a light chain variable region comprising CDR1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In one aspect, the disclosure features an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGT-TYYPDSVKR (SEQ ID NO:26), and GGDYSYALDY (SEQ ID NO:245), respectively.

In another aspect, the disclosure features an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGT-TYYPDSVER (SEQ ID NO:241), and GGDYSYALDY (SEQ ID NO:245), respectively.

In another aspect, the disclosure features an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSDGT-TYYPDSVKR (SEQ ID NO:242), and GGDYSYALDY (SEQ ID NO:245), respectively.

In another aspect, the disclosure features an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SIS-SGGTTDYPDSVKR (SEQ ID NO:243), and GGDYG-YALDY (SEQ ID NO:27), respectively.

In a further aspect, the disclosure features an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), GIS-SGGTTYYPDSVKR (SEQ ID NO:244), and GGDYG-YALDY (SEQ ID NO:27), respectively.

In yet another aspect, the disclosure provides an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGT-TYYPDSVKR (SEQ ID NO:26), and GGDYSYALDY (SEQ ID NO:245), respectively; and a light chain variable region comprising complementarity determining region (CDR)1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In yet another aspect, the disclosure provides an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSGGT-TYYPDSVER (SEQ ID NO:241), and GGDYSYALDY (SEQ ID NO:245), respectively; and a light chain variable region comprising complementarity determining region (CDR)1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In yet another aspect, the disclosure provides an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SISSDGT-TYYPDSVKR (SEQ ID NO:242), and GGDYSYALDY (SEQ ID NO:245), respectively; and a light chain variable region comprising complementarity determining region (CDR)1, CDR2, and CDR3, consisting of the amino acid sequences RASSSVNYMY (SEQ ID NO:28), YTSNLAP (SEQ ID NO:29), and QQFSSSPWT (SEQ ID NO:30), respectively.

In yet another aspect, the disclosure provides an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), SIS-SGGTTDYPDSVKR (SEQ ID NO:243), and GGDYG-YALDY (SEQ ID NO:27), respectively; and a light chain variable region comprising complementarity determining region (CDR)1, CDR2, and CDR3, consisting of the amino acid sequences RASSSVNYMY (SEQ ID NO:28), YTSN-LAP (SEQ ID NO:29), and QQFSSSPWT (SEQ ID NO:30), respectively.

In yet another aspect, the disclosure provides an antibody or antigen-binding fragment thereof that specifically binds to glycoprotein IIb/IIIa (GPIIb/IIIa), wherein the antibody or the antigen-binding fragment thereof comprises a heavy chain variable region comprising complementarity determining region (CDR)1, CDR2, and CDR3, consisting of the amino acid sequences AYAMS (SEQ ID NO:25), GIS-SGGTTYYPDSVKR (SEQ ID NO:244), and GGDYG-YALDY (SEQ ID NO:27), respectively; and a light chain variable region comprising complementarity determining region (CDR)1, CDR2, and CDR3, consisting of the amino acid sequences RASSSVNYMY (SEQ ID NO:28), YTSN-LAP (SEQ ID NO:29), and QQFSSSPWT (SEQ ID NO:30), respectively.

In certain embodiments of the above aspects, the antibody or antigen-binding fragment thereof has an apparent monovalent affinity that is about 1 to about $5 \times 10^{-8}$ M.

In certain embodiments of all of the above aspects, the antibody or the antigen-binding fragment thereof is an Fab, an Fab', an F(ab')2, an Facb, an Fv, an Fd, a diabody, an scFv, or an sc(Fv)2. In a specific embodiment, the antibody or the antigen-binding fragment thereof is an Fab.

In another aspect, the disclosure relates to a chimeric molecule comprising the anti-GPIIb/IIIa antibody or antigen-binding fragment thereof described herein and a heterologous moiety.

In certain embodiments of this aspect, the heterologous moiety of the chimeric molecule comprises a clotting factor. In some embodiments, the clotting factor is FVII, FIX, or FX. In some embodiments, the clotting factor is FVII zymogen (e.g., A or B isoform), activatable FVII, activated FVII (FVIIa), FIX zymogen, activatable FIX, activated FIX (FIXa), FX zymogen, activatable FX, or activated FX (FXa). In one embodiment, the clotting factor comprises a single polypeptide chain. In another embodiment, the clotting factor comprises two polypeptide chains. In certain embodiments, the heterologous moiety of the chimeric molecule comprises a small molecule drug.

In certain embodiments of this aspect, the chimeric molecule further includes a linker. In some embodiments, the linker is a peptide linker. The peptide linker can comprise at least two, at least three, at least four, at least five, at least 10, at least 15, at least 20, at least 25, at least 30, at least 35, at least 40, at least 50, at least 60, at least 70, at least 80, at least 90, or at least 100 amino acids. In some embodiments, the peptide linker comprises a peptide having the formula $[(Gly)_x$-$Ser_y]_z$ where x is from 1 to 4, y is 0 or 1, and z is from 1 to 50 (SEQ ID NO: 153).

In certain embodiments of this aspect, the chimeric molecule comprises a second heterologous moiety. In some embodiments, the second heterologous moiety comprises a half-life extending moiety. The half-life extending moiety can be, e.g., an XTEN, albumin, albumin binding polypeptide or fatty acid, an Fc region, transferrin, PAS, the C-terminal peptide (CTP) of the 13 subunit of human chorionic gonadotropin, polyethylene glycol (PEG), hydroxyethyl starch (HES), albumin-binding small molecules, vWF, and a clearance receptor or a fragment thereof which blocks binding of the chimeric molecule to a clearance receptor. In one embodiment, half-life extending moiety is an XTEN. In a specific embodiment, the XTEN is AE144. In another specific embodiment, the XTEN is AE288. In certain embodiments, the chimeric molecule comprises two half-life extending moieties. In certain embodiments, a linker connects the half-life extending molecule to the first heterologous moiety such as a clotting factor (e.g., Factor VII).

In a further aspect, the disclosure relates to a chimeric molecule comprising the anti-GPIIb/IIIa antibody or antigen-binding fragment thereof described herein, a Factor VII comprising a heavy chain and a light chain, and a half-life extending moiety. In certain embodiments, the antibody or antigen-binding fragment thereof is an Fab or an scFv. In one embodiment, the light chain of the Factor VII is linked to/associated with the heavy chain of the Factor VII, which in turn is linked to the half-life extending moiety, and the half-life extending moiety is linked to the anti-GPIIb/IIIa antibody or antigen-binding fragment thereof (e.g., Fab or scFv). The "linking" between these moieties can either be by direct covalent bonds between these moieties or via linkers (e.g., peptide linkers).

In another aspect, the disclosure features a chimeric molecule that has an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO: 74 or SEQ ID NO: 77. In certain embodiments, this chimeric molecule associates with an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO: 75 or SEQ ID NO: 76. In one embodiment, the chimeric molecule comprises, consists essentially of, or consists of the amino acid sequence set forth in SEQ ID NO: 74. In another embodiment, the chimeric molecule comprises, consists essentially of, or consists of the amino acid sequence set forth in or SEQ ID NO: 77. In certain embodiments, these chimeric molecules associates with an amino acid sequence comprising, consisting essentially of, or consisting of the amino acid sequence set forth in SEQ ID NO: 75. In certain embodiments, these chimeric molecules associates with an amino acid sequence comprising, consisting essentially of, or consisting of the amino acid sequence set forth in SEQ ID NO: 76. In certain embodiments, these chimeric molecules may comprise additional half-life extending moieties (e.g., AE144, AE288). In certain embodiments, these chimeric molecules may comprise one or more (e.g., 1, 2, 3, 4) linkers between Factor VII and the half-life extending moiety. In certain embodiments, these chimeric molecules may comprise additional linkers (e.g., 2, 3, 4) between the half-life extending moiety and the light chain of the Fab.

In another aspect, the disclosure features a chimeric molecule that has an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO: 247. In certain embodiments, this chimeric molecule includes at least one, at least two, or all three of CDRs of SEQ ID NO:4. In certain embodiments, the above-described chimeric molecule associates with an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO: 75. In one embodiment, the chimeric molecule comprises, consists essentially of, or consists of the amino acid sequence set forth in SEQ ID NO: 247. In certain embodiments, the chimeric molecule associates with an amino acid sequence comprising, consisting essentially of, or consisting of the amino acid sequence set forth in SEQ ID NO: 75. In certain embodiments, these chimeric molecules may comprise additional half-life extending moieties (e.g., AE144, AE288). In certain embodiments, these chimeric molecules may comprise one or more (e.g., 1, 2, 3, 4) linkers between Factor VII and the half-life extending moiety. In certain embodiments, these chimeric molecules may comprise additional linkers (e.g., 2, 3, 4) between the half-life extending moiety and the light chain of the Fab.

In another aspect, the disclosure features a chimeric molecule comprising a clotting factor (e.g., FVII, FIX, or FX), an anti-GPIIb/IIIa antibody or antigen-binding fragment thereof, and a half-life extending moiety (e.g., XTEN). This chimeric molecule may comprise one or more linkers (e.g., 6X(GGGGS) (SEQ ID NO:170)). The optional linker(s) can be between the clotting factor and the anti-GPIIb/IIIa antibody or antigen-binding fragment thereof and/or between the anti-GPIIb/IIIa antibody or antigen-binding fragment thereof and the half-life extending moiety. In certain embodiments of this aspect, the chimeric molecule comprises FVII, which may be the FVII zymogen (A or B isoform), activatable FVII, or activated FVII. In certain embodiments of this aspect, the chimeric molecule comprises FVII, a 6X(GGGGS) linker (SEQ ID NO:170), an Fab that binds GPIIb/IIIa, and an XTEN (e.g., AE288). In other embodiments of this aspect, the chimeric molecule comprises FVII, a 6X(GGGGS) linker (SEQ ID NO:170), an Fab that binds GPIIb/IIIa, two XTENs (e.g., AE288), and another linker. Non-limiting examples of chimeric molecules of this aspect are shown in FIGS. 17 and 20. In certain embodiments of this aspect, the chimeric molecule comprises an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO:74. In certain embodiments, this chimeric molecule includes at least one, at least two, or all three of the CDRs of SEQ ID NO:4. In certain embodiments of this aspect, the above-described chimeric molecule associates with a second chimeric molecule comprising an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO:252. In certain embodiments, this second chimeric molecule includes at least one, at least two, or all three of the CDRs of SEQ ID NO:7. In one embodiment, the chimeric molecule comprises, consists essentially of, or consists of the amino acid sequence set forth in SEQ ID NO:74 and associates with a second chimeric molecule with an amino acid sequence comprising, consisting essentially of, or consisting of the amino acid sequence set forth in SEQ ID NO:252. In certain embodiments, these chimeric molecules may comprise additional half-life extending moieties (e.g., AE144, AE288). In certain embodiments, these chimeric molecules may comprise one or more (e.g., 1, 2, 3, 4) linkers between Factor VII and the half-life extending moiety. In certain embodiments, these chimeric molecules may comprise additional linkers (e.g., 2, 3, 4) between the half-life extending moiety and the light and/or heavy chain of the Fab. In certain embodiments of this aspect, the chimeric molecule (e.g., polypeptides comprising SEQ ID NOs.: 74 and 252 that associate with each other) binds to the ectodomain of GP11b/IIIa with a KD of about $10^{-6}$ M to about $10^{-8}$M. In specific embodiments, the chimeric molecule (e.g., polypeptides comprising SEQ ID NOs.:74 and 252 that associate with each other) binds to the ectodomain of GP11b/IIIa with a KD of 1 to $10 \times 10^{-7}$M.

In one aspect, this disclosure provides a pharmaceutical composition comprising the anti-GPIIb/IIIa antibody or antigen-binding fragment thereof (e.g., Fab or scFv) and a pharmaceutically acceptable carrier. In another aspect, this disclosure provides a pharmaceutical composition comprising the chimeric molecules described herein and a pharmaceutically acceptable carrier.

In a different aspect, methods for reducing the frequency or degree of a bleeding episode in a subject in need thereof are provided. These methods involve administering to the subject (e.g., a human subject) an effective amount of a composition comprising the antibody or antigen-binding fragment thereof or the chimeric molecule described herein. In some embodiments, the subject has developed or has a tendency to develop an inhibitor against Factor VIII ("FVIII"), Factor IX ("FIX"), or both. The inhibitor against FVIII or FIX can be, e.g., a neutralizing antibody against FVIII, FIX, or both. In certain embodiments, the bleeding episode is the result of or caused by hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, or any combinations thereof.

In another aspect, the disclosure relates to a method of treating a blood coagulation disorder in a subject in need thereof. The method involves administering to the subject (e.g., a human subject) an effective amount of a composition comprising the antibody or antigen-binding fragment thereof, or the chimeric molecule described herein. In certain embodiments, the blood coagulation disorder is hemophilia A or hemophilia B.

In one aspect the disclosure provides a composition comprising the antibody or antigen-binding fragment thereof, or the chimeric molecule described herein for use in reducing the frequency or degree of a bleeding episode in a subject (e.g., human) in need thereof. In some embodiments, the subject has developed or has a tendency to develop an inhibitor against Factor VIII ("FVIII"), Factor IX ("FIX"), or both. The inhibitor against FVIII or FIX can be, e.g., a neutralizing antibody against FVIII, FIX, or both. In certain embodiments, the bleeding episode is the result of or caused by hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, or any combinations thereof.

In another aspect the disclosure provides a composition comprising the antibody or antigen-binding fragment thereof, or the chimeric molecule described herein for use in treating a blood coagulation disorder in a subject (e.g., human) in need thereof. In certain embodiments, the blood coagulation disorder is hemophilia A or hemophilia B.

In a further aspect, the disclosure relates to the use of a composition comprising the antibody or antigen-binding fragment thereof, or the chimeric molecule described herein in the preparation of a medicament for use in reducing the frequency or degree of a bleeding episode in a subject (e.g., human) in need thereof. In certain embodiments, the bleeding episode is the result of or caused by hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, or any combinations thereof.

In yet another aspect, the disclosure relates to the use of a composition comprising the antibody or antigen-binding fragment thereof, or the chimeric molecule described herein in the preparation of a medicament for use in treating a blood coagulation disorder in a subject (e.g., human) in need thereof. In certain embodiments, the blood coagulation disorder is hemophilia A or hemophilia B.

In a different aspect, the disclosure features a method of detecting platelets. The method involves contacting a human blood preparation with an anti-GPIIb/IIIa antibody or antigen-binding fragment thereof described herein and detecting cells in the blood preparation to which the antibody or antigen-binding fragment thereof binds. In some embodiments, the anti-GPIIb/IIIa antibody or antigen-binding fragment thereof is linked or conjugated to a detectable label (e.g., a fluorescent label, a radioactive label).

In yet another aspect, the disclosure provides a method for enriching platelets. This method comprises contacting a human blood preparation with an anti-GPIIb/IIIa antibody or antigen-binding fragment thereof described herein and enriching cells to which the antibody or antigen-binding fragment thereof are bound as compared to those cells in the blood preparation that are not bound by the antibody or antigen-binding fragment thereof.

In another aspect, the disclosure provides a method for isolating or enriching resting platelets (as opposed to activated platelets). This method comprises contacting a human blood preparation with an anti-GPIIb/IIIa antibody or antigen-binding fragment thereof described herein and enriching cells to which the antibody or antigen-binding fragment thereof are bound as compared to those cells in the blood preparation that are not bound by the antibody or antigen-binding fragment thereof.

The disclosure also provides an isolated nucleic acid comprising a nucleotide sequence that is at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to a nucleotide sequence selected from the group consisting of SEQ ID NOs: 13-22, 59-68, and 219-240.

In another aspect, the disclosure provides a nucleotide sequence that encodes a polypeptide comprising an amino acid sequence that is at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to an amino acid sequence selected from the group consisting of SEQ ID NOs: 3 to 12, 74-77, and 197-218.

In another aspect, the disclosure provides an isolated protein encoded by the above nucleic acid molecules. In yet another aspect, the disclosure provides a recombinant vector comprising the nucleic acids described herein. In a further aspect, the disclosure features a host cell comprising such recombinant vectors. In one embodiment, the disclosure provides an expression vector comprising a DNA comprising a nucleotide sequence that encodes the amino acid sequence set forth in SEQ ID NO:77. In another embodiment, the disclosure provides an expression vector comprising a DNA comprising a nucleotide sequence that encodes the amino acid sequence set forth in SEQ ID NO:247. In another embodiment, the disclosure provides an expression vector comprising a DNA comprising a nucleotide sequence that encodes the amino acid sequence set forth in SEQ ID NO:75. In yet another embodiment, the disclosure provides an expression vector comprising a DNA comprising a nucleotide sequence that encodes the amino acid sequence set forth in SEQ ID NO: 76. In certain embodiments, such expression vectors are either singly transformed/transfected into a host cell (e.g., 293, CHO) or transformed together (e.g., the expression vectors encoding the amino acid sequence set forth in SEQ ID NO:77 and 75; or the expression vectors encoding the amino acid sequence set forth in SEQ ID NO:77 and 76; or the expression vectors encoding the amino acid sequence set forth in SEQ ID NO:247 and 75). In certain embodiments, the host cell is cultured under conditions that allow the expression of the polypeptides encoded by these nucleic acids and involve isolating the polypeptides. In certain instances the Factor VII that is a component of SEQ ID NO:77 is activated. In certain instances the Factor VII that is a component of SEQ ID NO:247 is activated.

In another aspect, the disclosure provides a method of preparing an anti-GPIIb/IIIa antibody or antigen-binding fragment thereof. The method comprises culturing a host cell comprising recombinant vectors comprising the nucleic acid sequences set forth in SEQ ID NOs: 14 and 19; the nucleic acid sequences set forth in SEQ ID NOs: 15 and 19; the nucleic acid sequences set forth in SEQ ID NOs: 16 and 19; the nucleic acid sequences set forth in SEQ ID NOs: 17 and 19; the nucleic acid sequences set forth in SEQ ID NOs: 18 and 19; the nucleic acid sequences set forth in SEQ ID NOs: 13 and 22; the nucleic acid sequences set forth in SEQ ID NOs: 14 and 22; the nucleic acid sequences set forth in SEQ ID NOs: 15 and 22; the nucleic acid sequences set forth in SEQ ID NOs: 16 and 22; the nucleic acid sequences set forth in SEQ ID NOs: 17 and 22; the nucleic acid sequences set forth in SEQ ID NOs: 18 and 22; the nucleic acid sequences set forth in SEQ ID NOs: 18 and 21; the nucleic acid sequences set forth in SEQ ID NOs: 219 and 19; the nucleic acid sequences set forth in SEQ ID NOs: 220 and 19; the nucleic acid sequences set forth in SEQ ID NOs: 221 and 19; the nucleic acid sequences set forth in SEQ ID NOs: 222 and 19; the nucleic acid sequences set forth in SEQ ID NOs: 223 and 19; the nucleic acid sequences set forth in SEQ ID NOs: 224 and 19; the nucleic acid sequences set forth in SEQ ID NOs: 225 and 19; the nucleic acid sequences set forth in SEQ ID NOs: 226 and 19; the nucleic acid sequences set forth in SEQ ID NOs: 227 and 19; the nucleic acid sequences set forth in SEQ ID NOs: 228 and 19; the nucleic acid sequences set forth in SEQ ID NOs: 229 and 19; the nucleic acid sequences set forth in SEQ ID NOs: 230 and 19; the nucleic acid sequences set forth in SEQ ID NOs: 231 and 19; the nucleic acid sequences set forth in SEQ ID NOs: 232 and 19; the nucleic acid sequences set forth in SEQ ID NOs: 233 and 19; the nucleic acid sequences set forth in SEQ ID NOs: 234 and 19; the nucleic acid sequences set forth in SEQ ID NOs: 235 and 19; the nucleic acid sequences set forth in SEQ ID NOs: 236 and 19; the nucleic acid sequences set forth in SEQ ID NOs: 237 and 19; the nucleic acid sequences set forth in SEQ ID NOs: 238 and 19; the nucleic acid sequences set forth in SEQ ID NOs: 239 and 19; or the nucleic acid sequences set forth in SEQ ID NOs: 240 and 19, under conditions appropriate for expression and production of the antibody or antigen-binding fragment thereof. The method further comprises isolating the antibody or antigen-binding fragment thereof. In certain embodiments, the host cell is a 293 cell, a CHO cell or a DG44i cell.

In a further aspect, the disclosure features a method of preparing a chimeric molecule described herein. For example, the method comprises culturing a host cell comprising recombinant vectors comprising the nucleic acid sequences encoding the amino acid sequences set forth in SEQ ID NOs: 74 and 75; or the nucleic acid sequences encoding the amino acid sequences set forth in SEQ ID NOs: 74 and 76; under conditions appropriate for expression and production of the chimeric molecule. The method further comprises isolating the chimeric molecule. In certain embodiments, the host cell is a 293 cell, a CHO cell or a DG44i cell.

In one aspect, the disclosure features a method of preparing a chimeric molecule described herein. For example, the method comprises culturing a host cell comprising recombinant vectors comprising the nucleic acid sequences encoding the amino acid sequences set forth in SEQ ID NOs: 77 and 75; or the nucleic acid sequences encoding the amino acid sequences set forth in SEQ ID NOs: 77 and 76; under conditions appropriate for expression and production of the chimeric molecule. The method further comprises isolating the chimeric molecule. In certain embodiments, the host cell is a 293 cell, a CHO cell or a DG44i cell.

In another aspect, the disclosure features a method of preparing a chimeric molecule described herein. For example, the method comprises culturing a host cell comprising recombinant vectors comprising the nucleic acid sequences encoding the amino acid sequences set forth in SEQ ID NOs: 247 and 75; under conditions appropriate for expression and production of the chimeric molecule. The method further comprises isolating the chimeric molecule. In certain embodiments, the host cell is a 293 cell, a CHO cell or a DG44i cell.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is an alignment of the variable heavy chain (VH) amino acid sequences of six humanized 34D10 VH regions with the VH region of 34D10 (i.e., the murine anti-integrin GPIIb/IIIa antibody). The mutations in the humanized versions VH1 to VH5 compared to the humanized VH0 CDR graft are shown in bold, lower case font. The amino acids that differ between the 34D10 VH region and the humanized 34D10 VH CDR graft are highlighted in gray. The CDR regions (VHCDR1, VHCDR2, and VHCDR3) are underlined.

FIG. 2 is an alignment of the variable light chain (VL) amino acid sequences of four humanized 34D10 VL regions with the VL region of 34D10 (i.e., the murine anti-integrin GPIIb/IIIa antibody). The mutations in the humanized versions VL1 to VL3 compared to the humanized VL0 CDR graft are shown in bold, lower case font. The amino acids that differ between the 34D10 VL region and the humanized 34D10 VL CDR graft are highlighted in gray. The CDR regions (VLCDR1, VLCDR2, and VLCDR3) are underlined.

FIG. 5A is a diagrammatic representation of the structure of the chimeric molecules FVII-251/Fab-036 and FVII-251/Fab-037. The "6x(GGGGS) linker" has the amino acid sequence of SEQ ID NO: 170.

FIG. 5B is a graph comparing the clotting time (CT) in seconds for different concentrations (nM) of FactorVIIa-linked via XTEN AE288 and a linker to either Fab fragments of humanized 34D10 (FVII-251/Fab-036 (VL0/VH5) and FVII-251/Fab-037 (VL0/VH2)) or Fab fragments of murine 34D10 (FVII-200).

FIG. 5C is a graph comparing the clotting time (CT) in seconds for different concentrations (nM) of FVII-251/Fab-036 (VL0/VH5) against recombinant FVIIa.

FIG. 11 is an alignment of the variable heavy chain (VH) amino acid sequences of 22 affinity matured variants of the humanized 34D10 VH2 (SEQ ID NO: 7) (i.e., an anti-integrin GPIIb/IIIa antibody). The mutations identified in the humanized sequence compared to the humanized VH2 are shown in bold, lower case font. The CDR regions (VHCDR1, VHCDR2, and VHCDR3) are underlined.

FIG. 13 is a table listing the calculated melting temperatures for the indicated antibodies in the Fab format as performed by differential scanning fluorimetry.

FIG. 14A is a graphical depiction of the ex-vivo activity measured by rotational thromboelastometry (ROTEM) of FVII-265/Fab-037 and rFVIIa in human alphaIIb transgenic HemA mice with a fully humanized αIIb subunit in the αIIb/β3 integrin.

FIG. 14B depicts the ex-vivo activity of FVII-251/Fab-037 and rFVIIa in HemA mice, in which the murine αIIb/β3 integrin is not targeted by the Fab-037 moiety.

DETAILED DESCRIPTION

This disclosure features antibodies and antigen-binding fragments that specifically bind GPIIb/IIIa, an integrin that is expressed specifically and at high levels on platelets. Upon activation, the GPIIb/IIIa receptors change from a bent low ligand affinity conformation to an extended high ligand affinity conformation. Activated GPIIb/IIIa receptor binds fibrinogen and modulates platelet aggregation. The anti-GPIIb/IIIa antibodies described herein are capable of targeting the non-active form of the receptor. The anti-GPIIb/IIIa antibodies and antigen-binding fragments derived from these antibodies do not activate platelets, and can be used, for example, to target agents (e.g., therapeutic agents such as clotting factors or other molecules capable of having a pharmacological effect in platelets) to the platelet surface. In addition to their use as platelet-targeting moieties, these antibodies and antigen-binding fragments thereof can be used for diagnostics, for example, by conjugation to a detectable label, and also used for isolating and separating platelets from a sample.

Figure 7:
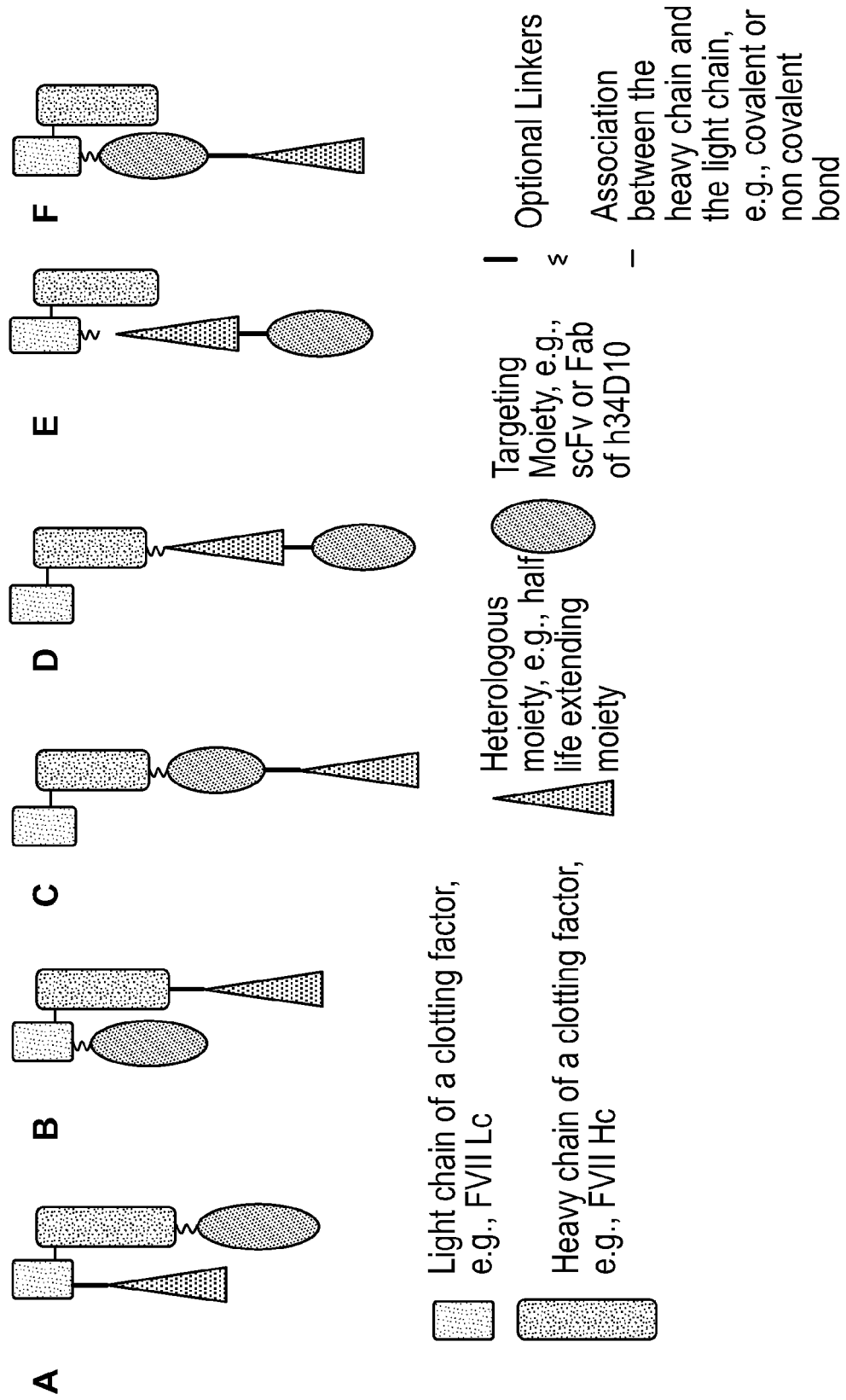
FIGS. 7A-F show possible configurations for chimeric molecules comprising the heavy and light chains of a clotting factor (e.g., a FVII), an Fab or scFv targeting moiety (e.g., derived for GPIIb/IIIa-specific antibodies), a heterologous moiety (e.g., a half-life extending moiety), and at least one optional linker.
Figure 8:
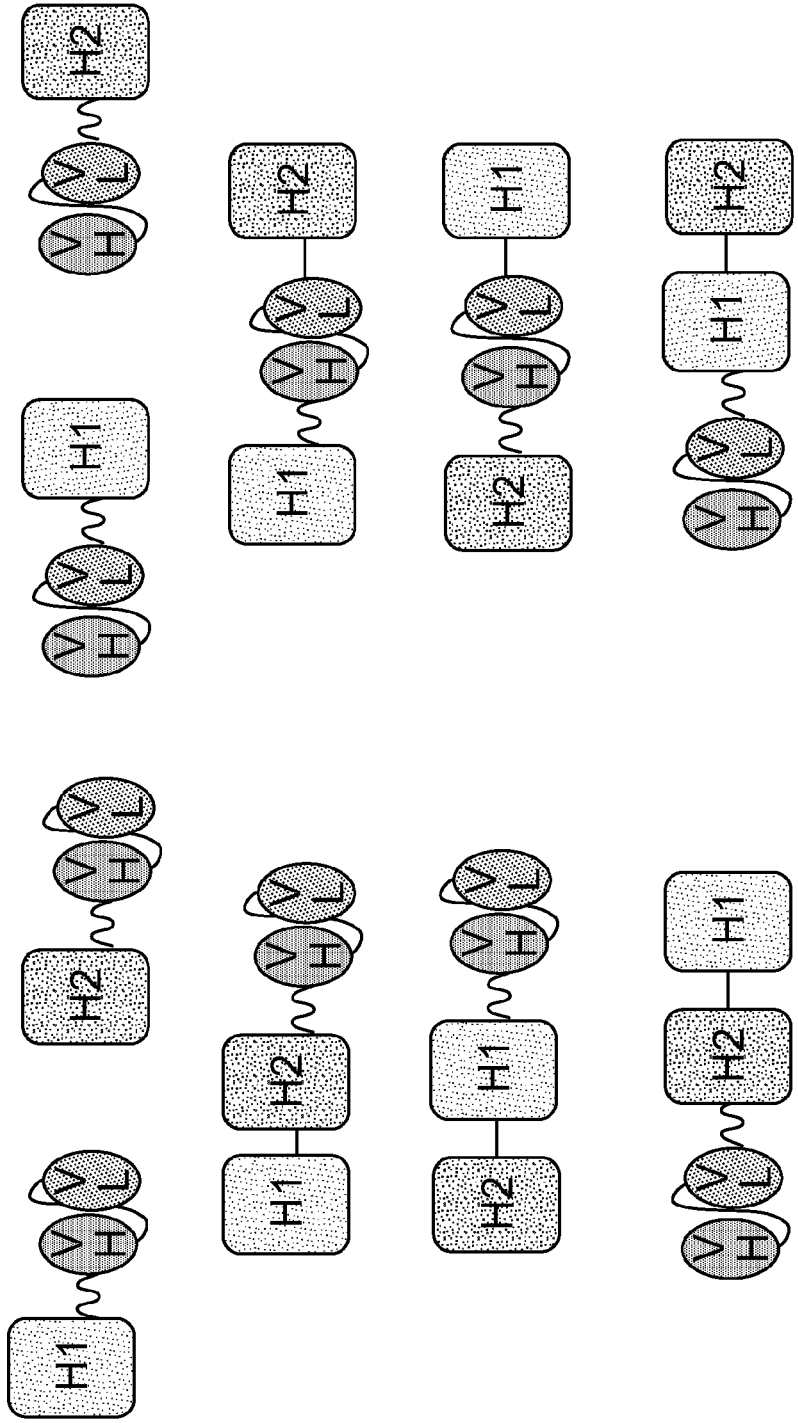
FIG. 8 shows possible configuration for chimeric molecules comprising one or two heterologous moieties (H1 and/or H2) and scFv moieties derived for GPIIb/IIIa-specific antibodies. It is to be understood that an Fab from the humanized anti-GPIIb/IIIa antibodies can be used instead of the scFv in these chimeric molecules.

This disclosure also provides chimeric molecules comprising the anti-GPIIb/IIIa antibodies and antigen-binding fragments thereof disclosed herein as targeting moieties, and one or more (e.g., one, two, three, four) heterologous moieties. For example, the chimeric molecules can comprise a heterologous moiety comprising a therapeutic molecule (e.g., a procoagulant molecule such as a clotting factor), and optionally a second heterologous moiety comprising, for example, a pharmacokinetic (PK) enhancing moiety (i.e., a molecule which can improve various pharmacokinetic properties, e.g., half-life). The heterologous moieties can optionally be connected by linkers (e.g., peptide linkers). In addition the targeting moiety of the chimeric molecule (e.g., an Fab or scFv of an anti-GPIIb/IIIa antibody described herein) can optionally be connected to the heterologous moiety or moieties by linkers (e.g., a peptide linker). Exemplary anti-GPIIb/IIIa antibodies and antigen-binding fragments thereof, as well as exemplary constructs (chimeric molecules) comprising such antibodies and antigen-binding fragments thereof (e.g., scFv or F(ab)) are illustrated in the instant description and figures. See, e.g., the chimeric molecules having the structures set forth in FIGS. 7 and 8.

The disclosure also provides polynucleotides encoding the antibodies and antigen-binding fragments thereof as well as the chimeric molecule constructs described herein.

In addition, this disclosure relates to methods of using the anti-GPIIb/IIIa antibodies and antigen-binding fragments thereof in the treatment of coagulation deficiencies such as hemophilia well as coagulation deficiencies other than hemophilia characterized by an impaired thrombin generation and life-threatening bleeding.

In order to provide a clear understanding of the specification and claims, the following definitions are provided below.

A. Definitions

It is understood that wherever embodiments are described herein with the language "comprising," otherwise analogous embodiments described in terms of "consisting of" and/or "consisting essentially of" are also provided.

The term "antibody" means an immunoglobulin molecule that recognizes and specifically binds to a target, such as a protein (e.g., the GPIIb/IIIa receptor, a subunit thereof, or the receptor complex), polypeptide, peptide, carbohydrate, polynucleotide, lipid, or combinations of the foregoing through at least one antigen recognition site within the variable region of the immunoglobulin molecule. A typical antibody comprises at least two heavy (HC) chains and two light (LC) chains interconnected by disulfide bonds. Each heavy chain is comprised of a "heavy chain variable region" or "heavy chain variable domain" (abbreviated herein as VH) and a heavy chain constant region. The heavy chain constant region is comprised of three domains, CH1, CH2, and CH3. Each light chain is comprised of a "light chain variable region" or "light chain variable domain" (abbreviated herein as VL) and a light chain constant region. The light chain constant region is comprised of one domain, Cl. The VH and VL regions can be further subdivided into regions of hypervariability, termed Complementarity Determining Regions (CDR), interspersed with regions that are more conserved, termed framework regions (FRs). Each VH and VL region is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. As used herein, the term "antibody" encompasses intact polyclonal antibodies, intact monoclonal antibodies, antibody fragments (such as Fab, Fab', F(ab')2, Fd, Facb, and Fv fragments), single chain Fv (scFv), minibodies (e.g., sc(Fv) 2, diabody), multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. Thus, the term "antibody" includes whole antibodies and any antigen-binding fragment or single chains thereof. Antibodies can be naked or conjugated to other molecules such as toxins, radioisotopes, small molecule drugs, polypeptides, etc.

The term "antigen binding fragment" refers to a portion of an intact antibody and refers to the antigenic determining variable regions of an intact antibody. It is known in the art that the antigen binding function of an antibody can be performed by fragments of a full-length antibody. Examples of antigen-binding antibody fragments include, but are not limited to Fab, Fab', F(ab')2, Facb, Fd, and Fv fragments, linear antibodies, single chain antibodies, and multispecific antibodies formed from antibody fragments. In some instances, antibody fragments may be prepared by proteolytic digestion of intact or whole antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments can be enzymatically or chemically produced by fragmentation of an intact antibody, recombinantly produced from a gene encoding the partial antibody sequence, or it can be wholly or partially synthetically produced. The term "F(ab')2" refers to an antibody fragment that is essentially equivalent to a fragment obtained by digestion of an immunoglobulin (typically IgG) with the enzyme pepsin at pH 4.0-4.5. Such fragments can be enzymatically or chemically produced by fragmentation of an intact antibody, recombinantly produced from a gene encoding the partial antibody sequence, or it can be wholly or partially synthetically produced. The term "Fv" refers to an antibody fragment that consists of one NH and one N domain held together by noncovalent interactions.

As used herein the term "scFv" or "scFv molecule" includes binding molecules which consist of one light chain variable domain (VL) or a portion thereof, and one heavy chain variable domain (VH) or a portion thereof, wherein each variable domain (or a portion thereof) is derived from the same or different antibodies. Single chain Fv molecules preferably comprise an scFv linker interposed between the VH domain and the VL domain. Exemplary scFv molecules are known in the art and are described, for example, in U.S. Pat. No. 5,892,019; Ho et al., *Gene,* 77:51 (1989); Bird et al., *Science,* 242:423 (1988); Pantoliano et al., *Biochemistry,* 30:10117 (1991); Milenic et al., *Cancer Research,* 51:6363 (1991); Takkinen et al., *Protein Engineering,* 4:837 (1991). The term "scFv linker" as used herein refers to a moiety interposed between the VL and VH domains of the scFv. The scFv linkers preferably maintain the scFv molecule in an antigen-binding conformation. In one embodiment, a scFv linker comprises or consists of an scFv linker peptide. In certain embodiments, an scFv linker peptide comprises or consists of a Gly-Ser peptide linker. In other embodiments, an scFv linker comprises a disulfide bond.

The terms "GPIIb/IIIa antibody," "anti-GPIIb/IIIa antibody," "anti-GPIIb/IIIa," "antibody that binds to GPIIb/IIIa" and any grammatical variations thereof refer to an antibody that is capable of specifically binding to the GPIIb/IIIa receptor with sufficient affinity such that the antibody is useful as a therapeutic agent or diagnostic reagent in targeting GPIIb/IIIa. The extent of binding of an anti-GPIIb/IIIa antibody disclosed herein to an unrelated, non-GPIIb/IIIa protein is less than about 10% of the binding of the antibody to GPIIb/IIIa as measured, e.g., by a radioimmunoassay (RIA), BIACORE™ (using recombinant GPIIb/IIIa as the analyte and antibody as the ligand, or vice versa), or other binding assays known in the art. In certain embodiments, an antibody that binds to GPIIb/IIIa has a dissociation constant (KD) of ≤1 µM, ≤100 nM, ≤50 nM, ≤10 nM, ≤1 nM, ≤0.1 nM, ≤10 pM, ≤1 pM, or ≤0.1 pM.

The term "% identical" between two polypeptide (or polynucleotide) sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence. One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org (ClustalX is a version of the ClustalW2 program ported to the Windows environment). Another suitable program is MUSCLE, available from www.drive5.com/muscle. ClustalW2 and MUSCLE are alternatively available, e.g., from the EBI.

As used herein, the term "targeting moiety" refers to a moiety capable of interacting with a target molecule (e.g., the GPIIb/IIIa receptor, or a molecule comprising the α and/or β subunits of the GPIIb/IIIa receptor). Targeting moieties having limited cross-reactivity are generally preferred. In certain embodiments, suitable targeting moieties include, for example, any member of a specific binding pair, antibodies, monoclonal antibodies, or derivatives or analogs thereof, including without limitation: Fv fragments, single chain Fv (scFv) fragments, Fab' fragments, F(ab')2 fragments, single domain antibodies, camelized antibodies and antibody fragments, humanized antibodies and antibody fragments, and multivalent versions of the foregoing; multivalent binding reagents including without limitation: monospecific or bispecific antibodies, such as disulfide stabilized Fv fragments, scFv tandems ((scFv) fragments), diabodies, tribodies or tetrabodies, which typically are covalently linked or otherwise stabilized (i.e., leucine zipper or helix stabilized) scFv fragments; and other targeting moieties include for example, aptamers, receptors, ligands, and fusion proteins.

The terms "linked" or "fused" refers to linkage via a peptide bonds (e.g., genetic fusion), chemical conjugation, or other means known in the art. For example, one way in which molecules or moieties can be linked employs peptide linkers that link the molecules or moieties via peptide bonds.

The term "associated with" refers to a covalent or non-covalent bond formed between a first amino acid chain and a second amino acid chain. In one embodiment, the term "associated with" means a covalent, non-peptide bond or a non-covalent bond. In another embodiment, the term "associated with" refers to a covalent, non-peptide bond or a non-covalent bond that is not chemically crosslinked. In another embodiment, it means a covalent bond except a peptide bond. In some embodiments this association is indicated by a colon, i.e., (:). For example, when representing the structure of the clotting factor, "CFH:CFL" refers to a dimer comprising a heavy chain of a clotting factor (CFH) disulfide bonded to a light chain of a clotting factor (CFL) in a N-terminus to C-terminus orientation.

The term "moiety" refers to a component part or constituent of a chimeric molecule of the present disclosure.

The term "heterologous moiety" refers to a moiety genetically fused, conjugated, and/or otherwise associated to a targeting molecule (e.g., GPIIb/IIIa antibody or antigen-binding molecule thereof).

The term "therapeutic agent" refers to any biological or chemical agent used in the treatment of a disease or disorder. Therapeutic agents include any suitable biologically active chemical compounds, biologically derived components such as cells, peptides, antibodies, and polynucleotides, and radiochemical therapeutic agents such as radioisotopes. In some embodiments, the therapeutic agent comprises a clotting factor.

The term "stability" refers to an art-recognized measure of the maintenance of one or more physical properties of the chimeric molecule in response to an environmental condition (e.g., an elevated or lowered temperature). In certain embodiments, the physical property can be the maintenance of the covalent structure of the chimeric molecule (e.g., the absence of proteolytic cleavage, unwanted oxidation or deamidation). In other embodiments, the physical property can also be the presence of the chimeric molecule in a properly folded state (e.g., the absence of soluble or insoluble aggregates or precipitates). In one embodiment, the stability of the chimeric molecule is measured by assaying a biophysical property of the chimeric molecule, for example thermal stability, pH unfolding profile, stable removal of glycosylation, solubility, biochemical function (e.g., ability to bind to a protein, receptor or ligand), etc., and/or combinations thereof. In another embodiment, biochemical function is demonstrated by the binding affinity of the interaction. In one embodiment, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

The term "clotting factor" refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. The term "clotting factor," as used herein encompasses clotting factors (e.g., vWF, FV, FVa, FVII, FVIIa, FVIII, FVIIIa, FIX, FIXa, FX, FXa, FXI, FXIa, FXII, FXIIa, FXIII, or FXIIIa), fragments, variants, analogs, or derivatives thereof, naturally occurring, recombinantly produced, or synthetically produced which prevent or decrease the duration of a bleeding episode in a subject.

The term "activatable clotting factor" refers to a clotting factor in an inactive form (e.g., in its zymogen form) that is capable of being converted to an active form.

As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor.

As used herein, the term "half-life extending moiety" refers to a heterologous moiety which increases the in vivo half-life of a protein, for example, a chimeric molecule. The term "half-life" refers to a biological half-life of a particular protein or polypeptide (e.g., a clotting factor or a chimeric molecule disclosed herein) in vivo. Half-life can be represented by the time required for half the quantity administered to a subject to be cleared from the circulation and/or other tissues in the animal. When a clearance curve of a given polypeptide or chimeric molecule of the invention is constructed as a function of time, the curve is usually biphasic with a rapid α-phase and longer β-phase. The α-phase typically represents an equilibration of the administered Fc polypeptide between the intra- and extra-vascular space and is, in part, determined by the size of the polypeptide. The β-phase typically represents the catabolism of the polypeptide in the intravascular space. In some embodiments, procoagulant compounds of the invention are monophasic, and thus do not have an alpha phase, but just the single beta phase. In certain embodiments, the term half-life as used herein refers to the half-life of the procoagulant compound in the β-phase. The typical β-phase half-life of a human antibody in humans is 21 days. In vivo half-life of a chimeric molecule can be determined by any method known to those of skill in the art. In certain embodiments, the half-life extending moiety can comprise an attachment site for a non-polypeptide moiety (e.g., PEG).

B. GPIIb/IIIa

The terms "GPIIb/IIIa" and "GPIIb/IIIa receptor" refer to glycoprotein IIb/IIIa (also known as integrin αIIbβ3), an integrin complex found on platelets. Integrins are composed of two chains, an α subunit and a β subunit, which are held together by noncovalent bonds in a calcium dependent manner. GPIIb constitutes the α subunit, which comprises divalent cation binding domains, whereas GPIIIa is a pro typical β subunit (β3). On each circulating platelet, there are about 35,000 to 100,000 GPIIb/IIIa complexes: most are distributed on the platelet surface, while a smaller pool is found in an internal reserve. The GPIIb/IIIa complex does not interact with its plasma ligands until platelets have been activated by exogenous agonists such as ADP or thrombin. When this occurs, an inside-out signal is generated that results in a conformational change in the extracellular portion of the complex that renders the molecule capable of binding fibrinogen and other ligands. The amino acid sequences of the two chains of this platelet receptor can be found in Uniprot entries P05106 (ITB3_HUMAN; GPIIIa: CD61; integrin beta-3; integrin β3) and P08514 (ITA2B_HUMAN; GPIIb; CD41; integrin alpha-2b; integrin αII) as published in Universal Protein Resource (Uniprot) database release 2013_05 (May 1, 2013), which are incorporated by reference in their entireties.

The amino acid sequence of human GPIIb is provided below:

```
                                           (SEQ ID NO: 23)
MARALCPLQALWLLEWVLLLLGPCAAPPAWALNLDPVQLTFYAGPNGSQF

GFSLDFHKDSHGRVAIVVGAPRTLGPSQEETGGVFLCPWRAEGGQCPSLL

FDLRDETRNVGSQTLQTFKARQGLGASVVSWSDVIVACAPWQHWNVLEKT

EEAEKTPVGSCFLAQPESGRRAEYSPCRGNTLSRIYVENDFSWDKRYCEA

GFSSVVTQAGELVLGAPGGYYFLGLLAQAPVADIFSSYRPGILLWHVSSQ

SLSFDSSNPEYFDGYWGYSVAVGEFDGDLNTTEYVVGAPTWSWTLGAVEI

LDSYYQRLHRLRGEQMASYFGHSVAVTDVNGDGRHDLLVGAPLYMESRAD

RKLAEVGRVYLFLQPRGPHALGAPSLLLTGTQLYGRFGSAIAPLGDLDRD

GYNDIAVAAPYGGPSGRGQVLVFLGQSEGLRSRPSQVLDSPFPTGSAFGF

SLRGAVDIDDNGYPDLIVGAYGANQVAVYRAQPVVKASVQLLVQDSLNPA

VKSCVLPQTKTPVSCFNIQMCVGATGHNIPQKLSLNAELQLDRQKPRQGR

RVLLLGSQQAGTTLNLDLGGKHSPICHTTMAFLRDEADFRDKLSPIVLSL

NVSLPPTEAGMAPAVVLHGDTHVQEQTRIVLDCGEDDVCVPQLQLTASVT
```

```
                                                    -continued
GSPLLVGADNVLELQMDAANEGEGAYEAELAVHLPQGAHYMRALSNVEGF

ERLICNQKKENETRVVLCELGNPMKKNAQIGIAMLVSVGNLEEAGESVSF

QLQIRSKNSQNPNSKIVLLDVPVRAEAQVELRGNSFPASLVVAAEEGERE

QNSLDSWGPKVEHTYELHNNGPGTVNGLHLSIHLPGQSQPSDLLYILDIQ

PQGGLQCFPQPPVNPLKVDWGLPIPSPSPIHPAHHKRDRRQIFLPEPEQP

SRLQDPVLVSCDSAPCTVVQCDLQEMARGQRAMVTVLAFLWLPSLYQRPL

DQFVLQSHAWFNVSSLPYAVPPLSLPRGEAQVWTQLLRALEERA
```

The amino acid sequence of human GPIIIa is provided below:

```
                                                    (SEQ ID NO: 24)
MRARPRPRPLWATVLALGALAGVGVGGPNICTTRGVSSCQQCLAVSPMCA

WCSDEALPLGSPRCDLKENLLKDNCAPESIEFPVSEARVLEDRPLSDKGS

GDSSQVTQVSPQRIALRLRPDDSKNFSIQVRQVEDYPVDIYYLMDLSYSM

KDDLWSIQNLGTKLATQMRKLTSNLRIGFGAFVDKPVSPYMYISPPEALE

NPCYDMKTTCLPMFGYKHVLTLTDQVTRFNEEVKKQSVSRNRDAPEGGFD

AIMQATVCDEKIGWRNDASHLLVFTTDAKTHIALDGRLAGIVQPNDGQCH

VGSDNHYSASTTMDYPSLGLMTEKLSQKNINLIFAVTENVVNLYQNYSEL

IPGTTVGVLSMDSSNVLQLIVDAYGKIRSKVELEVRDLPEELSLSFNATC

LNNEVIPGLKSCMGLKIGDTVSFSIEAKVRGCPQEKEKSFTIKPVGFKDS

LIVQVTFDCDCACQAQAEPNSHRCNNGNGTFECGVCRCGPGWLGSQCECS

EEDYRPSQQDECSPREGQPVCSQRGECLCGQCVCHSSDFGKITGKYCECD

DFSCVRYKGEMCSGHGQCSCGDCLCDSDWTGYYCNCTTRTDTCMSSNGLL

CSGRGKCECGSCVCIQPGSYGDTCEKCPTCPDACTFKKECVECKKFDRGA

LHDENTCNRYCRDEIESVKELKDTGKDAVNCTYKNEDDCVVRFQYYEDSS

GKSILYVVEEPECPKG
```

C. Anti-GPIIb/IIIa Antibodies

This disclosure provides antibodies and antigen-binding fragments thereof that specifically bind to GPIIb/IIIa. In certain embodiments, the antibodies and antigen-binding fragments thereof bind the GPIIb/IIIa receptors located on the surface of platelets. In other embodiments, the antibodies and antigen-binding fragments thereof bind the GPIIb/IIIa found within the platelets. The anti-GPIIb/IIIa antibodies and antigen binding fragments can bind the GPIIb subunit of the receptor and/or the GPIIb/IIIa complex. These antibodies do not activate the platelets and also do not compete with fibrinogen for binding to GPIIb/IIIa.

One example of an anti-GPIIb/IIIa antibody is the murine antibody, 34D10. This antibody was obtained as follows: Hybridomas were generated from BALB/C mice immunized with plasmids containing DNA sequences encoding GPIIb/IIIa according to methods known in the art. Hybridomas were then screened for binding to human and cynomolgus monkey platelets using flow cytometry, and for binding to GPIIb/IIIa using Enzyme-linked immunosorbent assays (ELISA). To determine binding to human and monkey platelets, gel-purified human or monkey (cynomolgus) platelets in Tyrode's buffer were incubated with hybridoma supernatant and antibody binding was detected by flow cytometry. The binding of supernatants from hybridomas to human GPIIb/IIIa (αIIbβ) was also determined by using ELISA. The supernatants from hybridomas which tested positive in the ELISA assays were mixed with platelets and screened for platelet activation using flow cytometry. The antibodies that did not activate platelets upon binding to GPIIb/IIIa were selected. The supernatants from non-activating hybridomas were subject to additional characterization assays (i) to confirm antibody binding to human and cynomolgus platelets, (ii) to determine antibody binding specificity for the α and/or β subunit of GPIIb/IIIa, and (iii) to determine whether the antibodies can compete with fibrinogen for binding to platelets. Fibrinogen is the natural ligand of GPIIb/IIIa and its binding to GPIIb/IIIa is essential to mediate platelet aggregation. Thus, the antibodies that compete with the binding of fibrinogen to GPIIb/IIIa were excluded from the selection. 34D10 was identified in the process and determined to be an antibody that does not activate platelets, that does not compete with the binding of fibrinogen to GPIIb/IIIa, and that binds both the a subunit of GPIIb/IIIa and the GPIIb/IIIa complex. The amino acid sequences of the heavy chain variable domain (VH) and light chain variable domain (VL) of the murine anti-GPIIb/IIIa antibody, 34D10, are provided below (the CDRs according to Kabat are underlined).

34D10 VH:

```
                                                    (SEQ ID NO: 1)
                        VHCDR1
EVKLVESGGGLVKPGGSLKLSCAASGFTFSAYAMSWVRQTPEKRLEWVA
IS

VHCDR2
SISSGGTTYYPDSVKRRF

VHCDR3
TRDNARNILYLQMSSLRSEDTAMYYCTRGGDYGYALDYWGQGTSVTVSS
```

34D10 VL:

```
                                                    (SEQ ID NO: 2)
                        VLCDR1
ENVLTQSPAIMSASLGEKVTMSCRASSSVNYMYWYQQKSDASPKLWIYY

VLCDR2                                    VLCDR3
TSNLAPGVPARFSGSGSGNSYSLTISSMEGEDAATYYCQQFSSSPWTFG

GGTKLEIK
```

The 34D10 antibody was humanized as described in Example 1. This example discloses six exemplary humanized heavy chain variable regions termed VH0, VH1, VH2, VH3, VH4, and VH5, with the amino acid sequences set forth in SEQ ID NOs: 3, 5, 7, 9, 11 and 12, respectively, and four exemplary humanized light chain variable regions termed VL0, VL1, VL2, and VL3, with the amino acid sequences set forth in SEQ ID NOs: 4, 6, 8, and 10, respectively. Each of these VH chains can pair with any of the VL chains: i.e., VH0 can pair with VL0, VL1, VL2, or VL3; VH1 can pair with VL0, VL1, VL2, or VL3; VH2 can pair with VL0, VL1, VL2, or VL3; VH3 can pair with VL0, VL1, VL2, or VL3; VH4 can pair with VL0, VL1, VL2, or VL3; and VH5 can pair with VL0, VL1, VL2, or VL3. Thus, the heavy chain variable region and light chain variable regions disclosed in Example 1 can form 24 different VH-VL pairs. All of these antibodies are considered part of this disclosure. In some embodiments, these antibodies can comprise a kappa light chain constant region. In other embodiments, these antibodies can comprise a lambda light chain constant region. In one embodiment, the light chain constant region comprises the following amino acid sequence:

(SEQ ID NO: 56)
RTVA APSVFIFPPS DEQLKSGTAS VVCLLNNFYP REAKVQWKVD

NALQSGNSQE SVTEQDSKDS TYSLSSTLTL SKADYEKHKV

YACEVTHQGL SSPVTKSFNR GEC.

In other embodiments, the light chain constant region comprises an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, or at least 99% identical to SEQ ID NO:56.

The antibodies of this disclosure can also comprise a heavy chain constant region. In certain embodiments the heavy chain constant region is from an IgG1 or IgG4 antibody. In one embodiment, the heavy chain constant region comprises the following amino acid sequence:

(SEQ ID NO: 57)
AS TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKKVEPKS C.

In other embodiments, the heavy chain constant region comprises an amino acid sequence that is at least 65% identical, at least 70% identical, at least 75% identical, at least 76% identical, at least 77% identical, at least 78% identical, at least 79% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, or at least 99% identical to SEQ ID NO:57. In another embodiment, the heavy chain constant region comprises the following amino acid sequence:

(SEQ ID NO: 58)
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFQSTYRVVSVLTVLHQDWLNG

KEYKCKVSNKGLPSSIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPG

The amino acid sequences of the heavy and light chain CDRs 1, 2, and 3, as well as the framework regions (FRs) 1, 2, 3, 4 of the six heavy chain variable regions and the four light chain variable regions of the exemplary humanized anti-GPIIb/IIIa antibodies described in Example 1 are provided below in Table 1. The CDRs are based upon the Kabat numbering system.

TABLE 1

Humanized 34D10 (h34D10) CDR and FR Amino Acid Sequences

| Domain | SEQ ID NO | Sequence |
| --- | --- | --- |
| VH CDR1 | 25 | AYAMS |
| VH CDR2 | 26 | SISSGGTTYYPDSVKR |
| VH101 CDR2 | 241 | SISSGGTTYYPDSVER |
| VH108 CDR2 | 242 | SISSDGTTYYPDSVKR |
| VH109 CDR2 | 243 | SISSGGTTDYPDSVKR |
| VH112 CDR2 | 244 | GISSGGTTYYPDSVKR |
| VH CDR3 | 27 | GGDYGYALDY |
| VH100 CDR3 | 245 | GGDYSYALDY |
| VL CDR1 | 28 | RASSSVNYMY |
| VL CDR2 | 29 | YTSNLAP |
| VL CDR3 | 30 | QQFSSSPWT |
| VH0 FR1 | 31 | EVQLVESGGGLVQPGGSLRLSCAASGFTFS |
| VH0 FR2 | 32 | WVRQAPGKGLVWV |
| VH0 FR3 | 33 | QFTISRDNAKNTLYLQMNSLRAEDMAVYYCTR |
| VH0 FR4 | 34 | WGQGTLVTVSS |
| VH1 FR1 | 35 | EVQLVQSGGGLVQPGESLRLSCAASGFTFS |
| VH1 FR2 | 36 | WVRQAPGKGLEWVS |
| VH1 FR3 | 33 | QFTISRDNAKNTLYLQMNSLRAEDMAVYYCTR |
| VH1 FR4 | 34 | WGQGTLVTVSS |
| VH2 FR1 | 37 | EVQLVESGGGLVKPGGSLRLSCAASGFTFS |
| VH2 FR2 | 38 | WVRQAPGKGLVWVA |
| VH2 FR3 | 39 | QFTISRDNAKNTLYLQMNSLRAEDTAVYYCTR |
| VH2 FR4 | 34 | WGQGTLVTVSS |
| VH3 FR1 | 40 | EVQLVQSGGGLVKPGESLRLSCAASGFTFS |
| VH3 FR2 | 41 | WVRQAPGKGLEWVA |
| VH3 FR3 | 42 | RFTISRDNAKNTLYLQMNSLRAEDTAVYYCTR |
| VH3 FR4 | 34 | WGQGTLVTVSS |
| VH4 FR1 | 40 | EVQLVQSGGGLVKPGESLRLSCAASGFTFS |
| VH4 FR2 | 41 | WVRQAPGKGLEWVA |
| VH4 FR3 | 43 | RFTISRDNSRNTLYLQMNSLRAEDTAVYYCTR |
| VH4 FR4 | 34 | WGQGTLVTVSS |
| VH5 FR1 | 44 | EVKLVESGGGLVKPGGSLRLSCAASGFTFS |
| VH5 FR2 | 41 | WVRQAPGKGLEWVA |
| VH5 FR3 | 45 | RFTISRDNARNTLYLQMNSLRAEDTAVYYCTR |

TABLE 1-continued

Humanized 34D10 (h34D10) CDR and FR Amino Acid Sequences

| Domain | SEQ ID NO | Sequence |
|---|---|---|
| VH5 FR4 | 34 | WGQGTLVTVSS |
| VL0 FR1 | 46 | EIVMTQSPATLSVSPGERATLSC |
| VL0 FR2 | 47 | WYQQKPGQAPRLLIY |
| VL0 FR3 | 48 | GIPARFSGSGSGTEFTLTISSLQSEDFAVYYC |
| VL0 FR4 | 49 | FGQGTKVEIK |
| VL1 FR1 | 50 | EIVLTQSPATLSVSPGERATLSC |
| VL1 FR2 | 47 | WYQQKPGQAPRLLIY |
| VL1 FR3 | 51 | GVPARFSGSGSGTEFTLTISSLQSEDFAVYYC |
| VL1 FR4 | 49 | FGQGTKVEIK |
| VL2 FR1 | 52 | EIVLTQSPATLSASPGERVTMSC |
| VL2 FR2 | 53 | WYQQKPGQSPRLLIY |
| VL2 FR3 | 54 | GVPARFSGSGSGTEYTLTISSLQSEDFAVYYC |
| VL2 FR4 | 49 | FGQGTKVEIK |
| VL3 FR1 | 55 | ENVMTQSPATLSASPGERVTMSC |
| VL3 FR2 | 53 | WYQQKPGQSPRLLIY |
| VL3 FR3 | 54 | GVPARFSGSGSGTEYTLTISSLQSEDFAVYYC |
| VL3 FR4 | 49 | FGQGTKVEIK |

Although the above Table discloses the CDRs according to Kabat (Kabat et al., Sequences of Proteins of Immunological Interest, 5th Ed. Public Health Service, National Institutes of Health, Bethesda, Md. (1991)), the antibodies of this disclosure can comprise CDRs of 34D10 according to any CDR definition (e.g., Kabat, Chothia, enhanced Chothia, contact, IMGT, AbM). The CDRs of an antibody according to the different CDR definitions can be determined, e.g., by using the AbYsis database (www.bioinforg.uk/abysis/sequence_input/key_annotation/key_annotation.cgi). According to the classical Kabat numbering, Kabat VH-CDR1 is at positions 31-35, VH-CDR2 is a positions 50-65, and VH-CDR3 is at positions 95-102; and, VL-CDR1, VL-CDR2, and VL-CDR3 are at positions 24-34, 50-56 and 89-97, respectively. According to the Chothia definition, VH-CDR1 is at positions 26-32 (Chothia numbering), VH-CDR2 is at positions 52-56, VH-CDR3 is at positions 95-102, VL-CDR1 is at positions 24-34, VL-CDR2 is at positions 50-56, and VL-CDR3 is at positions 89-97. According to the contact definition, VH-CDR1 is at positions 30-35 (Chothia numbering), VH-CDR2 is at positions 47-58, VH-CDR3 is at positions 93-101, VL-CDR1 is at positions 30-36, VL-CDR2 is at positions 46-55, and VL-CDR3 is at positions 89-96. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

The humanized antibodies can include the three CDRs of the VH of 34D10 (according to any CDR definition) in the context of any suitable heavy chain human acceptor framework. In one embodiment, a suitable heavy chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGHV3/OR16-13, with framework region 4 (FR4) from human consensus subgroup Heavy III. In one embodiment the heavy chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGHV3-15. In another embodiment the heavy chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGHV3-7. In yet another embodiment the heavy chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGHV3-53. In a further embodiment the heavy chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGHV3-66. The humanized antibodies can include the three CDRs of the VL of 34D10 (according to any CDR definition) in the context of any suitable light chain human acceptor framework. In one embodiment, a suitable light chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGKV3-15, with framework region 4 (FR4) from human consensus subgroup Kappa I. In another embodiment the light chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGKV1-NL1. In yet another embodiment the heavy chain human acceptor framework is an amino acid sequence that is at least 50%, at least 55%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of the germline humIGKV1D-43. Antibodies or antigen-binding fragments thereof can be selected for use based on higher affinity or avidity for GPIIb or the GPIIb/IIIa complex and/or reduced immunogenicity than previously known anti-GPIIb/IIIa antibodies. Methods of determining potency, affinity or avidity, and immunogenicity of antibodies are within the skill of the ordinary artisan.

This disclosure also includes antibodies or antigen-binding fragments thereof that specifically bind GPIIb and/or the GPIIb/IIIa complex that have heavy chain variable regions that are: at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequences set forth in any one of SEQ ID NOs.: 3, 5, 7, 9, 11, 12, or 197-218. This disclosure also provides antibodies or antigen-binding fragments thereof that specifically bind GPIIb and/or the GPIIb/IIIa complex that have heavy chain variable regions that are identical to the amino acid sequences set forth in any one of SEQ ID NOs.: 3, 5, 7, 9, 11, 12, or 197-218 except for a total of 1 to 40, 1 to 30, 1 to 20, 1 to 10, 1 to 9, 1 to 8, 1 to 7, 1 to 6, 1 to 5, 1 to 4, 1 to 3, 1 to 2, or 1 amino acid substitutions, deletions, or insertions. In certain embodiments, these antibodies or antigen-binding fragments thereof have at least one, at least two, at least three, at least four, at least five, or all six of the CDRs of 34D10 (wherein the CDRs can be according to any CDR definition). In some embodiments, these antibodies or antigen-binding fragments thereof have light chain variable regions that are: at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequences set forth in any one of SEQ ID NOs.: 4, 6, 8, or 10. This disclosure also provides antibodies or antigen-binding fragments thereof that specifically bind GPIIb and/or the GPIIb/IIIa complex that have light chain variable regions that are identical to the amino acid sequences set forth in any one of SEQ ID NOs.: 4, 6, 8, or 10 except for a total of 1 to 40, 1 to 30, 1 to 20, 1 to 10, 1 to 9, 1 to 8, 1 to 7, 1 to 6, 1 to 5, 1 to 4, 1 to 3, 1 to 2, or 1 amino acid substitutions, deletions, or insertions. In certain embodiments, these antibodies or antigen-binding fragments thereof have at least one, at least two, at least three, at least four, at least five, or all six of the CDRs of 34D10 (wherein the CDRs can be according to any CDR definition). In some embodiments, these antibodies or antigen-binding fragments thereof do not compete with fibrinogen for binding to GPIIb/IIIa. In some embodiments, these antibodies or antigen-binding fragments thereof do not activate platelets.

Exemplary antibodies or antigen-binding fragments thereof described herein that specifically bind GPIIb and/or the GPIIb/IIIa complex comprise amino acid sequences that are: at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequences set forth in: (i) SEQ ID NOs.: 5 and 4; (ii) SEQ ID NOs.: 7 and 4; (iii) SEQ ID NOs.: 9 and 4; (iv) SEQ ID NOs.: 11 and 4; (v) SEQ ID NOs.: 12 and 4; (vi) SEQ ID NOs.: 12 and 8; (vii) SEQ ID NOs.: 3 and 10; (viii) SEQ ID NOs.: 5 and 10; (ix) SEQ ID NOs.: 7 and 10; (x) SEQ ID NOs.: 9 and 10; (xi) SEQ ID NOs.: 11 and 10; and (xii) SEQ ID NOs.: 12 and 10. In certain embodiments, these antibodies or antigen-binding fragments thereof have at least one, at least two, at least three, at least four, at least five, or all six of the CDRs of 34D10 (wherein the CDRs can be according to any CDR definition). In some embodiments, these antibodies or antigen-binding fragments thereof do not compete with fibrinogen for binding to GPIIb/IIIa. In some embodiments, these antibodies or antigen-binding fragments thereof do not activate platelets.

The VH and or VL region of the anti-GPIIb/IIIa antibodies or antigen-binding fragments thereof described herein can be linked to a constant region (e.g., a wild-type human Fc region or an Fc region that includes one or more alterations). In some embodiments, the antibody has a light chain constant region derived from a human kappa sequence. In some embodiments, the antibody has a light chain constant region derived from a human lambda sequence. In a specific embodiment, the light chain constant region comprises a human subgroup kappa 1 sequence. In certain embodiments, the antibody has an isotype selected from the group consisting of IgG1, IgG2, IgG3, and IgG4. The heavy chain constant region can be a wild-type human Fc region, or a human Fc region that includes one or more amino acid substitutions. The antibodies can have mutations that stabilize the disulfide bond between the two heavy chains of an immunoglobulin, such as mutations in the hinge region of IgG4, as disclosed in the art (e.g., Angal et al., *Mol. Immunol.*, 30:105-08 (1993)). See also, e.g., U.S. 2005/0037000. The heavy chain constant region can also have substitutions that modify the properties of the antibody (e.g., decrease one or more of: Fc receptor binding, antibody glycosylation, deamidation, binding to complement, or methionine oxidation). In some instances, the antibodies may have mutations such as those described in U.S. Pat. Nos. 5,624,821 and 5,648,260. In some embodiments, the antibody is modified to reduce or eliminate effector function. In some embodiments, the heavy chain constant region has one or more of the following mutations: S228P; N297Q; and T299A (numbering according to Kabat). The heavy chain constant region can be chimeric, e.g., the Fc region can comprise the CH1 and CH2 domains of an IgG antibody of the IgG4 isotype, and the CH3 domain from an IgG antibody of the IgG1 isotype (see, e.g., U.S. Patent Appl. No. 2012/0100140A1 which is incorporated by reference in its entirety herein). In a specific embodiment, the humanized anti-GPIIb/IIIa antibodies described herein have a chimeric constant region comprising the CH1 and CH2 domains of an IgG antibody of the IgG4 isotype, and the CH3 domain from an IgG antibody of the IgG1 isotype and further contain the S228P and N297Q mutations (numbering according to Kabat).

Antigen-binding fragments of the anti-GPIIb/IIIa antibodies are also encompassed by this disclosure. In some embodiments, the anti-GPIIb/IIIa antibody or antigen-binding molecule thereof comprises or consists of (i) a single chain Fv ("scFv"); (ii) a diabody; (iii) an sc(Fv)2; (iv) a polypeptide chain of an antibody; (v) F(ab')2; or (vi) F(ab). In one embodiment, the antigen-binding fragment is an Fab molecule. The fragment antigen-binding (Fab fragment) is a region on an antibody that binds to antigens. It is composed of one constant and one variable domain of each of the heavy and the light chain. These domains shape the paratope, i.e., the antigen-binding site. The enzyme papain can be used to cleave an immunoglobulin monomer into two Fab fragments and an Fc fragment. Recombinant methods can also be used to make an Fab molecule. In another embodiment, the antigen-binding fragment is a single-chain fragment variable (scFv). An scFv is comprised of the variable regions of the heavy and light chains of an antibody. It is only half the size of the Fab fragment and yet retains the original specificity of the parent immunoglobulin. Methods of making an ScFv are well known in the art (see, e.g., Ahmad et al., *Clinical and Developmental Immunology*, vol. 2012, Article ID 980250, 15 pages, 2012. doi:10.1155/2012/980250).

In certain embodiments, the anti-GPIIb/IIIa antibody or antigen-binding molecule thereof can be a targeting moiety. These targeting moieties are useful in ferrying an agent of interest (e.g., a therapeutic agent, a coagulation factor, a small molecule drug) to platelets. In some embodiments, an anti-GPIIb/IIIa antibody or antigen-binding molecule thereof disclosed herein can target GPIIb/IIIa located on the surface of platelets.

D. Chimeric Molecules Comprising Anti-GPIIb/IIIa Antibodies

The present disclosure also provides "chimeric molecules" comprising, for example, at least one of the GPIIb/IIIa antibodies or antigen-binding fragments thereof disclosed herein that is linked and/or conjugated and/or otherwise associated with at least one heterologous moiety. In certain embodiments, the heterologous moiety is an agent that to be ferried or delivered to a platelet or its local environment. Such an agent can be e.g., a therapeutic agent such as a clotting factor (e.g., rFVIIa).

A chimeric molecule disclosed herein encompasses any molecule comprising (i) a GPIIb/IIIa antibody or antigen-binding molecule thereof disclosed herein (e.g., an Fab or scFv derived from a humanized 34D10 antibody), and (ii) at least one (e.g., one two, three, four) heterologous moiety (e.g., a therapeutic moiety, a clotting factor, a half-life extending moiety) and optionally including one or more linkers. In some embodiments, a chimeric molecule is a chimeric protein, i.e., a chimeric molecule in which all its components (heterologous moieties and/or linkers) are polypeptides. Other chimeric molecules can comprise non-polypeptide heterologous moieties (e.g., PEG, lipids, carbohydrates, nucleic acids, small molecule therapeutic agents, radionuclides, fluorescent probes, etc.) and/or non-polypeptide linkers.

In some embodiments, a chimeric molecule comprises a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric molecule can include for example, a protein derived from at least two different biological sources. A biological source can include any non-synthetically produced nucleic acid or amino acid sequence (e.g., a genomic or cDNA sequence, a plasmid or viral vector, a native virion or a mutant or analog, as further described herein, of any of the above). A synthetic source can include a protein or nucleic acid sequence produced chemically and not by a biological system (e.g., solid phase synthesis of amino acid sequences). A chimeric molecule can also include a protein derived from at least 2 different synthetic sources or a protein derived from at least one biological source and at least one synthetic source. A chimeric molecule can also comprise a first amino acid sequence derived from a first source, covalently or non-covalently linked to a nucleic acid, derived from any source or a small organic or inorganic molecule derived from any source. The chimeric molecule can also comprise a linker molecule between the first and second amino acid sequence or between the first amino acid sequence and the nucleic acid, or between the first amino acid sequence and the small organic or inorganic molecule.

In some embodiments, the chimeric molecule has, for example, a formula: (i) Ab-(L)-H or (ii) H-(L)-Ab, wherein, H is a heterologous moiety; L is an optional linker; and, Ab is an anti-GPIIb/IIIa antibody or antigen-binding molecule thereof disclosed herein. One or more copies (e.g., one, two, three, four) of the same heterologous moiety may be included in the chimeric molecule.

In some embodiments, the chimeric molecule further comprises a second heterologous moiety. Accordingly, in some embodiments, the chimeric molecule has a formula selected from:

(i) H1-(L1)-Ab-(L2)-H2;
(ii) H2-(L2)-Ab-(L1)-H1;
(iii) H1-(L1)-H2-(L2)-Ab;
(iv) H2-(L2)-H1-(L1)-Ab;
(v) Ab-(L1)-H1-(L2)-H2; or,
(vi) Ab-(L2)-H2-(L1)-H1;

wherein, Ab is an anti-GPIIb/IIIa antibody or antigen-binding molecule thereof disclosed herein; H1 is a first heterologous moiety, H2 is a second heterologous moiety, L1 is a first optional linker, and L2 is a second optional linker. One or more copies (e.g., one, two, three, four) of the same heterologous moiety may be included in the chimeric molecule.

In some embodiments, the first heterologous moiety and the second heterologous moiety are the same. In other embodiments, the first heterologous moiety and the second heterologous moiety are different. In some embodiments, L1 and L2 are the same. In other embodiments, L1 and L2 are different.

The chimeric molecule formulas disclosed are oriented from N-terminus (left) to C-terminus (right). One skilled in the art would understand that the chimeric molecule formulas disclosed herein are non-limiting examples of chimeric molecules comprising the disclosed anti-GPIIb/IIIa antibodies or antigen-binding fragments thereof. For example, the formulas can comprise further sequences at their N-terminal or C-terminal ends, or inserted between elements of the formula. Accordingly, a chimeric molecule can comprise one, two, three, four, five, or more than five heterologous moieties. In some embodiments, the hyphen (-) in a formula indicates a peptide bond or one or more amino acids. Exemplary chimeric molecules are presented in FIGS. 7 and 8.

In some embodiments, a chimeric protein comprises a first polypeptide chain and a second polypeptide chain, which are associated with each other. In some embodiments, the first polypeptide chain comprises a light chain of a clotting factor (e.g., FVII) and a heterologous moiety (e.g., a half-life extending moiety), and the second polypeptide chain comprises a heavy chain of the clotting factor (e.g., FVII) and a GPIIb/IIIa antibody or antigen-binding molecule thereof disclosed herein. In other embodiments, the first polypeptide chain comprises a light chain of a clotting factor (e.g., FVII) and a GPIIb/IIIa antibody or antigen-binding molecule thereof disclosed herein, and the second polypeptide chain comprises a heavy chain of the clotting factor (e.g., FVII) and a heterologous moiety (e.g., a half-life extending moiety). In yet another embodiment, the first polypeptide chain comprises a light chain of a clotting factor (e.g., FVII) and the second polypeptide chain comprises a heavy chain of the clotting factor (e.g., FVII), a GPIIb/IIIa antibody or antigen-binding molecule thereof disclosed herein, and a heterologous moiety (e.g., a half-life extending moiety). In some embodiments, the first polypeptide chain comprises a light chain of a clotting factor (e.g., FVII) and the second polypeptide chain comprises a heavy chain of the clotting factor (e.g., FVII), a heterologous moiety (e.g., a half-life extending moiety), and a GPIIb/IIIa antibody or antigen-binding molecule thereof disclosed herein. In other embodiments, the first polypeptide chain comprises a light chain of a clotting factor (e.g., FVII), a heterologous moiety (e.g., a half-life extending moiety), and a GPIIb/IIIa antibody or antigen-binding molecule thereof disclosed herein, and the second polypeptide chain comprises a heavy chain of the clotting factor (e.g., FVII). In some embodiments, the first polypeptide chain comprises a light chain of a clotting factor (e.g., FVII), a GPIIb/IIIa antibody or antigen-binding molecule thereof disclosed herein, and a heterologous moiety (e.g., a half-life extending moiety), and the second polypeptide chain comprises a heavy chain of the clotting factor (e.g., FVII).

In some embodiments, the chimeric molecule comprises a formula wherein:

(1) the first polypeptide chain comprises $CF_L$-H or H-$CF_L$ and the second polypeptide chain comprises CFH-Ab or Ab-CFH;

(2) the first polypeptide chain comprises $CF_L$-Ab or Ab-$CF_L$ and the second polypeptide chain comprises $CF_H$-H or H-$CF_H$;

(3) the first polypeptide chain comprises $CF_L$ and the second polypeptide chain comprises $CF_H$-Ab-H or H-Ab-$CF_H$;

(4) the first polypeptide chain comprises $CF_L$ and the second polypeptide chain comprises $CF_H$-H-Ab or Ab-H-$CF_H$;

(5) the first polypeptide chain comprises $CF_L$-H-Ab or Ab-H-$CF_L$ and the second polypeptide chain comprises $CF_H$; or (6) the first polypeptide chain comprises $CF_L$-Ab-H or H-Ab-$CF_L$ and the second polypeptide chain comprises $CF_H$;

wherein, $CF_L$ is a light chain of a clotting factor (e.g., FVII); $CF_H$ is a heavy chain of the clotting factor (e.g., FVII); Ab is an anti-GPIIb/IIIa antibody or antigen-binding molecule thereof; and H is a heterologous moiety (e.g., a half-life extending moiety). In some embodiments, the clotting factor is independently selected from the group consisting of FVII, FIX, FX, and any combinations thereof.

This disclosure also provides a chimeric molecule comprising a first polypeptide chain and a second polypeptide chain, which are associated with each other, (1) wherein the first polypeptide chain comprises a light chain of a clotting factor (e.g., FVII, FIX, or FX), and a targeting moiety, which binds to a platelet, and the second polypeptide chain comprises a heavy chain of the clotting factor (e.g., FVII, FIX, or FX) and a heterologous moiety (e.g., a half-life extending moiety); (2) wherein the first polypeptide chain comprises a light chain of a clotting factor (e.g., FVII) and a heterologous moiety (e.g., a half-life extending moiety), and the second polypeptide chain comprises a heavy chain of the clotting factor (e.g., FVII, FIX, or FX) and a targeting moiety, which binds to a platelet; (3) wherein the first polypeptide chain comprises a light chain of a clotting factor (e.g., FVII, FIX, or FX), a heterologous moiety (e.g., a half-life extending moiety), and a targeting moiety, which binds to a platelet, and the second polypeptide comprises a heavy chain of the clotting factor (e.g., FVII, FIX, or FX); or (4) wherein the first polypeptide chain comprises a light chain of a clotting factor (e.g., FVII, FIX, or FX), a targeting moiety, which binds to a platelet, and a heterologous moiety (e.g., a half-life extending moiety) and the second polypeptide chain comprises a heavy chain of the clotting factor (e.g., FVII, FIX, or FX). In some embodiments, the clotting factor is FVII, FIX, or FX.

As used herein, the phrases "which binds to a platelet," "binding to a platelet," and variants thereof generally refer to the specific binding of (i) a GPIIb/IIIa antibody or antigen-binding molecule thereof or (ii) a chimeric molecule of the present disclosure to an antigenic site on the surface of the platelet, e.g., an epitope on the extracellular domains of the α and/or β subunits of the GPIIb/IIIa receptor. It is known to a person skilled in the art that GPIIb/IIIa is present in two pools, a plasma membrane pool present in the platelet's resting state and an internal pool of GPIIb/IIIa which is expressed upon platelet activation. See, e.g., Quinn et al., J. Pharmacol. Exp. Ther., 297:496-500 (2001). Accordingly, in some specific embodiments, and particularly for diagnostic uses where the platelet's plasma membrane can be permeabilized, the binding of an anti-GPIIb/IIIa antibody or antigen-binding molecule thereof to platelets, or the binding of a chimeric molecule of the present disclosure to platelets can refer to binding to the plasma membrane pool and/or to the internal pool of GPIIb/IIIa.

In some embodiments, the chimeric molecule comprises a first polypeptide chain and a second polypeptide chain, which are associated with each other, (1) wherein the first polypeptide chain comprises $CF_L$-H or H-$CF_L$ and the second polypeptide chain comprises $CF_H$-Ab or Ab-$CF_H$; (2) wherein the first polypeptide chain comprises $CF_L$-Ab or Ab-$CF_L$ and the second polypeptide chain comprises $CF_H$-H or H-$CF_H$; (3) wherein the first polypeptide chain comprises $CF_L$-H-Ab or Ab-H-$CF_L$ and the second polypeptide chain comprises $CF_H$; or (4) wherein the first polypeptide chain comprises $CF_L$-Ab-H or H-Ab-$CF_L$ and the second polypeptide chain comprises $CF_H$; wherein, H is a heterologous moiety (e.g., a half-life extending moiety), $CF_H$ is a heavy chain of a clotting factor (e.g., FVII), $CF_L$ is a light chain of the clotting factor (e.g., FVII, FIX, or FX), Ab is an anti-GPIIb/IIIa antibody that binds to a platelet, and L is an optional linker.

In some embodiments, the association between the first polypeptide chain and the second polypeptide chain in the chimeric molecule is a covalent bond or a non-covalent bond. Thus, in other embodiments, the association between the first polypeptide chain and the second polypeptide chain in the chimeric molecule is a covalent bond between the heavy chain and the light chain of the clotting factor (e.g., FVII, FIX, or FX). In contrast, in some other embodiments, the covalent bond is a disulfide bond.

The present disclosure also provides a chimeric molecule comprising a single polypeptide chain, which comprises, from N terminus to C terminus, (i) a light chain of a clotting factor (e.g., FVII, FIX, or FX), a heterologous moiety (e.g., a half-life extending moiety), a protease cleavage site, a heavy chain of the clotting factor (e.g., FVII, FIX, or FX), and a targeting moiety (e.g., a GPIIb/IIIa antibody or antigen-binding molecule thereof) which binds to a platelet or (ii) a light chain of a clotting factor (e.g., FVII), a targeting moiety, which binds to a platelet, a protease cleavage site, a heavy chain of the clotting factor (e.g., FVII, FIX, or FX), and a heterologous moiety (e.g., a half-life extending moiety). In some embodiments, the clotting factor is FVII. In other embodiments, the clotting factor is FIX or FX. In yet other embodiments, the clotting factor is FVII, FIX, or FX. In some embodiments, the protease cleavage site is an intracellular processing site. In some embodiments, the intracellular processing site is processed by a proprotein convertase. In some embodiments, the proprotein convertase is selected from the group consisting of PC5, PACE, PC7, and any combinations thereof.

I. Heterologous Moieties

The heterologous moiety or moieties of the chimeric molecules disclosed herein can comprise, consist of, or consist essentially of, for example, prophylactic and/or therapeutic agents (e.g., clotting factors), molecules capable of improving a pharmacokinetic (PK) property (e.g., plasma half-life extending moieties), and detectable moieties (e.g., fluorescent molecules or radionuclides). In some embodiments, the heterologous moiety comprises a clotting factor (e.g., a Factor VII). In some embodiments, a heterologous moiety comprises a molecule that can modify a physicochemical property of a chimeric molecule lacking such heterologous moiety. For example, it can increase the hydrodynamic radius of a chimeric molecule. In other embodiments, the incorporation of a heterologous moiety into a chimeric molecule can improve one or more pharmacokinetic properties without significantly affecting its biological activity or function (e.g., procoagulant activity in chimeric molecules comprising a clotting factor). In other embodiments, a heterologous moiety increases stability of the chimeric molecule of the invention or a fragment thereof.

In some embodiments, the heterologous moiety is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

Non-limiting examples of the heterologous moieties are discussed below.

1. Clotting Factors

In some embodiments, the chimeric molecules of this disclosure comprise at least one polypeptide heterologous moiety which is (i) a clotting factor, or (ii) a procoagulant peptide (e.g., a synthetic procoagulant peptide). Blood coagulation is a process that involves a complex interaction of various blood factors that eventually result in a fibrin clot. Generally, the blood factor, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa). In some embodiments, the clotting factor is independently selected from the group consisting of factor FVII ("FVII"), factor IX ("FIX"), or factor X ("FX"), and any combinations thereof. As discussed in detail below, the clotting factor can be, for example, FVII zymogen, activatable FVII, activated FVII (FVIIa), FIX zymogen, activatable FIX, activated FIX (FIXa), FX zymogen, activatable FX, or activated FX (FXa). In some embodiments, the clotting factor can comprise a single polypeptide chain or two polypeptide chains (I the heavy chain and the light chain of FVII). In some embodiments, the chimeric molecule comprises a FVII or activated FVII (FVIIa) clotting factor. In some embodiments, the chimeric molecule of the invention comprises a FIX or activated FIX (FIXa) clotting factor. In other embodiments, the chimeric molecule comprises a FX or activated FX (FXa) clotting factor.

In some embodiments, the chimeric molecule comprises a single clotting factor, which in the chimeric molecule is represented by a formula as H, H1 or H2. In other embodiments, the chimeric molecule comprises two clotting factors. In some embodiments, the two clotting factors are the same, whereas in other embodiments, the two clotting factors are different. In some embodiments, one clotting factor is a fragment of a clotting factor (e.g., a heavy chain of a clotting factor such as FVII) and the second clotting factor is a fragment of the same clotting factor (e.g., a light chain of a clotting factor such as FVIII). In some embodiments, the chimeric molecule comprises more than two clotting factors.

a. Factor VII

In some embodiments, the chimeric molecule comprises a clotting factor which is a mature form of Factor VII or a variant thereof. Factor VII (FVII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. In some embodiments, the chimeric molecule comprises a Factor VIIa. In certain embodiments, the Factor VIIa is recombinant.

FVII can occur as a single chain zymogen, an activated zymogen-like two-chain polypeptide, or a fully activated two-chain form. The zymogen composed of a single chain polypeptide is converted to a two-chain form connected by disulfide bonds by the action of Factor Xa in the presence of calcium ions and phospholipids, thrombin, or by the action of factor XIIa (without additional cofactors). This hydrolysis of Factor VII is accompanied by an at least 85-fold increase in the Factor VII coagulant activity compared to the single chain form (see, e.g., Radcliffe et al., *J. Biol. Chem.*, 250(2):388-395 (1975) and Handbook of Enzymes, Class 3.4 Hydrolases II: EC3.4.21-3.4.22, Volume 7, coed. By Antje Chang, 2002, (Springer, 2$^{nd}$ edition)). Following vascular damage, blood clotting is triggered when factor VIIa (FVIIa) forms a complex with tissue factor (TF). In hemophilia A and B, the propagation phase of blood coagulation is disrupted due to the lack of factors VIII (FVIII) and IX (FIX), leading to excessive bleeding. However, high doses of recombinant FVIIa (rFVIIa) can bypass the FVIII/FIX deficiency and ameliorate bleeding problems.

The amino acid sequence of the B isoform of FVII zymogen is provided below (the signal sequence (boldened), propeptide sequence (underlined); the peptide bond between R and I (boldened and underlined) is cleaved to activate FVII):

This disclosure also encompasses any allelic variants of FVII.

Other exemplary FVII variants that are encompassed by this disclosure include those with increased specific activity, e.g., mutations that increase the activity of FVII by increasing its enzymatic activity ($K_{cat}$ or $K_m$). Such variants have been described in the art and include, e.g., mutant forms of the molecule as described for example in Persson, *Semin Hematol.*, 41 (1Suppl 1):89-92 (2004); Persson et al., *Proc. Natl. Acad Sci. USA* 98:13583 (2001); Petrovan and Ruf, *J. Biol. Chem.* 276:6616 (2001); Persson et al., *J. Biol. Chem.* 276:29195 (2001); Soejima et al., *J. Biol. Chem.* 276:17229 (2001); Soejima et al., *J. Biol. Chem.* 247:49027 (2002); and WO2002/022776.

```
                                                      (SEQ ID NO: 79)
  1  MVSQALRLLC LLLGLQGCLA AVFVTQEEAH GVLHRRRRAN AFLEELRPGS

51  LERECKEEQC SFEEAREIFK DAERTKLFWI SYSDGDQCAS SPCQNGGSCK

101  DQLQSYICFC LPAFEGRNCE THKDDQLICV NENGGCEQYC SDHTGTKRSC

151  RCHEGYSLLA DGVSCTPTVE YPCGKIPILE KRNASKPQGR IVGGKVCPKG

201  ECPWQVLLLV NGAQLCGGTL INTIWVVSAA HCFDKIKNWR NLIAVLGEHD

251  LSEHDGDEQS RRVAQVIIPS TYVPGTTNHD IALLRLHQPV VLTDHVVPLC

301  LPERTFSERT LAFVRFSLVS GWGQLLDRGA TALELMVLNV PRLMTQDCLQ

351  QSRKVGDSPN ITEYMFCAGY SDGSKDSCKG DSGGPHATHY RGTWYLTGIV

401  SWGQGCATVG HFGVYTRVSQ YIEWLQKLMR SEPRPGVLLR APFP
```

It is to be understood the chimeric molecules of this disclosure can include any FVII zymogen (e.g., the A or B isoforms) so long as intended results are achieved (e.g., effectiveness in treatment of a coagulation or hemostatic disorder).

The amino acid sequence of the light chain of FVII is provided below:

```
                                      (SEQ ID NO: 80)
ANAFLEELRP GSLERECKEE QCSFEEAREI FKDAERTKLF

WISYSDGDQC ASSPCQNGGS CKDQLQSYIC FCLPAFEGRN

CETHKDDQLI CVNENGGCEQ YCSDHTGTKR SCRCHEGYSL

LADGVSCTPT VEYPCGKIPI LEKRNASKPQ GR
```

The amino acid sequence of the heavy chain of FVII is provided below:

```
The amino acid sequence of the heavy chain
of FVII is provided below:
                                      (SEQ ID NO: 81)
   IVGGKVCP KGECPWQVLL LVNGAQLCGG TLINTIWVVS

AAHCFDKIKN WRNLIAVLGE HDLSEHDGDE QSRRVAQVII

PSTYVPGTTN HDIALLRLHQ PVVLTDHVVP LCLPERTFSE

RTLAFVRFSL VSGWGQLLDR GATALELMVL NVPRLMTQDC

LQQSRKVGDS PNITEYMFCA GYSDGSKDSC KGDSGGPHAT

HYRGTWYLTG IVSWGQGCAT VGHFGVYTRV SQYIEWLQKL

MRSEPRPGVL LRAPFP
```

In one embodiment, a variant form of FVII includes mutations, e.g., V158D-E296V-M298Q. In another embodiment, a variant form of FVII includes a replacement of amino acids 608-619 (LQQSRKVGDSPN (SEQ ID NO:82), corresponding to the 170-loop) from the FVII mature sequence with amino acids EASYPGK (SEQ ID NO:83) from the 170-loop of trypsin. High specific activity variants of FVII are also known in the art. For example, Simioni et al. (*N.E. Journal of Medicine* 361:1671, 2009) describe an R338L mutation. Chang et al. (*J. Biol. Chem.* 273:12089, 1988) and Pierri et al. (*Human Gene Therapy* 20:479, 2009) describe an R338A mutation. Other mutations are known in the art and include those described, e.g., in Zogg and Brandstetter, *Structure* 17:1669 (2009); Sichler et al., *J. Biol. Chem.* 278:4121 (2003); and Sturzebecher et al., *FEBS Lett.* 412:295 (1997). The contents of all of the references above are incorporated herein by reference.

Full activation, which occurs upon conformational change from a zymogen-like form, occurs upon binding to its co-factor, i.e., tissue factor. Also, mutations can be introduced that result in the conformation change in the absence of tissue factor. Hence, reference to FVIIa includes both two-chain forms thereof: the zymogen-like form, and the fully activated two-chain form.

b. Factor IX

In one embodiment, the chimeric molecule comprises a clotting factor which is a mature form of Factor IX or a variant thereof. Factor IX circulates as a 415 amino acid, single chain plasma zymogen. See, Vysotchin et al., *J. Biol. Chem.* 268:8436 (1993). The amino acid sequence of FIX zymogen is provided below (the signal sequence is underlined (1-28); the propeptide sequence (29-46) is boldened):

(SEQ ID NO: 84)
MQRVNMIMAESPGLITICLLGYLLSAECTVFLDHENANKILNRPKRYNS

GKLEEFVQGNLERECMEEKCSFEEAREVFENTERTTEFWKQYVDGDQCE

SNPCLNGGSCKDDINSYECWCPFGFEGKNCELDVTCNIKNGRCEQFCKN

SADNKVVCSCTEGYRLAENQKSCEPAVPFPCGRVSVSQTSKLTRAETVF

PDVDYVNSTEAETILDNITQSTQSFNDFTRVVGGEDAKPGQFPWQVVLN

GKVDAFCGGSIVNEKWIVTAAHCVETGVKITVVAGEHNIEETEHTEQKR

NVIRIIPHHNYNAAINKYNHDIALLELDEPLVLNSYVTPICIADKEYTN

IFLKFGSGYVSGWGRVFHKGRSALVLQYLRVPLVDRATCLRSTKFTIYN

NMFCAGFHEGGRDSCQGDSGGPHVTEVEGTSFLTGIISWGEECAMKGKY

GIYTKVSRYVNWIKEKTKLT

The zymogen of FIX is activated by FXIa or by the tissue factor/FVIIa complex. Specific cleavages between arginine-alanine 145-146 and arginine-valine 180-181 result in a light chain and a heavy chain linked by a single disulfide bond between cysteine 132 and cysteine 289 (Bajaj et al., *Biochemistry* 22:4047 (1983)).

The structural organization of FIX is similar to that of the vitamin K-dependent blood clotting proteins FVII, FX and protein C. The approximately 45 amino acids of the amino terminus comprise the gamma-carboxyglutamic acid, or Gla, domain. This is followed by two epidermal growth factor homology domains (EGF), an activation peptide and the catalytic "heavy chain" which is a member of the serine protease family (Vysotchin et al., *J. Biol. Chem.* 268:8436 (1993); Spitzer et al., *Biochemical Journal* 265:219 (1990); Brandstetter et al., *Proc. Natl. Acad Sci. USA* 92:9796 (1995)).

c. Factor X

In one embodiment, the chimeric molecule comprises a clotting factor which is a mature form of Factor X. Factor X is a vitamin-K dependent glycoprotein with a molecular weight of 58.5 kDa, which is secreted from liver cells into the plasma as a zymogen. Initially factor X is produced as a prepropeptide with a signal peptide consisting in total of 488 amino acids. The amino acid sequence of FX zymogen is provided below (the signal sequence (1-23) is underlined and the propeptide (24-40) is boldened):

(SEQ ID NO: 85)
MGRPLHLVLLSASLAGLLLLGESLFIRREQANNILARVTRANSFLEEMK

KGHLERECMEETCSYEEAREVFEDSDKTNEFWNKYKDGDQCETSPCQNQ

GKCKDGLGEYTCTCLEGFEGKNCELFTRKLCSLDNGDCDQFCHEEQNSV

VCSCARGYTLADNGKACIPTGPYPCGKQTLERRKRSVAQATSSSGEAPD

SITWKPYDAADLDPTENPFDLLDFNQTQPERGDNNLTRIVGGQECKDGE

CPWQALLINEENEGFCGGTILSEFYILTAAHCLYQAKRFKVRVGDRNTE

QEEGGEAVHEVEVVIKHNRFTKETYDFDIAVLRLKTPITFRMNVAPACL

PERDWAESTLMTQKTGIVSGFGRTHEKGRQSTRLKMLEVPYVDRNSCKL

SSSFIITQNMFCAGYDTKQEDACQGDSGGPHVTRFKDTYFVTGIVSWGE

GCARKGKYGIYTKVTAFLKWIDRSMKTRGLPKAKSHAPEVITSSPLK

The signal peptide is cleaved off by signal peptidase during export into the endoplasmic reticulum. The propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids (M, 16,200) and a C-terminal heavy chain of 306 amino acids (M, 42,000) which are covalently linked via a disulfide bridge between Cys172 and Cys342. Further posttranslational processing steps include the β-hydroxylation of Asp103 as well as N- and O-type glycosylation.

It will be understood that in addition to wild type (WT) versions of these clotting factors or biologically active portions thereof, the heterologous moieties in the chimeric molecules disclosed herein can also comprise precursor truncated forms thereof that have activity, allelic variants and species variants, variants encoded by splice variants, and other variants, including polypeptides that have at least 40%, 45%, 50%, 55%, 65%, 70%, 75%, 80%, 85%, 90%, 95%, 96%, 97%, 98%, 99% or more sequence identity to the mature form of the clotting factor and which retain the ability to promote clot formation. For example, modified FVII polypeptides and variants thereof which retain at least one activity of FVII, such as TF binding, factor X binding, phospholipid binding, and/or coagulant activity of FVII can be employed. By retaining activity, the activity can be altered, such as reduced or increased, as compared to a wild-type clotting factor so long as the level of activity retained is sufficient to yield a detectable effect.

Exemplary modified polypeptides include, but are not limited to, tissue-specific isoforms and allelic variants thereof, synthetic molecules prepared by translation of nucleic acids, proteins generated by chemical synthesis, such as syntheses that include ligation of shorter polypeptides, through recombinant methods, proteins isolated from human and non-human tissue and cells, chimeric polypeptides and modified forms thereof. The clotting factors can also consist of fragments or portions of WT molecules that are of sufficient length or include appropriate regions to retain at least one activity (upon activation if needed) of a full-length mature polypeptide. Exemplary clotting factor variants are known in the art.

The "Gla domain" refers to the conserved membrane binding motif which is present in vitamin K-dependent proteins, such as prothrombin, coagulation factors VII, IX and X, proteins C, S, and Z. These proteins require vitamin K for the posttranslational synthesis of γ-carboxyglutamic acid, an amino acid clustered in the N-terminal Gla domain of these proteins. All glutamic residues present in the domain are potential carboxylation sites and many of them are therefore modified by carboxylation. In the presence of calcium ions, the Gla domain interacts with phospholipid membranes that include phosphatidylserine. The Gla domain also plays a role in binding to the FVIIa cofactor, tissue factor (TF). Complexed with TF, the Gla domain of FVIIa is loaded with seven $Ca^{2+}$ ions, projects three hydrophobic side chains in the direction of the cell membrane for interaction with phospholipids on the cell surface, and has significant contact with the C-terminal domain of TF.

The Gla domain of factor VII comprises the uncommon amino acid γ-carboxyglutamic acid (Gla), which plays a vital role in the binding of clotting factors to negatively charged phospholipid surfaces. The Gla domain is responsible for the high-affinity binding of calcium ions. It starts at the N-terminal extremity of the mature form of proteins and ends with a conserved aromatic residue. A conserved Gla-x(3)-Gla-x-Cys motif is found in the middle of the domain which seems to be important for substrate recognition by the carboxylase. Using stopped-flow fluorescence kinetic measurements in combination with surface plasmon resonance analysis, the Gla domain has been found to be important in the sequence of events whereby the protease domain of FVIIa initiates contact with sTF (Osterlund et al., *Biochem. Biophys. Res. Commun.* 337:1276 (2005)). In addition, clearance of clotting factors can be significantly mediated through Gla interactions, e.g., on liver cells and clearance receptors, e.g., EPCR.

In one embodiment, the chimeric molecule comprises a heterologous moiety comprising a clotting factor modified to lack a Gla domain. The Gla domain is responsible for mediating clearance of clotting factors via multiple pathways, such as binding to liver cells, clearance receptors such as EPCR, etc. Thus, eliminating the Gla domain has beneficial effects on half-life of clotting factors. Though Gla domain is also generally required for activity by localizing clotting factors to sites of coagulation, the inclusion of a platelet targeting domain moiety (e.g., a GPIIb/IIIa antibody or antigen-binding molecule thereof) targets the Gla deleted clotting factor to platelets. Accordingly, in one embodiment, the chimeric molecule comprises a targeting moiety (e.g., a GPIIb/IIIa antibody or antigen-binding molecule thereof) and a heterologous moiety comprising a clotting factor that lacks a Gla domain. For example, in the case of Factor VII, the Gla domain is present at the amino terminus of the light chain and consists of amino acids 1-35. The Gla domains of the exemplary clotting factors disclosed herein are known in the art. The Gla domain can be removed using standard molecular biology techniques, replaced with a targeting domain, and the modified light chain incorporated into a construct of the invention. In one embodiment, a cleavage site can be introduced into constructs lacking a Gla domain to facilitate activation of the molecule. For example, in one embodiment, such a cleavage site can be introduced between the amino acids that are cleaved when the clotting factor is activated (e.g., between amino acids 152 and 153 in the case of Factor VII).

In one embodiment, a cleavage site can be introduced into chimeric molecules comprising a clotting factor that lacks a Gla domain to facilitate activation of the molecule. For example, in one embodiment, such a cleavage site can be introduced between the amino acids that are cleaved when the clotting factor is activated (e.g., between amino acids 152 and 153 in the case of Factor VII). Exemplary clotting factors lacking a Gla domain are known in the art. Exemplary clotting factors are those of mammalian, e.g., human, origin.

2. Half-Life Extending Moieties

In some embodiments, the chimeric molecule comprises at last one heterologous moiety that is a "half-life extending moiety." Half-life extending moieties, as discussed below in detail, can comprise, for example, (i) XTEN polypeptides; (ii) Fc; (iii) albumin, (iv) albumin binding polypeptide or fatty acid, (v) the C-terminal peptide (CTP) of the β subunit of human chorionic gonadotropin, (vi) PAS; (vii) HAP; (viii) transferrin; (ix) polyethylene glycol (PEG); (x) hydroxyethyl starch (HES), (xi) polysialic acids (PSAs); (xii) a clearance receptor or fragment thereof which blocks binding of the chimeric molecule to a clearance receptor; (xiii) low complexity peptides; (xiv) vWF; or (xv) any combinations thereof. In some embodiments, the half-life extending moiety comprises an Fc region. In other embodiments, the half-life extending moiety comprises two Fc regions fused by a linker. Exemplary heterologous moieties also include, e.g., FcRn binding moieties (e.g., complete Fc regions or portions thereof which bind to FcRn), single chain Fc regions (scFc regions, e.g., as described in U.S. Publ. No. 2008-0260738, and Intl. Publ. Nos. WO 2008-012543 and WO 2008-1439545), or processable scFc regions. In some embodiments, a heterologous moiety can include an attachment site for a non-polypeptide moiety such as polyethylene glycol (PEG), hydroxyethyl starch (HES), polysialic acid, or any derivatives, variants, or combinations of these moieties.

In certain embodiments, a chimeric molecule of the disclosure comprises at least one (e.g., one, two, three, or four) half-like extending moiety which increases the in vivo half-life of the chimeric molecule compared with the in vivo half-life of the corresponding chimeric molecule lacking such heterologous moiety. In vivo half-life of a chimeric molecule can be determined by any method known to those of skill in the art, e.g., activity assays (chromogenic assay or one stage clotting aPTT assay), ELISA, etc. In some embodiments, the presence of one or more half-life extending moiety results in the half-life of the chimeric molecule to be increased compared to the half-life of the corresponding chimeric molecule lacking such one or more half-life extending moieties. The half-life of the chimeric molecule comprising a half-life extending moiety is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding chimeric molecule lacking such half-life extending moiety.

In one embodiment, the half-life of the chimeric molecule comprising a half-life extending moiety is about 1.5-fold to about 20-fold, about 1.5 fold to about 15 fold, or about 1.5 fold to about 10 fold longer than the in vivo half-life of the corresponding chimeric molecule lacking such half-life extending moiety. In another embodiment, the half-life of chimeric molecule comprising a half-life extending moiety is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding chimeric molecule lacking such half-life extending moiety.

(i) XTEN Polypeptides

"XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a chimeric molecule partner, XTENs can serve as a carrier, conferring certain desirable pharmacokinetic, physicochemical and pharmaceutical properties when linked to a clotting factor, a heavy chain of a clotting factor, a light chain or a clotting factor, a targeting moiety, or any other sequences or molecules on the chimeric molecule. Such desirable properties include but are not limited to enhanced pharmacokinetic parameters and solubility characteristics.

As used herein, "XTEN" specifically excludes antibodies or antibody fragments such as single-chain antibodies or Fc fragments of a light chain or a heavy chain.

The chimeric molecules of the invention can include a single XTEN polypeptide or two or more (e.g., two, three, four, five) XTEN polypeptides. In one embodiment, a chimeric molecule comprises a FVII, a first XTEN polypeptide, a second XTEN polypeptide, and an anti-GPIIb/IIIa antibody or antigen-binding molecule thereof. The chimeric molecule thus can comprise a formula of FVII-(L1)-X1-(L2)-Ab-(L3)-X2, X2-(L1)-Ab-(L2)-X1-(L3)-FVII, FVII-(L1)-X1-(L2)-X2-(L3)-Ab, or Ab-(L3)-X2-(L2)-X1-(L1)-FVII, wherein FVII comprises FVIIa, X1 is a first XTEN polypeptide, X2 is a second XTEN polypeptide, Ab is an anti-GPIIb/IIIa antibody or antigen-binding molecule thereof as described above, L1 is a first optional linker, L2 is a second optional linker, and L3 is a third optional linker. In another embodiment, a chimeric molecule comprises two polypeptide chains associated with each other, the first polypeptide chain comprising a light chain of FVII and a first XTEN polypeptide the second polypeptide chain comprising a heavy chain of FVII, a second XTEN polypeptide, and a targeting moiety, which binds to a platelet, in any order. In other embodiments, a chimeric molecule comprises two polypeptide chains associated with each other, the first polypeptide chain comprising a light chain of FVII and the first XTEN polypeptide a second polypeptide chain comprising, from N-terminus to C-terminus, a heavy chain of FVII, a second XTEN polypeptide, and a targeting moiety, which binds to a platelet or a heavy chain of FVII, a targeting moiety, which binds to a platelet, and a second XTEN polypeptide.

Figure 17:
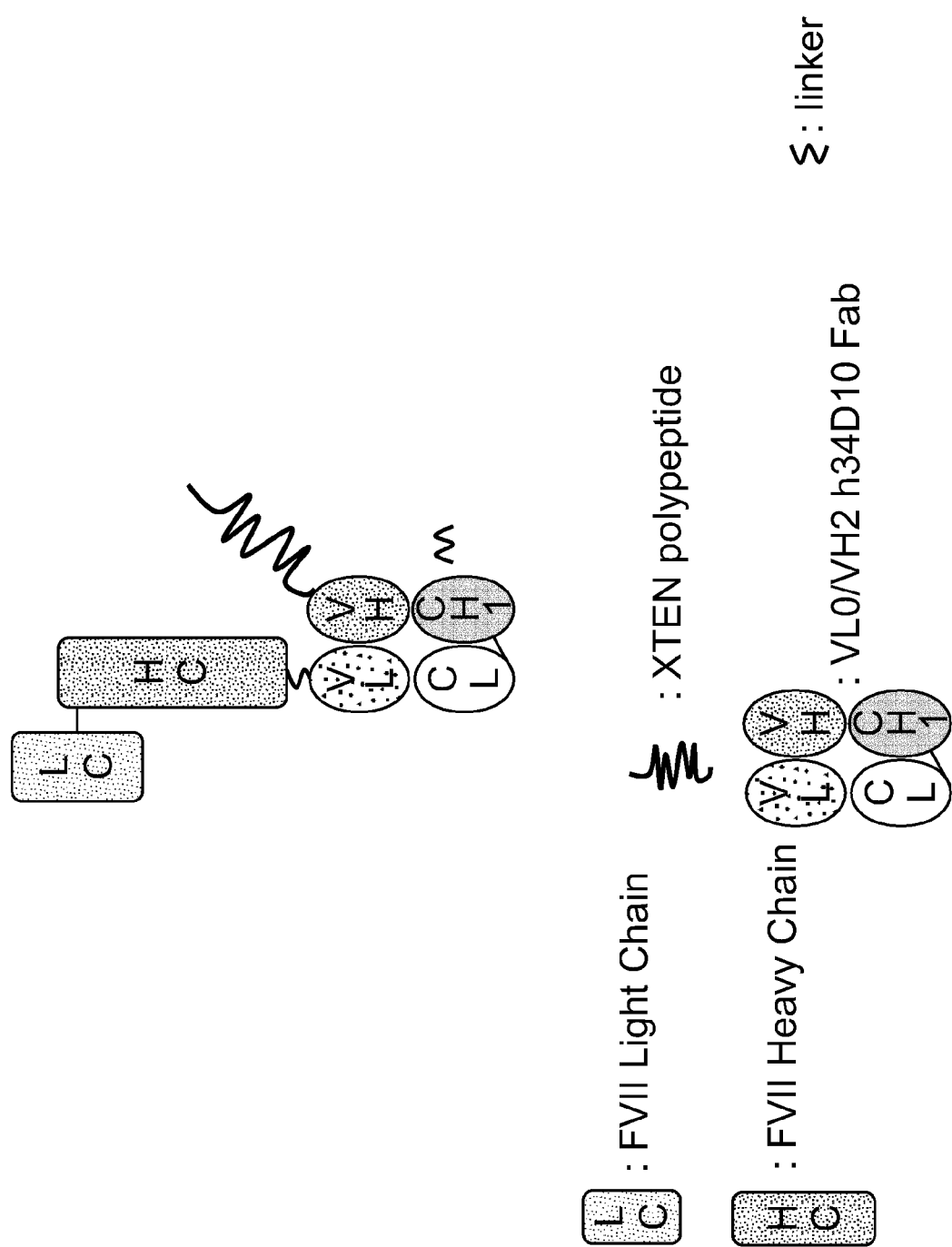
FIG. 17 shows the configuration of FVII-250 (SEQ ID NO:74)/Fab-062 (SEQ ID NO:252). The FVIIa molecule is fused to the Fab light chain VL0/CL via a 6x(GGGGS) linker (SEQ ID NO:170). VL0/CL forms a dimer with Fab-062 (Fab heavy chain) via a disulfide bond. Fab-062 comprises an XTEN fused to the N-terminus of the VH2/CH1 heavy chain.
Figure 20:
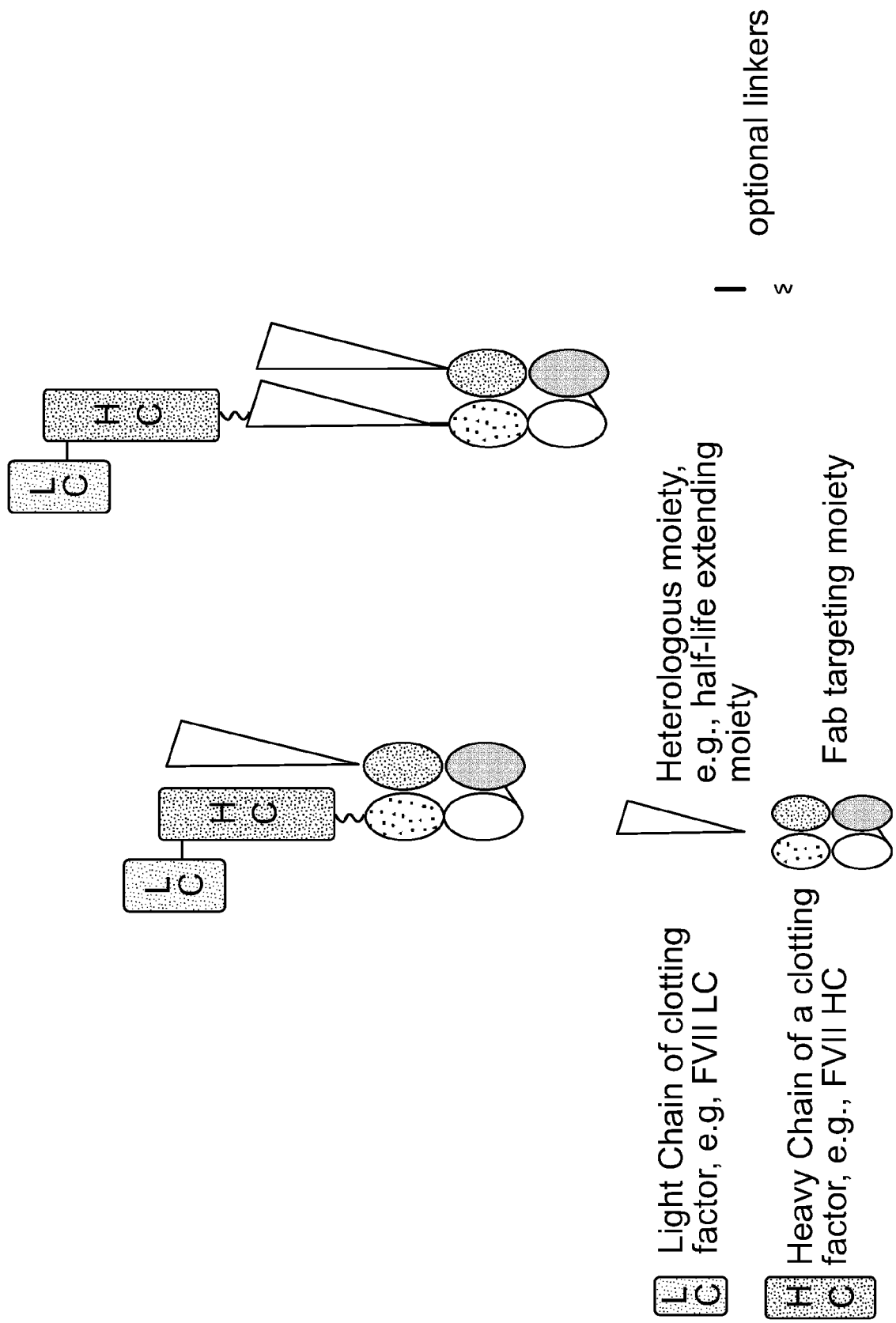
FIG. 20 illustrates non-limiting examples of possible configurations for chimeric molecules comprising the heavy and light chain of a clotting factor, a Fab targeting moiety, one or two heterologous moieties (e.g., half-life extension moieties), and optional linkers.

Other embodiments within the scope of this disclosure encompass a chimeric molecule represented by the following formula: FVII-(L1)-X1-(L2)-Ab-(L3)-X2 in which FVII comprises FVIIa, L1 is a first optional linker, X1 is a first optional XTEN polypeptide, L2 is a second optional linker, Ab is an anti-GPIIb/IIIa antibody or antigen-binding molecule thereof as described above (e.g., an Fab, scFv, etc.), L3 is a third optional linker, and X2 is a second XTEN polypeptide which may be the same of different from the first optional XTEN polypeptide. In a more specific embodiment, the first XTEN polypeptide is present in the molecule. Illustrative non-limiting examples of these embodiments are shown in FIGS. 17 and 20.

In some embodiments, the XTEN sequence of the invention is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues.

The XTEN sequence of the invention can comprise one or more sequence motif of 9 to 14 amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids selected from the group consisting of glycine (G), alanine (A), serine (S), threonine (T), glutamate (E) and proline (P). See US 2010-0239554 A1.

In some embodiments, the XTEN comprises non-overlapping sequence motifs in which about 80%, or at least about 85%, or at least about 90%, or about 91%, or about 92%, or about 93%, or about 94%, or about 95%, or about 96%, or about 97%, or about 98%, or about 99% or about 100% of the sequence consists of multiple units of non-overlapping sequences selected from a single motif family selected from TABLE 2, resulting in a family sequence. As used herein, "family" means that the XTEN has motifs selected only from a single motif category from TABLE 2; i.e., AD, AE, AF, AG, AM, AQ, BC, or BD XTEN, and that any other amino acids in the XTEN not from a family motif are selected to achieve a needed property, such as to permit incorporation of a restriction site by the encoding nucleotides, incorporation of a cleavage sequence, or to achieve a better linkage to FVII. In some embodiments of XTEN families, an XTEN sequence comprises multiple units of non-overlapping sequence motifs of the AD motif family, or of the AE motif family, or of the AF motif family, or of the AG motif family, or of the AM motif family, or of the AQ motif family, or of the BC family, or of the BD family, with the resulting XTEN exhibiting the range of homology described above. In other embodiments, the XTEN comprises multiple units of motif sequences from two or more of the motif families of TABLE 2. These sequences can be selected to achieve desired physical/chemical characteristics, including such properties as net charge, hydrophilicity, lack of secondary structure, or lack of repetitiveness that are conferred by the amino acid composition of the motifs, described more fully below. In the embodiments hereinabove described in this paragraph, the motifs incorporated into the XTEN can be selected and assembled using the methods described herein to achieve an XTEN of about 36 to about 3000 amino acid residues. Additional, non-limiting, examples of XTENs linked to FVII are disclosed in U.S. Patent Publication No. 2012/0263701, which is incorporated herein by reference in its entirety.

TABLE 2

XTEN Sequence Motifs of 12 Amino Acids and Motif Families

| Motif Family* | MOTIF SEQUENCE | SEQ ID NO: |
| --- | --- | --- |
| AD | GESPGGSSGSES | 86 |
| AD | GSEGSSGPGESS | 87 |
| AD | GSSESGSSEGGP | 88 |
| AD | GSGGEPSESGSS | 89 |
| AE, AM | GSPAGSPTSTEE | 90 |
| AE, AM, AQ | GSEPATSGSETP | 91 |
| AE, AM, AQ | GTSESATPESGP | 92 |
| AE, AM, AQ | GTSTEPSEGSAP | 93 |
| AF, AM | GSTSESPSGTAP | 94 |
| AF, AM | GTSTPESGSASP | 95 |
| AF, AM | GTSPSGESSTAP | 96 |
| AF, AM | GSTSSTAESPGP | 97 |

TABLE 2-continued

XTEN Sequence Motifs of 12 Amino Acids and Motif Families

| Motif Family* | MOTIF SEQUENCE | SEQ ID NO: |
|---|---|---|
| AG, AM | GTPGSGTASSSP | 98 |
| AG, AM | GSSTPSGATGSP | 99 |
| AG, AM | GSSPSASTGTGP | 100 |
| AG, AM | GASPGTSSTGSP | 101 |
| AQ | GEPAGSPTSTSE | 102 |
| AQ | GTGEPSSTPASE | 103 |
| AQ | GSGPSTESAPTE | 104 |
| AQ | GSETPSGPSETA | 105 |
| AQ | GPSETSTSEPGA | 106 |
| AQ | GSPSEPTEGTSA | 107 |
| BC | GSGASEPTSTEP | 108 |
| BC | GSEPATSGTEPS | 109 |
| BC | GTSEPSTSEPGA | 110 |
| BC | GTSTEPSEPGSA | 111 |
| BD | GSTAGSETSTEA | 112 |
| BD | GSETATSGSETA | 113 |
| BD | GTSESATSESGA | 114 |
| BD | GTSTEASEGSAS | 115 |

* Denotes individual motif sequences that, when used together in various permutations, results in a "family sequence"

XTEN can have varying lengths. In one embodiment, the length of the XTEN polypeptide(s) is chosen based on the property or function to be achieved in the fusion protein. Depending on the intended property or function, XTEN can be short or intermediate length sequence or longer sequence that can serve as carriers. In certain embodiments, the XTEN include short segments of about 6 to about 99 amino acid residues, intermediate lengths of about 100 to about 399 amino acid residues, and longer lengths of about 400 to about 1000 and up to about 3000 amino acid residues. Thus, the XTEN linked to FVII (e.g., heavy chain or light chain) or a targeting moiety can have lengths of about 6, about 12, about 36, about 40, about 42, about 72, about 96, about 144, about 288, about 400, about 500, about 576, about 600, about 700, about 800, about 864, about 900, about 1000, about 1500, about 2000, about 2500, or up to about 3000 amino acid residues in length. In other embodiments, the XTEN sequences is about 6 to about 50, about 50 to about 100, about 100 to 150, about 150 to 250, about 250 to 400, about 400 to about 500, about 500 to about 900, about 900 to 1500, about 1500 to 2000, or about 2000 to about 3000 amino acid residues in length. The precise length of an XTEN polypeptide that can be linked to FVII (e.g., light chain or heavy chain) or a targeting moiety (Ab) can vary without adversely affecting the activity of FVII. In one embodiment, one or more of the XTEN used herein has about 42 amino acids, about 72 amino acids, about 108 amino acids, about 144 amino acids, about 180 amino acids, about 216 amino acids, about 252 amino acids, about 288 amino acids, about 324 amino acids, about 360 amino acids, about 396 amino acids, about 432 amino acids, about 468 amino acids, about 504 amino acids, about 540 amino acids, about 576 amino acids, about 612 amino acids, about 624 amino acids, about 648 amino acids, about 684 amino acids, about 720 amino acids, about 756 amino acids, about 792 amino acids, about 828 amino acids, about 836 amino acids, about 864 amino acids, about 875 amino acids, about 912 amino acids, about 923 amino acids, about 948 amino acids, about 1044 amino acids, about 1140 amino acids, about 1236 amino acids, about 1318 amino acids, about 1332 amino acids, about 1428 amino acids, about 1524 amino acids, about 1620 amino acids, about 1716 amino acids, about 1812 amino acids, about 1908 amino acids, or about 2004 amino acids in length and can be selected from one or more of the XTEN family sequences; i.e., AD, AE, AF, AG, AM, AQ, BC, BD, or any combinations thereof.

In some embodiments, the XTEN polypeptide used in the invention is at least 60%, 70%, 80%, 85%, 90%, 91%, 92%, 93%, 94%, 95%, 96%, 97%, 98%, 99%, or 100% identical to a sequence selected from the group consisting of AE42, AG42, AE42_2, AE42_3, AE48, AM48, AE72, AE72_2, AE72_3, AG72, AE108, AG108, AE144, AF144, AE144_2, AE144_3, AG144, AE180, AG180, AE216, AG216, AE252, AG252, AE288, AG288, AE295, AE324, AG324, AE360, AG360, AE396, AG396, AE432, AG432, AE468, AG468, AE504, AG504, AF504, AE540, AG540, AF540, AD576, AE576, AF576, AG576, AE612, AG612, AE624, AE648, AG648, AG684, AE720, AG720, AE756, AG756, AE792, AG792, AE828, AG828, AD836, AE864, AF864, AG864, AE872, AE884, AM875, AE912, AM923, AM1318, BC864, BD864, AE948, AE1044, AE1140, AE1236, AE1332, AE1428, AE1524, AE1620, AE1716, AE1812, AE1908, AE2004A, AG948, AG1044, AG1140, AG1236, AG1332, AG1428, AG1524, AG1620, AG1716, AG1812, AG1908, AG2004, and any combinations thereof. See US 2010-0239554 A1.

In one embodiment, the XTEN sequence is at least 60%, 70%, 80%, 90%, 95%, 96%, 97%, 98%, 99% or 100% identical to an amino acid sequence selected from the group consisting of AE42, AE864, AE576, AE288, AE144, AG864, AG576, AG288, AG144, and any combinations thereof. In another embodiment, the XTEN sequence is selected from the group consisting of AE42, AE864, AE576, AE288, AE144, AG864, AG576, AG288, AG144, and any combinations thereof. In one embodiment, the XTEN sequence is AE144. In a specific embodiment, the XTEN sequence is AE288. The amino acid sequences for certain XTEN sequences of the invention are shown in TABLE 3.

TABLE 3

XTEN Sequences

| XTEN | Amino Acid Sequence |
|---|---|
| AE42<br>SEQ ID NO: 116 | GAPGSPAGSPTSTEEGTSESATPESGPGSEPATSGSETPASS |
| AE42_2<br>SEQ ID NO: 117 | TGGGSPAGSPTSTEEGTSESATPESGPGSEPATSGSETPASS |

TABLE 3-continued

XTEN Sequences

| XTEN | Amino Acid Sequence |
|---|---|
| AE42_3<br>SEQ ID NO: 118 | GTSESATPESGPGSEPATSGSETPGTSESATPESGPGSEPAT |
| AE72<br>SEQ ID NO: 119 | GAP TSESATPESG PGSEPATSGS ETPGTSESAT PESGPGSEPA TSGSETPGTS ESATPESGPG TSTEPSEGSA PGASS |
| AE72_2<br>SEQ ID NO: 120 | GTSESATPESGPGSEPATSGSETPGTSESATPESGPGSEPATSGSET PGTSESATPESGPGTSTEPSEGSAP |
| AE72_3<br>SEQ ID NO: 121 | SPAGSPTSTEEGTSESATPESGPGSEPATSGSETPGTSESATPESGP GTSTEPSEGSAPGTSTEPSEGSAPG |
| AE144<br>SEQ ID NO: 122 | GSEPATSGSETPGTSESATPESGPGSEPATSGSETPGSPAGSPTSTE EGTSTEPSEG SAPGSEPATSGSETPGSEPATSGSETPGSEPATSGSETPGTSTEPSE GSAPGTSESA PESGPGSEPATSGSETPGTSTEPSEGSAP |
| AE144_2<br>SEQ ID NO: 123 | GTSESATPESGPGSEPATSGSETPGTSESATPESGPGSEPATSGSET PGTSESATPESGPGTSTEPSEGSAPGSPAGSPTSTEEGTSESATPES GPGSEPATSGSETPGTSESATPESGPGSPAGSPTSTEEGSPAGSPTS TEE |
| AE144_3<br>SEQ ID NO: 124 | GSPAGSPTSTEEGTSESATPESGPGTSTEPSEGSAPGSPAGSPTSTE EGTSTEPSEGSAPGTSTEPSEGSAPGTSESATPESGPGSEPATSGSE TPGSEPATSGSETPGSPAGSPTSTEEGTSESATPESGPGTSTEPSEG SAP |
| AG144<br>SEQ ID NO: 125 | GTPGSGTASSSPGSSTPSGATGSPGSSPSASTGTGPGSSPSASTGTG PGASPGTSST GSPGASPGTSSTGSPGSSTPSGATGSPGSSPSASTGTGPGASPGTSS TGSPGSSPSA STGTGPGTPGSGTASSSPGSSTPSGATGSP |
| AE288<br>SEQ ID NO: 126 | GTSESATPESGPGSEPATSGSETPGTSESATPESGPGSEPATSGSET PGTSESATPESG PGTSTEPSEGSAPGSPAGSPTSTEEGTSESATPESGPGSEPATSGSE TPGTSESATPES GPGSPAGSPTSTEEGSPAGSPTSTEEGTSTEPSEGSAPGTSESATPE SGPGTSESATPE SGPGTSESATPESGPGSEPATSGSETPGSEPATSGSETPGSPAGSPT STEEGTSTEPSE GSAPGTSTEPSEGSAPGSEPATSGSETPGTSESATPESGPGTSTEPS EGSAP |
| AG288<br>SEQ ID NO: 127 | PGASPGTSSTGSPGASPGTSSTGSPGTPGSGTASSSPGSSTPSGATG SPGTPGSGTASS SPGSSTPSGATGSPGPTGSGTASSSPGSSTPSGATGSPGSSTPSGAT GSPGSSPSASTG TGPGSSPSASTGTGPGASPGTSSTGSPGTPGSGTASSSPGSSTPSGA TGSPGSSPSAST GTGPGSSPSASTGTGPGASPGTSSTGSPGASPGTSSTGSPGSSTPSG ATGSPGSSPSAS TGTGPGASPGTSSTGSPGSSPSASTGTGPGTPGSGTASSSPGSSTPS GATGS |
| AE576<br>SEQ ID NO: 128 | GSPAGSPTSTEEGTSESATPESGPGTSTEPSEGSAPGSPAGSPTSTE EGTSTEPSEGSA PGTSTEPSEGSAPGTSESATPESGPGSEPATSGSETPGSEPATSGSE TPGSPAGSPTST EEGTSESATPESGPGTSTEPSEGSAPGTSTEPSEGSAPGSPAGSPTS TEEGTSTEPSEG SAPGTSTEPSEGSAPGTSESATPESGPGTSTEPSEGSAPGTSESATP ESGPGSEPATSG SETPGTSTEPSEGSAPGTSTEPSEGSAPGTSESATPESGPGTSESAT PESGPGSPAGSP TSTEEGTSESATPESGPGSEPATSGSETPGTSESATPESGPGTSTEP SEGSAPGTSTEP SEGSAPGTSTEPSEGSAPGTSTEPSEGSAPGTSTEPSEGSAPGTSTE PSEGSAPGSPAG SPTSTEEGTSTEPSEGSAPGTSESATPESGPGSEPATSGSETPGTSE SATPESGPGSEP ATSGSETPGTSESATPESGPGTSTEPSEGSAPGTSESATPESGPGSP AGSPTSTEEGSP AGSPTSTEEGSPAGSPTSTEEGTSESATPESGPGTSTEPSEGSAP |

TABLE 3-continued

XTEN Sequences

| XTEN | Amino Acid Sequence |
|---|---|
| AG576<br>SEQ ID NO: 129 | PGTPGSGTASSSPGSSTPSGATGSPGSSPSASTGTGPGSSPSASTGTGPGSS<br>TPSGATG<br>SPGSSTPSGATGSPGASPGTSSTGSPGASPGTSSTGSPGASPGTSSTGSPGT<br>PGSGTAS<br>SSPGASPGTSSTGSPGASPGTSSTGSPGASPGTSSTGSPGSSPSASTGTGPG<br>TPGSGTA<br>SSSPGASPGTSSTGSPGASPGTSSTGSPGASPGTSSTGSPGSSTPSGATGSP<br>GSSTPSG<br>ATGSPGASPGTSSTGSPGTPGSGTASSSPGSSTPSGATGSPGSSTPSGATGS<br>PGSSTPS<br>GATGSPGSSPSASTGTGPGASPGTSSTGSPGASPGTSSTGSPGTPGSGTASS<br>SPGASPG<br>TSSTGSPGASPGTSSTGSPGASPGTSSTGSPGASPGTSSTGSPGTPGSGTAS<br>SSPGSST<br>PSGATGSPGTPGSGTASSSPGSSTPSGATGSPGTPGSGTASSSPGSSTPSGA<br>TGSPGSS<br>TPSGATGSPGSSPSASTGTGPGSSPSASTGTGPGASPGTSSTGSPGTPGSGT<br>ASSSPGS<br>STPSGATGSPGSSPSASTGTGPGSSPSASTGTGPGASPGTSSTGS |
| AE864<br>SEQ ID NO: 130 | GSPAGSPTSTEEGTSESATPESGPGTSTEPSEGSAPGSPAGSPTSTEEGTST<br>EPSEGSA<br>PGTSTEPSEGSAPGTSESATPESGPGSEPATSGSETPGSEPATSGSETPGSP<br>AGSPTST<br>EEGTSESATPESGPGTSTEPSEGSAPGTSTEPSEGSAPGSPAGSPTSTEEGT<br>STEPSEG<br>SAPGTSTEPSEGSAPGTSESATPESGPGTSTEPSEGSAPGTSESATPESGPG<br>SEPATSG<br>SETPGTSTEPSEGSAPGTSTEPSEGSAPGTSESATPESGPGTSESATPESGP<br>GSPAGSP<br>TSTEEGTSESATPESGPGSEPATSGSETPGTSESATPESGPGTSTEPSEGSA<br>PGTSTEP<br>SEGSAPGTSTEPSEGSAPGTSTEPSEGSAPGTSTEPSEGSAPGTSTEPSEGS<br>APGSPAG<br>SPTSTEEGTSTEPSEGSAPGTSESATPESGPGSEPATSGSETPGTSESATPE<br>SGPGSEP<br>ATSGSETPGTSESATPESGPGTSTEPSEGSAPGTSESATPESGPGSPAGSPT<br>STEEGSP<br>AGSPTSTEEGSPAGSPTSTEEGTSESATPESGPGTSTEPSEGSAPGTSESAT<br>PESGPGS<br>EPATSGSETPGTSESATPESGPGSEPATSGSETPGTSESATPESGPGTSTEP<br>SEGSAPG<br>SPAGSPTSTEEGTSESATPESGPGSEPATSGSETPGTSESATPESGPGSPAG<br>SPTSTEE<br>GSPAGSPTSTEEGTSTEPSEGSAPGTSESATPESGPGTSESATPESGPGTSE<br>SATPESG<br>PGSEPATSGSETPGSEPATSGSETPGSPAGSPTSTEEGTSTEPSEGSAPGTS<br>TEPSEGS<br>APGSEPATSGSETPGTSESATPESGPGTSTEPSEGSAP |
| AG864<br>SEQ ID NO: 131 | GASPGTSSTGSPGSSPSASTGTGPGSSPSASTGTGPGTPGSGTASSSPGSST<br>PSGATGS<br>PGSSPSASTGTGPGASPGTSSTGSPGTPGSGTASSSPGSSTPSGATGSPGTP<br>GSGTASS<br>SPGASPGTSSTGSPGASPGTSSTGSPGTPGSGTASSSPGSSTPSGATGSPGA<br>SPGTSST<br>GSPGTPGSGTASSSPGSSTPSGATGSPGSSPSASTGTGPGSSPSASTGTGPG<br>SSTPSGA<br>TGSPGSSTPSGATGSPGASPGTSSTGSPGASPGTSSTGSPGASPGTSSTGSP<br>GTPGSGT<br>ASSSPGASPGTSSTGSPGASPGTSSTGSPGASPGTSSTGSPGSSPSASTGTG<br>PGTPGSG<br>TASSSPGASPGTSSTGSPGASPGTSSTGSPGASPGTSSTGSPGSSTPSGATG<br>SPGSSTP<br>SGATGSPGASPGTSSTGSPGTPGSGTASSSPGSSTPSGATGSPGSSTPSGAT<br>GSPGSST<br>PSGATGSPGSSPSASTGTGPGASPGTSSTGSPGASPGTSSTGSPGTPGSGTA<br>SSSPGAS<br>PGTSSTGSPGASPGTSSTGSPGASPGTSSTGSPGASPGTSSTGSPGTPGSGT<br>ASSSPGS<br>STPSGATGSPGTPGSGTASSSPGSSTPSGATGSPGTPGSGTASSSPGSSTPS<br>GATGSPG<br>SSTPSGATGSPGSSPSASTGTGPGSSPSASTGTGPGASPGTSSTGSPGTPGS<br>GTASSSP |

TABLE 3-continued

XTEN Sequences

| XTEN | Amino Acid Sequence |
|---|---|
| | GSSTPSGATGSPGSSPSASTGTGPGSSPSASTGTGPGASPGTSSTGSPGASP<br>GTSSTGS<br>PGSSTPSGATGSPGSSPSASTGTGPGASPGTSSTGSPGSSPSASTGTGPGTP<br>GSGTASS<br>SPGSSTPSGATGSPGSSTPSGATGSPGASPGTSSTGSP |

In some embodiments wherein the XTEN has less than 100% of its amino acids consisting of 4, 5, or 6 types of amino acid selected from glycine (G), alanine (A), serine (S), threonine (T), glutamate (E) and proline (P), or less than 100% of the sequence consisting of the sequence motifs from Table 2 or the XTEN sequences of Table 3, the other amino acid residues of the XTEN are selected from any of the other 14 natural L-amino acids, but are preferentially selected from hydrophilic amino acids such that the XTEN sequence contains at least about 90%, 91%, 92%, 93%, 94%, 95%, 96%, 97%, 98%, or at least about 99% hydrophilic amino acids. An individual amino acid or a short sequence of amino acids other than glycine (G), alanine (A), serine (S), threonine (T), glutamate (E) and proline (P) may be incorporated into the XTEN to achieve a needed property, such as to permit incorporation of a restriction site by the encoding nucleotides, or to facilitate linking to a payload component, or incorporation of a cleavage sequence. The XTEN amino acids that are not glycine (G), alanine (A), serine (S), threonine (T), glutamate (E) and proline (P) are either interspersed throughout the XTEN sequence, are located within or between the sequence motifs, or are concentrated in one or more short stretches of the XTEN sequence such as at or near the N- or C-terminus. As hydrophobic amino acids impart structure to a polypeptide, the invention provides that the content of hydrophobic amino acids in the XTEN utilized in the conjugation constructs will typically be less than 5%, or less than 2%, or less than 1% hydrophobic amino acid content. Hydrophobic residues that are less favored in construction of XTEN include tryptophan, phenylalanine, tyrosine, leucine, isoleucine, valine, and methionine. Additionally, one can design the XTEN sequences to contain less than 5% or less than 4% or less than 3% or less than 2% or less than 1% or none of the following amino acids: methionine (to avoid oxidation), asparagine and glutamine (to avoid deamidation). In other embodiments, the amino acid content of methionine and tryptophan in the XTEN component used in the conjugation constructs is typically less than 5%, or less than 2%, and most preferably less than 1%. In other embodiments, the XTEN will have a sequence that has less than 10% amino acid residues with a positive charge, or less than about 7%, or less that about 5%, or less than about 2% amino acid residues with a positive charge, the sum of methionine and tryptophan residues will be less than 2%, and the sum of asparagine and glutamine residues will be less than 5% of the total XTEN sequence.

In further embodiments, the XTEN polypeptide used in the invention affects the physical or chemical property, e.g., pharmacokinetics, of the chimeric molecule of the present disclosure. The XTEN sequence used in the present disclosure can exhibit one or more of the following advantageous properties: conformational flexibility, enhanced aqueous solubility, high degree of protease resistance, low immunogenicity, low binding to mammalian receptors, or increased hydrodynamic (or Stokes) radii. In a specific embodiment, the XTEN polypeptide linked to FVII or a targeting moiety (e.g., an anti-GPIIb/IIIa antibody or antigen-binding molecule thereof) in in this invention increases pharmacokinetic properties such as longer terminal half-life or increased area under the curve (AUC), so that the chimeric molecule described herein stays in vivo for an increased period of time compared to wild type clotting factor. In further embodiments, the XTEN polypeptide used in this invention increases pharmacokinetic properties such as longer terminal half-life or increased area under the curve (AUC), so that the clotting factor stays in vivo for an increased period of time compared to wild type FVIIa.

A variety of methods and assays can be employed to determine the physical/chemical properties of proteins comprising the XTEN polypeptide. Such methods include, but are not limited to analytical centrifugation, EPR, HPLC-ion exchange, HPLC-size exclusion, HPLC-reverse phase, light scattering, capillary electrophoresis, circular dichroism, differential scanning calorimetry, fluorescence, HPLC-ion exchange, HPLC-size exclusion, IR, NMR, Raman spectroscopy, refractometry, and UV/Visible spectroscopy. Additional methods are disclosed in Amau et al., *Prot Expr and Purif* 48, 1-13 (2006).

Additional examples of XTEN polypeptides that can be used according to the present disclosure and are disclosed in U.S. Pat. Nos. 7,855,279 and 7,846,445, US Patent Publication Nos. 2009/0092582 A1, 2010/0239554 A1, 2010/0323956 A1, 2011/0046060 A1, 2011/0046061 A1, 2011/0077199 A1, 2011/0172146 A1, 2013/0017997 A1, or 2012/0263701 A1, International Patent Publication Nos. WO 2010091122 A1, WO 2010144502 A2, WO 2010144508 A1, WO 2011028228 A1, WO 2011028229 A1, or WO 2011028344 A2; or US 2012/0178691.

(ii) Fc and Single Chain Fc (scFc) Region

In certain embodiments, the chimeric molecule comprises at least one heterologous moiety comprising a Fc region. "Fc" or "Fc region" as used herein means a functional neonatal Fc receptor (FcRn) binding partner comprising an Fc domain, variant, or fragment thereof, unless otherwise specified. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al., *Nature*, 372:379 (1994), incorporated herein by reference in its entirety). The major contact area of the Fc with the FcRn is near the junction of the CH2 and CH3 domains. Fc-FcRn contacts are all within a single Ig heavy chain. FcRn binding partners include, but are not limited to, whole IgG, the Fc fragment of IgG, and other fragments of IgG that include the complete binding region of FcRn. An Fc can comprise the CH2 and CH3 domains of an immunoglobulin with or without the hinge region of the immunoglobulin. Also included are Fc fragments, variants, or derivatives which maintain the desirable properties of an Fc region in a chimeric molecule, e.g., an increase in half-life, e.g., in vivo half-life. Myriad mutants, fragments, variants, and derivatives are described, e.g., in PCT Publication Nos. WO2011/069164, WO2012/006623, WO2012/006635, or WO 2012/006633, all of which are incorporated herein by reference in their entireties. In some embodiments, the chimeric molecule comprises a clotting factor (e.g., a FVII), a targeting moiety (e.g., a GPIIb/IIIa antibody or antigen-binding molecule thereof), and an Fc region.

In one embodiment, the chimeric molecule comprises a heterologous moiety comprising one genetically fused Fc region or a portion thereof within a single polypeptide chain (i.e., a single-chain Fc (scFc) region). An exemplary single-chain human IgG1 Fc amino acid sequence is provided below (the Gly/Ser linker is underlined):

(SEQ ID NO: 132)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGK<u>GGGGSGGGGSGGGGSGGG</u>

<u>GS</u>DKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDK

SRWQQGNVFSCSVMHEALHNHYTQKSLSLSPGK

The unprocessed polypeptides comprise at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the invention is capable of binding, via its scFc region, to at least one Fc receptor (e.g., an FcRn, an FcγR receptor (e.g., FcγRIII), or a complement protein (e.g., C1q)) in order to improve half-life or trigger an immune effector function (e.g., antibody-dependent cytotoxicity (ADCC), phagocytosis, or complement-dependent cytotoxicity (CDCC) and/or to improve manufacturability). In some embodiments, the chimeric molecule comprises a clotting factor (e.g., a FVII), a targeting moiety (e.g., a GPIIb/IIIa antibody or antigen-binding molecule thereof), and an scFc region.

(iii) Albumins

In certain embodiments, the chimeric molecule comprises a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. US2008/0194481, US2008/0004206, US2008/ 0161243, US2008/0261877, or US2008/0153751 or PCT Appl. Publ. Nos. WO2008/033413, WO2009/058322, or WO2007/021494, which are incorporated herein by reference in their entireties. An exemplary mature human albumin amino acid sequence is provide below (NCBI Ref. Sequence NP_000468):

(SEQ ID NO: 133)
RGVFRRDAHKSEVAHRFKDLGEENFKALVLIAFAQYLQQCPFEDHVKLV

NEVTEFAKTCVADESAENCDKSLHTLFGDKLCTVATLRETYGEMADCCA

KQEPERNECFLQHKDDNPNLPRLVRPEVDVMCTAFHDNEETFLKKYLYE

IARRHPYFYAPELLFFAKRYKAAFTECCQAADKAACLLPKLDELRDEGK

ASSAKQRLKCASLQKFGERAFKAWAVARLSQRFPKAEFAEVSKLVTDLT

KVHTECCHGDLLECADDRADLAKYICENQDSISSKLKECCEKPLLEKSH

CIAEVENDEMPADLPSLAADFVESKDVCKNYAEAKDVFLGMFLYEYARR

HPDYSVVLLLRLAKTYETTLEKCCAAADPHECYAKVFDEFKPLVEEPQN

LIKQNCELFEQLGEYKFQNALLVRYTKKVPQVSTPTLVEVSRNLGKVGS

KCCKHPEAKRMPCAEDYLSVVLNQLCVLHEKTPVSDRVTKCCTESLVNR

RPCFSALEVDETYVPKEFNAETFTFHADICTLSEKERQIKKQTALVELV

KHKPKATKEQLKAVMDDFAAFVEKCCKADDKETCFAEEGKKLVAASQAA

LGL

In some embodiments, the chimeric molecule comprises a clotting factor (e.g., a FVII), a targeting moiety (e.g., a GPIIb/IIIa antibody or antigen-binding molecule thereof), and an albumin.

(iv) Albumin Binding Polypeptides and Lipids

In certain embodiments, a heterologous moiety can comprise an albumin binding moiety, which comprises an albumin binding peptide, a bacterial albumin binding domain, an albumin-binding antibody fragment, or any combinations thereof. For example, the albumin binding protein can be a bacterial albumin binding protein, an antibody or an antibody fragment including domain antibodies (see, e.g., U.S. Pat. No. 6,696,245). An albumin binding protein, for example, can be a bacterial albumin binding domain, such as the one of streptococcal protein G (Konig and Skerra (1998) *J. Immunol. Methods* 218, 73-83). Other examples of albumin binding peptides that can be used as conjugation partner are, for instance, those having a Cys-$Xaa_1$-$Xaa_2$-$Xaa_3$-$Xaa_4$-Cys consensus sequence (SEQ ID NO:134), wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in U.S. Pub. No. US2003/0069395 or Dennis et al. (2002) *J. Biol. Chem.* 277, 35035-35043.

Domain 3 from streptococcal protein G, as disclosed by Kraulis et al., *FEBS Lett.*, 378:190-194 (1996) and Linhult et al., *Protein Sci.*, 11:206-213 (2002) is an example of a bacterial albumin-binding domain. Examples of albumin-binding peptides include a series of peptides having the core sequence DICLPRWGCLW (SEQ ID NO:135) such as:

(SEQ ID NO: 136)
RLIE<u>DICLPRWGCLW</u>EDD;

(SEQ ID NO: 137)
QRLME<u>DICLPRWGCLW</u>EDDF ;

-continued

QGLIGDICLPRWGCLWGDSVK; (SEQ ID NO: 138)
and

GEWWEDICLPRWGCLWEEED. (SEQ ID NO: 139)

See, e.g., Dennis et al., *J. Biol. Chem.* 2002, 277: 35035-35043 (2002). Examples of albumin-binding antibody fragments are disclosed in Muller and Kontermann, *Curr. Opin. Mol. Ther.* 9:319-326 (2007); Roovers et al., *Cancer Immunol. Immunother.* 56:303-317 (2007), and Holt et al., *Prot. Eng. Design Sci.*, 21:283-288 (2008), which are incorporated herein by reference in their entireties. An example of such albumin binding moiety is 2-(3-maleimidopropanamido)-6-(4-(4-iodophenyl)butanamido) hexanoate ("Albu" tag) as disclosed by Trussel et al., *Bioconjugate Chem.* 20:2286-2292 (2009). Fatty acids, in particular long chain fatty acids (LCFA) and long chain fatty acid-like albumin-binding compounds can be used to extend the in vivo half-life of chimeric molecules of the invention. An example of a LCFA-like albumin-binding compound is 16-(1-(3-(9-(((2,5-dioxopyrrolidin-1-yloxy)carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

In some embodiments, the chimeric molecule comprises a clotting factor (e.g., a FVII), a targeting moiety (e.g., a GPIIb/IIIa antibody or antigen-binding molecule thereof), and an albumin binding polypeptide or lipid.

(v) CTP

In certain embodiments, a chimeric molecule disclosed herein comprises at least one heterologous moiety comprising one β subunit of the C-terminal peptide (CTP) of human chorionic gonadotropin or fragment, variant, or derivative thereof. The insertion of one or more CTP peptides into a recombinant protein is known to increase the in vivo half-life of that protein. See, e.g., U.S. Pat. No. 5,712,122, incorporated by reference herein in its entirety.

Exemplary CTP peptides include DPRFQDSSSSKAPPPSLPSPSRLPGPSDTPIL (SEQ ID NO:140) or SSSSKAPPPSLPSPSRLPGPSDTPILPQ (SEQ ID NO:141). See, e.g., U.S. Patent Appl. Publ. No. US 2009/0087411, incorporated by reference. In some embodiments, the chimeric molecule comprises two heterologous moieties that are CTP sequences. In some embodiments, three of the heterologous moieties are CTP sequences. In some embodiments, four of the heterologous moieties are CTP sequences. In some embodiments, five of the heterologous moieties are CTP sequences. In some embodiments, six or more of the heterologous moieties are CTP sequences.

In some embodiments, the chimeric molecule comprises a clotting factor (e.g., a FVII), a targeting moiety (e.g., a GPIIb/IIIa antibody or antigen-binding molecule thereof), and a CTP.

(vi) PAS

In other embodiments, at least one heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric molecule. Yet, the skilled person is aware that an amino acid polymer also can form random coil conformation when residues other than alanine, serine, and proline are added as a minor constituent in the PAS sequence.

The term "minor constituent" as used herein means that amino acids other than alanine, serine, and proline can be added in the PAS sequence to a certain degree, e.g., up to about 12%, i.e., about 12 of 100 amino acids of the PAS sequence, up to about 10%, i.e., about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids.

The amino acids different from alanine, serine and proline can be selected from Arg, Asn, Asp, Cys, Gln, Glu, Gly, His, Ile, Leu, Lys, Met, Phe, Thr, Trp, Tyr, and Val.

Under physiological conditions, the PAS sequence stretch forms a random coil conformation and thereby can mediate an increased in vivo and/or in vitro stability to the chimeric molecule. Since the random coil domain does not adopt a stable structure or function by itself, the biological activity mediated by the activatable clotting factor in the chimeric molecule is essentially preserved. In other embodiments, the PAS sequences that form random coil domain are biologically inert, especially with respect to proteolysis in blood plasma, immunogenicity, isoelectric point/electrostatic behavior, binding to cell surface receptors or internalization, but are still biodegradable, which provides clear advantages over synthetic polymers such as PEG.

Non-limiting examples of the PAS sequences forming random coil conformation comprise an amino acid sequence selected from the group consisting of ASPAAPA-PASPAAPAPSAPA (SEQ ID NO:142), AAPASPAPAAP-SAPAPAAPS (SEQ ID NO:143), APSSPSP-SAPSSPSPASPSS (SEQ ID NO:144), APSSPSPSAPSSPSPASPS (SEQ ID NO:145), SSP-SAPSPSSPASPSPSSPA (SEQ ID NO:146), AASPAAP-SAPPAAASPAAPSAPPA (SEQ ID NO:147), and ASAAAPAAASAAASAPSAAA (SEQ ID NO:148), or any combinations thereof. Additional examples of PAS sequences are known from, e.g., US Pat. Publ. No. 2010/0292130 and PCT Appl. Publ. No. WO2008/155134 A1.

In some embodiments, the chimeric molecule comprises a clotting factor (e.g., a FVII), a targeting moiety (e.g., a GPIIb/IIIa antibody or antigen-binding molecule thereof), and a PAS.

(vii) HAP

In certain embodiments, at least one heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to $(Gly)_n$, (SEQ ID NO:149), $(Gly_4Ser)_n$ (SEQ ID NO:150), or $Ser(Gly_4Ser)_n$ (SEQ ID NO:151), wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200. See, e.g., Schlapschy M et al., Protein Eng. Design Selection, 20: 273-284 (2007).

In some embodiments, the chimeric molecule comprises a clotting factor (e.g., a FVII), a targeting moiety (e.g., a GPIIb/IIIa antibody or antigen-binding molecule thereof), and a HAP.

(viii) Transferrin

In certain embodiments, at least one heterologous moiety is transferrin or a peptide or fragment, variant, or derivative thereof. Any transferrin can be used to make the chimeric molecules of the invention. As an example, wild-type human TF (TF) is a 679 amino acid protein, of approximately 75 KDa (not accounting for glycosylation), with two main domains, N (about 330 amino acids) and C (about 340 amino acids), which appear to originate from a gene duplication. N domain comprises two subdomains, N1 domain and N2 domain, and C domain comprises two subdomains, C1 domain and C2 domain. See GenBank accession numbers NM001063, XM002793, M12530, XM039845, XM 039847 and S95936 (www.ncbi.nlm.nih.gov), all of which are herein incorporated by reference in their entirety. In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric molecule includes one or more domains of the transferrin sequence, e.g., N domain, C domain, N1 domain, N2 domain, C1 domain, C2 domain or any combinations thereof.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., Trends Pharmacol. Sci. 23:206-209 (2002)). Transferrin fusion proteins have been studied for half-life extension, targeted deliver for cancer therapies, oral delivery and sustained activation of proinsulin (Brandsma et al., Biotechnol. Adv., 29: 230-238 (2011); Bai et al., Proc. Natl. Acad. Sci. USA 102:7292-7296 (2005); Kim et al., J. Pharmacol. Exp. Ther., 334:682-692 (2010); Wang et al., J. Controlled Release 155:386-392 (2011)).

In some embodiments, the chimeric molecule comprises a clotting factor (e.g., a FVII), a targeting moiety (e.g., a GPIIb/IIIa antibody or antigen-binding molecule thereof), and a transferrin.

(ix) PEG

In some embodiments, at least one heterologous moiety is a soluble polymer known in the art, including, but not limited to, polyethylene glycol, ethylene glycol/propylene glycol copolymers, carboxymethylcellulose, dextran, or polyvinyl alcohol. In some embodiments, the chimeric molecule comprising a PEG heterologous moiety further comprises a heterologous moiety selected from an immunoglobulin constant region or portion thereof (e.g., an Fc region), a PAS sequence, HES, and albumin, fragment, or variant thereof. In still other embodiments, the chimeric molecule comprises an activatable clotting factor or fragment thereof and a PEG heterologous moiety, wherein the chimeric molecule further comprises a heterologous moiety selected from an immunoglobulin constant region or portion thereof (e.g., an Fc moiety), a PAS sequence, HES, and albumin, fragment, or variant thereof. In yet other embodiments, the chimeric molecule comprises a clotting factor or fragment thereof, a second clotting factor or fragment thereof, and a PEG heterologous moiety, wherein the chimeric molecule further comprises a heterologous moiety selected from an immunoglobulin constant region or portion thereof (e.g., an Fc moiety), a PAS sequence, HES, and albumin, fragment, or variant thereof.

In other embodiments, the chimeric molecule comprises a clotting factor or fragment thereof, a synthetic procoagulant polypeptide, and a PEG heterologous moiety, wherein the chimeric molecule further comprises a heterologous moiety selected from an immunoglobulin constant region or portion thereof (e.g., an Fc region), a PAS sequence, HES, and albumin, fragment, or variant thereof. In other embodiments, the chimeric molecule comprises two synthetic procoagulant peptides and a PEG heterologous moiety, wherein the chimeric molecule further comprises a heterologous moiety selected from the group consisting of an immunoglobulin constant region or portion thereof (e.g., an Fc region), a PAS sequence, HES, and albumin, fragment, or variant thereof. In yet another embodiment, the chimeric molecule comprises a clotting factor or fragment thereof, a clotting factor cofactor (e.g., Tissue Factor if the clotting factor is Factor VII), and a PEG heterologous moiety, wherein the chimeric molecule further comprises a heterologous moiety selected from an immunoglobulin constant region or portion thereof (e.g., an Fc region), a PAS sequence, HES, and albumin, fragment, or variant thereof.

The polymer can be of any molecular weight, and can be branched or unbranched. For polyethylene glycol, in one embodiment, the molecular weight is between about 1 kDa and about 100 kDa for ease in handling and manufacturing. Other sizes can be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol can have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In some embodiments, the polyethylene glycol can have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

The number of polyethylene glycol moieties attached to each chimeric molecule of the invention (i.e., the degree of substitution) can also vary. For example, the PEGylated chimeric molecule can be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In some embodiments, the chimeric molecule can be PEGylated.

A PEGylated chimeric molecule comprises at least one polyethylene glycol (PEG) molecule. In other embodiments, the polymer can be water-soluble. Non-limiting examples of the polymer can be poly(alkylene oxide), poly(vinyl pyrrolidone), poly(vinyl alcohol), polyoxazoline, or poly(acryloylmorpholine). Additional types of polymer-conjugation to clotting factors are disclosed in U.S. Pat. No. 7,199,223. See also, Singh et al. Curr. Med. Chem. 15:1802-1826 (2008).

There are a number of PEG attachment methods available to those skilled in the art, for example Malik F et al., *Exp. Hematol.* 20:1028-35 (1992); Francis, *Focus on Growth Factors* 3(2):4-10 (1992); European Pat. Pub. Nos. EP0401384, EP0154316, and EP0401384; and International Pat. Appl. Pub. Nos. WO92/16221 and WO95/34326.

In some embodiments, the chimeric molecule comprises a clotting factor (e.g., a FVII), a targeting moiety (e.g., a GPIIb/IIIa antibody or antigen-binding molecule thereof), and a PEG.

(x) HES

In certain embodiments, at least one heterologous moiety is a polymer, e.g., hydroxyethyl starch (HES) or a derivative thereof. Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie*, 8(8), 271-278 (1987); and Weidler et al., *Arzneim.-Forschung/Drug Res.*, 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie*, 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be a mixture of hydroxyethyl starches having different mean molecular weights and/or different degrees of substitution and/or different ratios of C2:C6 substitution. Therefore, mixtures of hydroxyethyl starches can be employed having different mean molecular weights and different degrees of substitution and different ratios of C2:C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2:C6 substitution, or having about the same mean molecular weight and about the same degree of substitution and about the same ratio of C2:C6 substitution.

In some embodiments, the chimeric molecule comprises a clotting factor (e.g., a FVII), a targeting moiety (e.g., a GPIIb/IIIa antibody or antigen-binding molecule thereof), and a HES.

(xi) PSA

In certain embodiments, at least one heterologous moiety is a polymer, e.g., polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid: From Microbes to Man*, eds. Roth J., Rutishauser U., Troy F. A. (Birkhauser Verlag, Basel, Switzerland), pp 335-348. They can be produced in various degrees of polymerization from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist—such as the alternating alpha-2,8 alpha-2,9 polysialic acid of *E. coli* strain K92 and group C polysaccharides of *N. meningitidis*. Sialic acid can also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during fetal development (wherein the polymer has an anti-adhesive function) Cho and Troy, *P.N.A.S., USA*, 91 (1994) 11427-11431, although there are no known receptors for polysialic acids in mammals. The alpha-2,8-linked polysialic acid of *E. coli* strain K1 is also known as 'colominic acid' and is used (in various lengths) to exemplify the present disclosure. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

In some embodiments, the chimeric molecule comprises a clotting factor (e.g., FVII), a targeting moiety (e.g., a GPIIb/IIIa antibody or antigen-binding molecule thereof), and a PSA.

(xii) Clearance Receptors

In certain embodiments, the in vivo half-life of a chimeric molecule of the invention can be extended where the chimeric molecule comprises at least one heterologous molecule comprising a clearance receptor, fragment, variant, or derivative thereof. In specific embodiments wherein the chimeric molecule comprises Factor X, soluble forms of clearance receptors, such as the low density lipoprotein-related protein receptor LRP1, or fragments thereof, can block binding of Factor X to clearance receptors and thereby extend its in vivo half-life.

LRP1 is a 600 kDa integral membrane protein that is implicated in the receptor-mediate clearance of a variety of proteins, such as FVIII or X. See, e.g., Narita et al., Blood 91:555-560 (1998); Lenting et al., Haemophilia 16:6-16 (2010). The amino acid sequence of an exemplary human LRP1 protein is provided below (signal peptide underlined and transmembrane segment boldened; NCBI Reference Sequence: CAA32112):

```
                                        (SEQ ID NO: 152)
MLTPPLLLLLPLLSALVAAAIDAPKTCSPKQFACRDQITCISKGWRCDGE

RDCPDGSDEAPEICPQSKAQRCQPNEHNCLGTELCVPMSRLCNGVQDCMD

GSDEGPHCRELQGNCSRLGCQHHCVPTLDGPTCYCNSSFQLQADGKTCKD

FDECSVYGTCSQLCTNTDGSFICGCVEGYLLQPDNRSCKAKNEPVDRPPV

LLIANSQNILATYLSGAQVSTITPTSTRQTTAMDFSYANETVCWVHVGDS

AAQTQLKCARMPGLKGFVDEHTINISLSLHHVEQMAIDWLTGNFYFVDDI

DDRIFVCNRNGDTCVTLLDLELYNPKGIALDPAMGKVFFTDYGQIPKVER

CDMDGQNRTKLVDSKIVFPHGITLDLVSRLVYWADAYLDYIEVVDYEGKG

RQTIIQGILIEHLYGLTVFENYLYATNSDNANAQQKTSVIRVNRFNSTEY

QVVTRVDKGGALHIYHQRRQPRVRSHACENDQYGKPGGCSDICLLANSHK

ARTCRCRSGFSLGSDGKSCKKPEHELFLVYGKGRPGIIRGMDMGAKVPDE

HMIPIENLMNPRALDFHAETGFIYFADTTSYLIGRQKIDGTERETILKDG

IHNVEGVAVDWMGDNLYWTDDGPKKTISVARLEKAAQTRKTLIEGKMTHP
```

```
                              -continued
RAIVVDPLNGWMYWTDWEEDPKDSRRGRLERAWMDGSHRDIFVTSKTVLW

PNGLSLDIPAGRLYWVDAFYDRIETILLNGTDRKIVYEGPELNHAFGLCH

HGNYLFWTEYRSGSVYRLERGVGGAPPTVTLLRSERPPIFEIRMYDAQQQ

QVGTNKCRVNNGGCSSLCLATPGSRQCACAEDQVLDADGVTCLANPSYVP

PPQCQPGEFACANSRCIQERWKCDGDNDCLDNSDEAPALCHQHTCPSDRF

KCENNRCIPNRWLCDGDNDCGNSEDESNATCSARTCPPNQFSCASGRCIP

ISWTCDLDDDCGDRSDESASCAYPTCFPLTQFTCNNGRCININWRCDNDN

DCGDNSDEAGCSHSCSSTQFKCNSGRCIPEHWTCDGDNDCGDYSDETHAN

CTNQATRPPGGCHTDEFQCRLDGLCIPLRWRCDGDTDCMDSSDEKSCEGV

THVCDPSVKFGCKDSARCISKAWVCDGDNDCEDNSDEENCESLACRPPSH

PCANNTSVCLPPDKLCDGNDDCGDGSDEGELCDQCSLNNGGCSHNCSVAP

GEGIVCSCPLGMELGPDNHTCQIQSYCAKHLKCSQKCDQNKFSVKCSCYE

GWVLEPDGESCRSLDPFKPFIIFSNRHEIRRIDLHKGDYSVLVPGLRNTI

ALDFHLSQSALYWTDVVEDKIYRGKLLDNGALTSFEVVIQYGLATPEGLA

VDWIAGNIYWVESNLDQIEVAKLDGTLRTTLLAGDIEHPRAIALDPRDGI

LFWTDWDASLPRIEAASMSGAGRRTVHRETGSGGWPNGLTVDYLEKRILW

IDARSDAIYSARYDGSGHMEVLRGHEFLSHPFAVTLYGGEVYWTDWRTNT

LAKANKWTGHNVTVVQRTNTQPFDLQVYHPSRQPMAPNPCEANGGQGPCS

HLCLINYNRTVSCACPHLMKLHKDNTTCYEFKKFLLYARQMEIRGVDLDA

PYYNYIISFTVPDIDNVTVLDYDAREQRVYWSDVRTQAIKRAFINGTGVE

TVVSADLPNAHGLAVDWVSRNLFWTSYDTNKKQINVARLDGSFKNAVVQG

LEQPHGLVVHPLRGKLYWTDGDNISMANMDGSNRTLLFSGQKGPVGLAID

FPESKLYWISSGNHTINRCNLDGSGLEVIDAMRSQLGKATALAIMGDKLW

WADQVSEKMGTCSKADGSGSVVLRNSTTLVMHMKVYDESIQLDHKGTNPC

SVNNGDCSQLCLPTSETTRSCMCTAGYSLRSGQQACEGVGSFLLYSVHEG

IRGIPLDPNDKSDALVPVSGTSLAVGIDFHAENDTIYWVDMGLSTISRAK

RDQTWREDVVTNGIGRVEGIAVDWIAGNIYWTDQGFDVIEVARLNGSFRY

VVISQGLDKPRAITVHPEKGYLFWTEWGQYPRIERSRLDGTERVVLVNVS

ISWPNGISVDYQDGKLYWCDARTDKIERIDLETGENREVVLSSNNMDMFS

VSVFEDFIYWSDRTHANGSIKRGSKDNATDSVPLRTGIGVQLKDIKVFNR

DRQKGTNVCAVANGGCQQLCLYRGRGQRACACAHGMLAEDGASCREYAGY

LLYSERTILKSIHLSDERNLNAPVQPFEDPEHMKNVIALAFDYRAGTSPG

TPNRIFFSDIHFGNIQQINDDGSRRITIVENVGSVEGLAYHRGWDTLYWT

SYTTSTITRHTVDQTRPGAFERETVITMSGDDHPRAFVLDECQNLMFWTN

WNEQHPSIMRAALSGANVLTLIEKDIRTPNGLAIDHRAEKLYFSDATLDK

IERCEYDGSHRYVILKSEPVHPFGLAVYGEHIFWTDWVRRAVQRANKHVG

SNMKLLRVDIPQQPMGIIAVANDTNSCELSPCRINNGGCQDLCLLTHQGH

VNCSCRGGRILQDDLTCRAVNSSCRAQDEFECANGECINFSLTCDGVPHC

KDKSDEKPSYCNSRRCKKTFRQCSNGRCVSNMLWCNGADDCGDGSDEIPC

NKTACGVGEFRCRDGTCIGNSSRCNQFVDCEDASDEMNCSATDCSSYFRL
```

-continued
```
GVKGVLFQPCERTSLCYAPSWVCDGANDCGDYSDERDCPGVKRPRCPLNY

FACPSGRCIPMSWTCDKEDDCEHGEDETHCNKFCSEAQFECQNHRCISKQ

WLCDGSDDCGDGSDEAAHCEGKTCGPSSFSCPGTHVCVPERWLCDGDKDC

ADGADESIAAGCLYNSTCDDREFMCQNRQCIPKHFVCDHDRDCADGSDES

PECEYPTCGPSEFRCANGRCLSSRQWECDGENDCHDQSDEAPKNPHCTSP

EHKCNASSQFLCSSGRCVAEALLCNGQDDCGDSSDERGCHINECLSRKLS

GCSQDCEDLKIGFKCRCRPGFRLKDDGRTCADVDECSTTFPCSQRCINTH

GSYKCLCVEGYAPRGGDPHSCKAVTDEEPFLIFANRYYLRKLNLDGSNYT

LLKQGLNNAVALDFDYREQMIYWTDVTTQGSMIRRMHLNGSNVQVLHRTG

LSNPDGLAVDWVGGNLYWCDKGRDTIEVSKLNGAYRTVLVSSGLREPRAL

VVDVQNGYLYWTDWGDHSLIGRIGMDGSSRSVIVDTKITWPNGLTLDYVT

ERIYWADAREDYIEFASLDGSNRHVVLSQDIPHIFALTLFEDYVYWTDWE

TKSINRAHKTTGTNKTLLISTLHRPMDLHVFHALRQPDVPNHPCKVNNGG

CSNLCLLSPGGGHKCACPTNFYLGSDGRTCVSNCTASQFVCKNDKCIPFW

WKCDTEDDCGDHSDEPPDCPEFKCRPGQFQCSTGICTNPAFICDGDNDCQ

DNSDEANCDIHVCLPSQFKCTNTNRCIPGIFRCNGQDNCGDGEDERDCPE

VTCAPNQFQCSITKRCIPRVWVCDRDNDCVDGSDEPANCTQMTCGVDEFR

CKDSGRCIPARWKCDGEDDCGDGSDEPKEECDERTCEPYQFRCKNNRCVP

GRWQCDYDNDCGDNSDEESCTPRPCSESEFSCANGRCIAGRWKCDGDHDC

ADGSDEKDCTPRCDMDQFQCKSGHCIPLRWRCDADADCMDGSDEEACGTG

VRTCPLDEFQCNNTLCKPLAWKCDGEDDCGDNSDENPEECARFVCPPNRP

FRCKNDRVCLWIGRQCDGTDNCGDGTDEEDCEPPTAHTTHCKDKKEFLCR

NQRCLSSSLRCNMFDDCGDGSDEEDCSIDPKLTSCATNASICGDEARCVR

TEKAAYCACRSGFHTVPGQPGCQDINECLRFGTCSQLCNNTKGGHLCSCA

RNFMKTHNTCKAEGSEYQVLYIADDNEIRSLFPGHPHSAYEQAFQGDESV

RIDAMDVHVKAGRVYWTNWHTGTISYRSLPPAAPPTTSNRHRRQIDRGVT

HLNISGLKMPRGIAIDWVAGNVYWTDSGRDVIEVAQMKGENRKTLISGMI

DEPHAIVVDPLRGTMYWSDWGNHPKIETAAMDGTLRETLVQDNIQWPTGL

AVDYHNERLYWADAKLSVIGSIRLNGTDPIVAADSKRGLSHPFSIDVFED

YIYGVTYINNRVFKIHKFGHSPLVNLTGGLSHASDVVLYHQHKQPEVTNP

CDRKKCEWLCLLSPSGPVCTCPNGKRLDNGTCVPVPSPTPPPDAPRPGTC

NLQCFNGGSCFLNARRQPKCRCQPRYTGDKCELDQCWEHCRNGGTCAASP

SGMPTCRCPTGFTGPKCTQQVCAGYCANNSTCTVNQGNQPQCRCLPGFLG

DRCQYRQCSGYCENFGTCQMAADGSRQCRCTAYFEGSRCEVNKCSRCLEG

ACVVNKQSGDVTCNCTDGRVAPSCLTCVGHCSNGGSCTMNSKMMPECQCP

PHMTGPRCEEHVFSQQQPGHIASILIPLLLLLLLVLVAGVVFWYKRRVQG

AKGFQHQRMTNGAMNVEIGNPTYKMYEGGEPDDVGGLLDADFALDPDKPT

NFTNPVYATLYMGGHGSRHSLASTDEKRELLGRGPEDEIGDPLA
```

Other suitable clearance receptors are, e.g., LDLR (low-density lipoprotein receptor), VLDLR (very low-density lipoprotein receptor), and megalin (LRP-2), or fragments thereof. See, e.g., Bovenschen et al., *Blood* 106:906-912 (2005); Bovenschen, *Blood* 116:5439-5440 (2010); Martinelli et al., *Blood* 116:5688-5697 (2010).

In some embodiments, the chimeric molecule comprises a clotting factor (e.g., a FVII), a targeting moiety (e.g., a GPIIb/IIIa antibody or antigen-binding molecule thereof), and a clearance receptor, fragment, variant, or derivative thereof.

II. Linkers

The term "linker" or "linker moiety" (represented as L, L1, or L2 in the formulas disclosed herein) refers to a peptide or polypeptide sequence (e.g., a synthetic peptide or polypeptide sequence), or a non-peptide linker for which its main function is to connect two domains in a linear amino acid sequence of a polypeptide chain, for example, two heterologous moieties in a chimeric molecule of the invention. Accordingly, in some embodiments, linkers are interposed between two heterologous moieties, between a heterologous moiety and a targeting moiety, which binds to a platelet (e.g., an anti-GPIIb/IIIa antibody or antigen-binding molecule thereof disclosed herein), between a clotting factor (either the heavy chain or the light chain) and a targeting moiety, which binds to a platelet (e.g., an anti-GPIIb/IIIa antibody or antigen-binding molecule thereof disclosed herein), or between a clotting factor (either the heavy chain or the light chain) and a heterologous moiety.

When multiple linkers are present in a chimeric molecule of the invention, each of the linkers can be the same or different. Generally, linkers provide flexibility to the chimeric molecule. Linkers are not typically cleaved; however in certain embodiments, such cleavage can be desirable. Accordingly, in some embodiments a linker can comprise one or more protease-cleavable sites, which can be located within the sequence of the linker or flanking the linker at either end of the sequence of the linker.

In some embodiments, the chimeric molecule comprises one or more linkers, wherein one or more of the linkers comprise a peptide linker. In other embodiments, one or more of the linkers comprise a non-peptide linker. In some embodiments, the peptide linker can comprise at least two amino, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. In certain embodiments, the peptide linker can comprise 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids.

The peptide linker can comprise 1-5 amino acids, 1-10 amino acids, 1-20 amino acids, 1-30 amino acids, 5-25 amino acids, 5-30 amino acids, 10-30 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, 900-1000, 1000-1100, 1100-1200, 1200-1300, 1300-1400, 1400-1500, 1500-1600, 1600-1700, 1700-1800, 1800-1900, or 1900-2000 amino acids.

Examples of peptide linkers are well known in the art, for example peptide linkers according to the formula $[(Gly)_x\text{-}Ser_y]_z$ where x is from 1 to 4, y is 0 or 1, and z is from 1 to 50 (SEQ ID NO:153). In certain embodiments z is from 1 to 6. In one embodiment, the peptide linker comprises the sequence $G_n$, where n can be an integer from 1 to 100 (SEQ ID NO:249). In a specific embodiment, the specific embodiment, the sequence of the peptide linker is GGGG (SEQ ID NO:154). The peptide linker can comprise the sequence $(GA)_n$ (SEQ ID NO:163). The peptide linker can comprise the sequence $(GGS)_n$ (SEQ ID NO:155). In other embodiments, the peptide linker comprises the sequence $(GGGS)_n$ (SEQ ID NO:156). In still other embodiments, the peptide linker comprises the sequence $(GGS)_n(GGGGS)_n$ (SEQ ID NO:157). In these instances, n can be an integer from 1-100. In other instances, n can be an integer from 1-20, i.e., 1, 2, 3, 4, 5, 6, 7, 8, 9, 10, 11, 12, 13, 14, 15, 16, 17, 18, 19, or 20. Examples of linkers include, but are not limited to, GGG, SGGSGGS (SEQ ID NO:158), GGSGGSGGSGGSGGG (SEQ ID NO:159), GGSGGSGGGSGGGGS (SEQ ID NO:160), GGSGGSGGSGGSGGSGGS (SEQ ID NO:161), or GGGGSGGGGSGGGGS (SEQ ID NO:162). In other embodiments, the linker is a poly-G sequence $(GGGG)_n$, where n can be an integer from 1-100 (SEQ ID NO:164).

An exemplary Gly/Ser peptide linker comprises the amino acid sequence $(Gly_4Ser)_n$ (SEQ ID NO:250), wherein n is an integer that is the same or higher than 1, 2, 3, 4, 5, 6, 7, 8, 9, 10, 15, 20, 25, 30, 35, 40, 46, 50, 55, 60, 70, 80, 90, or 100. In one embodiment, n=1, i.e., the linker is $(Gly_4Ser)$ (SEQ ID NO:165). In one embodiment, n=2, i.e., the linker is $(Gly_4Ser)_2$ (SEQ ID NO:166). In another embodiment, n=3, i.e., the linker is $(Gly_4Ser)_3$ (SEQ ID NO:167). In another embodiment, n=4, i.e., the linker is $(Gly_4Ser)_4$ (SEQ ID NO:168). In another embodiment, n=5, i.e., the linker is $(Gly_4Ser)_5$ (SEQ ID NO:169). In yet another embodiment, n=6, i.e., the linker is $(Gly_4Ser)_6$ (SEQ ID NO:170). In another embodiment, n=7, i.e., the linker is $(Gly_4Ser)_7$ (SEQ ID NO:171). In yet another embodiment, n=8, i.e., the linker is $(Gly_4Ser)_8$ (SEQ ID NO:172). In another embodiment, n=9, i.e., the linker is $(Gly_4Ser)_9$ (SEQ ID NO:173). In yet another embodiment, n=10, i.e., the linker is $(Gly_4Ser)_{10}$ (SEQ ID NO:174).

Another exemplary Gly/Ser peptide linker comprises the amino acid sequence $Ser(Gly_4Ser)_n$ (SEQ ID NO:251), wherein n is an integer that is the same or higher than 1, 2, 3, 4, 5, 6, 7, 8, 9, 10, 15, 20, 25, 30, 35, 40, 46, 50, 55, 60, 70, 80, 90, or 100. In one embodiment, n=1, i.e., the linker is $Ser(Gly_4Ser)$ (SEQ ID NO:175). In one embodiment, n=2, i.e., the linker is $Ser(Gly_4Ser)_2$ (SEQ ID NO: 176). In another embodiment, n=3, i.e., the linker is $Ser(Gly_4Ser)_3$ (SEQ ID NO:177). In another embodiment, n=4, i.e., the linker is $Ser(Gly_4Ser)_4$ (SEQ ID NO:178). In another embodiment, n=5, i.e., the linker is $Ser(Gly_4Ser)_5$ (SEQ ID NO:179). In yet another embodiment, n=6, i.e., the linker is $Ser(Gly_4Ser)_6$ (SEQ ID NO:180). In yet another embodiment, n=7, i.e., the linker is $Ser(Gly_4Ser)_7$ (SEQ ID NO:181). In yet another embodiment, n=8, i.e., the linker is $Ser(Gly_4Ser)_8$ (SEQ ID NO:182). In yet another embodiment, n=9, i.e., the linker is $Ser(Gly_4Ser)_9$ (SEQ ID NO:183). In yet another embodiment, n=10, i.e., the linker is $Ser(Gly_4Ser)_{10}$ (SEQ ID NO:184).

In certain embodiments, said Gly/Ser peptide linker can be inserted between two other sequences of the peptide linker (e.g., any of the peptide linker sequences described herein). In other embodiments, a Gly/Ser peptide linker is attached at one or both ends of another sequence of the peptide linker (e.g., any of the peptide linker sequences described herein). In yet other embodiments, two or more Gly/Ser linkers are incorporated in series in a peptide linker. In one embodiment, a peptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of Gly/Ser amino acid residues (e.g., a Gly/Ser linker such as $(Gly_4Ser)_n$) (SEQ ID NO:165)).

A particular type of linker which can be present in an heterologous moiety, for example an activatable clotting factor, is herein referred to as a "cleavable linker" which comprises a heterologous protease-cleavage site (e.g., a factor XIa or thrombin cleavage site) that is not naturally occurring in the clotting factor and which can include additional linkers on either the N terminal of C terminal or both sides of the cleavage site. Exemplary locations for such sites include, e.g., placement between a heavy chain of a clotting factor zymogen and a light chain of a clotting factor zymogen.

Peptide linkers can be introduced into polypeptide sequences using techniques known in the art. Modifications can be confirmed by DNA sequence analysis. Plasmid DNA can be used to transform host cells for stable production of the polypeptides produced.

III. Protease Cleavage Site

In some embodiments, a chimeric molecule can comprise a protease cleavage site linking, for example, a light chain of a clotting factor zymogen and a heavy chain of the clotting factor zymogen (e.g., FVII). A protease-cleavage site linking a light chain of a clotting factor zymogen and a heavy chain of the clotting factor zymogen can be selected from any protease-cleavage site known in the art. In one embodiment, the protease-cleavage site is cleaved by a protease selected from the group consisting of factor XIa, factor XIIa, kallikrein, factor VIIa, factor IXa, factor Xa, factor IIa (thrombin), and any combinations thereof. The protease-cleavage sites allow the light chain and the heavy chain of the clotting factor to be cleaved and dissociated from each other at the site of injury. Exemplary FXIa cleavage sites include, e.g., KLTR (SEQ ID NO:185), DFTR (SEQ ID NO:186), TQSFNDFTR (SEQ ID NO:187) and SVSQTSKLTR (SEQ ID NO:188). Exemplary thrombin cleavage sites include, e.g., DFLAEGGGVR (SEQ ID NO:189), TTKIKPR (SEQ ID NO:190), LVPRG (SEQ ID NO:191) and ALRPR (SEQ ID NO:192).

In some embodiments, the protease-cleavage site can be combined with an intracellular processing site for efficient cleavage and activation. For example, an activatable clotting factor in the chimeric molecule can comprise a heterodimer, which comprises a light chain of a clotting factor associated with a heavy chain of the clotting factor by a covalent bond, wherein the N-terminus of the heavy chain of the clotting factor is linked to a protease-cleavage site. The protease-cleavage site can be cleaved off at the site of coagulation, thus activating the clotting factor. Such constructs can be designed by inserting an intracellular processing site between the light chain of the clotting factor zymogen and the protease-cleavage site, which is linked to the heavy chain of the clotting factor zymogen. The intracellular processing site inserted therein can be processed (cleaved) by an intracellular processing enzyme upon expression in a host cell, thereby allowing formation of a zymogen-like heterodimer.

Examples of the intracellular processing enzymes include furin, a yeast Kex2, PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art. In constructs that include more than one processing or cleavage site, it will be understood that such sites can be the same or different.

E. Exemplary Chimeric Molecules

In one embodiment, the chimeric molecule comprises, consists essentially of, or consists of, a polypeptide that has an amino acid sequence that is at least 60%, at least 65%, at least 70%, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO:74.

least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID Nos. 75 or 76.

In one embodiment, the chimeric molecule comprises, consists essentially of, or consists of, a polypeptide that has an amino acid sequence that is at least 60%, at least 65%, at least 70%, at least 75% identical, at least 80% identical, at least 81% identical, at least 82% identical, at least 83% identical, at least 84% identical, at least 85% identical, at least 86% identical, at least 87% identical, at least 88%

```
                                                            (SEQ ID NO: 74)
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

351 HYRGTWYLTG IVSWGQGCAT VGHFGVYTRV SQYIEWLQKL MRSEPRPGVL

401 LRAPFPGGGG SGGGGSGGGG SGGGGSGGGG SGGGGSEIVM TQSPATLSVS

451 PGERATLSCR ASSSVNYMYW YQQKPGQAPR LLIYYTSNLA PGIPARFSGS

501 GSGTEFTLTI SSLQSEDFAV YYCQQFSSSP WTFGQGTKVE IKRTVAAPSV

551 FIFPPSDEQL KSGTASVVCL LNNFYPREAK VQWKVDNALQ SGNSQESVTE

601 QDSKDSTYSL SSTLTLSKAD YEKHKVYACE VTHQGLSSPV TKSFNRGEC*
```

In certain embodiments, one or more (e.g., 1, 2, 3, 4) linkers can be introduced between the light and heavy chain of Factor VII. The linker(s) can be a peptide linker.

The Fab light chain of this chimeric molecule can associate, e.g., with the Fab heavy chain comprising a polypeptide sequence that has an amino acid sequence that is at least 60%, at least 65%, at least 70%, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to the amino acid sequence set forth in SEQ ID NO: 77.

```
                                                            (SEQ ID NO: 77)
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

351 HYRGTWYLTG IVSWGQGCAT VGHFGVYTRV SQYIEWLQKL MRSEPRPGVL

401 LRAPFPGSPG TSESATPESG PGSEPATSGS ETPGTSESAT PESGPGSEPA
```

```
451 TSGSETPGTS ESATPESGPG TSTEPSEGSA PGSPAGSPTS TEEGTSESAT

501 PESGPGSEPA TSGSETPGTS ESATPESGPG SPAGSPTSTE EGSPAGSPTS

551 TEEGTSTEPS EGSAPGTSES ATPESGPGTS ESATPESGPG TSESATPESG

601 PGSEPATSGS ETPGSEPATS GSETPGSPAG SPTSTEEGTS TEPSEGSAPG

651 TSTEPSEGSA PGSEPATSGS ETPGTSESAT PESGPGTSTE PSEGSAPGSS

701 SGGGGSGGGG SGGGGSGGGG SGGGGSGGGG SEIVMTQSPA TLSVSPGERA

751 TLSCRASSSV NYMYWYQQKP GQAPRLLIYY TSNLAPGIPA RFSGSGSGTE

801 FTLTISSLQS EDFAVYYCQQ FSSSPWTFGQ GTKVEIKRTV AAPSVFIFPP

851 SDEQLKSGTA SVVCLLNNFY PREAKVQWKV DNALQSGNSQ ESVTEQDSKD

901 STYSLSSTLT LSKADYEKHK VYACEVTHQG LSSPVTKSFN RGEC*
```

This chimeric molecule includes the light and heavy chains of Factor VII, a linker having the amino acid sequence: GSPGTSESATPESGPGSEPATSGSETP (SEQ ID NO: 195), an XTEN termed AE288 (a half-life extending moiety), a GSSS (SEQ ID NO: 196) linker, a (G4S)6 (SEQ ID NO:170) linker, and the Fab light chain of a humanized GPIIb/IIIa antibody described herein. In certain embodiments, one or more of the linkers noted above can be eliminated (e.g., SEQ ID NOs: 195 and/or 196) from the chimeric molecule. In certain embodiments, one or more (e.g., 1, 2, 3, 4) linkers can be introduced between the light and heavy chain of Factor VII. The linker(s) can be a peptide linker. In certain embodiments, the heavy chain of Factor VII can precede the light chain of Factor VII in the chimeric molecule. The Fab light chain of this chimeric molecule can associate, e.g., with a polypeptide comprising an amino acid sequence that is at least 60%, at least 65%, at least 70%, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or 100% identical to an amino acid sequence set forth in SEQ ID Nos: 75 or 76.

The above-described chimeric molecules can be modified, e.g., to include additional linkers (e.g., between the Factor VII and the half-life extending moiety and between the half-life extending moiety and the anti-GPIIb/IIIa antibody or antigen-binding fragment thereof). In certain instances there can be one or more (e.g., 1, 2, 3, 4) linkers between these components of the chimeric molecule. These chimeric molecules can also be modified to include one or more half-life extending moieties (e.g., AE144, AE288). In addition, instead of an Fab fragment, the chimeric molecules can comprise an scFv of the anti-GPIIb/IIIa antibody, a diabody, sc(Fv)2, or a whole anti-GPIIb/IIIa antibody. In instances where the targeting moiety is an scFv, the chimeric molecule is a two polypeptide chain comprising either (i) the light chain of Factor VII and the heavy chain of Factor VII-scFv or heavy chain of Factor VII-half-life extending moiety-scFv chimeric molecule; or (ii) the heavy chain of Factor VII and the light chain of Factor VII-scFv or light chain of Factor VII-half-life extending moiety-scFv chimeric molecule.

In certain embodiments, the Factor VII of the chimeric molecule is activated. Activation of Factor VII can occur by the cleavage of the Arg152-Ile153 peptide bond of Factor VII to create a two chain FVII polypeptide. In one embodiment, the Factor VII of the chimeric molecule is activated by concentrating the chimeric polypeptide to about 4 mg/ml at a pH of 8.0 and incubating the polypeptide at 4° C. for several minutes to an hour (e.g., 1, 2, 4, 5, 10, 15, 20, 25, 30, 35, 40, 45, 50, 55 or 60 minutes).

F. Methods of Preparation

The present disclosure also provides a nucleic acid molecule or a set of nucleic acid molecules encoding (i) a GPIIb/IIIa antibody or antigen-binding molecule thereof disclosed herein, or (ii) any of the chimeric molecules disclosed herein, or (iii) a complement thereof.

In one embodiment, the invention includes a nucleic acid molecule encoding a polypeptide chain, which comprises a light chain of a clotting factor (e.g., FVII, FIX, or FX), a heterologous moiety (e.g., a half-life extending moiety), an intracellular processing site, a heavy chain of the clotting factor (e.g., FVII, FIX, or FX), and a targeting moiety which binds to a platelet (e.g., an anti-GPIIb/IIIa antibody or antigen-binding molecule thereof). In another embodiment, the nucleic acid molecule of the invention encodes a polypeptide chain comprising a light chain of a clotting factor (e.g., FVII, FIX, or FX), a targeting moiety which binds to a platelet (e.g., an anti-GPIIb/IIIa antibody or antigen-binding molecule thereof), an intracellular processing site, a heavy chain of the clotting factor (e.g., FVII, FIX, or FX), and a heterologous moiety (e.g., a half-life extending moiety). In other embodiments, the nucleic acid molecule encodes a polypeptide chain comprising a light chain of a clotting factor (e.g., FVII, FIX, or FX), an intracellular processing site, a heavy chain of the clotting factor (e.g., FVII, FIX, or FX), a heterologous moiety (e.g., a half-life extending moiety), and a targeting moiety which binds to a platelet (e.g., an anti-GPIIb/IIIa antibody or antigen-binding molecule thereof). In some embodiments, the nucleic acid molecule encodes a polypeptide chain comprising a light chain of a clotting factor (e.g., FVII, FIX, or FX), an intracellular processing site, a heavy chain of the clotting factor (e.g., FVII, FIX, or FX), a targeting moiety which binds to a platelet (e.g., an anti-GPIIb/IIIa antibody or antigen-binding molecule thereof), and a heterologous moiety (e.g., a half-life extending moiety). In certain embodiments, the nucleic acid molecule encodes a polypeptide chain comprising a light chain of a clotting factor (e.g., FVII, FIX, or FX), a heavy chain of the clotting factor (e.g., FVII, FIX, or FX), at least one (e.g., one two, three, four)

heterologous moiety (e.g., a half-life extending moiety such as the XTEN, AE144 or AE288), and a targeting moiety which binds to a platelet (e.g., an anti-GPIIb/IIIa antibody or antigen-binding molecule thereof such as an scFv, or the light and/or heavy chain of an Fab).

In some embodiments, the nucleic acid molecule comprises a set of nucleotide sequences, a first nucleotide sequence encoding a first polypeptide chain comprising a light chain of a clotting factor (e.g., FVII, FIX, or FX) and a heterologous moiety (e.g., a half-life extending moiety) and a second nucleotide sequence encoding a second polypeptide chain comprising a heavy chain of the clotting factor (e.g., FVII, FIX, or FX) and a targeting moiety which binds to a platelet (e.g., an anti-GPIIb/IIIa antibody or antigen-binding molecule thereof). In other embodiments, the nucleic acid molecule comprises a set of nucleotide sequences, a first nucleotide sequence encoding a first polypeptide chain comprising a light chain of a clotting factor (e.g., FVII, FIX, or FX) and a targeting moiety which binds to a platelet (e.g., an anti-GPIIb/IIIa antibody or antigen-binding molecule thereof) and a second nucleotide sequence encoding a second polypeptide chain comprising a heavy chain of the clotting factor (e.g., FVII, FIX, or FX) and a heterologous moiety (e.g., a half-life extending moiety). In other embodiments, the nucleic acid molecule comprises a set of nucleotide sequences, a first nucleotide sequence encoding a light chain of a clotting factor (e.g., FVII, FIX, or FX) and a second nucleotide sequence encoding a heavy chain of the clotting factor (e.g., FVII, FIX, or FX), a heterologous moiety (e.g., a half-life extending moiety), and a targeting moiety which binds to a platelet (e.g., an anti-GPIIb/IIIa antibody or antigen-binding molecule thereof). In some embodiments, the nucleic acid molecule comprises a set of nucleotide sequences, a first nucleotide sequence encoding a light chain of a clotting factor (e.g., FVII, FIX, or FX) and a second nucleotide sequence encoding a heavy chain of the clotting factor (e.g., FVII, FIX, or FX), a targeting moiety which binds to a platelet (e.g., an anti-GPIIb/IIIa antibody or antigen-binding molecule thereof), and a heterologous moiety (e.g., a half-life extending moiety). In other embodiments, the nucleic acid molecule comprises a set of nucleotide sequences, a first nucleotide sequence encoding a first polypeptide chain comprising a light chain of a clotting factor (e.g., FVII, FIX, or FX), a heavy chain of the clotting factor (e.g., FVII, FIX, or FX), at least one (e.g., one two, three, four) heterologous moiety (e.g., a half-life extending moiety such as the XTEN, AE144 or AE288), and either the light chain or the heavy chain of an Fab of an anti-GPIIb/IIIa antibody described herein; and a second nucleotide sequence encoding the corresponding heavy or light chain of the Fab of the anti-GPIIb/IIIa antibody. It is to be understood that by "heavy chain of the Fab" is meant the VH region attached to CH1 of the heavy chain of the antibody.

Also provided are a vector or a set of vectors comprising such nucleic acid molecule or the set of the nucleic acid molecules or a complement thereof, as well as a host cell comprising the vector.

The instant disclosure also provides a method for producing a GPIIb/IIIa antibody or antigen-binding molecule thereof or chimeric molecule disclosed herein, such method comprising culturing the host cell disclosed herein and recovering the antibody, antigen-binding molecule thereof, or the chimeric molecule from the culture medium.

A variety of methods are available for recombinantly producing a GPIIb/IIIa antibody or antigen-binding molecule thereof disclosed herein, or a chimeric molecule disclosed herein. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

In one embodiment a first expression vector comprising a DNA comprising a nucleic acid encoding the amino acid sequence of the chimeric polypeptide set forth in SEQ ID NO:77 is transfected into a host cell (e.g., 293, CHO, COS) and the host cell is cultured under conditions that allow for the expression of the chimeric polypeptide. The chimeric polypeptide is recovered from the cell or culture medium. A second expression vector comprising a DNA comprising a nucleic acid encoding the amino acid sequence of the heavy chain of the Fab set forth in SEQ ID NOs. 75 or 76 is transfected into a host cell (e.g., 293, CHO, COS) and the host cell is cultured under conditions that allow for the expression of the heavy chain of the Fab. The heavy chain of the Fab is recovered from the cell or culture medium. The chimeric polypeptide and the heavy chain of the Fab are contacted together to permit the heavy chain of the Fab to associate with the light chain of the Fab in the chimeric polypeptide. In another embodiment, a host cell (e.g., 293, CHO, COS) is co-transfected with the first and second expression vectors described above and the host cell is cultured under conditions that allow for the expression of the chimeric polypeptide and the heavy chain of the Fab. The chimeric polypeptide and the heavy chain are isolated from the cell or culture medium. In certain instances, the heavy chain of the Fab is already associated with the light chain of the Fab in the chimeric polypeptide when the polypeptides are isolated from the cell or culture medium. In other instances, the heavy chain of the Fab is not already associated with the light chain of the Fab in the chimeric polypeptide when the polypeptides are isolated from the cell or culture medium and an additional step is required to facilitate their association. In certain embodiments, the Factor VII of the chimeric molecule is activated. Activation of Factor VII can occur by the cleavage of the Arg152-Ile153 peptide bond of Factor VII to create a two chain FVII polypeptide. In one embodiment, the Factor VII of the chimeric molecule is activated by concentrating the chimeric polypeptide (with or without the heavy chain Fab that associates with the light chain Fab of the chimeric polypeptide) to about 4 mg/ml at a pH of 8.0 and incubating the polypeptide at 4° C. for several minutes to an hour (e.g., 1, 2, 4, 5, 10, 15, 20, 25, 30, 35, 40, 45, 50, 55 or 60 minutes).

Oligonucleotide-mediated mutagenesis is one method for preparing a substitution, in-frame insertion, or alteration (e.g., altered codon) to introduce a codon encoding an amino acid substitution (e.g., into a GPIIb/IIIa antibody variant). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a GPIIb/IIIa antibody or antigen-binding molecule thereof disclosed herein, or any of the chimeric molecules disclosed herein.

For recombinant production, a polynucleotide sequence encoding a polypeptide (e.g., a GPIIb/IIIa antibody or antigen-binding molecule thereof disclosed herein, or any of the chimeric molecules disclosed herein) is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the polypeptide (e.g., a GPIIb/IIIa antibody or antigen-binding molecule thereof disclosed herein, or any of the chimeric molecules disclosed herein) is inserted into the vector in proper reading frame. The expression vector is then transfected into a suitable target cell which will express the polypeptide. Transfection techniques known in the art include, but are not limited to, calcium phosphate precipitation (Wigler et al. 1978, *Cell* 14:725) and electroporation (Neumann et al. 1982, *EMBO J.* 1:841). A variety of host-expression vector systems can be utilized to express the polypeptides described herein (e.g., a GPIIb/IIIa antibody or antigen-binding molecule thereof disclosed herein, or any of the chimeric molecules disclosed herein) in eukaryotic cells. In one embodiment, the eukaryotic cell is an animal cell, including mammalian cells (e.g., 293 cells, PerC6, CHO, BHK, Cos, HeLa cells). When the polypeptide is expressed in a eukaryotic cell, the DNA encoding the polypeptide (e.g., a GPIIb/IIIa antibody or antigen-binding molecule thereof disclosed herein, or any of the chimeric molecules disclosed herein) can also code for a signal sequence that will permit the polypeptide to be secreted. One skilled in the art will understand that while the polypeptide is translated, the signal sequence is cleaved by the cell to form the mature chimeric molecule. Various signal sequences are known in the art, e.g., native FVII signal sequence, native FIX signal sequence, native FX signal sequence, native GPIIb signal sequence, native GPIIIa signal sequence, and the mouse IgK light chain signal sequence. Alternatively, where a signal sequence is not included, the polypeptide (e.g., a GPIIb/IIIa antibody or antigen-binding molecule thereof disclosed herein, or any of the chimeric molecules disclosed herein) can be recovered by lysing the cells.

The GPIIb/IIIa antibody or antigen-binding molecule thereof disclosed herein, or any of the chimeric molecules disclosed herein can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, *Proc. Natl. Acad. Sci. USA* 82:4438). Methods of producing transgenic animals are known in the art including transgenics that produce immunoglobulin molecules (Wagner et al. 1981, *Proc. Natl. Acad. Sci. USA* 78:6376; McKnight et al. 1983, *Cell* 34:335; Brinster et al. 1983, *Nature* 306:332; Ritchie et al. 1984, *Nature* 312:517; Baldassarre et al. 2003, *Theriogenology* 59:831; Robl et al. 2003, *Theriogenology* 59:107; Malassagne et al. 2003, *Xenotransplantation* 10: 267).

The expression vectors can encode for tags that permit for easy purification or identification of the recombinantly produced polypeptide. Examples include, but are not limited to, vector pUR278 (Ruther et al. 1983, *EMBO J.* 2:1791) in which the polypeptide (e.g., a GPIIb/IIIa antibody or antigen-binding molecule thereof disclosed herein, or any of the chimeric molecules disclosed herein) coding sequence can be ligated into the vector in frame with the lac z coding region so that a hybrid polypeptide is produced; pGEX vectors can be used to express proteins with a glutathione S-transferase (GST) tag. These proteins are usually soluble and can easily be purified from cells by adsorption to glutathione-agarose beads followed by elution in the presence of free glutathione. The vectors include cleavage sites, e.g., for PreCission Protease (Pharmacia, Peapack, N.J.) for easy removal of the tag after purification.

Numerous expression vector systems can be employed. These expression vectors are typically replicable in the host organisms either as episomes or as an integral part of the host chromosomal DNA. Expression vectors can include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors can also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly used expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes can be selected by introducing one or more markers which allow selection of transfected host cells. The marker can provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

An exemplary expression vector is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments, polypeptides of the invention (e.g., a GPIIb/IIIa antibody or antigen-binding molecule thereof disclosed herein, or any of the chimeric molecules disclosed herein) can be expressed using polycistronic constructs. In these expression systems, multiple gene products of interest such as multiple polypeptides of multimer binding protein can be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems can be used to effectively produce the full range of polypeptides disclosed in the instant application.

More generally, once the vector or DNA sequence encoding a polypeptide has been prepared, the expression vector can be introduced into an appropriate host cell. That is, the host cells can be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), flow cytometry, immunohistochemistry, and the like.

As used herein, the term "transformation" refers in a broad sense to the introduction of DNA into a recipient host cell that changes the genotype and consequently results in a change in the recipient cell. Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" can mean either from spun down whole cells, or from the cell culture containing both the medium and the suspended cells.

In one embodiment, a host cell endogenously expresses an enzyme (or the enzymes) necessary to cleave a scFc linker (e.g., if such a linker is present and contains intracellular processing site(s)) during processing to form the mature polypeptide. During this processing, the scFc linker can be substantially removed to reduce the presence of extraneous amino acids. In another embodiment of the invention, a host cell is transformed to express one or more enzymes which are exogenous to the cell such that processing of a scFc linker occurs or is improved.

In one embodiment an enzyme which can be endogenously or exogenously expressed by a cell is a member of the furin family of enzymes. Complete cDNA and amino acid sequences of human furin (i.e., PACE) were published in 1990. Van den Ouweland A M et al. (1990) Nucleic Acids Res. 18:664; Erratum in: Nucleic Acids Res. 18:1332 (1990). U.S. Pat. No. 5,460,950, issued to Barr et al., describes recombinant PACE and the coexpression of PACE with a substrate precursor polypeptide of a heterologous protein to improve expression of active, mature heterologous protein. U.S. Pat. No. 5,935,815, likewise describes recombinant human furin (i.e., PACE) and the coexpression of furin with a substrate precursor polypeptide of a heterologous protein to improve expression of active, mature heterologous protein. Possible substrate precursors disclosed in this patent include a precursor of Factor IX. Other family members in the mammalian furin/subtilisin/Kex2p-like proprotein convertase (PC) family in addition to PACE are reported to include PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). While these various members share certain conserved overall structural features, they differ in their tissue distribution, subcellular localization, cleavage specificities, and preferred substrates. For a review, see Nakayama K (1997) *Biochem J.* 327:625-35. Similar to PACE, these proprotein convertases generally include, beginning from the amino terminus, a signal peptide, a propeptide (that can be autocatalytically cleaved), a subtilisin-like catalytic domain characterized by Asp, His, Ser, and Asn/Asp residues, and a Homo B domain that is also essential for catalytic activity and characterized by an Arg-Gly-Asp (RGD) sequence. PACE, PACE4, and PC5 also include a Cys-rich domain, the function of which is unknown. In addition, PC5 has isoforms with and without a transmembrane domain; these different isoforms are known as PC5B and PC5A, respectively. Comparison between the amino acid sequence of the catalytic domain of PACE and the amino acid sequences of the catalytic domains of other members of this family of proprotein convertases reveals the following degrees of identity: 70 percent for PC4; 65 percent for PACE4 and PC5; 61 percent for PC1/PC3; 54 percent for PC2; and 51 percent for LPC/PC7/PC8/SPC7. Nakayama K (1997) *Biochem J.,* 327:625-35.

PACE and PACE4 have been reported to have partially overlapping but distinct substrates. In particular, PACE4, in striking contrast to PACE, has been reported to be incapable of processing the precursor polypeptide of FIX. Wasley et al. (1993) J. Biol. Chem. 268:8458-65; Rehemtulla et al. (1993) Biochemistry. 32:11586-90. U.S. Pat. No. 5,840,529, discloses nucleotide and amino acid sequences for human PC7 and the notable ability of PC7, as compared to other PC family members, to cleave HIV gp160 to gp120 and gp41.

Nucleotide and amino acid sequences of rodent PC5 were first described as PC5 by Lusson et al. (1993) Proc Natl Acad Sci USA 90:6691-5 and as PC6 by Nakagawa et al. (1993) J Biochem (Tokyo) 113:132-5. U.S. Pat. No. 6,380,171 discloses nucleotide and amino acid sequences for human PC5A, the isoform without the transmembrane domain. The sequences of these enzymes and method of cloning them are known in the art.

Genes encoding the polypeptides of the invention (e.g., a GPIIb/IIIa antibody or antigen-binding molecule thereof disclosed herein, or any of the chimeric molecules disclosed herein) can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryotes, eukaryotic microbes can also be used. *Saccharomyces cerevisiae*, or common baker's yeast, is the most commonly used among eukaryotic microorganisms although a number of other strains are commonly available.

For expression in *Saccharomyces*, the plasmid YRp7, for example, (Stinchcomb et al., *Nature,* 282:39 (1979); Kingsman et al., *Gene,* 7:141 (1979); Tschemper et al., *Gene,* 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

Other yeast hosts such *Pichia* can also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, polypeptide-coding nucleotide sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-) affinity chromatography, e.g., after preferential biosynthesis of a synthetic hinge region polypeptide or prior to or subsequent to the HIC chromatography step described herein. An affinity tag sequence (e.g. a His(6) tag (SEQ ID NO: 246)) can optionally be attached or included within the polypeptide sequence to facilitate downstream purification.

Once expressed, the chimeric molecules can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)) and see specifically the methods used in the instant Examples. Substantially pure proteins of at least about 90 to 95% homogeneity are preferred, and 98 to 99% or more homogeneity most preferred, for pharmaceutical uses.

G. Pharmaceutical Compositions

The present disclosure also provides pharmaceutical compositions comprising one or more of:
(i) a GPIIb/IIIa antibody or antigen-binding molecule thereof disclosed herein;
(ii) a chimeric molecule disclosed herein;
(iii) a nucleic acid molecule or the set of nucleic acid molecules disclosed herein; or
(iv) a vector or set of vectors disclosed herein,
and a pharmaceutically acceptable carrier.

In some embodiments, administering (i) a chimeric molecule disclosed herein, (ii) a nucleic acid molecule or a set of nucleic acid molecules disclosed herein, (iii) a vector or a set of vectors disclosed herein, or (iii) a pharmaceutical composition disclosed herein, can be used, for example, to reduce the frequency or degree of a bleeding episode in a subject in need, and/or reducing or preventing an occurrence of a bleeding episode in a subject in need thereof. In some embodiments, the subject has developed or has a tendency to develop an inhibitor against treatment with FVIII, FIX, or both. In some embodiments, the inhibitor against FVIII or FIX is a neutralizing antibody against FVIII, FIX, or both. In some embodiments, the bleeding episode can be caused by a blood coagulation disorder, for example, hemophilia A or hemophilia B. In other embodiments, the bleeding episode can be the result of hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, bleeding in the illiopsoas sheath, or any combinations thereof. In certain embodiments, the subject is a human subject.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

In one embodiment, the pharmaceutical composition (e.g., a composition comprising the polypeptide(s) or nucleic acid molecule(s) encoding the polypeptide(s)) is one in which the clotting factor is present in activatable form when administered to a subject. Such an activatable molecule can be activated in vivo at the site of clotting after administration to a subject.

H. Methods of Treatment

The antibodies, antigen-binding fragments thereof and chimeric molecules of the disclosure can be useful in methods of treating a subject with a disease or condition. The disease or condition can include, but is not limited to, hemostatic or coagulation disorders.

For example, this disclosure provides a method of treating, ameliorating, or preventing a hemostatic disorder to a subject comprising administering a therapeutically effective amount of a chimeric molecule of the disclosure which comprises a clotting factor. The treatment, amelioration, and prevention by the chimeric molecule can be a bypass therapy. The subject in the bypass therapy can have already developed an inhibitor to a clotting factor, e.g., FVIII or FIX, or is subject to developing a clotting factor inhibitor. In one embodiment, a chimeric molecule composition of the invention is administered in combination with at least one other agent that promotes hemostasis. As an example, but not as a limitation, hemostatic agent can include a FV, FVII, FVIII, FIX, FX, FXI, FXII, FXIII, prothrombin, or fibrinogen or activated forms of any of the preceding. The clotting factor or hemostatic agent can also include anti-fibrinolytic drugs, e.g., epsilon-amino-caproic acid, tranexamic acid.

The chimeric molecules of the invention treat or prevent a hemostatic disorder by promoting the formation of a fibrin clot. The chimeric molecule of the invention can activate any member of a coagulation cascade. The clotting factor can be a participant in the extrinsic pathway, the intrinsic pathway or both. A chimeric molecule of the invention can be used to treat hemostatic disorders, e.g., those known to be treatable with the particular clotting factor present in the chimeric molecule. The hemostatic disorders that can be treated by administration of the chimeric molecule of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII.

In one embodiment, the hemostatic disorder is an inherited disorder. In one embodiment, the subject has hemophilia A, and the chimeric molecule comprises activated or protease-activatable FVII linked to or associated with a GPIIb/IIIa antibody or antigen-binding molecule thereof and a half-life extending heterologous moiety. In another embodiment, the subject has hemophilia A and the chimeric molecule comprises activated or protease-activatable FVII linked to or associated with an Fab or scFv of an GPIIb/IIIa antibody and a half-life extending heterologous moiety. In other embodiments, the subject has hemophilia B and the chimeric molecule comprises activated or protease-activatable FVII or FX linked to or associated with a GPIIb/IIIa antibody or antigen-binding molecule thereof and a half-life extending heterologous moiety. In some embodiments, the subject has inhibitory antibodies to FVIII or FVIIIa and the chimeric molecule comprises activated or protease-activatable FVII linked to or associated with a GPIIb/IIIa antibody or antigen-binding molecule thereof and a half-life extending heterologous moiety. In yet other embodiments, the subject has inhibitory antibodies against FIX or FIXa and the chimeric molecule comprises activated or protease-activatable FVII linked to or associated with a GPIIb/IIIa antibody or antigen-binding molecule thereof and a half-life extending heterologous moiety. In still other embodiments, the subject has inhibitory antibodies to FVIII or FVIIIa and the chimeric molecule comprises activated or protease-activatable FX linked to or associated with a GPIIb/IIIa antibody or antigen-binding molecule thereof and a half-life extending heterologous moiety. In certain embodiments, the subject has inhibitory antibodies against FIX or FIXa and the chimeric molecule comprises activated or protease-activatable FX linked to or associated with a GPIIb/IIIa antibody or antigen-binding molecule thereof and a half-life extending heterologous moiety.

Chimeric molecules of the invention comprising a clotting factor (e.g., FVII) can be used to prophylactically treat a subject with a hemostatic or coagulation disorder. Chimeric molecules of the invention comprising a clotting factor (e.g., FVII) can be used to treat an acute bleeding episode in a subject with a hemostatic disorder.

In one embodiment, the hemostatic disorder is the result of a deficiency in a clotting factor, e.g., FVII, FIX, or FVIII. In another embodiment, the hemostatic disorder can be the result of a defective clotting factor. In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention thus relates to a method of treating a subject in need of a general hemostatic agent comprising administering a therapeutically effective amount of at least one chimeric molecule of the invention. For example, in one embodiment, the subject in need of a general hemostatic agent is undergoing, or is about to undergo, surgery. The chimeric molecule of the invention can be administered prior to or after surgery as a prophylactic. The chimeric molecule of the invention can be administered during or after surgery to control an acute bleeding episode. The surgery can include, but is not limited to, liver transplantation, liver resection, or stem cell transplantation. In another embodiment, the chimeric molecule of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

I. Administration

The antibodies, antigen-binding fragments thereof, chimeric molecules, or nucleic acids encoding same of the disclosure can be administered intravenously, subcutaneously, intramuscularly, or via any mucosal surface, e.g., orally, sublingually, buccally, sublingually, nasally, rectally, vaginally or via pulmonary route. The chimeric molecule can be implanted within or linked to a biopolymer solid support that allows for the slow release of the chimeric molecule to the desired site. The route and/or mode of administration of the antibody or antigen-binding fragment thereof can also be tailored for the individual case, e.g., by monitoring the subject, For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle. For buccal and sublingual administration the composition can take the form of tablets, lozenges or fast dissolving films according to conventional protocols. For administration by inhalation, the chimeric molecules for use according to the present disclosure are conveniently delivered in the form of an aerosol spray from a pressurized pack or nebulizer (e.g., in PBS), with a suitable propellant.

In one embodiment, the route of administration of the polypeptides of the invention is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the invention, a form for administration would be a solution for injection, in particular for intravenous or intraarterial injection or drip. Usually, a suitable pharmaceutical composition for injection can comprise a buffer (e.g., acetate, phosphate or citrate buffer), a surfactant (e.g. polysorbate), optionally a stabilizer agent (e.g., human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

In one embodiment, the dose of a biologically active moiety (e.g., comprising FVII), can range from about 90 to 270 µg/kg or 0.090 to 0.270 mg/kg. In another embodiment, the dose of a biologically active moiety (e.g., comprising FX), can range from about 1 µg/kg to 400 mg/kg.

Dosages can range from 1000 µg/kg to 0.1 ng/kg body weight. In one embodiment, the dosing range is 1 ug/kg to 100 µg/kg. The protein can be administered continuously or at specific timed intervals. In vitro assays can be employed to determine optimal dose ranges and/or schedules for administration. In vitro assays that measure clotting factor activity are known in the art, e.g., STA-CLOT VIIa-rTF clotting assay. Additionally, effective doses can be extrapolated from dose-response curves obtained from animal models, e.g., a hemophiliac dog (Mount et al. 2002, *Blood* 99: 2670).

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

Polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

Polypeptides of the invention can optionally be administered in combination with other agents that are effective in treating the disorder or condition in need of treatment (e.g., prophylactic or therapeutic).

As used herein, the administration of polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g., a physician) would be readily be able to discern effective combined therapeutic regimens without undue experimentation based on the selected adjunct therapy and the teachings of the instant specification.

It will further be appreciated that the polypeptides of the instant invention can be used in conjunction or combination with an agent or agents (e.g., to provide a combined therapeutic regimen). Exemplary agents with which a polypeptide of the invention can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with the polypeptides of the instant invention can vary by subject or can be administered according to what is known in the art. See for example, Bruce A Chabner et al., Antineoplastic Agents, in Goodman & Gilman's The Pharmacological Basis of Therapeutics 1233-1287 ((Hardman et al., eds., 9th ed. 1996). In another embodiment, an amount of such an agent consistent with the standard of care is administered.

As previously discussed, the polypeptides of the present disclosure, can be administered in a pharmaceutically effective amount for the in vivo treatment of clotting disorders. In this regard, it will be appreciated that the polypeptides of the invention can be formulated to facilitate administration and promote stability of the active agent. Preferably, pharmaceutical compositions in accordance with the present disclosure comprise a pharmaceutically acceptable, non-toxic, sterile carrier such as physiological saline, non-toxic buffers, preservatives and the like. Of course, the pharmaceutical compositions of the present disclosure can be administered in single or multiple doses to provide for a pharmaceutically effective amount of the polypeptide.

In one embodiment, a chimeric molecule of the invention is administered as a nucleic acid molecule. Nucleic acid molecules can be administered using techniques known in the art, including via vector, plasmid, liposome, DNA injection, electroporation, gene gun, intravenously injection or hepatic artery infusion. Vectors for use in gene therapy embodiments are known in the art.

In keeping with the scope of the present disclosure, the chimeric molecule of the invention can be administered to a human or other animal in accordance with the aforementioned methods of treatment in an amount sufficient to produce a therapeutic or prophylactic effect.

J. Other Methods of Use

The instant disclosure also provides a method to target or deliver a therapeutic or prophylactic agent (e.g., a clotting factor such as FVII) to the surface of platelets, wherein the method comprises fusing the agent to one of the GPIIb/IIIa antibodies or antigen-binding fragments thereof disclosed herein.

In addition, the disclosure provides a method to increase the activity of a therapeutic or prophylactic agent (e.g., a clotting factor such as FVII) comprising fusing the agent to a GPIIb/IIIa antibody or antigen-binding molecule thereof disclosed herein.

Further, the disclosure provides a method to improve the pharmacokinetic properties of a clotting factor comprising fusing the clotting factor to the GPIIb/IIIa antibody or antigen-binding molecule thereof disclosed herein.

In some embodiments, these methods further comprise fusing or conjugating a clotting factor and/or the GPIIb/IIIa antibody or antigen-binding molecule thereof disclosed herein to a half-life extending moiety. In some embodiments, the therapeutic or prophylactic agent is a FVII, a FIX, or a FX.

The present disclosure also provides a method of measuring the level of platelets in plasma of a subject in need thereof comprising contacting the GPIIb/IIIa antibody or antigen binding molecule thereof disclosed herein with the plasma from the subject and measuring the level of platelets in plasma. This method can further comprise fusing or conjugating the clotting factor and/or the GPIIb/IIIa antibody or antigen-binding molecule thereof disclosed herein to a detectable heterologous moiety, for example, a fluorescent molecule or a radionuclide.

This disclosure also provides a method of isolating or separating platelets from other cells in a sample (e.g., a blood sample). The method comprises contacting the sample with an GPIIb/IIIa antibody or antigen binding molecule thereof disclosed herein and separating the cells that have bound to the GPIIb/IIIa antibody or antigen binding molecule thereof from the unbound fraction.

In addition, the disclosure also provides a method of detecting platelets in a sample (e.g., blood sample) of a subject comprising contacting the sample with a detectably labeled GPIIb/IIIa antibody or antigen binding molecule. The detectable label can be, for example, a fluorescent molecule or a radionuclide.

The following examples are included for purposes of illustration only and are not intended to be limiting of the invention. All patents and publications referred to herein are expressly incorporated by reference in their entireties.

EXAMPLES

Example 1: Humanized Anti-GPIIb/IIIa Antibody Designs

The CDRs (CDR-H1, CDR-H2, and CDR-H3 for the heavy chain region and CDR-L1, CDR-L2, and CDR-L3 for the light chain region) of the murine anti-integrin GPIIb/IIIa antibody, 34D10, were grafted onto human acceptor frameworks to create CDR-grafted variable heavy chain, VH0, and variable light chain, VL0, respectively. Five additional heavy chain regions (VH1 to 5) and three additional light chain regions (VL1 to 3) were created by combining several mutations in the human acceptor frameworks of the CDR grafts compared to the CDR-grafted chains (i.e., VH0 and VL0). The majority of the mutations that were made in the human acceptor frameworks were backmutations to the amino acid of the mature murine framework to help maintain the structure of the 34D10 CDRs.

The germline humIGKV3-15 with framework region FR4 from human consensus subgroup Kappa I was chosen as the light chain acceptor framework. As the humIGKV3-15 germline sequence lacks the final framework region, FR4, the VL0 CDR graft employed the FR4 region from the corresponding human consensus subgroup, Kappa III, which is the same as the FR4 sequence of the human consensus subgroup most similar to the mature murine, Kappa I, namely FGQGTKVEIK (SEQ ID NO:49). This FR4 sequence differs at two positions from 34D10's FR4, FG G GTK L EIK (SEQ ID NO: 193).

The germline humIGHV3/OR16-13 with framework region FR4 from human consensus subgroup Heavy III was chosen as the heavy chain acceptor framework. As the humIGHV3/OR16-13 germline sequence lacks the final framework region FR4, the VH0 CDR graft used the FR4 region from the human consensus that best matched 34D10 VH, human consensus subgroup Heavy III. This framework region 4 sequence is WGQGTLVTVSS (SEQ ID NO: 34), differing from murine only by having that L108, which is S in the 34D10 VH and the murine consensus Heavy III(D).

The sequences of the 34D10 VH and VL regions, as well as the six humanized 34D10 variable heavy chain regions and four humanized 34D10 variable light chain regions are shown below. CDRs 1, 2, and 3 are underlined in each amino acid sequence.

Variable Heavy Chain Sequences:
34D10 VH Variable Heavy Chain Amino Acid Sequence (SEQ ID NO: 1)
EVKLVESGGGLVKPGGSLKLSCAASGFTFSAYAMSWVRQTPEKRLEWVAS
ISSGGTTYYPDSVKRRFTISRDNARNILYLQMSSLRSEDTAMYYCTRGGD
YGYALDYWGQGTSVTVSS h34D10 VH0 Variable Heavy Chain Amino Acid Sequence (SEQ ID NO: 3)
EVQLVESGGGLVQPGGSLRLSCAASGFTFSAYAMSWVRQAPGKGLVWVSS
ISSGGTTYYPDSVKRQFTISRDNAKNTLYLQMNSLRAEDMAVYYCTRGGD
YGYALDYWGQGTLVTVSS h34D10 VH0 Variable Heavy Chain Nucleic Acid Sequence (SEQ ID NO: 13)
```
  1 GAGGTGCAGC TGGTGGAGTC TGGAGGAGGC TTGGTACAGC CTGGAGGGTC
    CCTGAGACTC
 61 TCCTGTGCAG CCTCTGGATT CACCTTTAGC GCCTATGCCA TGAGCTGGGT
    CCGCCAGGCT
121 CCAGGGAAGG GCTGGTGTG GGTCTCAAGC ATTAGTAGTG GTGGTACCAC
    ATACTACCCA
181 GACTCCGTGA AGAGGCAGTT CACCATCTCC AGAGACAATG CCAAGAACAC
    GCTGTATCTG
241 CAAATGAACA GCCTGAGAGC CGAGGACATG GCCGTATATT ACTGTACCAG
    AGGAGGGGAT
301 TATGGCTACG CTCTCGACTA CTGGGGCCAG GGAACCCTGG TCACCGTCTC CTCA
``` h34D10 VH0 Heavy Chain Nucleic Acid Sequence (SEQ ID NO: 59)
```
  1 GAGGTGCAGC TGGTGGAGTC TGGAGGAGGC TTGGTACAGC CTGGAGGGTC
    CCTGAGACTC
 61 TCCTGTGCAG CCTCTGGATT CACCTTTAGC GCCTATGCCA TGAGCTGGGT
    CCGCCAGGCT
121 CCAGGGAAGG GCTGGTGTG GGTCTCAAGC ATTAGTAGTG GTGGTACCAC
    ATACTACCCA
181 GACTCCGTGA AGAGGCAGTT CACCATCTCC AGAGACAATG CCAAGAACAC
    GCTGTATCTG
241 CAAATGAACA GCCTGAGAGC CGAGGACATG GCCGTATATT ACTGTACCAG
    AGGAGGGGAT
301 TATGGCTACG CTCTCGACTA CTGGGGCCAG GGAACCCTGG TCACCGTCTC
    CTCAGCCTCC
361 ACCAAGGGCC CATCGGTCTT CCCGCTAGCA CCCTCCTCCA AGAGCACCTC
    TGGGGGCACA
```

```
421 GCGGCCCTGG GCTGCCTGGT CAAGGACTAC TTCCCCGAAC CGGTGACGGT
    GTCGTGGAAC
481 TCAGGCGCCC TGACCAGCGG CGTCCACACC TTCCCGGCTG TCCTACAGTC
    TAGCGGACTC
541 TACTCCCTCA GCAGCGTAGT GACCGTGCCC TCTTCTAGCT TGGGCACCCA
    GACCTACATC
601 TGCAACGTGA ATCACAAGCC CAGCAACACC AAGGTGGACA AGAAAGTTGA
    GCCCAAATCT
661 TGTTAG
``` h34D10 VH1 Variable Heavy Chain Amino Acid Sequence (SEQ ID NO: 5)
EVQLVQSGGGLVQPGESLRLSCAASGFTFS<u>AYAMS</u>WVRQAPGKGLEWVS<u>S</u>
<u>ISSGGTTYYPDSVKR</u>RFTISRDNAKNTLYLQMNSLRAEDMAVYYCTR<u>GGD</u>
<u>YGYALDY</u>WGQGTLVTVSS h34D10 VH1 Variable Heavy Chain Nucleic Acid Sequence

```
                                                    (SEQ ID NO: 14)
  1 GAGGTGCAGC TGGTGCAGTC TGGAGGAGGC TTGGTACAGC CTGGAGAGTC
    CCTGAGACTC
 61 TCCTGTGCAG CCTCTGGATT CACCTTTAGC GCCTATGCCA TGAGCTGGGT
    CCGCCAGGCT
121 CCAGGGAAGG GGCTGGAGTG GGTCTCAAGC ATTAGTAGTG GTGGTACCAC
    ATACTACCCA
181 GACTCCGTGA AGAGGAGATT CACCATCTCC AGAGACAATG CCAAGAACAC
    GCTGTATCTG
241 CAAATGAACA GCCTGAGAGC CGAGGACATG GCCGTATATT ACTGTACCAG
    AGGAGGGGAT
301 TATGGCTACG CTCTCGACTA CTGGGGCCAG GGAACCCTGG TCACCGTCTC CTCA
``` h34D10 VH1 Heavy Chain Nucleic Acid Sequence

```
                                                    (SEQ ID NO: 60)
  1 GAGGTGCAGC TGGTGCAGTC TGGAGGAGGC TTGGTACAGC CTGGAGAGTC
    CCTGAGACTC
 61 TCCTGTGCAG CCTCTGGATT CACCTTTAGC GCCTATGCCA TGAGCTGGGT
    CCGCCAGGCT
121 CCAGGGAAGG GGCTGGAGTG GGTCTCAAGC ATTAGTAGTG GTGGTACCAC
    ATACTACCCA
181 GACTCCGTGA AGAGGAGATT CACCATCTCC AGAGACAATG CCAAGAACAC
    GCTGTATCTG
241 CAAATGAACA GCCTGAGAGC CGAGGACATG GCCGTATATT ACTGTACCAG
    AGGAGGGGAT
```

```
301 TATGGCTACG CTCTCGACTA CTGGGGCCAG GGAACCCTGG TCACCGTCTC
    CTCAGCCTCC
361 ACCAAGGGCC CATCGGTCTT CCCGCTAGCA CCCTCCTCCA AGAGCACCTC
    TGGGGGCACA
421 GCGGCCCTGG GCTGCCTGGT CAAGGACTAC TTCCCCGAAC CGGTGACGGT
    GTCGTGGAAC
481 TCAGGCGCCC TGACCAGCGG CGTCCACACC TTCCCGGCTG TCCTACAGTC
    TAGCGGACTC
541 TACTCCCTCA GCAGCGTAGT GACCGTGCCC TCTTCTAGCT TGGGCACCCA
    GACCTACATC
601 TGCAACGTGA ATCACAAGCC CAGCAACACC AAGGTGGACA AGAAAGTTGA
    GCCCAAATCT
661 TGTTAG
``` h34D10 VH2 Variable Heavy Chain Amino Acid Sequence (SEQ ID NO: 7)
EVQLVESGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQMNSLRAEDTAVYYCTR<u>GGD</u>
<u>YGYALDY</u>WGQGTLVTVSS h34D10 VH2 Variable Heavy Chain Nucleic Acid Sequence

```
                                                (SEQ ID NO: 15)
  1 GAGGTGCAGC TGGTGGAGTC TGGAGGAGGC TTGGTAAAGC CTGGAGGATC
    CCTGAGACTC
 61 TCCTGTGCAG CCTCTGGATT CACCTTTAGC GCCTATGCCA TGAGCTGGGT
    CCGCCAGGCT
121 CCAGGGAAGG GGCTGGTCTG GGTCGCTAGC ATTAGTAGTG GTGGTACCAC
    ATACTACCCA
181 GACTCCGTGA AGAGGCAGTT CACCATCTCC AGAGACAATG CCAAGAACAC
    GCTGTATCTG
241 CAAATGAACA GCCTGAGAGC CGAGGACACA GCCGTATATT ACTGTACCAG
    AGGAGGGGAT
301 TATGGCTACG CTCTCGACTA CTGGGGCCAG GGAACCCTGG TCACCGTCTC CTCA
``` h34D10 VH2 Heavy Chain Nucleic Acid Sequence

```
                                                (SEQ ID NO: 61)
  1 GAGGTGCAGC TGGTGGAGTC TGGAGGAGGC TTGGTAAAGC CTGGAGGATC
    CCTGAGACTC
 61 TCCTGTGCAG CCTCTGGATT CACCTTTAGC GCCTATGCCA TGAGCTGGGT
    CCGCCAGGCT
121 CCAGGGAAGG GGCTGGTCTG GGTCGCTAGC ATTAGTAGTG GTGGTACCAC
    ATACTACCCA
```

-continued

```
181 GACTCCGTGA AGAGGCAGTT CACCATCTCC AGAGACAATG CCAAGAACAC
    GCTGTATCTG
241 CAAATGAACA GCCTGAGAGC CGAGGACACA GCCGTATATT ACTGTACCAG
    AGGAGGGGAT
301 TATGGCTACG CTCTCGACTA CTGGGGCCAG GGAACCCTGG TCACCGTCTC
    CTCAGCCTCC
361 ACCAAGGGCC CATCGGTCTT CCCGCTAGCA CCCTCCTCCA AGAGCACCTC
    TGGGGGCACA
421 GCGGCCCTGG GCTGCCTGGT CAAGGACTAC TTCCCCGAAC CGGTGACGGT
    GTCGTGGAAC
481 TCAGGCGCCC TGACCAGCGG CGTCCACACC TTCCCGGCTG TCCTACAGTC
    TAGCGGACTC
541 TACTCCCTCA GCAGCGTAGT GACCGTGCCC TCTTCTAGCT TGGGCACCCA
    GACCTACATC
601 TGCAACGTGA ATCACAAGCC CAGCAACACC AAGGTGGACA AGAAAGTTGA
    GCCCAAATCT
661 TGTTAG
``` h34D10 VH3 Variable Heavy Chain Amino Acid Sequence (SEQ ID NO: 9)
EVQLVQSGGGLVKPGESLRLSCAASGFTFS<u>AYAMS</u>WVRQAPGKGLEWVA<u>S
ISSGGTTYYPDSVKR</u>RFTISRDNAKNTLYLQMNSLRAEDTAVYYCTR<u>GGD
YGYALDY</u>WGQGTLVTVSS h34D10 VH3 Variable Heavy Chain Nucleic Acid Sequence

```
                                             (SEQ ID NO: 16)
  1 GAGGTGCAGC TGGTGCAGTC TGGAGGAGGC TTGGTAAAGC CTGGAGAGTC
    CCTGAGACTC
 61 TCCTGTGCAG CCTCTGGATT CACCTTTAGC GCCTATGCCA TGAGCTGGGT
    CCGCCAGGCT
121 CCAGGGAAGG GGCTGGAGTG GGTCGCTAGC ATTAGTAGTG GTGGTACCAC
    ATACTACCCA
181 GACTCCGTGA AGAGGAGATT CACCATCTCC AGAGACAATG CCAAGAACAC
    GCTGTATCTG
241 CAAATGAACA GCCTGAGAGC CGAGGACACA GCCGTATATT ACTGTACCAG
    AGGAGGGGAT
301 TATGGCTACG CTCTCGACTA CTGGGGCCAG GGAACCCTGG TCACCGTCTC CTCA
``` h34D10 VH3 Heavy Chain Nucleic Acid Sequence (SEQ ID NO: 62)
```
  1 GAGGTGCAGC TGGTGCAGTC TGGAGGAGGC TTGGTAAAGC CTGGAGAGTC
    CCTGAGACTC
 61 TCCTGTGCAG CCTCTGGATT CACCTTTAGC GCCTATGCCA TGAGCTGGGT
    CCGCCAGGCT
121 CCAGGGAAGG GGCTGGAGTG GGTCGCTAGC ATTAGTAGTG GTGGTACCAC
    ATACTACCCA
181 GACTCCGTGA AGAGGAGATT CACCATCTCC AGAGACAATG CCAAGAACAC
    GCTGTATCTG
241 CAAATGAACA GCCTGAGAGC CGAGGACACA GCCGTATATT ACTGTACCAG
    AGGAGGGGAT
301 TATGGCTACG CTCTCGACTA CTGGGGCCAG GGAACCCTGG TCACCGTCTC
    CTCAGCCTCC
361 ACCAAGGGCC CATCGGTCTT CCCGCTAGCA CCCTCCTCCA AGAGCACCTC
    TGGGGGCACA
421 GCGGCCCTGG GCTGCCTGGT CAAGGACTAC TTCCCCGAAC CGGTGACGGT
    GTCGTGGAAC
481 TCAGGCGCCC TGACCAGCGG CGTCCACACC TTCCCGGCTG TCCTACAGTC
    TAGCGGACTC
541 TACTCCCTCA GCAGCGTAGT GACCGTGCCC TCTTCTAGCT TGGGCACCCA
    GACCTACATC
601 TGCAACGTGA ATCACAAGCC CAGCAACACC AAGGTGGACA AGAAAGTTGA
    GCCCAAATCT
661 TGTTAG
``` h34D10 VH4 Variable Heavy Chain Amino Acid Sequence (SEQ ID NO: 11)
EVQLVQSGGGLVKPGESLRLSCAASGFTFS<u>AYAMS</u>WVRQAPGKGLEWVA<u>S</u>

<u>ISSGGTTYYPDSVKR</u>RFTISRDNSRNTLYLQMNSLRAEDTAVYYCTR<u>GGD</u>

<u>YGYALDY</u>WGQGTLVTVSS h34D10 VH4 Variable Heavy Chain Nucleic Acid Sequence (SEQ ID NO: 17)
```
  1 GAGGTGCAGC TGGTGCAGTC TGGAGGAGGC TTGGTAAAGC
    CTGGAGAGTC CCTGAGACTC
 61 TCCTGTGCAG CCTCTGGATT CACCTTTAGC GCCTATGCCA
    TGAGCTGGGT CCGCCAGGCT
121 CCAGGGAAGG GGCTGGAGTG GGTCGCTAGC ATTAGTAGTG
    GTGGTACCAC ATACTACCCA
181 GACTCCGTGA AGAGGAGATT CACCATCTCC AGAGACAATA
    GTCGCAACAC GCTGTATCTG
241 CAAATGAACA GCCTGAGAGC CGAGGACACA GCCGTATATT
    ACTGTACCAG AGGAGGGGAT
301 TATGGCTACG CTCTCGACTA CTGGGGCCAG GGAACCCTGG
    TCACCGTCTC CTCA
``` h34D10 VH4 Heavy Chain Nucleic Acid Sequence (SEQ ID NO: 63)
```
  1 GAGGTGCAGC TGGTGCAGTC TGGAGGAGGC TTGGTAAAGC
    CTGGAGAGTC CCTGAGACTC
 61 TCCTGTGCAG CCTCTGGATT CACCTTTAGC GCCTATGCCA
    TGAGCTGGGT CCGCCAGGCT
121 CCAGGGAAGG GGCTGGAGTG GGTCGCTAGC ATTAGTAGTG
    GTGGTACCAC ATACTACCCA
181 GACTCCGTGA AGAGGAGATT CACCATCTCC AGAGACAATA
    GTCGCAACAC GCTGTATCTG
241 CAAATGAACA GCCTGAGAGC CGAGGACACA GCCGTATATT
    ACTGTACCAG AGGAGGGGAT
301 TATGGCTACG CTCTCGACTA CTGGGGCCAG GGAACCCTGG
    TCACCGTCTC CTCAGCCTCC
361 ACCAAGGGCC CATCGGTCTT CCCGCTAGCA CCCTCCTCCA
    AGAGCACCTC TGGGGGCACA
``` h34D10 VH5 Variable Heavy Chain Amino Acid Sequence (SEQ ID NO: 12)
EVKLVESGGGLVKPGGSLRLSCAASGFTFS<u>AYAMS</u>WVRQAPGKGLEWVA<u>S ISSGGTTYYPDSVKR</u>RFTISRDNARNTLYLQMNSLRAEDTAVYYCTR<u>GGD YGYALDY</u>WGQGTLVTVSS h34D10 VH5 Variable Heavy Chain Nucleic Acid Sequence (SEQ ID NO: 18)
```
  1 GAGGTGAAGC TGGTGGAGTC TGGAGGAGGC TTGGTAAAGC
    CTGGAGGCTC CCTGAGACTC
 61 TCCTGTGCAG CCTCTGGATT CACCTTTAGC GCCTATGCCA
    TGAGCTGGGT CCGCCAGGCT
121 CCAGGGAAGG GGCTGGAGTG GTCGCTAGC ATTAGTAGTG
    GTGGTACCAC ATACTACCCA
181 GACTCCGTGA AGAGGAGATT CACCATCTCC AGAGACAATG
    CTCGCAACAC GCTGTATCTG
241 CAAATGAACA GCCTGAGAGC CGAGGACACA GCCGTATATT
    ACTGTACCAG AGGAGGGGAT
301 TATGGCTACG CTCTCGACTA CTGGGGCCAG GGAACCCTGG
    TCACCGTCTC CTCA
``` h34D10 VH5 Heavy Chain Nucleic Acid Sequence (SEQ ID NO: 64)
```
  1 GAGGTGAAGC TGGTGGAGTC TGGAGGAGGC TTGGTAAAGC
    CTGGAGGCTC CCTGAGACTC
 61 TCCTGTGCAG CCTCTGGATT CACCTTTAGC GCCTATGCCA
    TGAGCTGGGT CCGCCAGGCT
121 CCAGGGAAGG GGCTGGAGTG GTCGCTAGC ATTAGTAGTG
    GTGGTACCAC ATACTACCCA
181 GACTCCGTGA AGAGGAGATT CACCATCTCC AGAGACAATG
    CTCGCAACAC GCTGTATCTG
241 CAAATGAACA GCCTGAGAGC CGAGGACACA GCCGTATATT
    ACTGTACCAG AGGAGGGGAT
301 TATGGCTACG CTCTCGACTA CTGGGGCCAG GGAACCCTGG
    TCACCGTCTC CTCAGCCTCC
361 ACCAAGGGCC CATCGGTCTT CCCGCTAGCA CCCTCCTCCA
    AGAGCACCTC TGGGGGCACA
421 GCGGCCCTGG GCTGCCTGGT CAAGGACTAC TTCCCCGAAC
    CGGTGACGGT GTCGTGGAAC
481 TCAGGCGCCC TGACCAGCGG CGTCCACACC TTCCCGGCTG
    TCCTACAGTC TAGCGGACTC
541 TACTCCCTCA GCAGCGTAGT GACCGTGCCC TCTTCTAGCT
    TGGGCACCCA GACCTACATC
601 TGCAACGTGA ATCACAAGCC CAGCAACACC AAGGTGGACA
    AGAAAGTTGA GCCCAAATCT
661 TGTTAG
```

Variable Light Chain Sequences:

34D10 VL Variable Light Chain Amino Acid Sequence (SEQ ID NO: 2)
ENVLTQSPAIMSASLGEKVTMSC<u>RASSSVNYMY</u>WYQQKSDASPKLWIY<u>YT SNLAP</u>GVPARFSGSGSGNSYSLTISSMEGEDAATYYC<u>QQFSSSPWT</u>FGGG

TKLEIK h34D10 VL0 Variable Light Chain Amino Acid Sequence (SEQ ID NO: 4)
EIVMTQSPATLSVSPGERATLSC<u>RASSSVNYMY</u>WYQQKPGQAPRLLIY<u>YT SNLAP</u>GIPARFSGSGSGTEFTLTISSLQSEDFAVYYC<u>QQFSSSPWT</u>FGQG

TKVEIK h34D10 VL0 Variable Light Chain Nucleic Acid Sequence (SEQ ID NO: 19)
```
  1 GAAATTGTAA TGACACAGTC TCCAGCCACC CTGTCTGTGT
    CTCCTGGCGA AAGAGCCACC
 61 CTCTCCTGCC GCGCCAGTAG CAGTGTTAAC TACATGTACT
    GGTATCAACA GAAACCTGGC
121 CAGGCTCCCA GGCTCCTCAT CTATTACACA TCCAACTTGG
    CCCCTGGCAT CCCAGCCAGG
181 TTCAGTGGCA GTGGGTCTGG GACAGAGTTC ACTCTCACCA
    TCAGCAGCCT ACAGAGCGAA
241 GATTTTGCAG TTTATTACTG TCAGCAGTTC AGCAGTTCAC
    CTTGGACGTT CGGCCAAGGG
301 ACCAAGGTGG AAATCAAA
``` h34D10 VL0 Light Chain Nucleic Acid Sequence (with signal sequence: MDMRVPAQLL GLLLLWLPGARC (SEQ ID NO:194); the nucleic acid sequence encoding the mature light chain sequence is underlined)

(SEQ ID NO: 65)
```
  1 ATGGACATGA GGGTCCCCGC TCAGCTCCTG GGGCTCCTTC
    TGCTCTGGCT CCCTGGAGCA
 61 CGATGTGAAA TTGTAATGAC ACAGTCTCCA GCCACCCTGT
    CTGTGTCTCC TGGCGAAAGA
121 GCCACCCTCT CCTGCCGCGC CAGTAGCAGT GTTAACTACA
    TGTACTGGTA TCAACAGAAA
181 CCTGGCCAGG CTCCCAGGCT CCTCATCTAT TACACATCCA
    ACTTGGCCCC TGGCATCCCA
241 GCCAGGTTCA GTGGCAGTGG GTCTGGGACA GAGTTCACTC
    TCACCATCAG CAGCCTACAG
301 AGCGAAGATT TTGCAGTTTA TTACTGTCAG CAGTTCAGCA
    GTTCACCTTG GACGTTCGGC
361 CAAGGGACCA AGGTGGAAAT CAAACGTACG GTGGCTGCAC
    CATCTGTCTT CATCTTCCCG
421 CCATCTGATG AGCAGTTGAA ATCTGGAACT GCCTCTGTTG
    TGTGCCTGCT GAATAACTTC
```

-continued

```
481 TATCCCAGAG AGGCCAAAGT ACAGTGGAAG GTGGATAACG
    CCCTCCAATC GGGTAACTCC

541 CAGGAGAGTG TCACAGAGCA GGACAGCAAG GACAGCACCT
    ACAGCCTCAG CAGCACCCTG

601 ACGCTGAGCA AAGCAGACTA CGAGAAACAC AAAGTCTACG
    CCTGCGAAGT CACCCATCAG

661 GGCCTGAGCT CGCCCGTCAC AAAGAGCTTC AACAGGGGAG
    AGTGTTAG
``` h34D10 VL1 Variable Light Chain Amino Acid Sequence (SEQ ID NO: 6)
EIVLTQSPATLSVSPGERATLSC<u>RASSSVNYMY</u>WYQQKPGQAPRLLIY<u>YT
SNLAP</u>GVPARFSGSGSGTEFTLTISSLQSEDFAVYYC<u>QQFSSSPWT</u>FGQG
TKVEIK h34D10 VL1 Variable Light Chain Nucleic Acid Sequence

```
                                          (SEQ ID NO: 20)
  1 GAAATTGTAC TCACACAGTC TCCAGCCACC CTGTCTGTGT
    CTCCTGGCGA AAGAGCCACC

61 CTCTCCTGCC GCGCCAGTAG CAGTGTTAAC TACATGTACT
    GGTATCAACA GAAACCTGGC

121 CAGGCTCCCA GGCTCCTCAT CTATTACACA TCCAACTTGG
    CCCCTGGCGT TCCAGCCAGG

181 TTCAGTGGCA GTGGGTCTGG GACAGAGTTC ACTCTCACCA
    TCAGCAGCCT ACAGAGCGAA

241 GATTTTGCAG TTTATTACTG TCAGCAGTTC AGCAGTTCAC
    CTTGGACGTT CGGCCAAGGG

301 ACCAAGGTGG AAATCAAA
``` h34D10 VL1 Light Chain Nucleic Acid Sequence

```
                                          (SEQ ID NO: 66)
  1 GAAATTGTAC TCACACAGTC TCCAGCCACC CTGTCTGTGT
    CTCCTGGCGA AAGAGCCACC

61 CTCTCCTGCC GCGCCAGTAG CAGTGTTAAC TACATGTACT
    GGTATCAACA GAAACCTGGC

121 CAGGCTCCCA GGCTCCTCAT CTATTACACA TCCAACTTGG
    CCCCTGGCGT TCCAGCCAGG

181 TTCAGTGGCA GTGGGTCTGG GACAGAGTTC ACTCTCACCA
    TCAGCAGCCT ACAGAGCGAA

241 GATTTTGCAG TTTATTACTG TCAGCAGTTC AGCAGTTCAC
    CTTGGACGTT CGGCCAAGGG

301 ACCAAGGTGG AAATCAAACG TACGGTGGCT GCACCATCTG
    TCTTCATCTT CCCGCCATCT

361 GATGAGCAGT TGAAATCTGG AACTGCCTCT GTTGTGTGCC
    TGCTGAATAA CTTCTATCCC

421 AGAGAGGCCA AAGTACAGTG GAAGGTGGAT AACGCCCTCC
    AATCGGGTAA CTCCCAGGAG

481 AGTGTCACAG AGCAGGACAG CAAGGACAGC ACCTACAGCC
    TCAGCAGCAC CCTGACGCTG

541 AGCAAAGCAG ACTACGAGAA ACACAAAGTC TACGCCTGCG
    AAGTCACCCA TCAGGGCCTG

601 AGCTCGCCCG TCACAAAGAG CTTCAACAGG GGAGAGTGTT
    AG
``` h34D10 VL2 Variable Light Chain Amino Acid Sequence (SEQ ID NO: 8)
EIVLTQSPATLSASPGERVTMSC<u>RASSSVNYMY</u>WYQQKPGQSPRLLIY<u>YT
SNLAP</u>GVPARFSGSGSGTEYTLTISSLQSEDFAVYYC<u>QQFSSSPWT</u>FGQG
TKVEIK h34D10 VL2 Variable Light Chain Nucleic Acid Sequence

```
                                          (SEQ ID NO: 21)
  1 GAAATTGTAC TCACACAGTC TCCAGCCACC CTGTCTGCCT
    CTCCTGGCGA AAGAGTGACC

61 ATGTCCTGCC GCGCCAGTAG CAGTGTTAAC TACATGTACT
    GGTATCAACA GAAACCTGGC

121 CAGTCACCCA GGCTCCTCAT CTATTACACA TCCAACTTGG
    CCCCTGGCGT TCCAGCCAGG

181 TTCAGTGGCA GTGGGTCTGG GACAGAGTAC ACTCTCACCA
    TCAGCAGCCT ACAGAGCGAA

241 GATTTTGCAG TTTATTACTG TCAGCAGTTC AGCAGTTCAC
    CTTGGACGTT CGGCCAAGGG

301 ACCAAGGTGG AAATCAAA
``` h34D10 VL2 Light Chain Nucleic Acid Sequence

```
                                          (SEQ ID NO: 67)
  1 GAAATTGTAC TCACACAGTC TCCAGCCACC CTGTCTGCCT CTCCTGGCGA
    AAGAGTGACC

61 ATGTCCTGCC GCGCCAGTAG CAGTGTTAAC TACATGTACT GGTATCAACA
    GAAACCTGGC

121 CAGTCACCCA GGCTCCTCAT CTATTACACA TCCAACTTGG CCCCTGGCGT
    TCCAGCCAGG
```

```
181 TTCAGTGGCA GTGGGTCTGG ACAGAGTAC ACTCTCACCA TCAGCAGCCT
    ACAGAGCGAA

241 GATTTTGCAG TTTATTACTG TCAGCAGTTC AGCAGTTCAC CTTGGACGTT
    CGGCCAAGGG

301 ACCAAGGTGG AAATCAAACG TACGGTGGCT GCACCATCTG TCTTCATCTT
    CCCGCCATCT

361 GATGAGCAGT TGAAATCTGG AACTGCCTCT GTTGTGTGCC TGCTGAATAA
    CTTCTATCCC

421 AGAGAGGCCA AGTACAGTG GAAGGTGGAT AACGCCCTCC AATCGGGTAA
    CTCCCAGGAG

481 AGTGTCACAG AGCAGGACAG CAAGGACAGC ACCTACAGCC TCAGCAGCAC
    CCTGACGCTG

541 AGCAAAGCAG ACTACGAGAA ACACAAAGTC TACGCCTGCG AAGTCACCCA
    TCAGGGCCTG

601 AGCTCGCCCG TCACAAAGAG CTTCAACAGG GGAGAGTGTT AG
``` h34D10 VL3 Variable Light Chain Amino Acid Sequence (SEQ ID NO: 10)
ENVMTQSPATLSASPGERVTMSCRASSSVNYMYWYQQKPGQSPRLLIYYT

SNLAPGVPARFSGSGSGTEYTLTISSLQSEDFAVYYCQQFSSSPWTFGQG

TKVEIK h34D10 VL3 Variable Light Chain Nucleic Acid Sequence

```
                                             (SEQ ID NO: 22)
  1 GAAAACGTAA TGACACAGTC TCCAGCCACC CTGTCTGCCT CTCCTGGCGA
    AAGAGTGACC

61 ATGTCCTGCC GCGCCAGTAG CAGTGTTAAC TACATGTACT GGTATCAACA
    GAAACCTGGC

121 CAGTCACCCA GGCTCCTCAT CTATTACACA TCCAACTTGG CCCCTGGCGT
    TCCAGCCAGG

181 TTCAGTGGCA GTGGGTCTGG ACAGAGTAC ACTCTCACCA TCAGCAGCCT
    ACAGAGCGAA

241 GATTTTGCAG TTTATTACTG TCAGCAGTTC AGCAGTTCAC CTTGGACGTT
    CGGCCAAGGG

301 ACCAAGGTGG AAATCAAA
``` h34D10 VL3 Light Chain Nucleic Acid Sequence

```
                                             (SEQ ID NO: 68)
  1 GAAAACGTAA TGACACAGTC TCCAGCCACC CTGTCTGCCT CTCCTGGCGA
    AAGAGTGACC

61 ATGTCCTGCC GCGCCAGTAG CAGTGTTAAC TACATGTACT GGTATCAACA
    GAAACCTGGC

121 CAGTCACCCA GGCTCCTCAT CTATTACACA TCCAACTTGG CCCCTGGCGT
    TCCAGCCAGG

181 TTCAGTGGCA GTGGGTCTGG ACAGAGTAC ACTCTCACCA TCAGCAGCCT
    ACAGAGCGAA

241 GATTTTGCAG TTTATTACTG TCAGCAGTTC AGCAGTTCAC CTTGGACGTT
    CGGCCAAGGG

301 ACCAAGGTGG AAATCAAACG TACGGTGGCT GCACCATCTG TCTTCATCTT
    CCCGCCATCT
```

-continued

```
361 GATGAGCAGT TGAAATCTGG AACTGCCTCT GTTGTGTGCC TGCTGAATAA
    CTTCTATCCC

421 AGAGAGGCCA AAGTACAGTG GAAGGTGGAT AACGCCCTCC AATCGGGTAA
    CTCCCAGGAG

481 AGTGTCACAG AGCAGGACAG CAAGGACAGC ACCTACAGCC TCAGCAGCAC
    CCTGACGCTG

541 AGCAAAGCAG ACTACGAGAA ACACAAAGTC TACGCCTGCG AAGTCACCCA
    TCAGGGCCTG

601 AGCTCGCCCG TCACAAAGAG CTTCAACAGG GGAGAGTGTT AG
```

Alignments of the amino acid sequences of 34D10 VH and VL with the six humanized 34D10 variable heavy chain regions and four humanized 34D10 variable light chain regions are shown in FIGS. 1 and 2, respectively.

Figure 3:
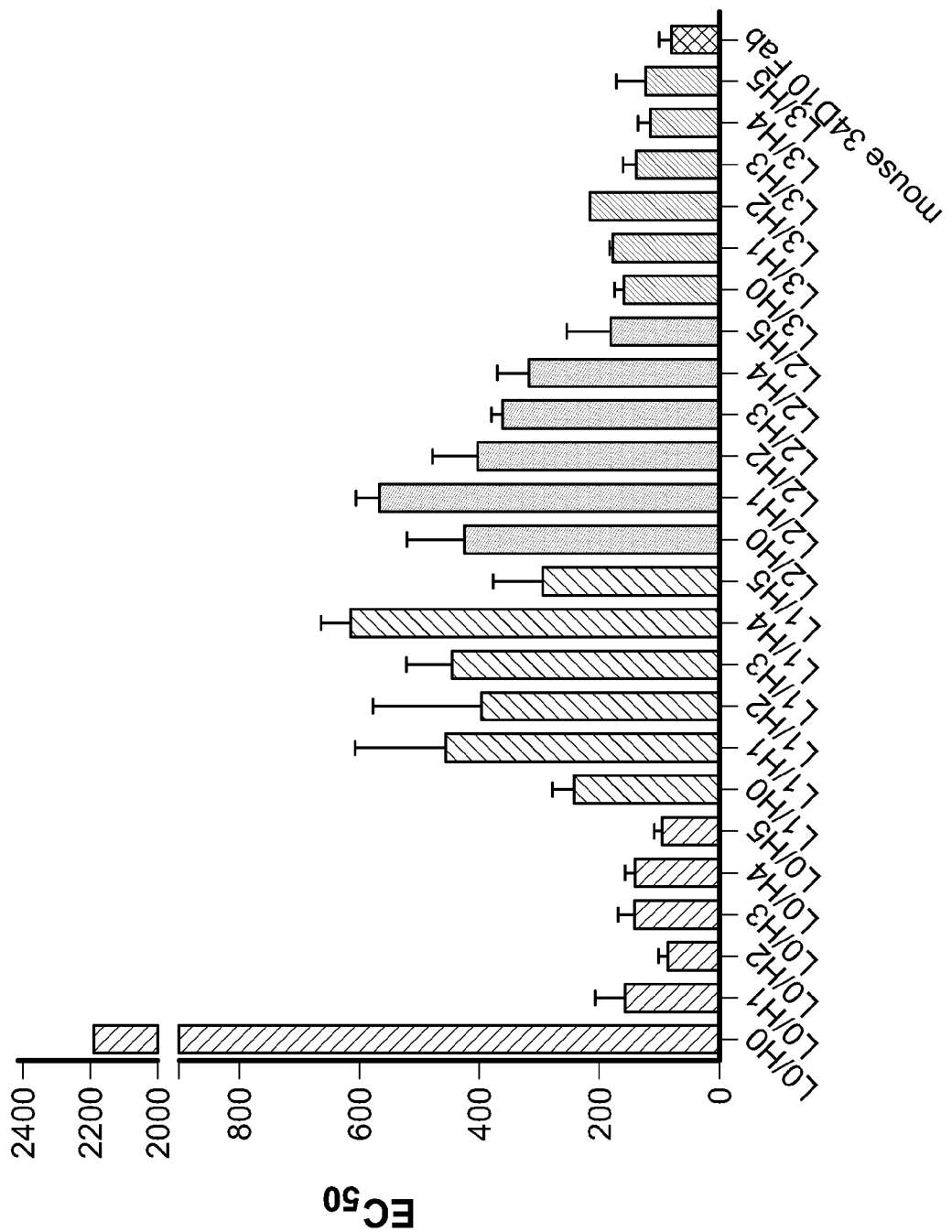
FIG. 3 is a bar graph depicting the binding affinity for GPIIb/IIIa of humanized Fab fragments of 34D10.

Example 2: Flow Cytometry Studies to Determine the Binding of the Humanized Fabs to Human Platelets and Surface Plasmon Resonance Studies to Determine the Affinity of Humanized Fabs for Purified GPIIb/IIIa Human platelets were purified from platelet-rich plasma (PRP) using a Sepharose CL-2B column (GE Healthcare) in platelet buffer (15 mM HEPES, 138 mM NaCl, 5 mM $CaCl_2$, 2.7 mM KCl, 1 mM $MgCl_2$, 5.5 mM dextrose, 1 mg/ml BSA, pH 7.4) following methods known in the art. Humanized Fab at different increasing concentrations was incubated with the gel-purified platelets for 20 minutes at room temperature. Next platelets were washed with citrate buffer (5.4 mM trisodium citrate, 146 mM NaCl, 5.5 mM dextrose, pH 6.8) and resuspended in platelet buffer. R-phycoerythrin-labeled anti-human Fab polyclonal antibody (Southern Biotech) was added to the samples and incubated for 20 minutes at room temperature in the dark. Finally the cells were fixed with paraformaldehyde (final concentration 1%) and binding of the Fab to platelets was measured by standard flow cytometry techniques. $EC_{50}$ was calculated as the Fab concentration that shows a mean fluorescence signal (MFI) equal to one half of the maximal mean fluorescence signal (maximal signal observed at saturation of Fab binding). As a control, binding of the mouse Fab (34D10) was also measured. With the exception of Fab L0/H0, all Fabs with L0 light chain showed binding comparable to the mouse Fab (FIG. 3). L0/H2 and L0/H5 showed the best binding. All the Fabs with the L3 light chain also showed binding comparable to the mouse Fab. In general, Fabs with the L1 or L2 light chains showed weaker binding.

To confirm the binding profiles observed in the flow cytometry experiments, binding assays were performed using surface plasmon resonance (SPR) technology. For this purpose biotinylated human GPIIb/IIIa ectodomain protein was generated as described in Zhu et al. *Molecular Cell*, 32(6): 849-861 (2008). The GPIIb/IIIa ectodomain protein was immobilized on an SPR chip coated with streptavidin (GE Healthcare). Next, the association and dissociation rates of Fab binding to GPIIb/IIIa at sequentially increasing concentrations of the Fab were measured following methods known in the art. The kinetic parameters were derived from a 1:1 binding model. Fab L0/H2 ($K_D$=2.8 nM) and L0/H5 ($K_D$=5.3 nM) displayed affinities comparable to the mouse 34D10 Fab ($K_D$=2.8 nM), while Fab L1/H3 displays significantly lower affinity (110 nM) (data not shown). These results are consistent with the flow cytometry binding data and show that the humanized Fabs L0/H2 and L0/H5 and the mouse Fab 34D10 bind to GPIIb/IIIa with similar affinity.

Example 3: Generation of FVII-245/Fab033, FVII-250/Fab-036, FVII-250/Fab-037, FVII-251/Fab-036, FVII-251-Fab-037 and FVII-200

As shown above, the binding of humanized Fabs L0/H2 and L0/H5 and mouse Fab (34D10) to platelets and purified GPIIb/IIIa was similar. To determine if the properties of the humanized Fabs and the mouse Fab were similar when fused to FVIIa, a number of FVIIa fusion proteins were generated. Specifically, the following chimeric proteins were generated: (i) mouse Fab fused to FVIIa (FVII-245/Fab-033, FIG. 4A), (ii) humanized Fab L0/H2 fused to FVIIa to generate FVII-250/Fab-037 or (iii) humanized Fab L0/H5 fused to FVIIa to generate FVII-250/Fab-036. In all of these fusions, the N-terminus of the light chain variable domain of the Fab was recombinantly fused to the C-terminus of heavy chain FVIIa via a linker($Gly_4Ser)_6$ (SEQ ID NO:170), and the light chain of rFVIIa associates with the heavy chain FVIIa while the heavy chain component of the Fab associates with the light chain component of the Fab.

The amino acid sequence of the light chain (underlined) followed by the heavy chain (boldened) of FVII are provided below:

(SEQ ID NO: 69)
1   ANAFLEELRP GSLERECKEE QCSFEEAREI FKDAERTKLF WISYSDGDQC

51  ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

```
351 HYRGTWYLTG IVSWGQGCAT VGHFGVYTRV SQYIEWLQKL MRSEPRPGVL

401 LRAPFP
```

The amino acid sequence of the Fab light chain in FVII-245 that associates with the Fab heavy chain of Fab-033 (the VL domain is underlined and the constant region boldened) is provided below:

(SEQ ID NO: 70)
ENVLTQSPAIMSASLGEKVTMSCRASSSVNYMYWYQQKSDASPKLWIYYT
SNLAPGVPARFSGSGSGNSYSLTISSMEGEDAATYYCQQFSSSPWTFGGG
TKLEIKRADAAPTVSIFPPSSEQLTSGGASVVCFLNNFYPKDINVKWKID
GSERQNGVLNSWTDQDSKDSTYSMSSTLTLTKDEYERHNSYTCEATHKTS
TSPIVKSFNRNEC

The amino acid sequence of FVII-245 (i.e., the fusion of the light and heavy chain of FVII via a linker (underlined) to the light chain domain of 34D10 (variable domain boldened; constant region italicized) is provided below:

```
                                            (SEQ ID NO: 71)
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

351 HYRGTWYLTG IVSWGQGCAT VGHFGVYTRV SQYIEWLQKL MRSEPRPGVL

401 LRAPFPGGGG SGGGGSGGGG SGGGGSGGGG SGGGGSENVL TQSPAIMSAS

451 LGEKVTMSCR ASSSVNYMYW YQQKSDASPK LWIYYTSNLA PGVPARFSGS

501 GSGNSYSLTI SSMEGEDAAT YYCQQFSSSP WTFGGGTKLE IKRADAAPTV

551 SIFPPSSEQL TSGGASVVCF LNNFYPKDIN VKWKIDGSER QNGVLNSWTD

601 QDSKDSTYSM SSTLTLTKDE YERHNSYTCE ATHKTSTSPI VKSFNRNEC*
```

The amino acid sequence of the Fab heavy chain of Fab-033 (the VH domain is underlined; the constant region is boldened) is provided below:

```
                                            (SEQ ID NO: 72)
  1 EVKLVESGGG LVKPGGSLKL SCAASGFTFS AYAMSWVRQT PEKRLEWVAS

51 ISSGGTTYYP DSVKRRFTIS RDNARNILYL QMSSLRSEDT AMYYCTRGGD

101 YGYALDYWGQ GTSVTVSSAK TTAPSVYPLA PVCGDTTGSS VTLGCLVKGY

151 FPEPVTLTWN SGSLSSGVHT FPAVLQSDLY TLSSSVTVTS STWPSQSITC

201 NVAHPASSTK VDKKIEPR
```

This Fab heavy chain associates with the Fab light chain in FVII-245.

The amino acid sequence of the L0 Fab light chain in FVII-250 that associates with the Fab heavy chains of Fab-036 and Fab-037 (the VL0 domain is underlined, the constant region of the Fab is boldened) is provided below:

(SEQ ID NO: 73)
  1 EIVMTQSPAT LSVSPGERAT LSCRASSSVN YMYWYQQKPG QAPRLLIYYT

51 SNLAPGIPAR FSGSGSGTEF TLTISSLQSE DFAVYYCQQF SSSPWTFGQG

-continued

```
101 TKVEIKRTVA APSVFIFPPS DEQLKSGTAS VVCLLNNFYP REAKVQWKVD

151 NALQSGNSQE SVTEQDSKDS TYSLSSTLTL SKADYEKHKV YACEVTHQGL

201 SSPVTKSFNR GEC*
```

The amino acid sequence of FVII-250 (i.e., the fusion of the light and heavy chain of FVII via a linker (underlined) to the L0 Fab light chain (boldened)) is provided below:

```
                                                    (SEQ ID NO: 74)
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

351 HYRGTWYLTG IVSWGQGCAT VGHFGVYTRV SQYIEWLQKL MRSEPRPGVL

401 LRAPFPGGGG SGGGGSGGGG SGGGGSGGGG SGGGGSEIVM TQSPATLSVS

451 PGERATLSCR ASSSVNYMYW YQQKPGQAPR LLIYYTSNLA PGIPARFSGS

501 GSGTEFTLTI SSLQSEDFAV YYCQQFSSSP WTFGQGTKVE IKRTVAAPSV

551 FIFPPSDEQL KSGTASVVCL LNNFYPREAK VQWKVDNALQ SGNSQESVTE

601 QDSKDSTYSL SSTLTLSKAD YEKHKVYACE VTHQGLSSPV TKSFNRGEC*
```

The amino acid sequence of the H2 chain of Fab-037 (the VH2 domain is underlined) is provided below:

```
                                                    (SEQ ID NO: 75)
  1 EVQLVESGGG LVKPGGSLRL SCAASGFTFS AYAMSWVRQA PGKGLVWVAS

51 ISSGGTTYYP DSVKRQFTIS RDNAKNTLYL QMNSLRAEDT AVYYCTRGGD

101 YGYALDYWGQ GTLVTVSSAS TKGPSVFPLA PSSKSTSGGT AALGCLVKDY

151 FPEPVTVSWN SGALTSGVHT FPAVLQSSGL YSLSSVVTVP SSSLGTQTYI

201 CNVNHKPSNT KVDKKVEPKS C*
```

The amino acid sequence of the H5 chain of Fab-036 (the VH5 domain is underlined) is provided below:

```
                                                    (SEQ ID NO: 76)
  1 EVKLVESGGG LVKPGGSLRL SCAASGFTFS AYAMSWVRQA PGKGLEWVAS

51 ISSGGTTYYP DSVKRRFTIS RDNARNTLYL QMNSLRAEDT AVYYCTRGGD

101 YGYALDYWGQ GTLVTVSSAS TKGPSVFPLA PSSKSTSGGT AALGCLVKDY

151 FPEPVTVSWN SGALTSGVHT FPAVLQSSGL YSLSSVVTVP SSSLGTQTYI

201 CNVNHKPSNT KVDKKVEPKS C*
```

The above two Fab heavy chains associate with the Fab light chain in FVII-250.

Figure 4:
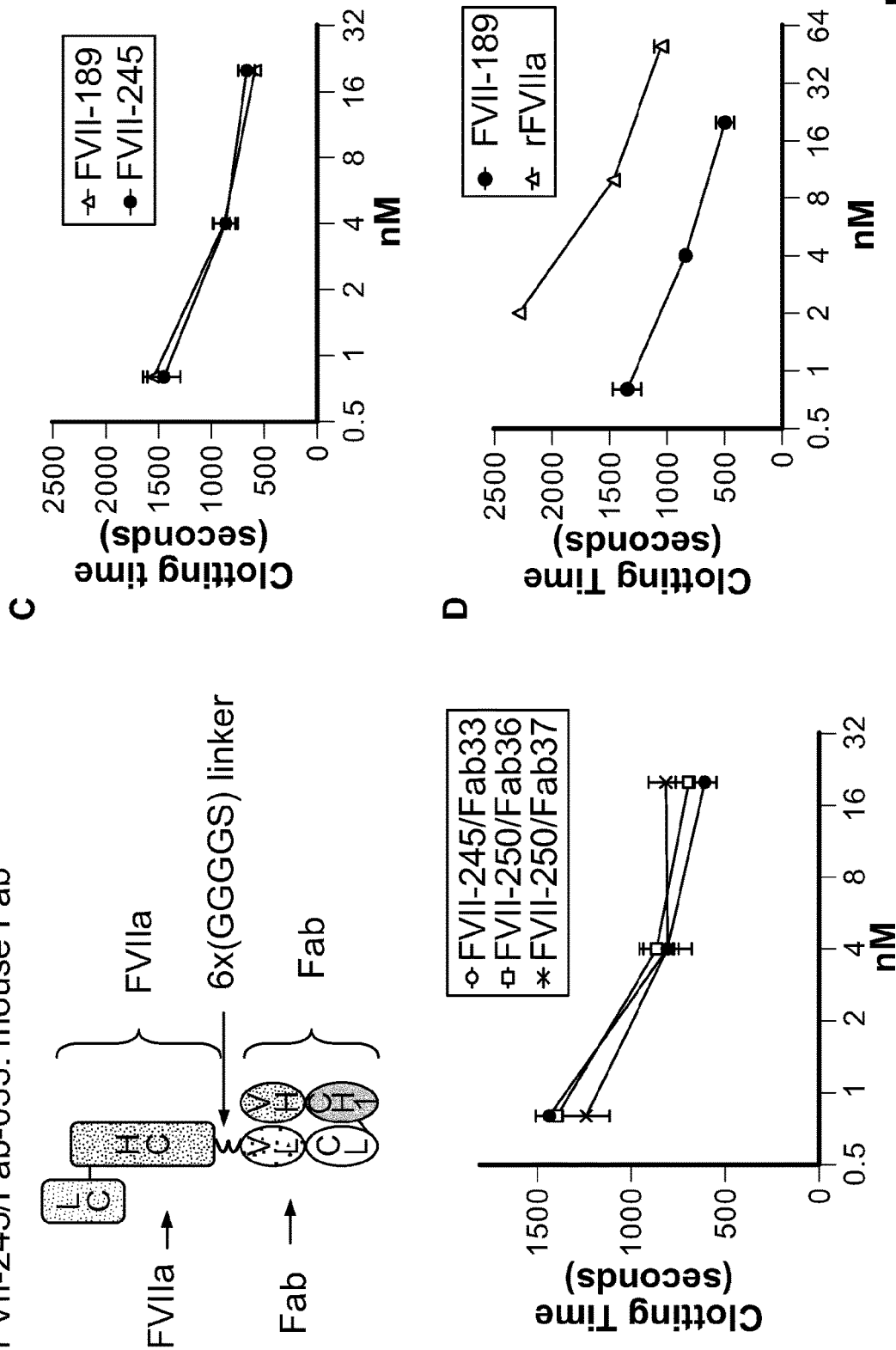
FIG. 4A is a diagrammatic representation of the structure of the chimeric molecules FVII-245/Fab-033, FVII-250/Fab-036, and FVII-250/Fab-037. The "6x(GGGGS) linker" has the amino acid sequence of SEQ ID NO: 170.
FIG. 4B is a graph comparing the clotting time (CT) in seconds for different concentrations (nM) of FactorVIIa-linked Fab fragments of murine 34D10 (FVII-245/Fab-033) and humanized 34D10 (FVII-250/Fab-036 (VL0/VH5) and FVII-250/Fab-037 (VL0/VH2)).
FIG. 4C is a graph comparing the clotting time (CT) in seconds for different concentrations (nM) of FactorVIIa-linked Fab fragments of murine 34D10 (FVII-245/Fab-033) and mouse 34D10 in scFv format recombinantly fused to rFVIIa (FVII-189).
FIG. 4D is a graph comparing the clotting time (CT) in seconds for different concentrations (nM) of mouse 34D10 in scFv format recombinantly fused to rFVIIa (FVII-189) and recombinant FVIIa.

A schematic diagram of these chimeric constructs is depicted in FIG. 4A.

In addition the same Fabs were fused to FVIIa-XTEN (AE288) as shown in FIG. 5A to generate FVII-251/Fab-037 and FVII-251/Fab-036. FVII-200, was also generated with the same structural organization as FVII-251, but where the targeting moiety was an scFv version of mouse 34D10 (instead of an Fab).

The amino acid sequence of FVII-251 (i.e., the fusion of the light and heavy chain of FVII via a linker (SEQ ID NO:195) to an XTEN (AE288) (italicized and underlined) and linkers (SEQ ID NO:196 and 170) (bold italics (SEQ ID NO:196) and underlined (SEQ ID NO:170)) to the Fab light chain L0 (boldened)) is provided below:

```
                                                           (SEQ ID NO: 77)
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

351 HYRGTWYLTG IVSWGQGCAT VGHFGVYTRV SQYIEWLQKL MRSEPRPGVL

401 LRAPFPGSPG TSESATPESG PGSEPATSGS ETP*GTSESAT PESGPGSEPA*

451 *TSGSETPGTS ESATPESGPG TSTEPSEGSA PGSPAGSPTS TEEGTSESAT*

501 *PESGPGSEPA TSGSETPGTS ESATPESGPG SPAGSPTSTE EGSPAGSPTS*

551 *TEEGTSTEPS EGSAPGTSES ATPESGPGTS ESATPESGPG TSESATPESG*

601 *PGSEPATSGS ETPGSEPATS GSETPGSPAG SPTSTEEGTS TEPSEGSAPG*

651 *TSTEPSEGSA PGSEPATSGS ETPGTSESAT PESGPGTSTE PSEGSAP*GSS

701 S*GGGGSGGGG SGGGGSGGGG SGGGGSGGGG S*EIVMTQSPA TLSVSPGERA

751 TLSCRASSSV NYMYWYQQKP GQAPRLLIYY TSNLAPGIPA RFSGSGSGTE

801 FTLTISSLQS EDFAVYYCQQ FSSSPWTFGQ GTKVEIKRTV *AAPSVFIFPP*

851 *SDEQLKSGTA SVVCLLNNFY PREAKVQWKV DNALQSGNSQ ESVTEQDSKD*

901 *STYSLSSTLT LSKADYEKHK VYACEVTHQG LSSPVTKSFN RGEC**
```

The two Fab heavy chains discussed above (Fab-037 and Fab-036) associate with the Fab light chain in FVII-251.

The amino acid sequence of FVII-200 is provided below. The structure of this construct is as follows: light chain of FVII followed by heavy chain of FVII fused to a linker (SEQ ID NO: 195) followed by XTEN followed by a GSSS linker (SEQ ID NO:196) and a (G4S)6 (SEQ ID NO: 170) linker fused to the VL domain of 34D10 fused to (G4S)4 (SEQ ID NO:168) linker fused to the VH domain of 34D10 (the XTEN, AE288 is italicized and underlined; the G4S (SEQ ID NO:165) linkers are underlined; the VL of the 34D10 scFv is boldened and the VH of the 34D10 scFv is italicized):

```
                                                           (SEQ ID NO: 78)
  1 ANAFLEELRP GSLERECKEE QCSFEEAREI FKDAERTKLF WISYSDGDQC

51 ASSPCQNGGS CKDQLQSYIC FCLPAFEGRN CETHKDDQLI CVNENGGCEQ

101 YCSDHTGTKR SCRCHEGYSL LADGVSCTPT VEYPCGKIPI LEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

351 HYRGTWYLTG IVSWGQGCAT VGHFGVYTRV SQYIEWLQKL MRSEPRPGVL

401 LRAPFPGSPG TSESATPESG PGSEPATSGS ETP*GTSESAT PESGPGSEPA*

451 *TSGSETPGTS ESATPESGPG TSTEPSEGSA PGSPAGSPTS TEEGTSESAT*

501 *PESGPGSEPA TSGSETPGTS ESATPESGPG SPAGSPTSTE EGSPAGSPTS*

551 *TEEGTSTEPS EGSAPGTSES ATPESGPGTS ESATPESGPG TSESATPESG*

601 *PGSEPATSGS ETPGSEPATS GSETPGSPAG SPTSTEEGTS TEPSEGSAPG*

651 *TSTEPSEGSA PGSEPATSGS ETPGTSESAT PESGPGTSTE PSEGSAP*GSS

701 S*GGGGSGGGG SGGGGSGGGG SGGGGSGGGG S*ENVLTQSPA IMSASLGEKV
```

```
751 TMSCRASSSV NYMYWYQQKS DASPKLWIYY TSNLAPGVPA RFSGSGSGNS

801 YSLTISSMEG EDAATYYCQQ FSSSPWTFGG GTKLEIKRGG GGSGGGGSGG

851 GGSGGGGSEV KLVESGGGLV KPGGSLKLSC AASGFTFSAY AMSWVRQTPE

901 KRLEWVASIS SGGTTYYPDS VKRRFTISRD NARNILYLQM SSLRSEDTAM

951 YYCTRGGDYG YALDYWGQGT SVTVSS
```

To generate all these fusion proteins, DNA encoding the protein sequences were synthesized, cloned into an expression vector, and expressed in HEK 293 cells by transient transfection following methods known in the art. Protein was purified from the conditioned media following methods known in the art.

Example 4: FVIIa-Humanized Fab and FVIIa-Mouse Fab Fusion Proteins Show Comparable Activity in Whole Blood Assays These experiments were directed at determining whether the activity associated with platelet-targeted FVIIa was similar for variants fused to the mouse 34D10 Fab and the humanized Fabs. The activity of FVII-245/Fab-033, FVII-250/Fab-037 and FVII-250/Fab-036 was determined by rotational thromboelastometry (ROTEM) assays using whole blood from hemophilia donors. The activity in whole blood is platelet-dependent, and coagulation was initiated by recalcification of the blood. In these assays all three proteins showed similar clotting times at all the concentrations tested (FIG. 4B), indicating that the humanized Fabs maintain their properties after humanization.

FVII-245//Fab-033 and FVII-189 (mouse 34D10 in scFv format recombinantly fused to rFVIIa) also showed comparable activity by ROTEM (FIG. 4C), demonstrating that the targeting moiety works equally well as an scFv or Fab format.

In addition, FVII-189 displays much higher activity than rFVIIa by ROTEM (FIG. 4D) and from this it can be inferred that FVII-250 with the humanized Fab also displays activity by ROTEM much greater than rFVIIa.

The same experiments were performed with the FVIIa-XTEN fusion proteins (FIG. 5A). First, FVII-251/Fab-037 and FVII-251/Fab-036 were compared to FVII-200 carrying the mouse version of the targeting moiety. FIG. 5B shows that the activity of all three proteins is similar, indicating that the humanized and mouse targeting moieties have similar properties. Next FVII-251/Fab-037 was compared to recombinant FVIIa (rFVIIa) (FIG. 5C). FVII-251/Fab-037 displays greater activity than rFVIIa, demonstrating that the humanized targeting moiety (L0/H2) can target FVIIa to platelets and increase its activity.

Figure 6:
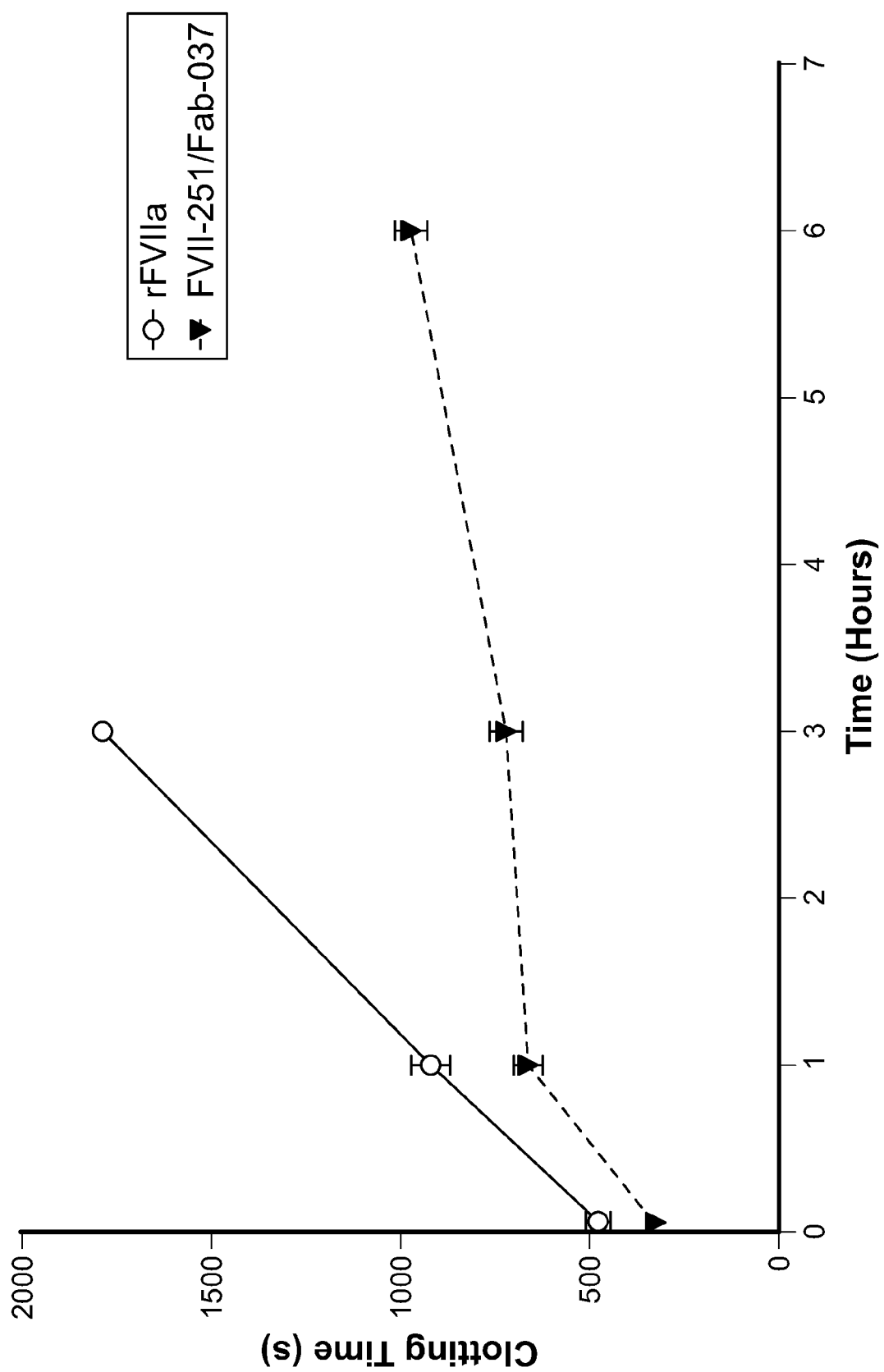
FIG. 6 is a graphical depiction of the ex vivo activity measured by rotational thromboelastometry (ROTEM) of FVII-251/Fab-037 and rFVIIa in transgenic hemophilia A mice with a fully humanized αIIb subunit in the αIIb/β3 integrin. Mice were dosed with 10 nmol/kg of rFVIIa or FVII-251/Fab-037. The data each time point is the average+/−standard deviation of 3 mice.

Example 5: Ex Vivo Activity of Humanized 34D10 Fab Linked to Factor VIIa Compared with Recombinant Factor VIIa (rFVIIa) in Transgenic Hemophilia a Mice Transgenic hemophilia A mice with a fully humanized αIIb subunit in the αIIb/β3 integrin were dosed with 10 nmol/kg of rFVIIa or FVII-251/Fab-037 (i.e., Factor VIIa linked to XTEN linked to the VL0/VH2 h34D10 Fab). For each molecule and time point 3 mice were dosed. At different times post-dosing (FIG. 6), mice were euthanized and blood was collected. Three hundred microliters of blood were analyzed by rotational thromboelastometry (ROTEM) assay, and coagulation was initiated by recalcification of the blood. FVII-251/Fab-037, showed shorter clotting times at 5 minutes post-dosing, indicating increased acute ex vivo activity. FVII-251/Fab-037 displayed shorter clotting times than rFVIIa at all the timepoints, and the clotting time for FVII-251/Fab-037 at 6 hours post-dosing was comparable to the clotting time of rFVIIa at 1 hour post-dosing, suggesting a 6-fold improvement in the prolonged ex vivo efficacy for FVII-251/Fab-037 compared with rFVIIa.

Figure 9:
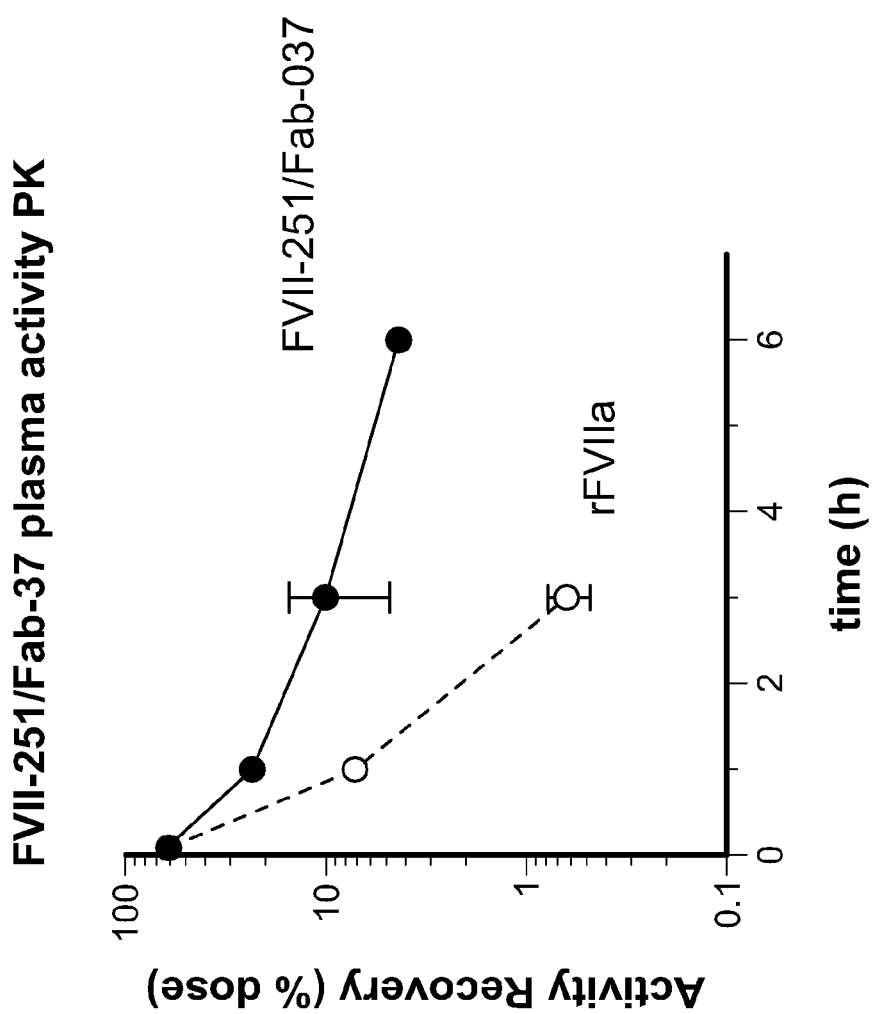
FIG. 9 depicts the plasma activity of both rFVIIa (open circles) and FVII-251/Fab-037 (black circles) as percentile of injected dose over time (hours) as determined by the VIIa-rTF FVIIa-activity assay, using rFVIIa or FVII-251/Fab037 as respective matched self standards. Mean±SD.

Example 6: Improved Plasma Pharmacokinetics of FVII-251/Fab-037 in Human Alpha IIb Transgenic Hemophilia a Mice Plasma samples from Example 5, in which transgenic hemophilia A mice with a fully humanized αIIb subunit in the αIIb/β3 integrin were dosed with 10 nmol/kg of rFVIIa (n=3) or FVII-251/Fab-037 (n=4) were taken. For each molecule and time point 3-4 mice were dosed. At different times post-dosing (FIG. 9), mice were euthanized and blood was collected. One fraction of the citrated whole blood was used for ex-vivo rotational thromboelastometry (ROTEM) assay as described in Example 5. From the remaining blood, plasma was isolated by centrifugation and the FVIIa plasma activity levels of rFVIIa or FVII-251/Fab037 were determined using the Staclot VIIa-rTF assay (Diagnostica Stago) on a Sysmex CA-1500, using the respective dosing material as self-standard.

In these experiments, rFVIIa and FVII-251/Fab-037 showed comparable plasma recovery at 5 minutes post-dosing and FVII-251/Fab-037 showed decreased clearance and higher plasma activity levels compared to equal molar dosed rFVIIa over all time points measured, consistent with improved pharmacokinetic properties.

Example 7: FVII-251/Fab-037 is Efficacious in Acute Efficacy Murine Bleeding Models Factor VIII deficient mice expressing only human alphaIIb in place of murine alphaIIb on platelets (HemA-Tg-hu-alphaIIb mice), were created by crossing hemophilia A (HemA) knock-out mice (exon 16, Bi et al., *Nat. Genet.*, 10(1):119-121, 1995) with mouse alphaIIb knock-out mice (Emambokus et al., *Immunity*, 19(1):33-45, 2003), which were transgenic for human alphaIIb integrin expression (Thornton et al., *Blood*, 100(10):3588-3596, 2002). For experiments the mice were crossed to homogeneity, resulting in HemA mice, expressing human aIIb, murine beta3 integrin heterodimers on all platelets.

Figure 10:
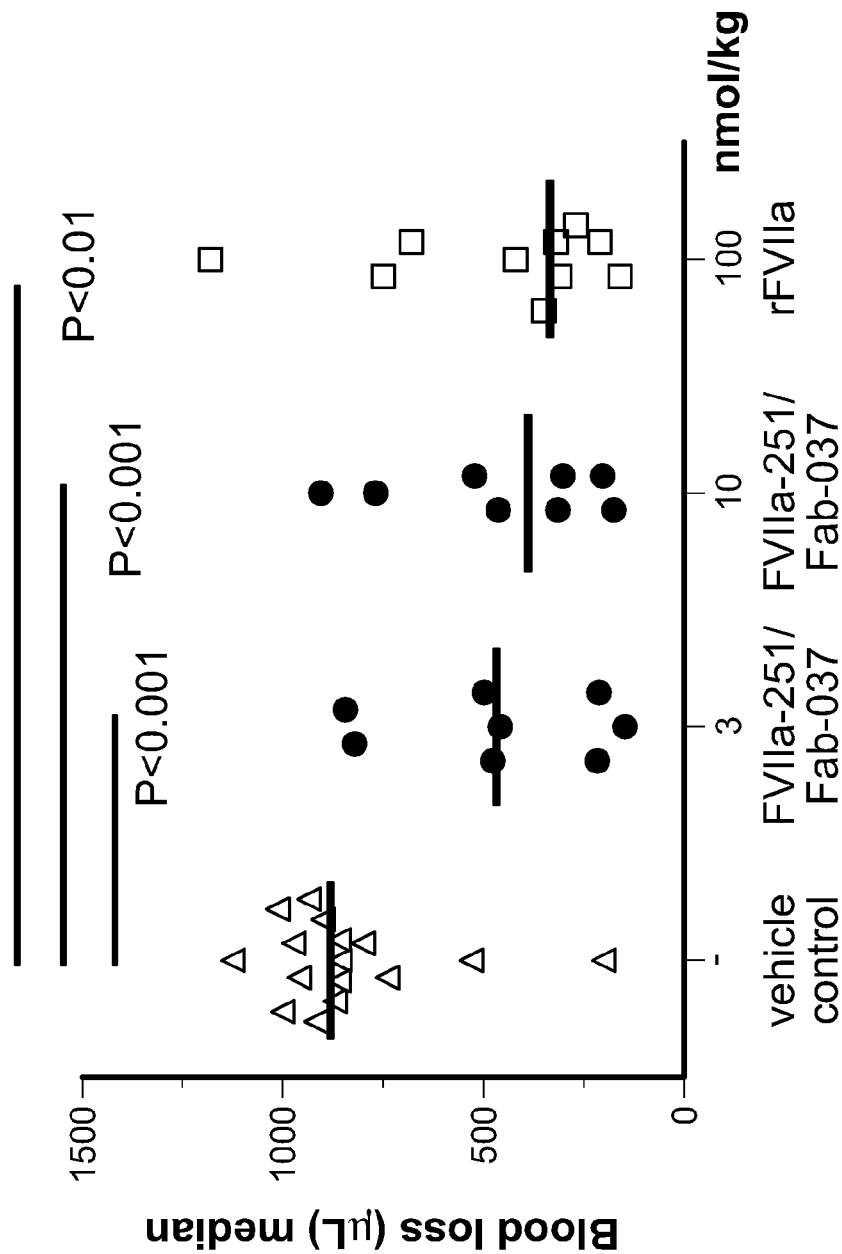
FIG. 10 is a graph showing the acute efficacy of FVII-251/Fab-037 compared to rFVIIa in tail clip bleeding model. Results presented are individual and median blood loss over 30 minutes for treatments and dosing as indicated. P values for vehicle versus all other treatments are indicated. Data indicate similar or improved efficacy in mice dosed with 3 nmol/kg and 10 nmol/kg FVII-251/Fab-037 compared to mice dosed with 100 nmol/kg rFVIIa.

Acute efficacy was studied in a blinded murine tail-clip bleeding model, in which total blood loss in dosed mice is measured after tail tip amputation, as described previously (Dumont et al., *Blood*, 119(13):3024-3030, 2012). Briefly, male HemA-Tg hu-αIIb mice (8-13 wks) were anesthetized with a cocktail of 50 mg/kg ketamine and 0.5 mg/kg dexmedetomidine. The tails were immersed in 37° C. saline for 10 minutes, to dilate the lateral vein followed by intravenous tail vein injection of either vehicle (20 mM 2-amino-2-hydroxymethyl-propane-1,3-diol (TRIS), pH 8.0; 150 mM NaCl; 3% human serum albumin (n=13)), rFVIIa at 100 nmol/kg (n=10) or FVII-251/Fab-037 at 3 nmol/kg (n=8) or 10 nmole/kg, (n=8). Five minutes post-dosing, the 4 mm distal tip of the tail was clipped and submerged into a pre-weighted tube containing 11 mL saline for the period of 30 minutes. Blood loss was quantified by weight. Statistical significance was calculated using unpaired two-tailed t-test in GraphPad Prism 6. Such two tailed t-tests showed that the 3 and 10 nmol/kg doses of FVII-251/Fab-037 and rFVIIa were significantly different from vehicle (p-value<0.001), but not significantly different from each other (p-value>0.9) (see, FIG. 10).

These results demonstrate equal or improved acute efficacy for FVII-251/Fab-037 compared to rFVIIa in this bleeding model.

Example 8: Affinity Maturation of a Humanized 34D10 Antibody

The nucleic acid sequence encoding humanized 34D10 VH2 (the amino acid sequence is set forth in SEQ ID NO: 7) was subjected to multiple cycles of error-prone polymerase chain reaction (PCR) according to published methods (Zaccolo et al., *J. Mol. Biol.*, 255(4):589-603, 1996; Van Deventer and Wittrup, *Methods Mol. Biol.*, 1131:151-81, 2014). The pool of mutated 34D10 VH2 nucleic acid sequences and a nucleic acid sequence encoding 34D10 VL0 (SEQ ID NO: 19) were then introduced into the Adimab platform, resulting in an Adimab expression library size of approximately $10^6$ antibodies (see, US Patent Publications 20100056386 and 20090181855 to Adimab, Inc. as well as references cited therein). For comparison purposes, a nucleic acid sequence encoding 34D10 VH2 (SEQ ID NO: 15) and a nucleic acid sequence encoding 34D10 VL0 (SEQ ID NO: 19) were introduced into the Adimab yeast platform. To identify anti-GPIIb/IIIa antibodies with improvements in affinity (over the parental VH—i.e., h34D10 VH2), expression libraries were screened in accordance with the methodologies disclosed in the US Patent Publications 20100056386 and 20090181855. After iterative rounds of selective pressure towards the target antigen, GPIIb/IIIa (SEQ ID NOs: 23 and 24), and efforts to improve antibody off-rate, colonies were sequenced to identify unique antibodies, according to methods known in the art. 45 unique VH sequences were discovered and subsequently expressed and purified from yeast by protein A purification followed by standard Fab generation, according to methods known in the art.

Figure 12:
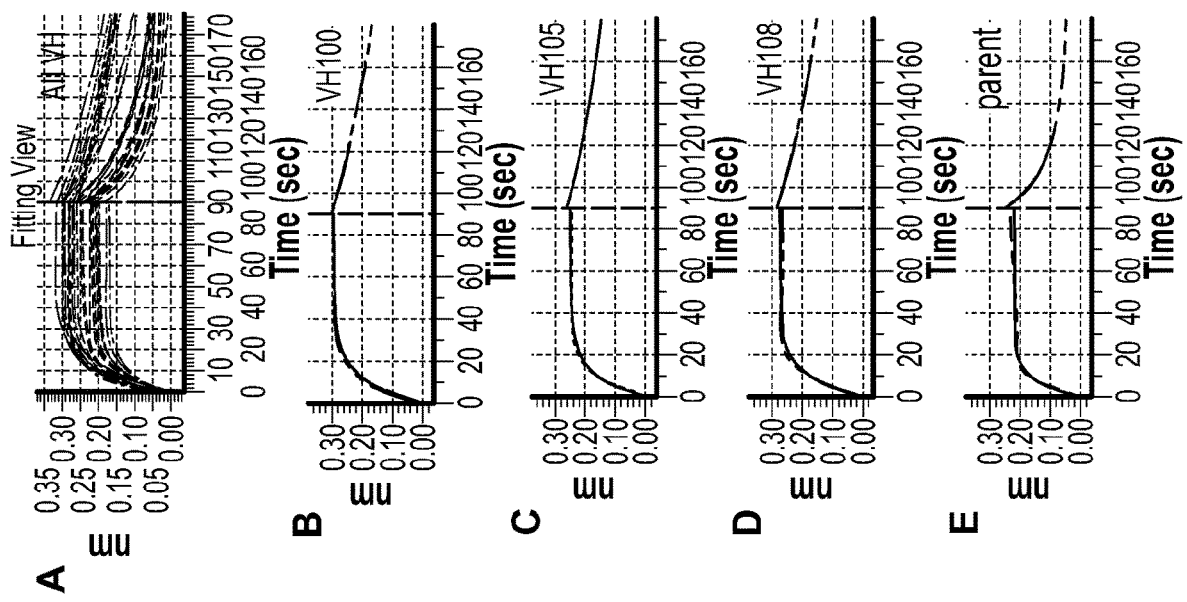
FIG. 12A-E shows the measurement of binding by Bio-Layer Interferometry (BLI) of the indicated yeast purified Fab to sensor-associated GPIIb/IIIa (SEQ ID NOs.: 23 and 24), as a function of time.
FIG. 12F is a table listing the apparent monovalent affinity ($K_D$) and apparent dissociation rate ($K_{dis}$) of the indicated yeast purified Fab.

To identify antibodies discovered from our selections that displayed improvements in affinity and/or off-rate when compared to the parental VH (amino acid sequence: SEQ ID NO:7; nucleic acid sequence: SEQ ID NO:15), the antibodies purified from yeast were screened for binding to target antigen (hGPIIb-SEQ ID NO:23 and hGPIIIa-SEQ ID NO:24) using Bio-Layer Interferometry (BLI) in a monovalent assay format. BLI was performed on the OctetRed94 instrument, manufactured by ForteBio, according to standard procedures. The present disclosure identifies 22 unique VH sequences with improvements in affinity and/or off-rate when compared to the parental VH (amino acid sequence: SEQ ID NO:7; nucleic acid sequence: SEQ ID NO: 15) (FIG. 11). The BLI binding profiles of all VH (FIG. 12A) as well as examples of individual affinity matured VH sequences (SEQ ID NOs: 197, 202, 205) in comparison to the parental clone (amino acid sequences: SEQ ID NOs: 7 and 4; nucleic acid sequences: SEQ ID NOs: 15 and 19) are disclosed herein (FIGS. 12B-E). A table listing the apparent monovalent affinity and dissociation rates of the 22 disclosed VH sequences paired with the parental 34D10 VL0 (amino acid sequence: SEQ ID NO:4; nucleic acid sequence: SEQ ID NO: 19) purified from yeast, as determined by BLI in the monovalent format, is depicted in FIG. 12F.

To determine if mutations introduced into the humanized 34D10 VH2 sequence (amino acid sequence: SEQ ID NO:7; nucleic acid sequence: SEQ ID NO: 15) during error-prone PCR had adverse effects on protein stability, yeast purified Fab of the 22 unique VH (FIG. 11) with parental VL0 were subjected to thermal denaturation by differential scanning fluorimetry (DSF). Measurements were conducted on an Mx3005p real-time PCR system (Agilent Technologies) in a 96-well format using 10 μg of Fab in 50 μl PBS (at pH 7.0) supplemented with SYPRO orange fluorophor. Derivation of the melting temperature ($T_m$) was performed as described in Pepinsky et al., *Protein Sci.*, 19(5):954-662010. A table listing the calculated $T_m$ is provided in FIG. 13.

The amino acid and nucleic acid sequences of the 22 VH sequences obtained by the affinity maturation of h34D10 VH2 by the methods described above are provided below:

VH100 Variable Heavy Chain Amino Acid Sequence (SEQ ID NO: 197)
EVQLVESGGGLVKPGGSLRLSCAASGFTFG<u>AYAM</u>SWVRQAPGKGLVWVA<u>S</u>

<u>ISSGGTTYYPDSVKR</u>QFTISRDNAKNTLYLQMNSLRAEDTAVYYCTR<u>GGD</u>

<u>YSYALD</u>YWGQGTLVTVSS

VH100 Variable Heavy Chain Nucleic Acid Sequence (SEQ ID NO: 219)
GAGGTGCAGCTGGTGGAGTCTGGAGGAGGCTTGGTAAAGCCTGGAGGATC

CCTGAGACTCTCCTGTGCAGCCTCTGGATTCACCTTTGGCGCCTATGCCA

TGAGCTGGGTCCGCCAGGCTCCAGGGAAGGGGCTGGTCTGGGTCGCTAGC

ATTAGTAGTGGTGGTACCACATACTACCCAGACTCCGTGAAGAGGCAGTT

CACCATCTCCAGAGACAATGCCAAGAACACGCTGTATCTGCAAATGAACA

GCCTGAGAGCCGAGGACACAGCCGTATATTACTGTACCAGAGGAGGGGAT

TATAGCTACGCTCTCGACTACTGGGGCCAGGGAACCCTGGTCACCGTCTC

CTCA

VH101 Variable Heavy Chain Amino Acid Sequence (SEQ ID NO: 198)
EVQLVESGGGLVKPGGSLRLSCAASGFTFS<u>AYAM</u>SWVRQAPGKGLVWVA<u>S</u>

<u>ISSGGTTYYPDSVER</u>QFTISRDNAKNTLYLQMNSLRAEDTAVYYCTR<u>GGD</u>

<u>YSYALD</u>YWGQGTLVTVSS

VH101 Variable Heavy Chain Nucleic Acid Sequence (SEQ ID NO: 220)
GAGGTGCAGCTGGTGGAGTCTGGAGGAGGCTTGGTAAAGCCTGGAGGATC

CCTGAGACTCTCCTGTGCAGCCTCTGGATTCACCTTTAGCGCCTATGCCA

TGAGCTGGGTCCGCCAGGCTCCAGGGAAGGGGCTGGTCTGGGTCGCTAGC

-continued

ATTAGTAGTGGTGGTACCACATACTACCCAGACTCCGTGGAGAGGCAGTT

CACCATCTCCAGAGACAATGCCAAGAACACGCTGTATCTGCAAATGAACA

GCCTGAGAGCCGAGGACACAGCCGTATATTACTGTACCAGAGGAGGGGAT

TATAGCTACGCTCTCGACTACTGGGGCCAGGGAACCCTGGTCACCGTCTC

CTCA

VH102 Variable Heavy Chain Amino Acid Sequence (SEQ ID NO: 199)
EVQLVESGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQMNSLRAEDTAVYYCTR<u>GGD</u>
<u>YSYALDY</u>WGQGTLVTVSF VH102 Variable Heavy Chain Nucleic Acid Sequence (SEQ ID NO: 221)
GAGGTGCAGCTGGTGGAGTCTGGAGGAGGCTTGGTAAAGCCTGGAGGATC

CCTGAGACTCTCCTGTGCAGCCTCTGGATTCACCTTTAGCGCCTATGCCA

TGAGCTGGGTCCGCCAGGCTCCAGGGAAGGGGCTGGTCTGGGTCGCTAGC

ATTAGTAGTGGTGGTACCACATACTACCCAGACTCCGTGAAGAGGCAGTT

CACCATCTCCAGAGACAATGCCAAGAACACGCTGTATCTGCAAATGAACA

GCCTGAGAGCCGAGGACACAGCCGTATATTACTGTACCAGAGGAGGGGAT

TATAGCTACGCTCTCGACTACTGGGGCCAGGGAACCCTGGTCACCGTCTC

CTTCAGC

VH103 Variable Heavy Chain Amino Acid Sequence (SEQ ID NO: 200)
EVQLVESGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQVNSLRAEDTAVYYCTR<u>GGD</u>
<u>YSYALDY</u>WGQGTLVTVSS VH103 Variable Heavy Chain Nucleic Acid Sequence (SEQ ID NO: 222)
GAGGTGCAGCTGGTGGAGTCTGGAGGAGGCTTGGTAAAGCCTGGAGGATC

CCTGAGACTCTCCTGTGCAGCCTCTGGATTCACCTTTAGCGCCTATGCCA

TGAGCTGGGTCCGCCAGGCTCCAGGGAAGGGGCTGGTCTGGGTCGCTAGC

ATTAGTAGTGGTGGTACCACATACTACCCAGACTCCGTGAAGAGGCAGTT

CACCATCTCCAGAGACAATGCCAAGAACACGCTGTATCTGCAAGTGAACA

GCCTGAGAGCCGAGGACACAGCCGTATATTACTGTACCAGAGGAGGGGAT

TATAGCTACGCTCTCGACTACTGGGGCCAGGGAACCCTGGTCACCGTCTC

CTCA

VH104 Variable Heavy Chain Amino Acid Sequence (SEQ ID NO: 201)
EVQLVESGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQMNSLRAEDTAVYYCTR<u>GGD</u>
<u>YSYALDY</u>WGRGTLVTVSS VH104 Variable Heavy Chain Nucleic Acid Sequence (SEQ ID NO: 223)
GAGGTGCAGCTGGTGGAGTCTGGAGGAGGCTTGGTAAAGCCTGGAGGATC

CCTGAGACTCTCCTGTGCAGCCTCTGGATTCACCTTTAGCGCCTATGCCA

TGAGCTGGGTCCGCCAGGCTCCAGGGAAGGGGCTGGTCTGGGTCGCTAGC

ATTAGTAGTGGTGGTACCACATACTACCCAGACTCCGTGAAGAGGCAGTT

CACCATCTCCAGAGACAATGCCAAGAACACGCTGTATTTGCAAATGAACA

GCCTGAGAGCCGAGGACACAGCCGTATATTACTGTACCAGAGGAGGGGAT

TATAGCTACGCTCTCGACTACTGGGGCCGGGGAACCCTGGTCACCGTCTC

CTCA

VH105 Variable Heavy Chain Amino Acid Sequence (SEQ ID NO: 202)
EVQLVESGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQMNSLRAEDTAVYYCTR<u>GGD</u>
<u>YSYALDY</u>WGQGTLVTVSS VH105 Variable Heavy Chain Nucleic Acid Sequence (SEQ ID NO: 224)
GAGGTGCAGCTGGTGGAGTCTGGAGGAGGCTTGGTAAAGCCTGGAGGATC

CCTGAGACTCTCCTGTGCAGCCTCTGGATTCACCTTTAGCGCCTATGCCA

TGAGCTGGGTCCGCCAGGCTCCAGGGAAGGGGCTGGTCTGGGTCGCTAGC

ATTAGTAGTGGTGGTACCACATACTACCCAGACTCCGTGAAGAGGCAGTT

CACCATCTCCAGAGACAATGCCAAGAACACGCTGTATCTGCAAATGAACA

GCCTGAGAGCCGAGGACACAGCCGTATATTACTGTACCAGAGGAGGGGAT

TATAGCTACGCTCTCGACTACTGGGGCCAGGGAACCCTGGTCACCGTCTC

CTCA

VH106 Variable Heavy Chain Amino Acid Sequence (SEQ ID NO: 203)
EVQLVECGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQMNSLRAEDTAVYYCTR<u>GGD</u>
<u>YSYALDY</u>WGQGTLVTVSS VH106 Variable Heavy Chain Nucleic Acid Sequence (SEQ ID NO: 225)
GAGGTGCAGCTGGTGGAGTGTGAGGAGGCTTGGTAAAGCCTGGAGGATC

CCTGAGACTCTCCTGTGCAGCCTCTGGATTCACCTTTAGCGCCTATGCCA

TGAGCTGGGTCCGCCAGGCTCCAGGGAAGGGGCTGGTCTGGGTCGCTAGC

ATTAGTAGTGGTGGTACCACATACTACCCAGACTCCGTGAAGAGGCAGTT

CACCATCTCCAGAGACAATGCCAAGAACACGCTGTATCTGCAAATGAACA

GCCTGAGAGCCGAGGACACAGCCGTATATTACTGTACCAGAGGAGGGGAT

TATAGCTACGCTCTCGACTACTGGGGCCAGGGAACCCTGGTCACCGTCTC

CTCA

VH107 Variable Heavy Chain Amino Acid Sequence (SEQ ID NO: 204)
EVQLVESGGGLVKPGESLRLSCAASGFTF<u>AYAMS</u>WVRQAPGEGLVWVA<u>S
ISSGGTTYYPDSVKR</u>QFTISRDNAKNTLYLQMNSLRAEDTAVYYCTR<u>GGD
YSYALD</u>YWGQGTLVTVSS VH107 Variable Heavy Chain Nucleic Acid Sequence (SEQ ID NO: 226)
GAGGTGCAGCTGGTGGAGTCTGGAGGAGGCTTGGTAAAGCCTGGAGAATC
CCTGAGACTCTCCTGTGCAGCCTCGGGATTCACCTTTAGCGCCTATGCCA
TGAGCTGGGTCCGCCAGGCTCCAGGGGAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATAGCTACGCTCTCGACTACTGGGGCCAGGGAACCCTGGTCACCGTCTC
CTCA VH108 Variable Heavy Chain Amino Acid Sequence (SEQ ID NO: 205)
EVQLVESGGGLVKPGGSLRLSCAASGFTF<u>SAYAMS</u>WVRQAPGKGLVWVA<u>S
ISSDGTTYYPDSVKR</u>QFTISRDNARNTLYLQMNSLRAEDTAVYYCTR<u>GGD
YSYALD</u>YWGQGTLVTVSS VH108 Variable Heavy Chain Nucleic Acid Sequence (SEQ ID NO: 227)
GAGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGATGGTACCACATACTACCCAGACTCCGTGAAGAGGCAGTT
CACCATCTCCAGAGACAATGCCAGGAACACGCTGTATCTGCAAATGAACA
GCCTGAGAGCCGAGGACACAGCCGTATATTACTGTACCAGAGGAGGGGAC
TATAGCTACGCTCTCGACTACTGGGGCCAGGGGACCCTGGTCACCGTCTC
CTCA VH109 Variable Heavy Chain Amino Acid Sequence (SEQ ID NO: 206)
EVQLVESGGGLVKPGGSLRLSCAASGFTF<u>SAYAMS</u>WVRQAPGKGLVWVA<u>S
ISSGGTTDYPDSVKR</u>QFTISRDNAKNTLYLQMNSLRAEDTAVYYCTR<u>GGD
YGYALD</u>YWGQGTLVTVSS VH109 Variable Heavy Chain Nucleic Acid Sequence (SEQ ID NO: 228)
GAGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGGTGGTACCACAGACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH110 Variable Heavy Chain Amino Acid Sequence (SEQ ID NO: 207)
EVQLVESGGGLVKPGGSLRLSCAASGFTF<u>NAYAMS</u>WVRQAPGKGLVWVA<u>S
ISSGGTTYYPDSVKR</u>QFTISRDNAKNTLYLQMNSLRAEDTAVYYCTR<u>GGD
YGYALD</u>YWGQGTLVTVSS VH110 Variable Heavy Chain Nucleic Acid Sequence (SEQ ID NO: 229)
GAGGTGCAGCTGGTGGAGTCTGGAGGAGGCTTGGTAAAGCCTGGAGGATC
CCTGAGACTCTCCTGTGCAGCCTCTGGATTCACCTTTAACGCCTATGCAA
TGAGCTGGGTCCGCCAGGCTCCAGGGAAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH111 Variable Heavy Chain Amino Acid Sequence (SEQ ID NO: 208)
EVQLVESGGGLVKPGGSLRLSCAASGFTF<u>NAYAMS</u>WVRQAPGEGLVWVA<u>S
ISSGGTTYYPDSVKR</u>QFTISRDNAKNTLYLQMNSLRAEDTAVYYCTR<u>GGD
YGYALD</u>YWGQGTLVTVSS VH111 Variable Heavy Chain Nucleic Acid Sequence (SEQ ID NO: 230)
GAGGTGCAGCTGGTGGAGTCTGGAGGAGGCTTGGTAAAGCCTGGAGGATC
CCTGAGACTCTCCTGTGCAGCCTCTGGATTCACCTTTAACGCCTATGCCA
TGAGCTGGGTCCGCCAGGCTCCAGGGGAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGCACCAGAGGAGGGGAT
TATGGCTACGCTCTCGACTACTGGGGCCAGGGAACCCTGGTCACCGTCTC
CTCA VH112 Variable Heavy Chain Amino Acid Sequence (SEQ ID NO: 209)
EVQLVESGGGLVKPGGSLRLSCAASGFTFS<u>AYAMS</u>WVRQAPGEGLVWVA<u>G</u>
<u>ISSGGTTYYPDSVKR</u>QFTISRDNAKNTLYLQMNSLRAEDTAVYYCTR<u>GGD</u>
<u>YGYALDY</u>WGQGTLVTVSS VH112 Variable Heavy Chain Nucleic Acid Sequence (SEQ ID NO: 231)
GAGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGGAGGGGCTGGTCTGGGTCGCTGGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH113 Variable Heavy Chain Amino Acid Sequence (SEQ ID NO: 210)
EVQLVESGGGLVKPGGSLRLSCAASGFTFS<u>AYAMS</u>WVRQAPGKGLVWVA<u>G</u>
<u>ISSGGTTYYPDSVKR</u>QFTISRDNAKNTLYLQMNSLRAEDTAVYYCTR<u>GGD</u>
<u>YGYALDY</u>WGQGTLVTVSS VH113 Variable Heavy Chain Nucleic Acid Sequence (SEQ ID NO: 232)
GAGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTGGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH114 Variable Heavy Chain Amino Acid Sequence (SEQ ID NO: 211)
EMQLVESGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQMNSLRAEDTAVYYCTR<u>GGD</u>
<u>YGYALDY</u>WGQGTLVTVSS VH114 Variable Heavy Chain Nucleic Acid Sequence (SEQ ID NO: 233)
GAGATGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH115 Variable Heavy Chain Amino Acid Sequence (SEQ ID NO: 212)
GVQLVESGGGLVKPGGSLRLSCAASGFTFS<u>AYAMS</u>WVRQAPGKGLVWVA<u>S</u>
<u>ISSGGTTYYPDSVKR</u>QFTISRDDAKNTLYLQMNSLRAEDTAVYYCTR<u>GGD</u>
<u>YGYALDY</u>WGQGTLVTVSS VH115 Variable Heavy Chain Nucleic Acid Sequence (SEQ ID NO: 234)
GGGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGGTGGTACCACATACTACCCAGACTCCGTGAAGAGGCAGTT
CACCATCTCCAGAGACGATGCCAAGAACACGCTGTATCTGCAAATGAACA
GCCTGAGAGCCGAGGACACAGCCGTATATTACTGTACTAGAGGGGGGGAT
TATGGCTACGCTCTCGACTACTGGGGCCAGGGAACCCTGGTCACCGTCTC
CTCA VH116 Variable Heavy Chain Amino Acid Sequence (SEQ ID NO: 213)
EVQLVESGGGLVKPGGSLRLSCAASGFTFS<u>AYAMS</u>WVRQAPGKGLVWVA<u>S</u>
<u>ISSGGTTYYPDSVKR</u>QFTISRDDAKNTLYLQMNSLRAEDTAVYYCTR<u>GGD</u>
<u>YGYALDY</u>WGQGTLVTVSS VH116 Variable Heavy Chain Nucleic Acid Sequence (SEQ ID NO: 235)
GAGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGGTGGTACCACATACTACCCAGACTCCGTGAAGAGGCAGTT
CACCATCTCCAGAGACGATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH117 Variable Heavy Chain Amino Acid Sequence (SEQ ID NO: 214)
EAQLVESGGGLVKPGGSLRLSCAASGFTFS<u>AYAMS</u>WVRQAPGKGLVWVA<u>S</u>
<u>ISSGGTTYYPDSVKR</u>QFTISRDNAKNTLYLQMNSLRAEDTAVYYCTR<u>GGD</u>
<u>YGYALDY</u>WGQGTLVTVSS VH117 Variable Heavy Chain Nucleic Acid Sequence (SEQ ID NO: 236)
GAGGCGCAGCTGGTGGAGTCTGGAGGAGGCTTGGTGAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH118 Variable Heavy Chain Amino Acid Sequence (SEQ ID NO: 215)
GVQLVESGGGLVKPGGSLRLSCAASGFTFS<u>AYAMS</u>WVRQAPGKGLVWVA<u>S
ISSGGTTYYPDSVKR</u>QFTISRDNAKNTLYLQMNSLRAEDTAVYYCTR<u>GGD
YGYALD</u>YWGQGALVTVSS VH118 Variable Heavy Chain Nucleic Acid Sequence (SEQ ID NO: 237)
GGGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAGCCCTGGTCACCGTCTC
CTCA VH119 Variable Heavy Chain Amino Acid Sequence (SEQ ID NO: 216)
GVQLVESGGGLVKPGGSLRLSCAASGFTFS<u>AYAMS</u>WVRQAPGKGLVWVA<u>S
ISSGGTTYYPDSVKR</u>QFTISRDNAKNTLYLQMNSLRAEDTAVYYCTR<u>GGD
YGYALD</u>YWGQGTLVTVSS VH119 Variable Heavy Chain Nucleic Acid Sequence (SEQ ID NO: 238)
GGGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGAAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH120 Variable Heavy Chain Amino Acid Sequence (SEQ ID NO: 217)
EVQLVESGGGLVEPGGSLRLSCAASGFTFS<u>AYAMS</u>WVRQAPGKGLVWVA<u>S
ISSGGTTYYPDSVKR</u>QFTISRDNAKNTLYLQMNSLRAEDTAVYYCTR<u>GGD
YGYALD</u>YWGQGTLVTVSS VH120 Variable Heavy Chain Nucleic Acid Sequence (SEQ ID NO: 239)
GAGGTGCAGCTGGTGGAGTCTGGAGGAGGCTTGGTAGAGCCTGGAGGATC
CCTGAGACTCTCCTGTGCAGCCTCTGGATTCACCTTTAGCGCCTACGCCA
TGAGCTGGGTCCGCCAGGCTCCAGGGAAGGGGCTGGTCTGGGTCGCTAGC
ATTAGTAGTGGCGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA VH121 Variable Heavy Chain Amino Acid Sequence (SEQ ID NO: 218)
EVQLVESGGGLVKPGGSLRLSCAASGFTFS<u>AYAMS</u>WVRQAPGEGLVWVA<u>S
ISSGGTTYYPDSVKR</u>QFTISRDNAKNTLYLQMNSLRAEDTAVYYCTR<u>GGD
YGYALD</u>YWGQGTLVTVSS VH121 Variable Heavy Chain Nucleic Acid Sequence (SEQ ID NO: 240)
GAGGTGCAGCTGGTGGAGTCTGGAGGAGGCTTGGTAAAGCCTGGAGGATC
CCTGAGACTCTCCTGTGCAGCCTCTGGATTCACCTTTAGCGCCTATGCCA
TGAGCTGGGTCCGCCAGGCTCCAGGGGAGGGGCTGGTCTGGGTCGCTAGC
ATTAGTAGTGGTGGTACCACATACTACCCAGACTCCGTGAAGAGGCAGTT
CACCATCTCCAGAGACAATGCCAAGAACACGCTGTATCTGCAAATGAACA
GCCTGAGAGCCGAGGACACAGCCGTATATTACTGTACCAGAGGAGGGGAT
TATGGCTACGCTCTCGACTACTGGGGCCAGGGAACCCTGGTCACCGTCTC
CTCA Example 9: Generation of FVII-265

FVII-265 was generated to remove a GSSS (SEQ ID NO: 196) linker sequence in FVII-251 (see, Example 3) located between the XTEN sequence and the (Gly$_4$Ser)$_6$ (SEQ ID NO:170) linker. The amino acid sequence of FVII-265 is provided below (from N terminus to C-terminus: the amino acid sequence of the light chain of FVII is underlined; this is followed by the amino acid sequence of the heavy chain of FVII, which is boldened and italicized; this is followed by a linker having the amino acid sequence set forth in SEQ ID NO:195; which is followed by the XTEN (AE288) sequence which is both italicized and underlined; followed by a (Gly$_4$Ser)$_6$ (SEQ ID NO:170) linker that is double underlined; and which is followed by the Fab light chain L0 (boldened)):

(SEQ ID NO: 247)

```
  1 ANAFLEELRPGSLERECKEEQCSFEEAREIFKDAERTKLFWISYSDGDQC

51 ASSPCQNGGSCKDQLQSYICFCLPAFEGRNCETHKDDQLICVNENGGCEQ

101 YCSDHTGTKRSCRCHEGYSLLADGVSCTPTVEYPCGKIPILEKRNASKPQ

151 GRIVGGKVCP KGECPWQVLL LVNGAQLCGG TLINTIWVVS AAHCFDKIKN

201 WRNLIAVLGE HDLSEHDGDE QSRRVAQVII PSTYVPGTTN HDIALLRLHQ

251 PVVLTDHVVP LCLPERTFSE RTLAFVRFSL VSGWGQLLDR GATALELMVL

301 NVPRLMTQDC LQQSRKVGDS PNITEYMFCA GYSDGSKDSC KGDSGGPHAT

351 HYRGTWYLTG IVSWGQGCAT VGHFGVYTRV SQYIEWLQKL MRSEPRPGVL

401 LRAPFPGSPG TSESATPESG PGSEPATSGS ETPGTSESATPESGPGSEPA

451 TSGSETPGTSESATPESGPGTSTEPSEGSAPGSPAGSPTSTEEGTSESAT

501 PESGPGSEPATSGSETPGTSESATPESGPGSPAGSPTSTEEGSPAGSPTS

551 TEEGTSTEPSEGSAPGTSESATPESGPGTSESATPESGPGTSESATPESG

601 PGSEPATSGSETPGSEPATSGSETPGSPAGSPTSTEEGTSTEPSEGSAPG

651 TSTEPSEGSAPGSEPATSGSETPGTSESATPESGPGTSTEPSEGSAPGGG

701 GSGGGGSGGGGSGGGGSGGGGSGGGGSEIV MTQSPATLSV SPGERATLSC

751 RASSSVNYMY WYQQKPGQAP RLLIYYTSNL APGIPARFSG SGSGTEFTLT

801 ISSLQSEDFA VYYCQQFSSS PWTFGQGTKV EIKRTVAAPS VFIFPPSDEQ

851 LKSGTASVVC LLNNFYPREA KVQWKVDNAL QSGNSQESVT EQDSKDSTYS

901 LSSTLTLSKA DYEKHKVYAC EVTHQGLSSP VTKSFNRGEC *
```

The Fab heavy chain discussed above in Example 3, Fab-037 (SEQ ID NO:75) associates with the Fab light chain in FVII-265.

Example 10: FVII-265/Fab-037 Shows More Potent ROTEM Activity than rFVIIa in a Platelet Targeting-Dependent Manner Human αIIb transgenic HemA mice were dosed with the indicated doses of 0.3, 1, 3, 10, 30, and 100 nmol/kg of FVII-265/Fab-037 (solid dots in FIGS. 14A and B) or 3, 10, 30,100 nmol/kg of rFVIIa (open circles in FIG. 14) or vehicle (open triangle in FIGS. 14A and 14B). Five minutes post-dosing mice were euthanized and blood was collected from the vena cava. Whole blood clotting times were analyzed by ROTEM as described in Example 5 above. FVII-265/Fab-037 showed increased clotting activity in a platelet targeting-dependent manner compared to FVIIa (FIG. 14A), whereas, in HemA mice in which the murine αIIb/β3 integrin is not targeted by FVII-251/Fab-037, similar clotting times of FVII-251/Fab-037 and FVIIa were measured. The data for each time point is the average+/− standard deviation of 3 to 4 mice (FIG. 14B).

Figure 15:
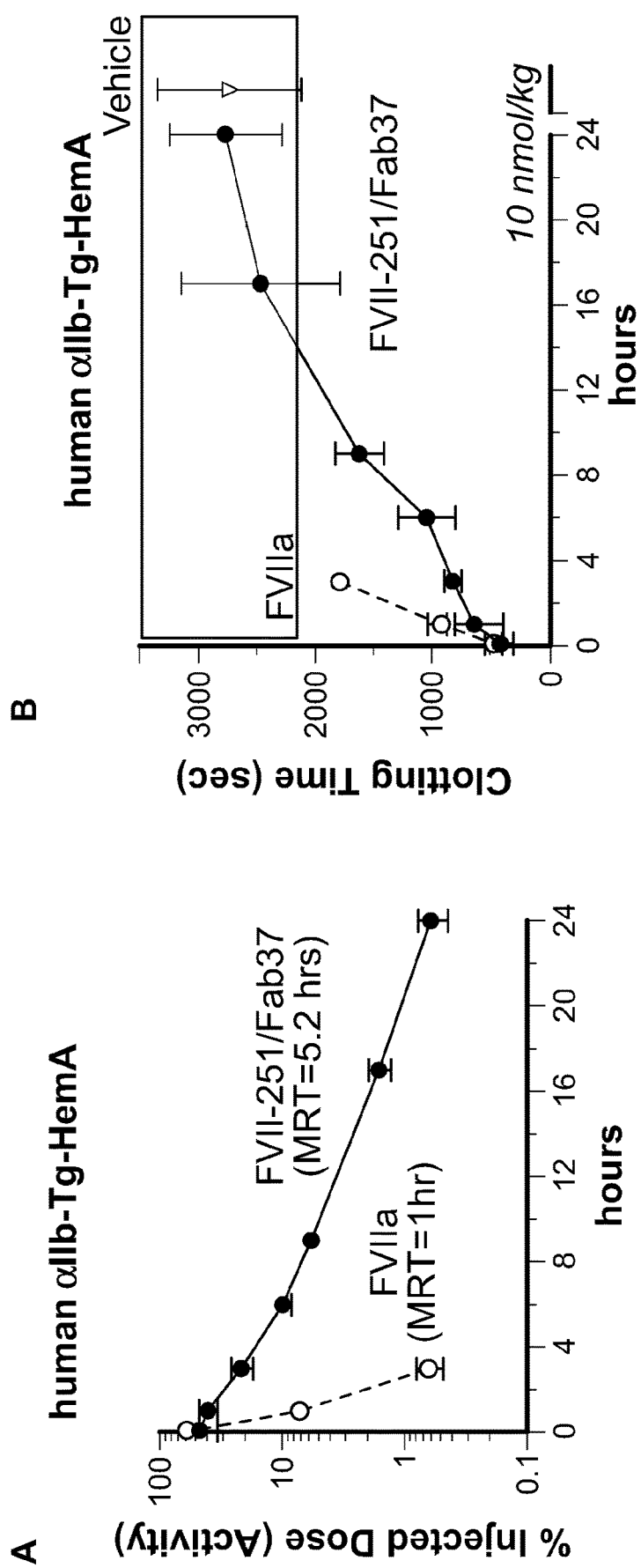
FIG. 15A is a graph showing the plasma PK as measured by soluble tissue factor (sTF)-prothrombin time (PT) activity of FVIIa and FVII-251/Fab-037 dosed at 10 nmol/kg, showing an approximately 5-fold decreased clearance of plasma levels of FVII-251/Fab-037 compared to rFVIIa.
FIG. 15B is a graph comparing the clotting time (CT) in seconds as measured in whole blood by ROTEM at the indicated time points, comparing recombinant FVII-251/Fab37 to FVIIa both dosed at 10 nmol/kg over time in human αIIb transgenic HemA mice.

Example 11: Improved Pharmacokinetics of FVII-251/Fab-037 Compared with rFVIIa in Human αIIb Transgenic HemA Mice Correlates with Prolonged and Improved ROTEM Clotting Time Efficacy Human αIIb-transgenic HemA mice were dosed with either 10 nmol/kg rFVIIa, FVII-251/Fab-037 or vehicle. Blood was collected from the vena cava at t=5 min, 1, 3, 6, 9, 17, or 24 hours post dosing with FVII-251/Fab37, or at t=5 min, 1, or 3 hours for FVIIa. Plasma levels of FVII-251/Fab-037 or FVIIa were determined by soluble tissue factor (sTF)-prothrombin time (PT) activity using dosing material as activity standards. In FIG. 15A, plasma activity is plotted as % of injected dose. Mean Residence Time (MRT) and other pharmacokinetic (PK) parameters were calculated using Phoenix WinNonLin 6.2.1 (Pharsight, Certara) by NCA analysis. Clotting times in the freshly isolated whole blood samples were determined in a ROTEM machine (FIG. 15B). As indicated in FIG. 15B, FVII-251/Fab-037 shows, when dosed at equal molar doses, improved clotting times compared to FVIIa over a longer time interval, which correlates with the improved plasma PK profile of FVII-251/Fab-037.

Figure 16:
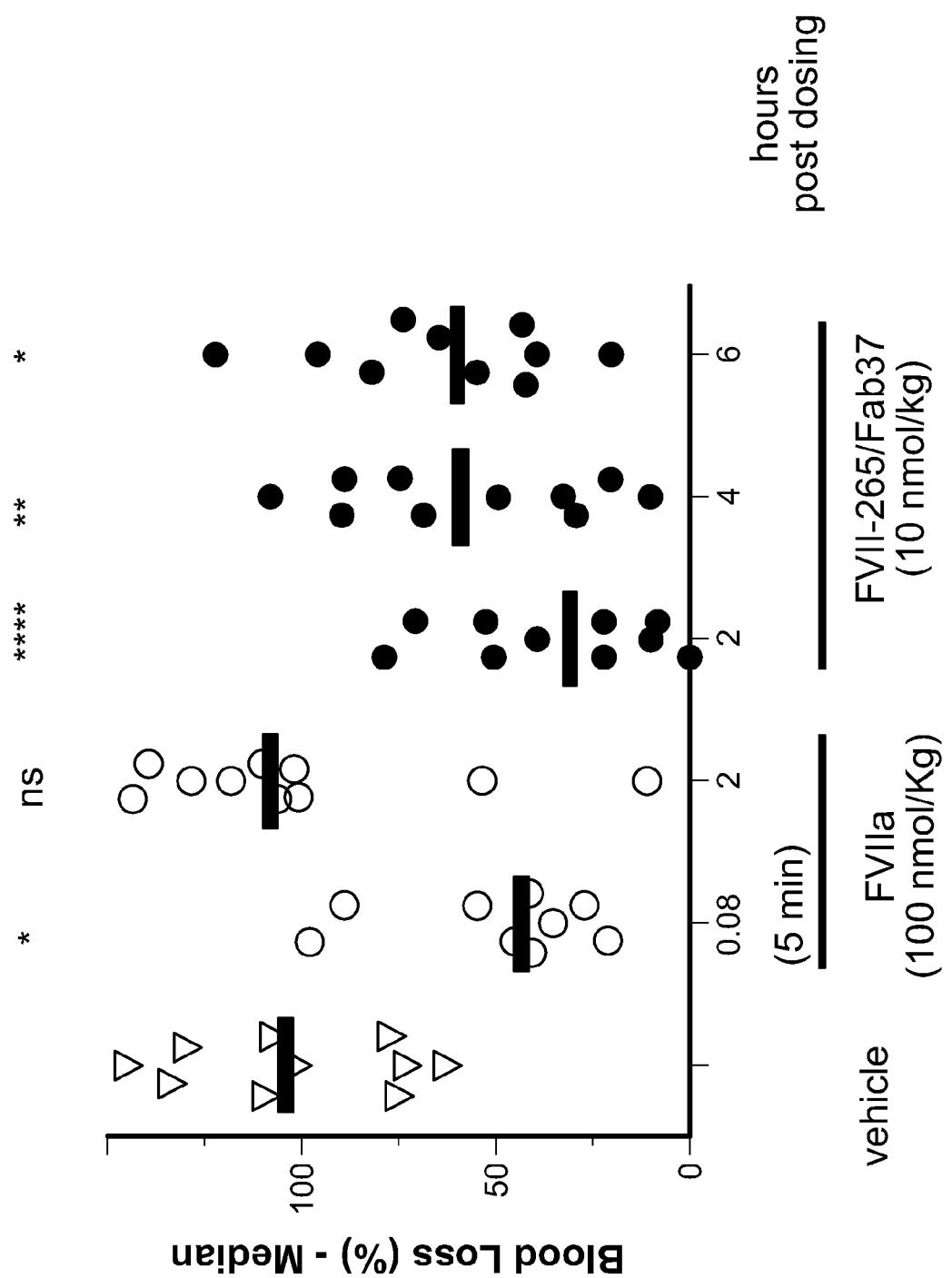
FIG. 16 is a graph showing the prolonged efficacy of 10 nmol/kg FVII-265/Fab-037 compared with 100 nmol/kg rFVIIa in a modified prolonged tail clip bleeding efficacy model.

Example 12: FVII-265/Fab-037 is Efficacious in a Prolonged Tail-Clip Bleeding Efficacy Model in Tg-HemA Mice Prolonged bleeding efficacy was studied in a blinded murine tail-clip bleeding model in human αIIb-transgenic HemA mice (FIG. 16). Prolonged protection was determined in a modified version of the acute tail-clip amputation efficacy model as described in Example 7. In Example 7, blood loss over a 30 minute time frame was measured after a tail-tip amputation applied 5 minutes post-dosing. In the novel prolonged modified model, the tail-tip amputations are performed at a later time points post-dosing, blood loss is again measured over a 30 minute period. After the dosing of 10 nmol/kg FVII-265/Fab-037, tail-tip amputations were performed at 2, 4 and 6 hours post-dosing. Similarly, blood loss was measured at 5 min and 2 hours-post dosing of 100 nmol/kg intravenous dosed FVIIa. Blood loss is indicated as % blood loss, compared to blood loss as measured in vehicle dosed mice at similar time points post-dosing. Indicated are the median blood loss and the statistical significance. The latter was calculated using unpaired two-tailed t-test in GraphPad Prism 6. Such two tailed t-tests showed that the 100 nmol/kg dose of FVIIa significant reduces blood loss at 5 minutes post-dosing and is not advantageous at 2 hours post-dosing. In contrast, a ten-fold lower dose of 10 nmol/kg of FVII-265/Fab-037 shows a similar and efficacious reduction in blood loss 2 hours post-dosing as 100 nmol/kg FVIIa at five minutes post-dosing. In addition, significant reduction in blood loss compared to vehicle treated mice was observed at 4 and 6 hours post-dosing.

Example 13. Generation of FVII-250/Fab-062

In this configuration the Fab light chain within FVII-250 (described in Example 3; SEQ ID NO:74) was dimerized to the Fab heavy chain Fab-062, which comprises an XTEN (AE288) moiety fused to the N-terminus of the Fab heavy chain as illustrated in FIG. 17.

Figure 18:
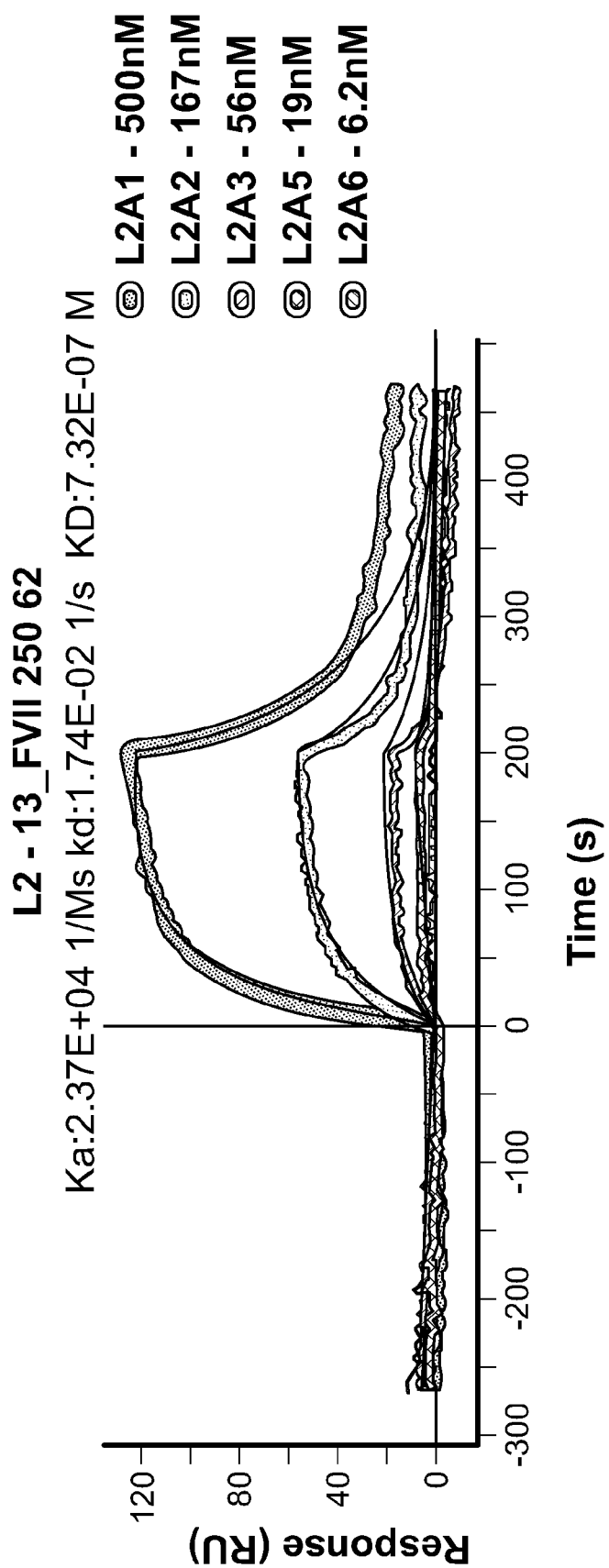
FIG. 18 displays the results of surface plasmon resonance experiments showing the binding of FVII-250/Fab-062 to biotinylated GPIIb/IIIa immobilized on a streptavidin chip.

The amino acid sequence of the Fab-062 is provided below. The XTEN sequence is in bold (note that a glutamic acid (E) is added at the N-terminus of AE288) and the VH2 domain of the Fab is underlined.

resonance (SPR) technology. For this purpose, biotinylated human GPIIb/IIIa ectodomain protein was generated as described in Zhu et al. *Molecular Cell,* 32(6): 849-861 (2008). The GPIIb/IIIa ectodomain protein was immobilized on an SPR chip coated with streptavidin (GE Healthcare). Next, the association and dissociation rates of FVII-250/Fab-062 binding to GPIIb/IIIa at sequentially increasing concentrations of FVII-250/Fab-062 were measured. The kinetic parameters were derived from a 1:1 binding model, and FVII-250/Fab-062 displayed a $K_D=7.3\times10^{-7}$M for its association with GPIIb/IIIa (FIG. 18). These results indicate that Fab-250/Fab-062 can associate with GPIIb/IIIa.

Figure 19:
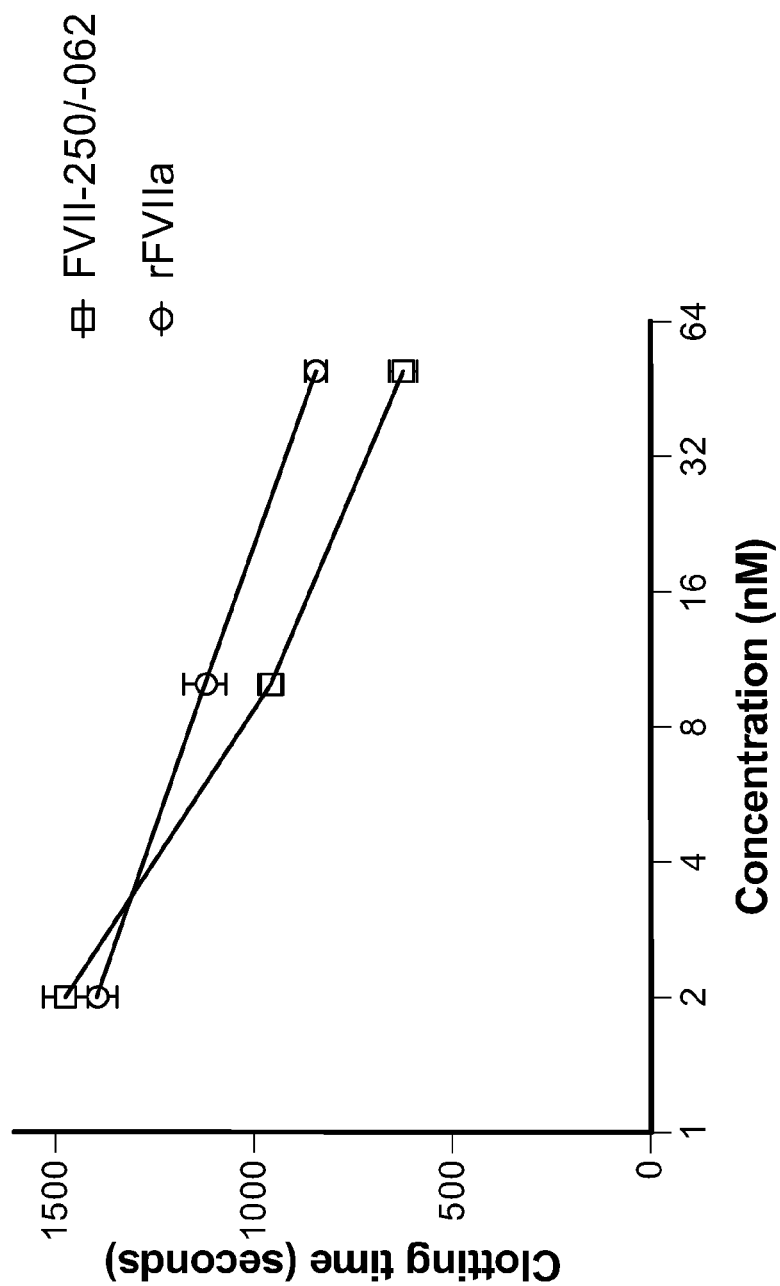
FIG. 19 shows the results of rotational thromboelastometry (ROTEM) experiments measuring the activities of FVII-250/Fab-062 and recombinant FVIIa in whole blood from a hemophilia donor.

Example 15. FVII-250/Fab-062 Shows Improved Activity Compared to FVIIa in Whole Blood Assays The activity of FVII-250/Fab-062 was determined by rotational thromboelastometry (ROTEM) assays using whole blood from hemophilia donors. The activity in whole blood is platelet-dependent, and coagulation was initiated by recalcification of the blood. FVII-250/Fab-062 displays enhanced activity compared to FVIIa, indicated by faster clotting times for FVII-250/Fab-062 than FVIIa at equivalent concentrations (FIG. 19). These data demonstrate that this Fab targeting moiety, with an XTEN moiety at the

```
                                                            (SEQ ID NO: 252)
  1 EGTSESATPE SGPGSEPATS GSETPGTSES ATPESGPGSE PATSGSETPG

51 TSESATPESG PGTSTEPSEG SAPGSPAGSP TSTEEGTSES ATPESGPGSE

101 PATSGSETPG TSESATPESG PGSPAGSPTS TEEGSPAGSP TSTEEGTSTE

151 PSEGSAPGTS ESATPESGPG TSESATPESG PGTSESATPE SGPGSEPATS

201 GSETPGSEPA TSGSETPGSP AGSPTSTEEG TSTEPSEGSA PGTSTEPSEG

251 SAPGSEPATS GSETPGTSES ATPESGPGTS TEPSEGSAPEVQLVESGGGL

301 VKPGGSLRLSCAASGFTFSAYAMSWVRQAPGKGLVWVASISSGGTTYYPD

351 SVKRQFTISRDNAKNTLYLQMNSLRAEDTAVYYCTRGGDYGYALDYWGQG

401 TLVTVSSAST KGPSVFPLAP SSKSTSGGTA ALGCLVKDYF PEPVTVSWNS

451 GALTSGVHTF PAVLQSSGLY SLSSVVTVPS SSLGTQTYIC NVNHKPSNTK

501 VDKKVEPKSC *
```

To generate this fusion protein, DNA encoding the above protein sequence was synthesized, cloned into an expression vector, and expressed in HEK 293 cells by transient transfection. The fusion protein was then purified from the conditioned media.

Example 14. Surface Plasmon Resonance Studies to Determine the Affinity of FVII-250/Fab-062 for Purified GPIIb/IIIa To measure the affinity of FVII-250/Fab-062 for GPIIb/IIIa, binding assays were performed using surface plasmon N-terminus of the Fab heavy chain, can target FVIIa to platelets and increase its potency.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that binds to glycoprotein IIb/IIIa (GPIIb/IIIa), wherein the antibody or the antigen-binding fragment thereof comprises a heavy chain variable region that is at least 95% identical to the amino acid sequence set forth in SEQ ID NO:7 and a light chain variable region that is at least 95% identical to the amino acid sequence set forth in SEQ ID NO:4, wherein the heavy chain variable region comprises complementarity determining region (CDR)1, CDR2, and CDR3 consisting of the amino acid sequences AYAMS (SEQ ID NO:25), SISSGGTTYYPDSVKR (SEQ ID NO:26), and GGDYGYALDY (SEQ ID NO:27), respectively, and wherein the light chain variable region comprises CDR1, CDR2, and CDR3 consisting of the amino acid sequences RASSSVNYMY (SEQ ID NO:28), YTSNLAP (SEQ ID NO:29), and QQFSSSPWT (SEQ ID NO:30), respectively.

2. The antibody or antigen-binding fragment thereof of claim 1, wherein the heavy chain variable region is at least 98% identical to the amino acid sequence set forth in SEQ ID NO:7 and the light chain variable region is at least 98% identical to the amino acid sequence set forth in SEQ ID NO:4.

3. The antibody or antigen-binding fragment thereof of claim 1, wherein the heavy chain variable region is at least 99% identical to the amino acid sequence set forth in SEQ ID NO:7 and the light chain variable region is at least 99% identical to the amino acid sequence set forth in SEQ ID NO:4.

4. An antibody or antigen-binding fragment thereof that binds to glycoprotein IIb/IIIa (GPIIb/IIIa), wherein the antibody or the antigen-binding fragment thereof comprises a heavy chain variable region comprising the amino acid sequence set forth in SEQ ID NO:7 and a light chain variable region comprising the amino acid sequence set forth in SEQ ID NO:4.

5. The antibody or antigen-binding fragment thereof of claim 1, wherein the antigen-binding fragment is selected from the group consisting of an Fab, an Fab', an F(ab')$_2$, an Fv, an Fd, a diabody, an scFv, and an sc(Fv)$_2$.

6. The antibody or antigen-binding fragment thereof of claim 2, wherein the antigen-binding fragment is selected from the group consisting of an Fab, an Fab', an F(ab')$_2$, an Fv, an Fd, a diabody, an scFv, and an sc(Fv)$_2$.

7. The antibody or antigen-binding fragment thereof of claim 3, wherein the antigen-binding fragment is selected from the group consisting of an Fab, an Fab', an F(ab')$_2$, an Fv, an Fd, a diabody, an scFv, and an sc(Fv)$_2$.

8. The antibody or antigen-binding fragment thereof of claim 4, wherein the antigen-binding fragment is selected from the group consisting of an Fab, an Fab', an F(ab')$_2$, an Fv, an Fd, a diabody, an scFv, and an sc(Fv)$_2$.

9. A pharmaceutical composition comprising the antibody or antigen-binding fragment thereof of claim 1, and a pharmaceutically acceptable carrier.

10. A pharmaceutical composition comprising the antibody or antigen-binding fragment thereof of claim 2, and a pharmaceutically acceptable carrier.

11. A pharmaceutical composition comprising the antibody or antigen-binding fragment thereof of claim 3, and a pharmaceutically acceptable carrier.

12. A pharmaceutical composition comprising the antibody or antigen-binding fragment thereof of claim 4, and a pharmaceutically acceptable carrier.

13. A pharmaceutical composition comprising the antibody or antigen-binding fragment thereof of claim 5, and a pharmaceutically acceptable carrier.

14. A pharmaceutical composition comprising the antibody or antigen-binding fragment thereof of claim 6, and a pharmaceutically acceptable carrier.

15. A pharmaceutical composition comprising the antibody or antigen-binding fragment thereof of claim 7, and a pharmaceutically acceptable carrier.

16. A pharmaceutical composition comprising the antibody or antigen-binding fragment thereof of claim 8, and a pharmaceutically acceptable carrier.

* * * * *